(12) United States Patent
Parham et al.

(10) Patent No.: US 12,250,880 B2
(45) Date of Patent: Mar. 11, 2025

(54) COMPOUNDS FOR ELECTRONIC DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Anja Jatsch, Frankfurt am Main (DE); Christian Eickhoff, Mannheim (DE); Christian Ehrenreich, Darmstadt (DE); Jens Kaiser, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 839 days.

(21) Appl. No.: 17/298,555

(22) PCT Filed: Nov. 28, 2019

(86) PCT No.: PCT/EP2019/082821
§ 371 (c)(1),
(2) Date: May 29, 2021

(87) PCT Pub. No.: WO2020/109434
PCT Pub. Date: Jun. 4, 2020

(65) Prior Publication Data
US 2022/0013730 A1    Jan. 13, 2022

(30) Foreign Application Priority Data

Nov. 30, 2018    (EP) .................... 18209646

(51) Int. Cl.
| | |
|---|---|
| H10K 85/60 | (2023.01) |
| C07D 471/04 | (2006.01) |
| C07D 471/14 | (2006.01) |
| C07D 519/00 | (2006.01) |
| C09K 11/06 | (2006.01) |
| H10K 50/11 | (2023.01) |
| H10K 50/16 | (2023.01) |
| H10K 50/17 | (2023.01) |
| H10K 50/18 | (2023.01) |
| H10K 101/10 | (2023.01) |

(52) U.S. Cl.
CPC ......... *H10K 85/657* (2023.02); *C07D 471/04* (2013.01); *C07D 471/14* (2013.01); *C07D 519/00* (2013.01); *C09K 11/06* (2013.01); *H10K 85/6572* (2023.02); *H10K 85/6574* (2023.02); *C09K 2211/1018* (2013.01); *H10K 50/11* (2023.02); *H10K 50/16* (2023.02); *H10K 50/171* (2023.02); *H10K 50/18* (2023.02); *H10K 2101/10* (2023.02)

(58) Field of Classification Search
CPC ............. H10K 85/657; H10K 85/6574; H10K 85/6572; H10K 2101/10; H10K 50/16; H10K 50/18; H10K 50/11; H10K 50/171; C07D 471/04; C07D 471/14; C07D 519/00; C09K 11/06; C09K 2211/1018
See application file for complete search history.

(56) References Cited

U.S. PATENT DOCUMENTS

| | | |
|---|---|---|
| 2015/0340621 A1 | 11/2015 | Parham et al. |
| 2017/0141328 A1 | 5/2017 | Hayer et al. |
| 2017/0141329 A1 | 5/2017 | Koenen et al. |

FOREIGN PATENT DOCUMENTS

| | | |
|---|---|---|
| CN | 102869662 A | 1/2013 |
| CN | 104024371 A | 9/2014 |
| CN | 104871329 A | 8/2015 |
| CN | 106459747 A | 2/2017 |
| DE | 102010019306 A1 | 11/2011 |
| WO | 2013/064206 A1 | 5/2013 |
| WO | 2014/056567 A1 | 4/2014 |
| WO | 2014/094964 A1 | 6/2014 |
| WO | 2018/099846 A1 | 6/2018 |

OTHER PUBLICATIONS

International Preliminary Report on Patentability received for PCT Patent Application No. PCT/EP2019/082821, mailed on Jun. 10, 2021, 13 pages (8 pages of English Translation and 5 pages of Original Document).
International Search Report and Written Opinion received for PCT Patent Application No. PCT/EP2019/082821, mailed on Jan. 21, 2020, 16 pages (7 pages of English Translation and 9 pages of Original Document).

*Primary Examiner* — Shane Fang
(74) *Attorney, Agent, or Firm* — Faegre Drinker Biddle & Reath LLP

(57) ABSTRACT

The present invention relates to compounds of formula (I), to processes for producing the compounds, and to electronic devices containing at least one compound of formula (I).

19 Claims, No Drawings

COMPOUNDS FOR ELECTRONIC DEVICES

CROSS-REFERENCE TO RELATED APPLICATIONS

This application is a national stage application (under 35 U.S.C. § 371) of PCT/EP2019/082821, filed Nov. 28, 2019, which claims benefit of European Application No. 18209646.1, filed Nov. 30, 2018, both of which are incorporated herein by reference in their entirety.

The present application relates to compounds containing a cyclic lactam group. The compounds are suitable for use in electronic devices.

Electronic devices in the context of this application are understood to mean what are called organic electronic devices, which comprise organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in an improvement in the performance data, especially lifetime, efficiency, operating voltage and color purity. In these aspects, it has not yet been possible to find any entirely satisfactory solution. There is also a need for novel, alternative compounds for use in electronic devices, especially in OLEDs.

A great influence on the performance data of electronic devices is possessed by emitting layers, especially phosphorescent emitting layers, and very especially red-phosphorescing emitting layers. Novel compounds are also being sought for use in these layers, especially compounds that can serve as matrix material, especially for red- or green-phosphorescing emitters, in an emitting layer. More particularly, there is a search for compounds that have a high glass transition temperature $T_G$ and high oxidation and thermal stability, and that result in a high efficiency of the devices when used in OLEDs.

The prior art discloses a multitude of heteroaromatic compounds for use as matrix material for phosphorescent emitting layers, for example carbazole derivatives and quinazoline derivatives.

However, there is still a need for alternative compounds suitable for use in electronic devices, especially for compounds having one or more of the abovementioned advantageous properties. There is still a need for improvement in the performance data achieved when the compounds are used in electronic devices, especially in respect of lifetime, operating voltage, efficiency and color purity of the devices.

It has been found that particular compounds containing a cyclic lactam group are of excellent suitability for use in electronic devices, especially for use in OLEDs, more especially for use therein as matrix materials for phosphorescent emitters, especially red- or green-phosphorescing emitters. The compounds lead to high lifetime, high efficiency, low operating voltage and high color purity of the devices. Further preferably, the compounds have a high glass transition temperature $T_G$ and high oxidation stability and thermal stability.

The compounds conform to a formula (I)

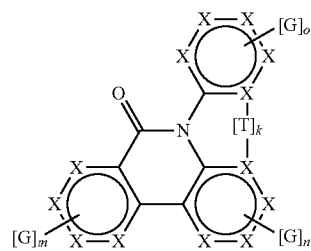

Formula (I)

where the variables that occur are as follows:
G is the same or different at each instance and is selected from a group of the formula (G-1)

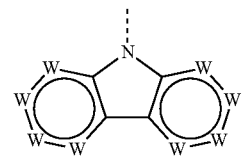

Formula (G-1)

attached via the dotted bond,
where, in formula (G-1), W is the same or different at each instance and is $CR^2$ or N; or one or more units from any two adjacent W groups are the same or different at each instance and are selected from units of the formulae (W-1) to (W-2)

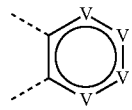

Formula (W-1)

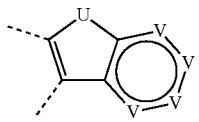

Formula (W-2)

where the dotted bonds represent the bonds to the rest of the formula (G-1);
where U is the same or different at each instance and is selected from O, S, $NR^3$ and $C(R^3)_2$, and
where, in formula (W-1) to (W-2), V is the same or different at each instance and is $CR^2$ or N; or one or more units from any two adjacent V groups are the same or different at each instance and are selected from units of the formulae (V-1) to (V-2)

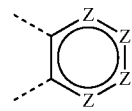

Formula (V-1)

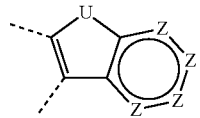

Formula (V-2)

where the dotted bonds represent the bonds to the rest of the formulae (W-1) to (W-2);

where Z is the same or different at each instance and is $CR^2$ or N;

X, when no G or T is bonded thereto, is the same or different at each instance and is N or $CR^1$; and X, when G or T is bonded thereto, is C;

T is a single bond that connects the X groups in question;

$R^1$ is the same or different at each instance and is selected from H, D, F, Cl, Br, I, C(=O)$R^4$, CN, Si($R^4$)$_3$, N($R^4$)$_2$, P(=O)($R^4$)$_2$, O$R^4$, S(=O)$R^4$, S(=O)$_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more $CH_2$ groups in the alkyl, alkoxy, alkenyl and alkynyl groups mentioned may be replaced by —$R^4C$=$CR^4$—, —C≡C—, Si($R^4$)$_2$, C=O, C=N$R^4$, —C(=O)O—, —C(=O)N$R^4$—, N$R^4$, P(=O)($R^4$), —O—, —S—, SO or $SO_2$;

$R^2$ is the same or different at each instance and is selected from H, D, F, Cl, Br, I, C(=O)$R^4$, CN, Si($R^4$)$_3$, N($R^4$)$_2$, P(=O)($R^4$)$_2$, O$R^4$, S(=O)$R^4$, S(=O)$_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more $CH_2$ groups in the alkyl, alkoxy, alkenyl and alkynyl groups mentioned may be replaced by —$R^4C$=$CR^4$—, —C≡C—, Si($R^4$)$_2$, C=O, C=N$R^4$, —C(=O)O—, —C(=O)N$R^4$—, N$R^4$, P(=O)($R^4$), —O—, —S—, SO or $SO_2$;

$R^3$ is the same or different at each instance and is selected from H, D, F, Cl, Br, I, CN, Si($R^4$)$_3$, N($R^4$)$_2$, straight-chain alkyl groups having 1 to 20 carbon atoms, branched or cyclic alkyl groups having 3 to 20 carbon atoms, aromatic ring systems having 6 to 40 aromatic ring atoms, and heteroaromatic ring systems having 5 to 40 aromatic ring atoms; where two or more $R^3$ radicals may be joined to one another and may form a ring;

where the alkyl groups mentioned and the aromatic ring systems and heteroaromatic ring systems mentioned are each substituted by $R^4$ radicals;

$R^4$ is the same or different at each instance and is selected from H, D, F, Cl, Br, I, C(=O)$R^5$, CN, Si($R^5$)$_3$, N($R^5$)$_2$, P(=O)($R^5$)$_2$, O$R^5$, S(=O)$R^5$, S(=O)$_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^4$ radicals may be joined to one another and may form a ring; where the alkyl, alkoxy, alkenyl and alkynyl groups mentioned and the aromatic ring systems and heteroaromatic ring systems mentioned are each substituted by $R^5$ radicals; and where one or more $CH_2$ groups in the alkyl, alkoxy, alkenyl and alkynyl groups mentioned may be replaced by —$R^5C$=$CR^5$—, —C≡C—, Si($R^5$)$_2$, C=O, C=N$R^5$, —C(=O)O—, —C(=O)N$R^5$—, N$R^5$, P(=O)($R^5$), —O—, —S—, SO or $SO_2$;

$R^5$ is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^5$ radicals may be joined to one another and may form a ring; and where the alkyl, alkoxy, alkenyl and alkynyl groups, aromatic ring systems and heteroaromatic ring systems mentioned may be substituted by one or more radicals selected from F and CN;

k is 0 or 1, where, when k is 0, T is absent, and the X groups in question are not bonded to one another;

m, n, o is the same or different at each instance and is selected from 0 and 1, where at least one of the indices m, n and o must be 1;

where at least one X group in at least one of the rings to which a G group is bonded is N.

A circle drawn within a ring means that the ring in question has aromaticity, preferably from three delocalized double bonds.

The definitions which follow are applicable to the chemical groups that are used in the present application. They are applicable unless any more specific definitions are given.

An aryl group in the context of this invention is understood to mean either a single aromatic cycle, i.e. benzene, or a fused aromatic polycycle, for example naphthalene, phenanthrene or anthracene. A fused aromatic polycycle in the context of the present application consists of two or more single aromatic cycles fused to one another. Fusion between cycles is understood here to mean that the cycles share at least one edge with one another. An aryl group in the context of this invention contains 6 to 40 aromatic ring atoms of which none is a heteroatom.

A heteroaryl group in the context of this invention is understood to mean either a single heteroaromatic cycle, for example pyridine, pyrimidine or thiophene, or a fused heteroaromatic polycycle, for example quinoline or carbazole. A fused heteroaromatic polycycle in the context of the present application consists of two or more single aromatic or heteroaromatic cycles that are fused to one another, where at least one of the aromatic and heteroaromatic cycles is a heteroaromatic cycle. Fusion between cycles is understood here to mean that the cycles share at least one edge with one another. A heteroaryl group in the context of this invention contains 5 to 40 aromatic ring atoms of which at least one is a heteroatom. The heteroatoms of the heteroaryl group are preferably selected from N, O and S.

An aryl or heteroaryl group, each of which may be substituted by the abovementioned radicals, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, benzimidazole[1,2-a]benzimidazole, naphthimidazole, phenanthroimidazole, pyridoimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention is a system which does not necessarily contain solely aryl groups, but which may additionally contain one or more nonaromatic rings fused to at least one aryl group. These nonaromatic rings contain exclusively carbon atoms as ring atoms. Examples of groups covered by this definition are tetrahydronaphthalene, fluorene and spirobifluorene. In addition, the term "aromatic ring system" includes systems that consist of two or more aromatic ring systems joined to one another via single bonds, for example biphenyl, terphenyl, 7-phenyl-2-fluorenyl, quaterphenyl and 3,5-diphenyl-1-phenyl. An aromatic ring system in the context of this invention contains 6 to 40 carbon atoms and no heteroatoms in the ring system. The definition of "aromatic ring system" does not include heteroaryl groups.

A heteroaromatic ring system conforms to the abovementioned definition of an aromatic ring system, except that it must contain at least one heteroatom as ring atom. As is the case for the aromatic ring system, the heteroaromatic ring system need not contain exclusively aryl groups and heteroaryl groups, but may additionally contain one or more nonaromatic rings fused to at least one aryl or heteroaryl group. The nonaromatic rings may contain exclusively carbon atoms as ring atoms, or they may additionally contain one or more heteroatoms, where the heteroatoms are preferably selected from N, O and S. One example of such a heteroaromatic ring system is benzopyranyl. In addition, the term "heteroaromatic ring system" is understood to mean systems that consist of two or more aromatic or heteroaromatic ring systems that are bonded to one another via single bonds, for example 4,6-diphenyl-2-triazinyl. A heteroaromatic ring system in the context of this invention contains 5 to 40 ring atoms selected from carbon and heteroatoms, where at least one of the ring atoms is a heteroatom. The heteroatoms of the heteroaromatic ring system are preferably selected from N, O and S.

The terms "heteroaromatic ring system" and "aromatic ring system" as defined in the present application thus differ from one another in that an aromatic ring system cannot have a heteroatom as ring atom, whereas a heteroaromatic ring system must have at least one heteroatom as ring atom. This heteroatom may be present as a ring atom of a nonaromatic heterocyclic ring or as a ring atom of an aromatic heterocyclic ring.

In accordance with the above definitions, any aryl group is covered by the term "aromatic ring system", and any heteroaryl group is covered by the term "heteroaromatic ring system".

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethenylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, one, two, three or four X groups in formula (I) are N, more preferably two or three, most preferably two.

Preferably, in one of the three rings in formula (I) containing X groups, two X groups are N.

Preferably, in a ring to which a G group binds, exactly one or two, more preferably two, X groups are N. Preferably, in a ring to which a G group binds, one or two X groups adjacent to the bond to G are N. More preferably, in the ring to which a G group binds, two X groups are adjacent to the bond to G, and both are N.

Preferably, k is 0.

Preferably, the sum total of the indices m, n and o is 1, such that exactly one G group is present in formula (I). More preferably, at least one of the indices m and n is 1; most preferably, one of the indices m and n is 1, and the other of the indices m and n is 0. It is further preferable that index o is 0.

It is preferable that, in a ring in formula (I) to which a G group binds, no $R^1$ radical is H or D, and at least one X group is N; in particular, two X groups are N. Preferably, in a ring in formula (I) to which a G group binds, all $R^1$ radicals are selected from F, CN, $Si(R^4)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups mentioned, the aromatic ring systems mentioned and the heteroaromatic ring systems mentioned are each substituted by $R^4$ radicals, and at least one X group is N; in particular, two X groups are N. More preferably, in a ring in formula (I) to which a G group binds, all $R^1$ radicals are selected from aromatic ring systems that have 6 to 40 aromatic ring atoms and are substituted by one or more $R^4$ radicals, and heteroaromatic ring systems that have 5 to 40 aromatic ring atoms and are substituted by one or more $R^4$ radicals, and at least one X group is N; in particular, two X groups are N. It is further preferable that this preferred embodiment occurs in combination with that preferred embodiment in which, in a ring to which a G group binds, one or two X groups adjacent to the bond to G are N; in particular, two X groups adjacent to the bond to G are N.

Preferably, $R^1$ is the same or different at each instance and is selected from H, D, F, CN, $Si(R^4)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned are each substituted by $R^4$ radicals; and where one or more $CH_2$ groups in the alkyl groups mentioned may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—. More preferably, $R^1$ is the same or different at each instance and is selected from H, aromatic ring systems that have 6 to aromatic ring atoms and are substituted by $R^4$ radicals, and heteroaromatic ring systems that have 5 to 40 aromatic ring atoms and are substituted by $R^4$ radicals. Preferably, $R^1$ in a ring to which a G group binds is selected from F, CN, $Si(R^4)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups mentioned, the aromatic ring systems mentioned and the heteroaromatic ring systems mentioned are each substituted by $R^4$ radicals. More preferably, $R^1$ in a ring to which a G group binds is selected from aromatic ring systems having 6 to 40 aromatic ring atoms and heteroaromatic ring systems having 5 to 40 aromatic ring atoms, each of which are substituted by $R^4$ radicals.

Preferably, $R^2$ is the same or different at each instance and is selected from H, D, F, CN, $Si(R^4)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned are each substituted by $R^4$ radicals; and where one or more $CH_2$ groups in the alkyl groups mentioned may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—. More preferably, $R^2$ is the same or different at each instance and is selected from H, aromatic ring systems that have 6 to aromatic ring atoms and are substituted by $R^4$ radicals, and heteroaromatic ring systems that have 5 to 40 aromatic ring atoms and are substituted by $R^4$ radicals. Even more preferably, $R^2$ is H.

Preferably, $R^3$ is the same or different at each instance and is selected from H, straight-chain alkyl groups having 1 to 20 carbon atoms, branched or cyclic alkyl groups having 3 to 20 carbon atoms, aromatic ring systems having 6 to 40 aromatic ring atoms, and heteroaromatic ring systems having 5 to 40 aromatic ring atoms; where two $R^3$ radicals may be joined to one another and may form a ring; where the alkyl groups mentioned and the aromatic ring systems and heteroaromatic ring systems mentioned are each substituted by $R^4$ radicals. Most preferably, $R^3$ is the same or different at each instance and is selected from straight-chain alkyl groups having 1 to 20 carbon atoms, branched or cyclic alkyl groups having 3 to 20 carbon atoms, aromatic ring systems having 6 to 40 aromatic ring atoms, and heteroaromatic ring systems having 5 to 40 aromatic ring atoms; where two $R^3$ radicals may be joined to one another and may form a ring; where the alkyl groups mentioned and the aromatic ring systems and heteroaromatic ring systems mentioned are each substituted by $R^4$ radicals.

In the case of linkage of two $R^3$ radicals that form a ring, it is preferable that these two radicals are constituents of a U group that is $C(R^3)_2$, so as to form a spiro system. Preferably, in this case, the two $R^3$ radicals are selected from aromatic ring systems having 6 to 40 aromatic ring atoms and heteroaromatic ring systems having 5 to 40 aromatic ring atoms, each of which are substituted by $R^4$ radicals, more preferably from phenyl groups each substituted by $R^4$ radicals, so as to form a spirobifluorene unit.

Preferably, $R^4$ is the same or different at each instance and is selected from H, D, F, CN, $Si(R^5)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned are each substituted by $R^5$ radicals; and where one or more $CH_2$ groups in the alkyl groups mentioned may be replaced by —C≡C—, —$R^5$C=C$R^5$—, $Si(R^5)_2$, C=O, C=N$R^5$, —N$R^5$—, —O—, —S—, —C(=O)O— or —C(=O)N$R^5$—. More preferably, $R^4$ is the same or different at each instance and is selected from H, aromatic ring systems that have 6 to aromatic ring atoms and are substituted by $R^5$ radicals, and heteroaromatic ring systems that have 5 to 40 aromatic ring atoms and are substituted by $R^5$ radicals. Even more preferably, $R^4$ is H.

Preferably, in formula (G-1), one unit consisting of any two adjacent W groups is selected from units of the formulae (W-1) and (W-2), preferably (W-2), and the remaining W groups are the same or different at each instance and are N or $CR^2$, preferably $CR^2$.

In an alternative, likewise preferred embodiment, in formula (G-1), all W groups are the same or different and are selected from N and $CR^2$, preferably $CR^2$. In this case, it is preferable that one or more of the $R^2$ radicals are carbazole, preferably C-bonded carbazole, in each case substituted by $R^4$ radicals, or contain a carbazole unit, in each case substituted by $R^4$ radicals. C-bonded carbazole is understood to mean carbazole bonded via one of its carbon atoms.

In an alternative, likewise preferred embodiment, in formula (G-1), two units consisting of any two adjacent W groups are selected from units of the formulae (W-1) to (W-2), and the remaining W groups are the same or different at each instance and are N or $CR^2$, preferably $CR^2$. In this embodiment, it is particularly preferable that, of the two units consisting of any two adjacent W groups, one unit conforms to the formula (W-1), where V is preferably $CR^2$, and the other unit conforms to the formula (W-2), where V is preferably $CR^2$.

Preferably, in formula (W-1), one unit consisting of two adjacent V groups is selected from units of the formulae (V-1) and (V-2), and the remaining V groups are the same or different at each instance and are N or $CR^2$, preferably $CR^2$.

In an alternative, likewise preferred embodiment, in formula (W-1), all V groups are the same or different and are selected from N and $CR^2$, preferably $CR^2$.

Preferably, in formula (W-2), one unit consisting of two adjacent V groups is selected from units of the formulae (V-1) and (V-2), and the remaining V groups are the same or different at each instance and are N or $CR^2$, preferably $CR^2$.

In an alternative, likewise preferred embodiment, in formula (W-2), all V groups are the same or different and are selected from N and $CR^2$, preferably $CR^2$.

Preferably, Z is $CR^2$.

Preferred groups of the formula (G-1) conform to one of the following formulae:

Formula (G-1-1)

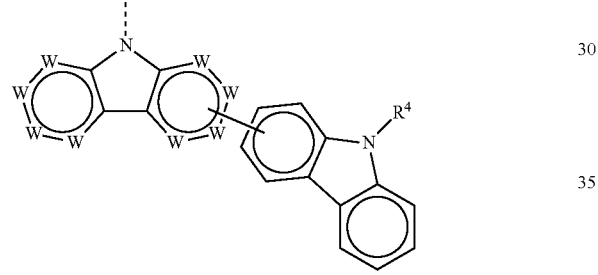

Formula (G-1-2)

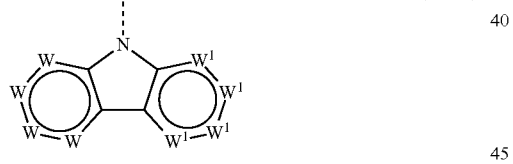

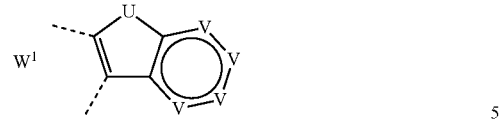

Formula (G-1-3)

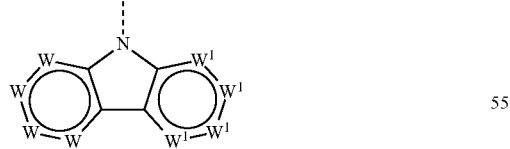

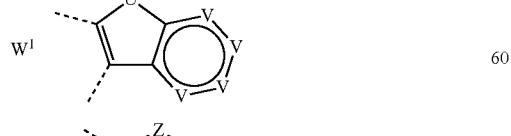

Formula (G-1-4)

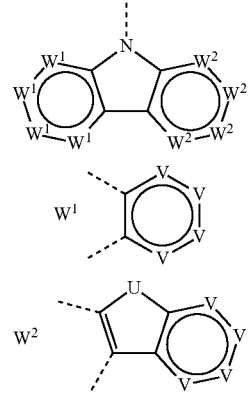

Formula (G-1-5)

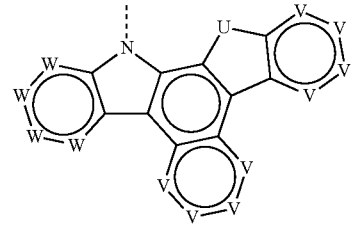

Formula (G-1-6)

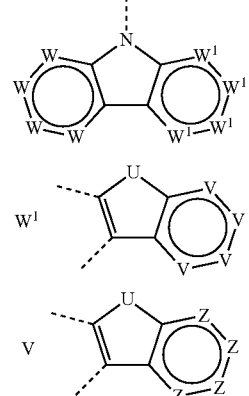

Formula (G-1-7)

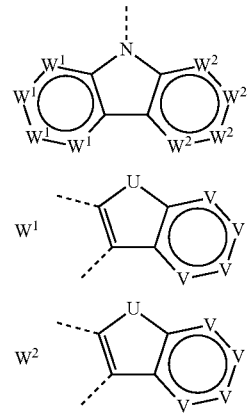

where, in formula (G-1-1), W is as defined above, and W is preferably $CR^2$ or N, more preferably $CR^2$; and where the positions shown as unsubstituted in formula (G-1-1) are substituted by $R^4$ radicals;

where, in formula (G-1-2), a $W^1$—$W^1$ unit is selected from the lower formula, where the dotted lines are the bonds of the unit to the rest of the formula (G-1-2), and where the remaining $W^1$ groups are the same or different and are selected from $CR^2$ and N, and are preferably $CR^2$; and where W is as defined above, and is preferably $CR^2$ or N, more preferably $CR^2$; and where U is as defined above, and is preferably selected from O, $NR^3$ and $C(R^3)_2$, more preferably from $NR^3$; and where V is as defined above, and is preferably N or $CR^2$, more preferably $CR^2$;

where, in formula (G-1-3), a $W^1$—$W^1$ unit is selected from the middle formula, where the dotted lines are the bonds of the unit to the rest of the formula (G-1-3), and where the remaining $W^1$ groups are the same or different and are selected from $CR^2$ and N, and are preferably $CR^2$;

and where W is as defined above, and W is preferably $CR^2$ or N, more preferably $CR^2$; and where, in formula (G-1-3), a V—V unit is selected from the lower formula, where the dotted lines are the bonds of the unit to the rest of the formula (G-1-3), and where the remaining V groups are the same or different and are selected from $CR^2$ and N, and are preferably $CR^2$; and where U is as defined above, and is preferably selected from O, $NR^3$ and $C(R^3)_2$; and where Z is as defined above and is preferably $CR^2$, where, in formula (G-1-4), a $W^1$—$W^1$ unit is selected from the middle formula, where the dotted lines are the bonds of the unit to the rest of the formula (G-1-4), and where the remaining $W^1$ groups are the same or different and are selected from $CR^2$ and N, and are preferably $CR^2$, and where a $W^2$—$W^2$ unit is selected from the lower formula, where the dotted lines are the bonds of the unit to the rest of the formula (G-1-4), and where the remaining $W^2$ groups are the same or different and are selected from $CR^2$ and N, and are preferably $CR^2$, and where V is as defined above, and V is preferably the same or different and is selected from $CR^2$ and N, and is preferably $CR^2$, and where U is as defined above, and is preferably selected from O, $NR^3$ and $C(R^3)_2$;

where, in formula (G-1-5), W is as defined above, and W is preferably $CR^2$ or N, more preferably $CR^2$, and where U is as defined above, and is preferably selected from S; and where V is as defined above, and is preferably N or $CR^2$, more preferably $CR^2$;

where, in formula (G-1-6), a $W^1$—$W^1$ unit is selected from the middle formula, where the dotted lines are the bonds of the unit to the rest of the formula (G-1-6), and where the remaining $W^1$ groups are the same or different and are selected from $CR^2$ and N, and are preferably $CR^2$; and where W is as defined above, and W is preferably $CR^2$ or N, more preferably $CR^2$; and where, in formula (G-1-6), a V—V unit is selected from the lower formula, where the dotted lines are the bonds of the unit to the rest of the formula (G-1-6), and where the remaining V groups are the same or different and are selected from $CR^2$ and N, and are preferably $CR^2$; and where U is as defined above, and is preferably selected from $C(R^3)_2$; and where Z is as defined above and is preferably $CR^2$, where, in formula (G-1-7), a $W^1$—$W^1$ unit is selected from the middle formula, where the dotted lines are the bonds of the unit to the rest of the formula (G-1-7), and where the remaining $W^1$ groups are the same or different and are selected from $CR^2$ and N, and are preferably $CR^2$; and where, in formula (G-1-7), a $W^2$—$W^2$ unit is selected from the lower formula, where the dotted lines are the bonds of the unit to the rest of the formula (G-1-7), and where the remaining $W^2$ groups are the same or different and are selected from $CR^2$ and N, and are preferably $CR^2$; and where U is as defined above, and is preferably $C(R^3)_2$; and where V is as defined above, and is preferably the same or different at each instance and $CR^2$ or N, more preferably $CR^2$.

Among the formulae (G-1-1) to (G-1-7), preference is given to the formulae (G-1-1) to (G-1-5), particular preference to the formula (G-1-1).

The formula (G-1-1) preferably conforms to the following formula (G-1-1-1)

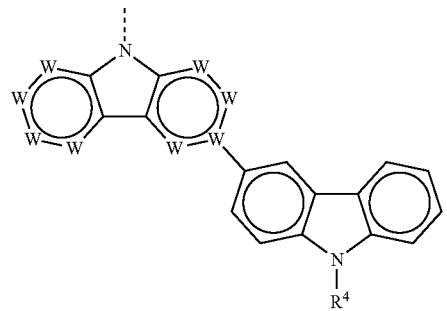

Formula (G-1-1-1)

where the positions shown as unsubstituted are substituted by $R^4$ radicals, and where W is selected from N and $CR^2$ and is preferably $CR^2$.

The formula (G-1-2) preferably conforms to one of the following formulae:

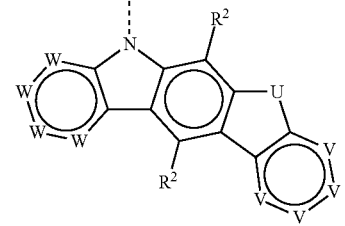

Formula (G-1-2-1)

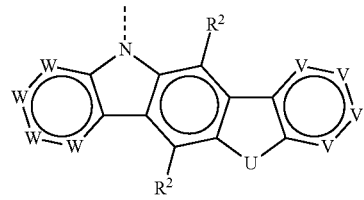

Formula (G-1-2-2)

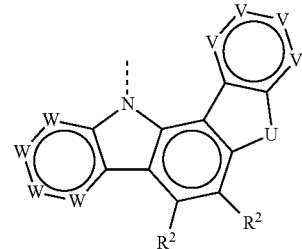

Formula (G-1-2-3)

-continued

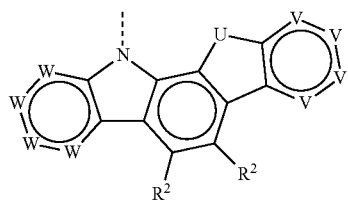

Formula (G-1-2-4)

where W, U and V are as defined above, and where W is preferably the same or different at each instance and is $CR^2$ or N and more preferably $CR^2$; and where U is preferably $C(R^3)_2$, and where V is preferably the same or different at each instance and is $CR^2$ or N and is more preferably $CR^2$.

The formula (G-1-3) preferably conforms to the following formula:

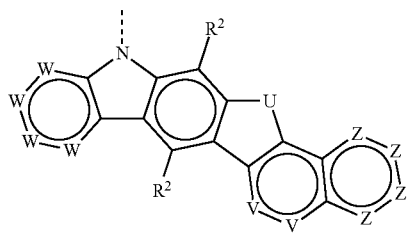

Formula (G-1-3-1)

where W, U, V and Z are as defined above, and where W is preferably the same or different at each instance and is $CR^2$ or N and more preferably $CR^2$, and where U is preferably $C(R^3)_2$, and where V is preferably the same or different at each instance and is $CR^2$ or N and is more preferably $CR^2$; and where Z is preferably $CR^2$.

The formula (G-1-4) preferably conforms to the following formula:

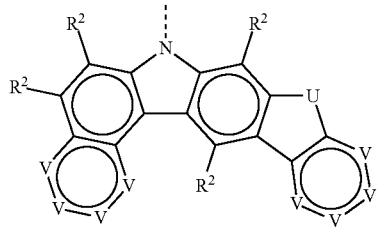

Formula (G-1-4-1)

where U and V are as defined above, and where V is preferably the same or different at each instance and is $CR^2$ or N and is more preferably $CR^2$; and where U is preferably $C(R^3)_2$.

The formula (G-1-5) preferably conforms to the following formula:

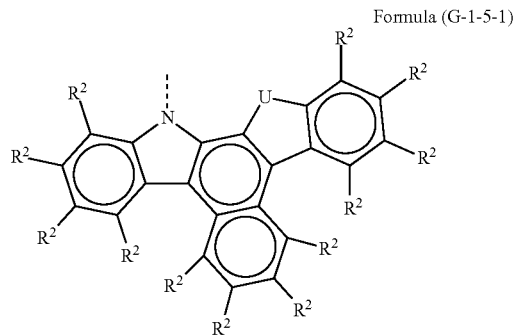

Formula (G-1-5-1)

where U is as defined above and is preferably S.

A preferred embodiment of the formula (G-1-6) corresponds to the following formula:

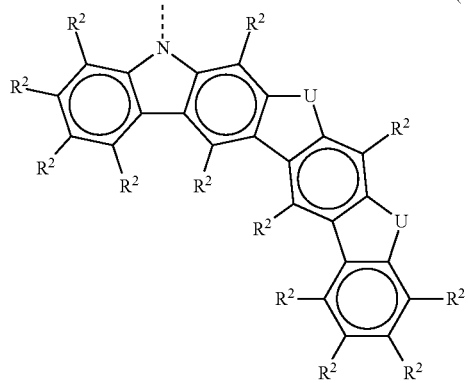

Formula (G-1-6-1)

where U is as defined above and is preferably $C(R^3)_2$.

A preferred embodiment of the formula (G-1-7) corresponds to the following formula:

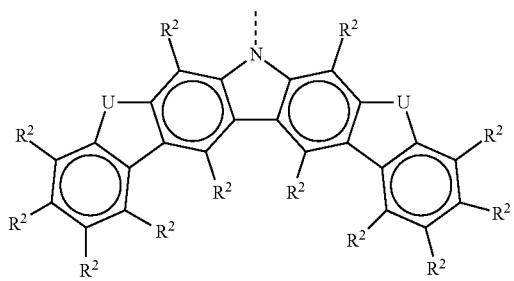

Formula (G-1-7-1)

where U is as defined above and is preferably $C(R^3)_2$.

Preferred embodiments of the formula (I) conform to the following formulae:

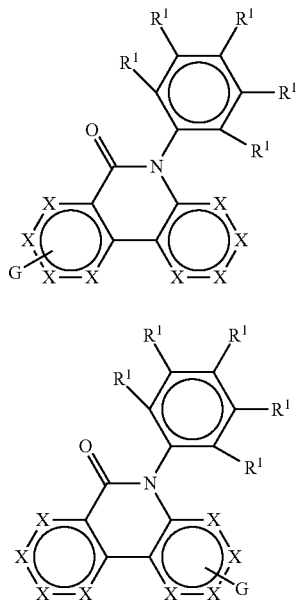

Formula (I-1)

Formula (I-2)

where the symbols that occur are as defined above, and where, in the ring to which the G group is bonded, at least one X is N. More preferably, G is selected from the abovementioned preferred embodiments. It is further preferable that, in the ring to which the G group is bonded, two X groups are N. It is further preferable that, if there are two X groups adjacent to the bond to the G group, at least one of them is N, more preferably both of them. It is further preferable that, if there is only one X group adjacent to the bond to the G group, this X group is N.

Preferred embodiments of the formulae (I-1) and (I-2) conform to the following formulae in which the G group is selected from formulae (G-1-1) to (G-1-7):

| Formula | Base formula | Formula of the G group |
| --- | --- | --- |
| (I-1-1) | (I-1) | (G-1-1) |
| (I-1-2) | (I-1) | (G-1-2) |
| (I-1-3) | (I-1) | (G-1-3) |
| (I-1-4) | (I-1) | (G-1-4) |
| (I-1-5) | (I-1) | (G-1-5) |
| (I-1-6) | (I-1) | (G-1-6) |
| (I-1-7) | (I-1) | (G-1-7) |
| (I-2-1) | (I-2) | (G-1-1) |
| (I-2-2) | (I-2) | (G-1-2) |
| (I-2-3) | (I-2) | (G-1-3) |
| (I-2-4) | (I-2) | (G-1-4) |
| (I-2-5) | (I-2) | (G-1-5) |
| (I-2-6) | (I-2) | (G-1-6) |
| (I-2-7) | (I-2) | (G-1-7) |

Preferred embodiments of the formulae (I-1) and (I-2) conform to the formulae shown below:

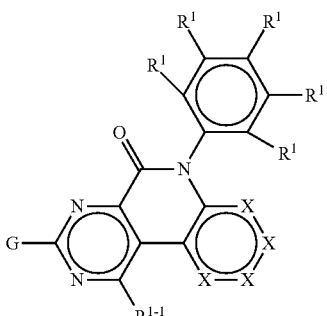

Formula (I-1-A)

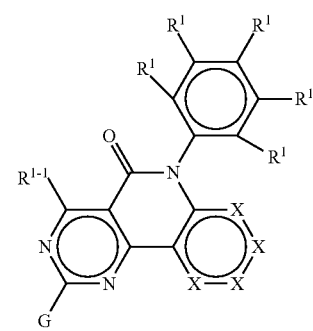

Formula (I-1-B)

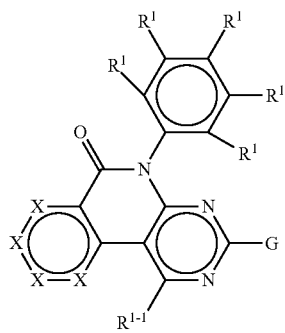

Formula (I-2-A)

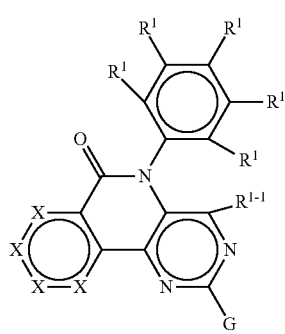

Formula (I-2-B)

where the symbols that occur are as defined above, and where $R^{1-1}$ is as defined for $R^1$ above. Preferably, G is selected from the abovementioned preferred embodiments. Preferably, $R^{1-1}$ is selected from F, CN, $Si(R^4)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups mentioned, the aromatic ring systems mentioned and the heteroaromatic ring systems mentioned are each substituted by $R^4$ radicals. More preferably, $R^{1-1}$ is selected from aromatic ring systems having 6 to 40 aromatic ring atoms and heteroaromatic ring systems having 5 to 40 aromatic ring atoms, each of which are substituted by $R^4$ radicals. In a preferred embodiment, one of the X groups in the above formulae is N. In an alternative preferred embodiment, all X groups in the above formulae are $CR^1$.

Preferred embodiments of the formulae (I-1-A), (I-1-B), (I-2-A) and (I-2-B) conform to the following formulae in which the G group is selected from formulae (G-1-1-1) to (G-1-7-1):

| Formula | Base formula | Formula of the G group |
| --- | --- | --- |
| (I-1-A-1) | (I-1-A) | (G-1-1-1) |
| (I-1-A-2) | (I-1-A) | (G-1-2-1) |
| (I-1-A-3) | (I-1-A) | (G-1-2-2) |
| (I-1-A-4) | (I-1-A) | (G-1-2-3) |
| (I-1-A-5) | (I-1-A) | (G-1-2-4) |
| (I-1-A-6) | (I-1-A) | (G-1-3-1) |
| (I-1-A-7) | (I-1-A) | (G-1-4-1) |
| (I-1-A-8) | (I-1-A) | (G-1-5-1) |
| (I-1-A-9) | (I-1-A) | (G-1-6-1) |
| (I-1-A-10) | (I-1-A) | (G-1-7-1) |
| (I-1-B-1) | (I-1-B) | (G-1-1-1) |
| (I-1-B-2) | (I-1-B) | (G-1-2-1) |
| (I-1-B-3) | (I-1-B) | (G-1-2-2) |
| (I-1-B-4) | (I-1-B) | (G-1-2-3) |
| (I-1-B-5) | (I-1-B) | (G-1-2-4) |
| (I-1-B-6) | (I-1-B) | (G-1-3-1) |
| (I-1-B-7) | (I-1-B) | (G-1-4-1) |
| (I-1-B-8) | (I-1-B) | (G-1-5-1) |
| (I-1-B-9) | (I-1-B) | (G-1-6-1) |
| (I-1-B-10) | (I-1-B) | (G-1-7-1) |
| (I-2-A-1) | (I-2-A) | (G-1-1-1) |
| (I-2-A-2) | (I-2-A) | (G-1-2-1) |
| (I-2-A-3) | (I-2-A) | (G-1-2-2) |
| (I-2-A-4) | (I-2-A) | (G-1-2-3) |
| (I-2-A-5) | (I-2-A) | (G-1-2-4) |
| (I-2-A-6) | (I-2-A) | (G-1-3-1) |
| (I-2-A-7) | (I-2-A) | (G-1-4-1) |
| (I-2-A-8) | (I-2-A) | (G-1-5-1) |
| (I-2-A-9) | (I-2-A) | (G-1-6-1) |
| (I-2-A-10) | (I-2-A) | (G-1-7-1) |
| (I-2-B-1) | (I-2-B) | (G-1-1-1) |
| (I-2-B-2) | (I-2-B) | (G-1-2-1) |
| (I-2-B-3) | (I-2-B) | (G-1-2-2) |
| (I-2-B-4) | (I-2-B) | (G-1-2-3) |
| (I-2-B-5) | (I-2-B) | (G-1-2-4) |
| (I-2-B-6) | (I-2-B) | (G-1-3-1) |
| (I-2-B-7) | (I-2-B) | (G-1-4-1) |
| (I-2-B-8) | (I-2-B) | (G-1-5-1) |
| (I-2-B-9) | (I-2-B) | (G-1-6-1) |
| (I-2-B-10) | (I-2-B) | (G-1-7-1) |

Preferred compounds of formula (I) are depicted below:

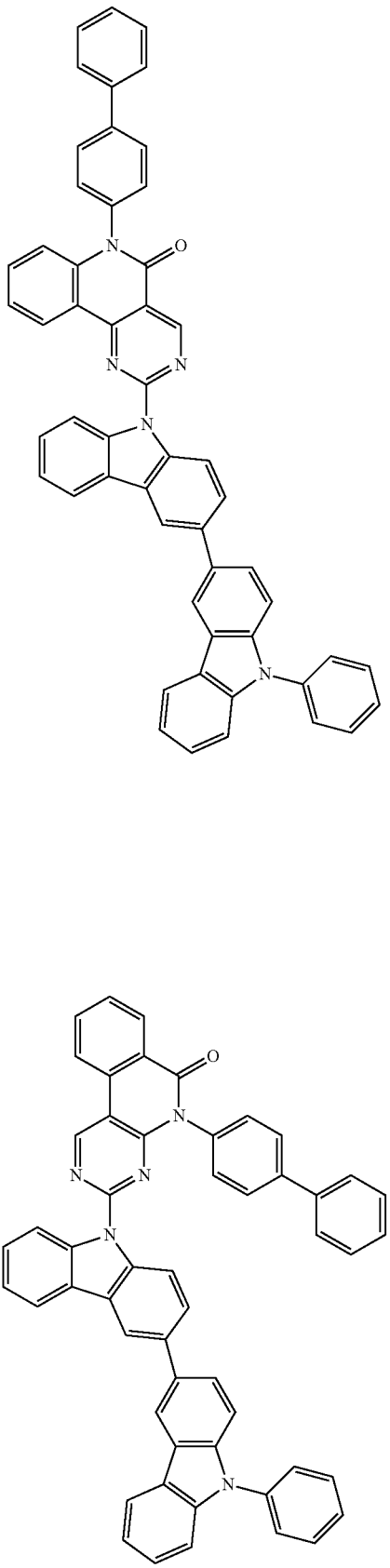

-continued
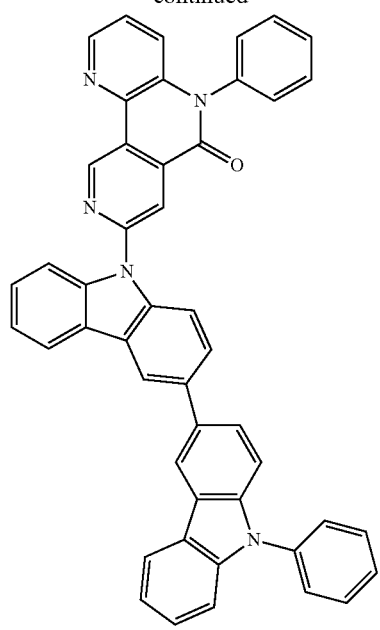
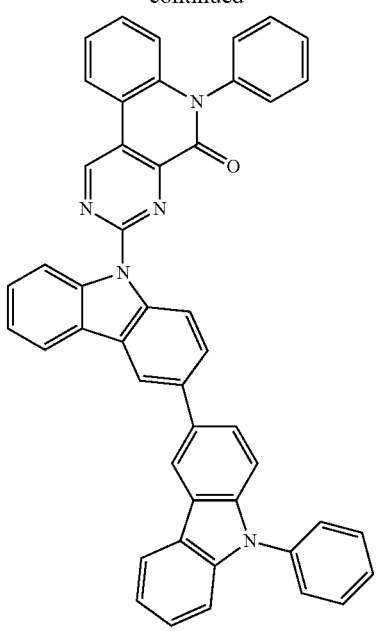
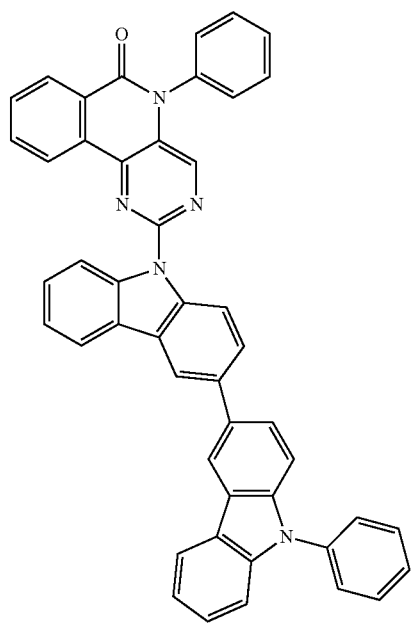
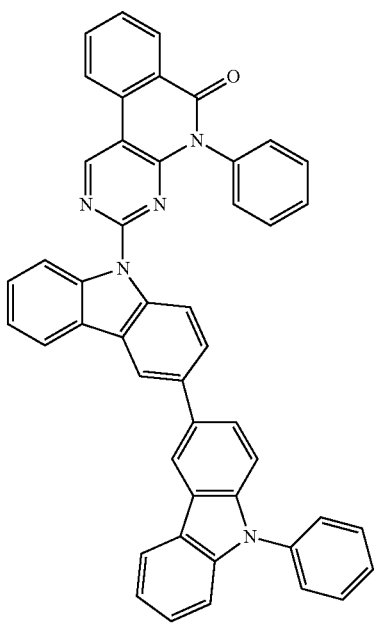

21
-continued
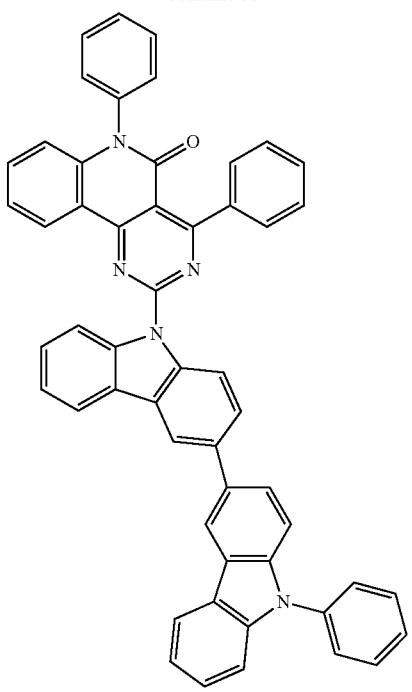
22
-continued
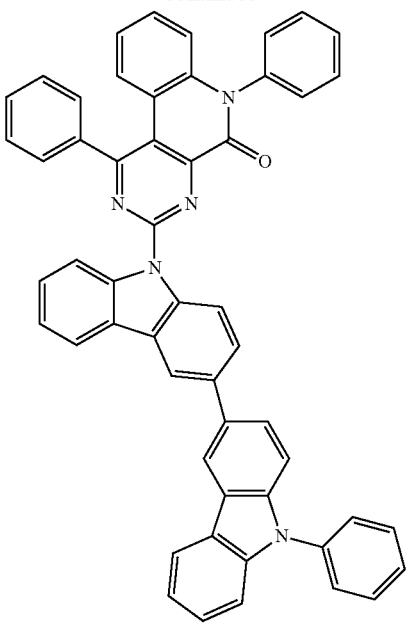
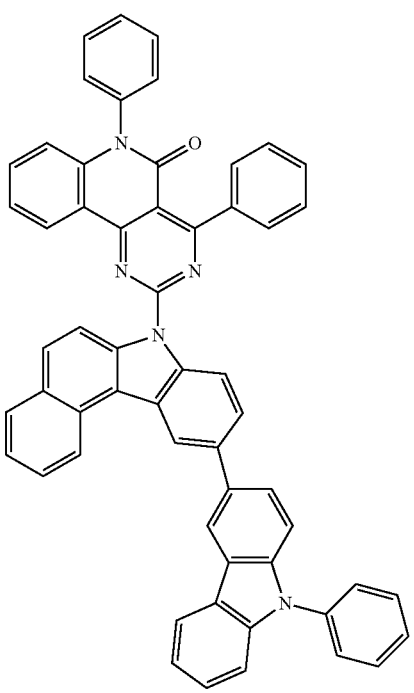
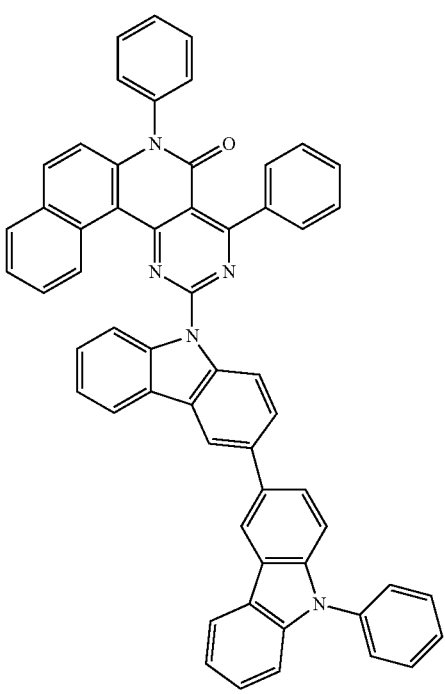

23
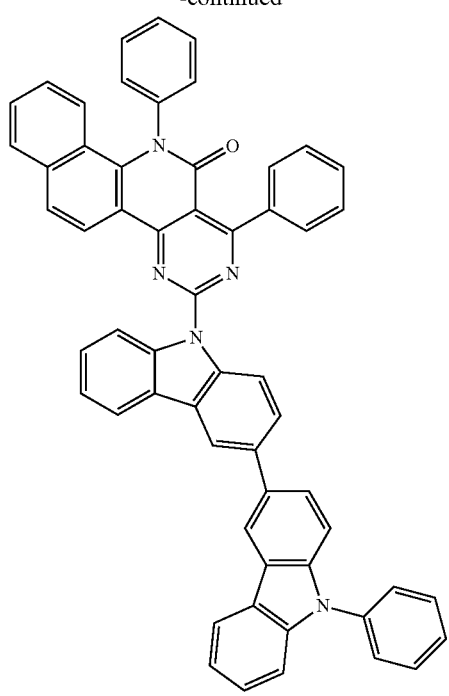
24
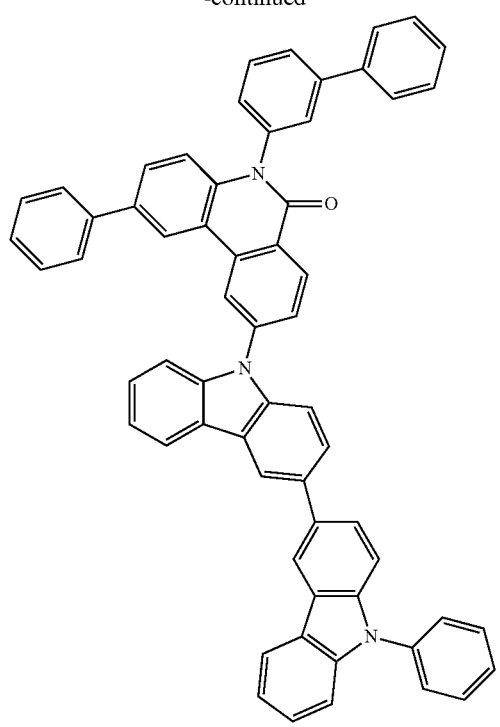
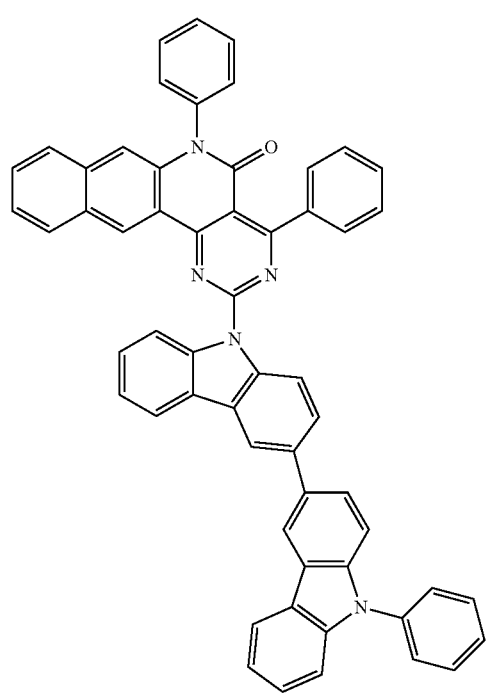
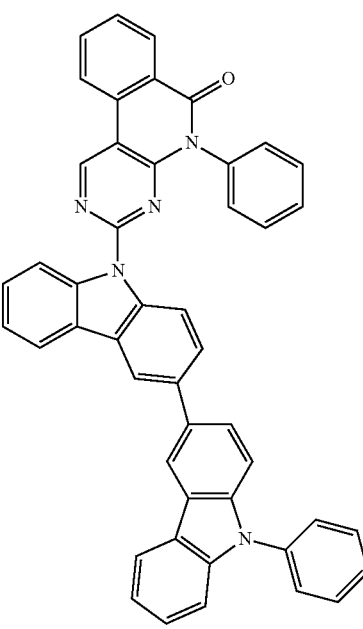

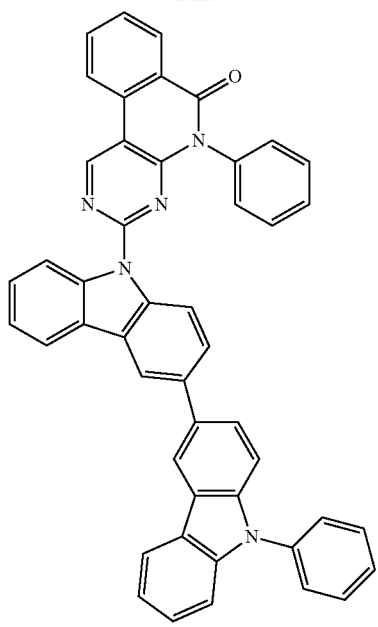
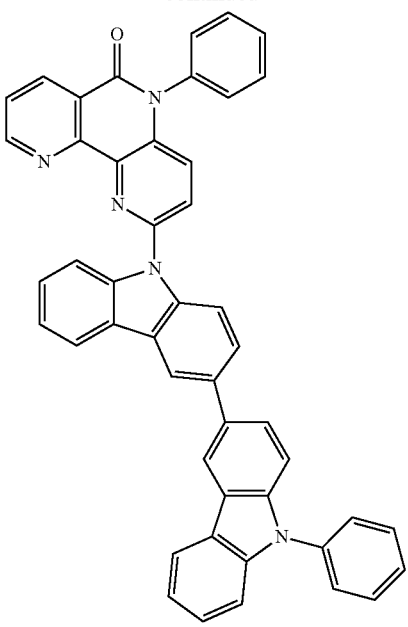
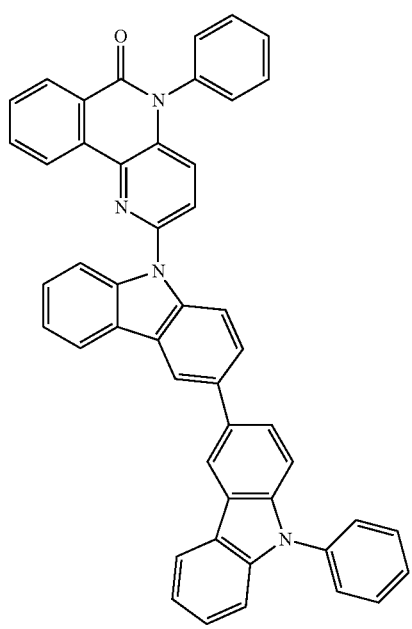
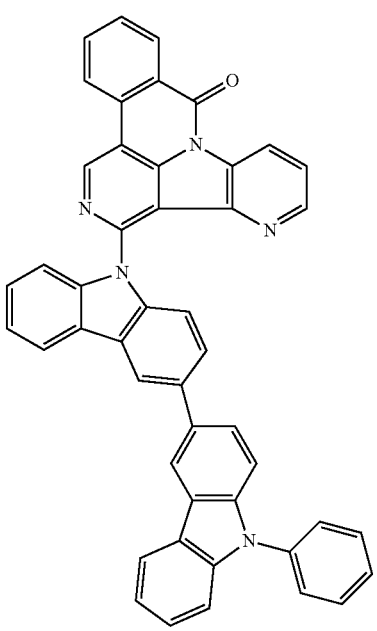

27
-continued
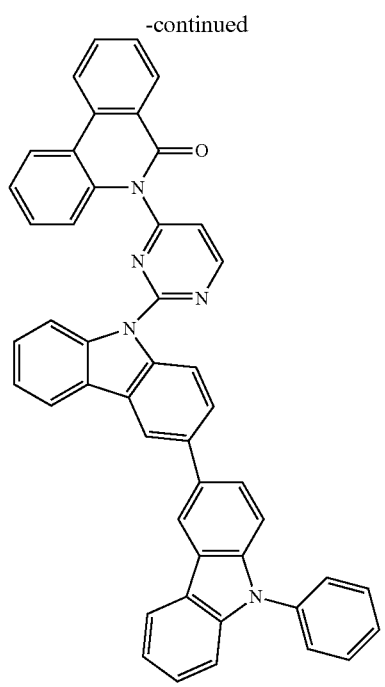
28
-continued
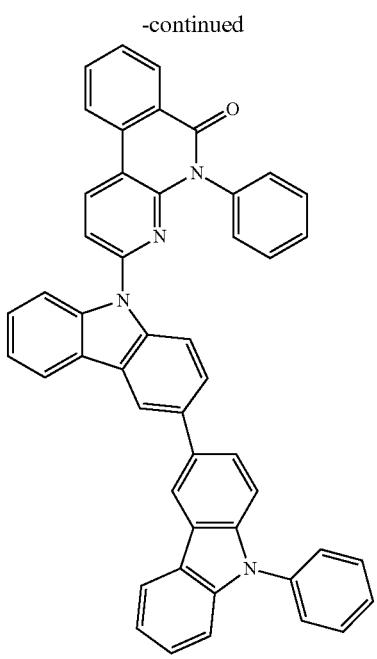
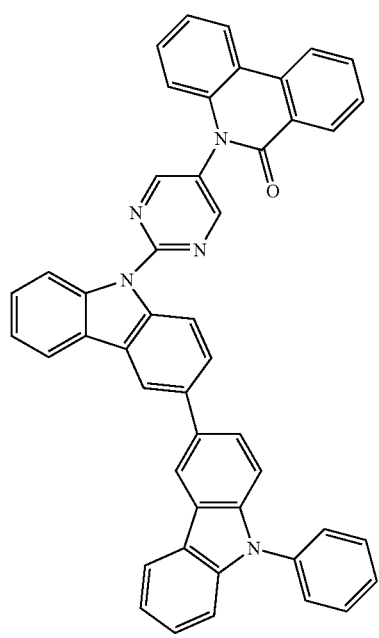

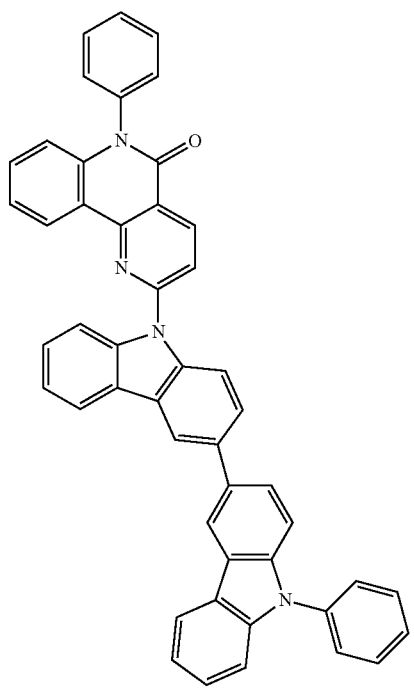
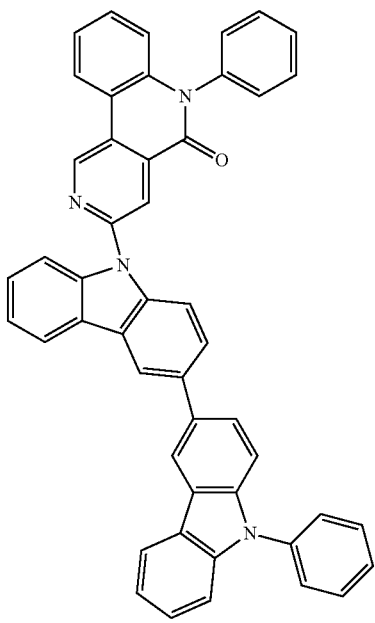
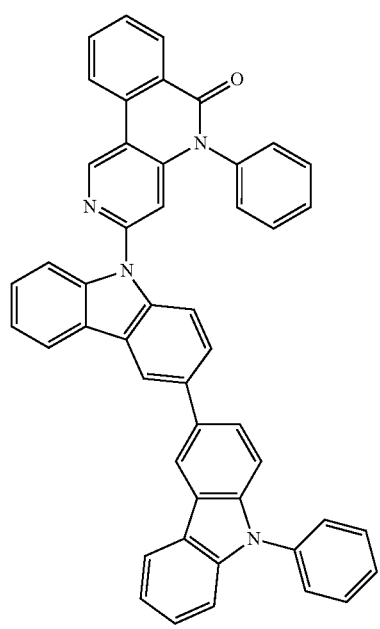
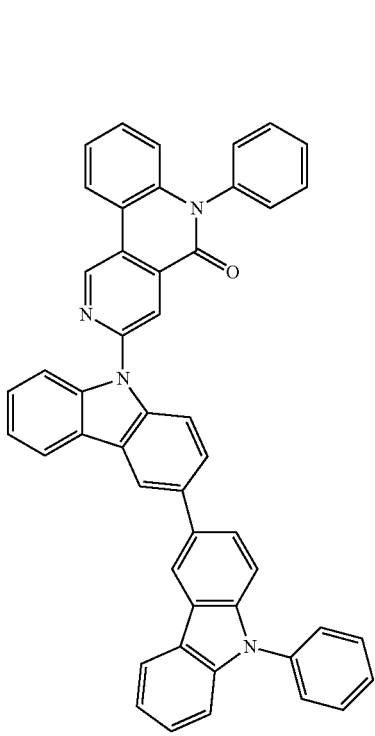

31
-continued
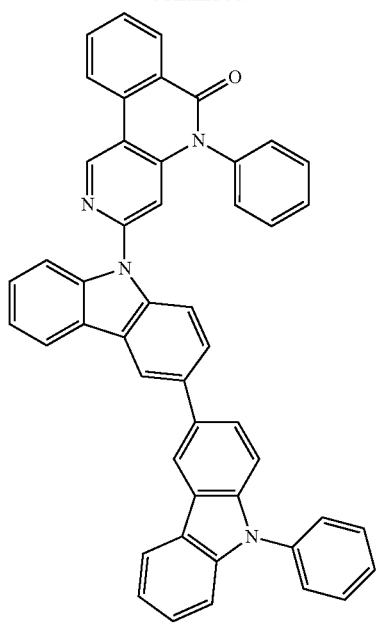
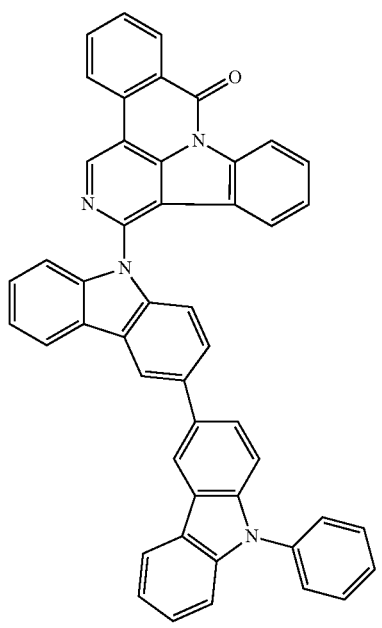
32
-continued
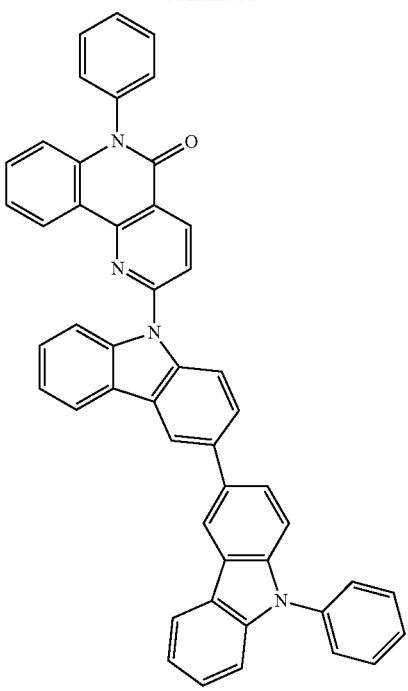
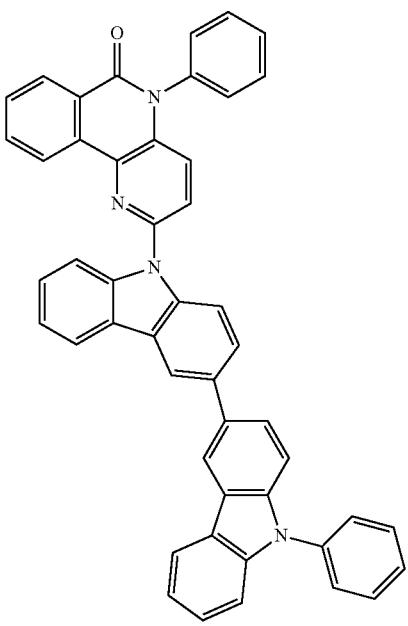

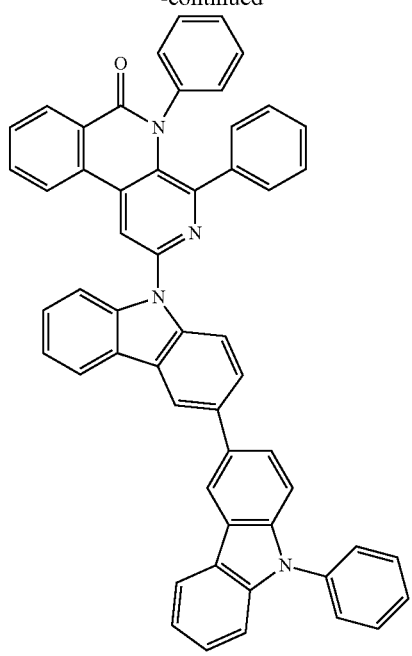
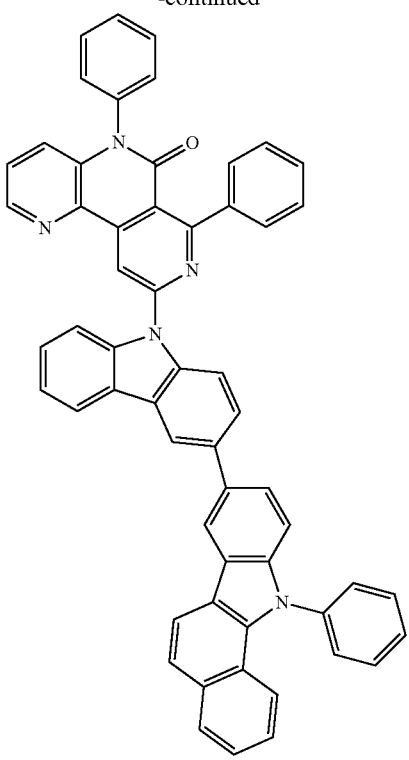
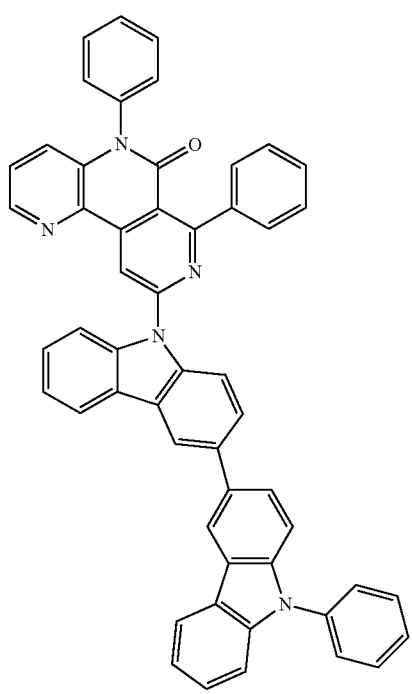
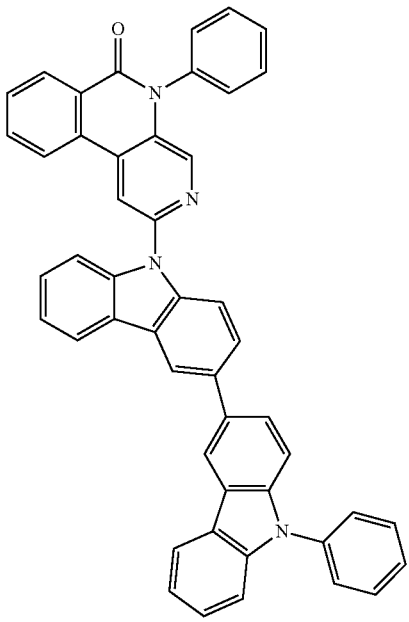

35
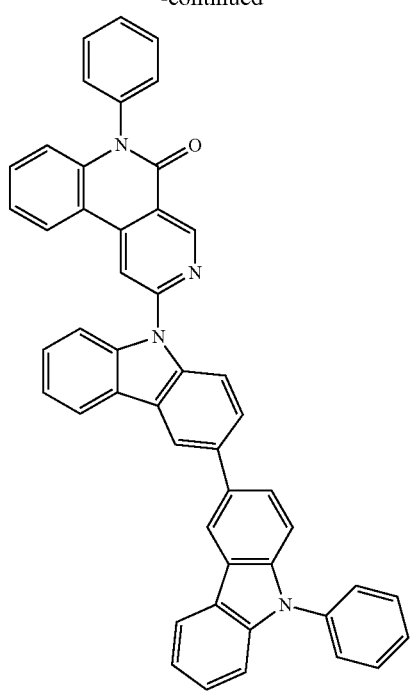
36
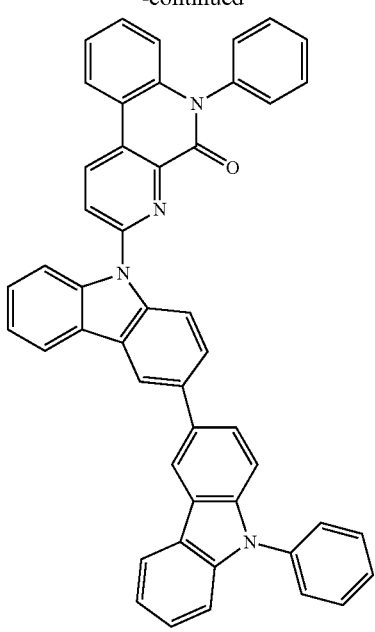
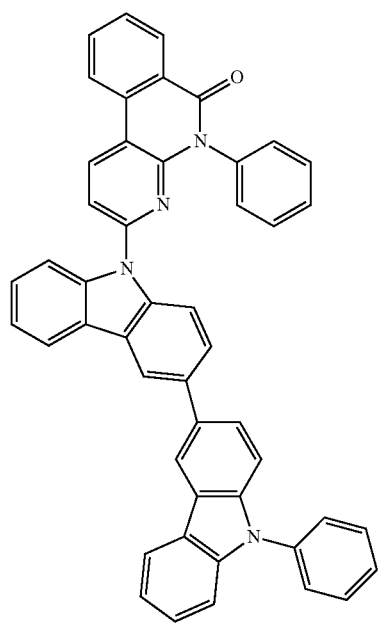
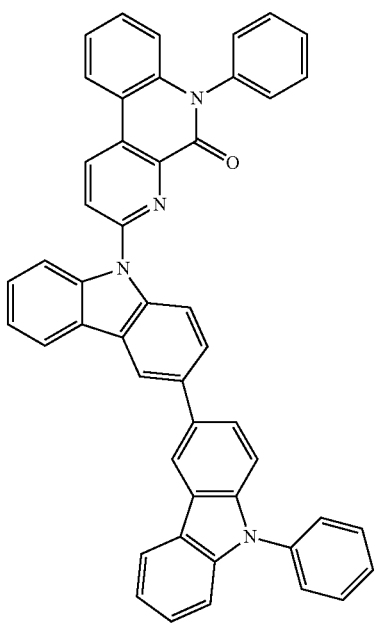

37
-continued

38
-continued

39
-continued
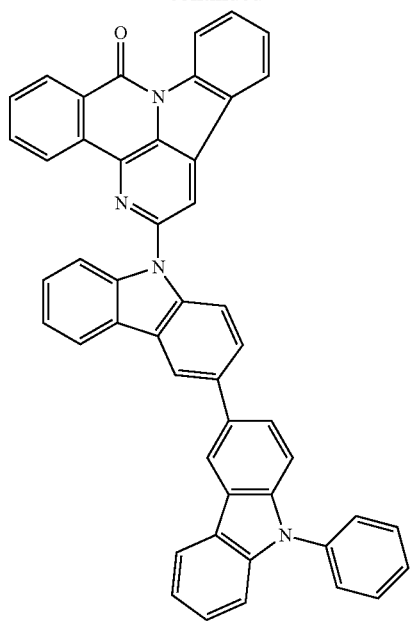
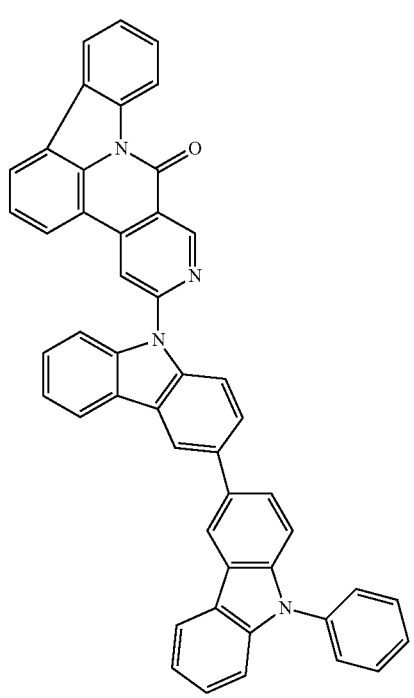
40
-continued
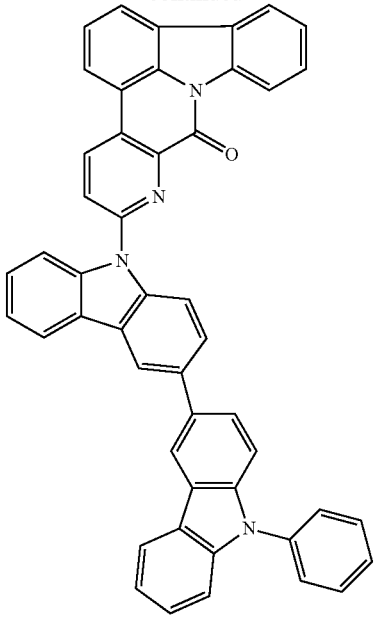
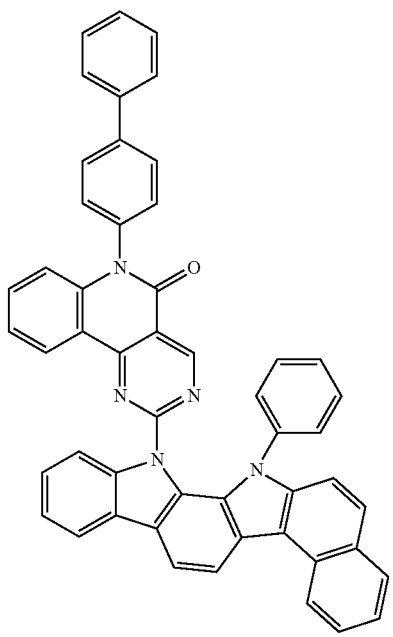

41
-continued
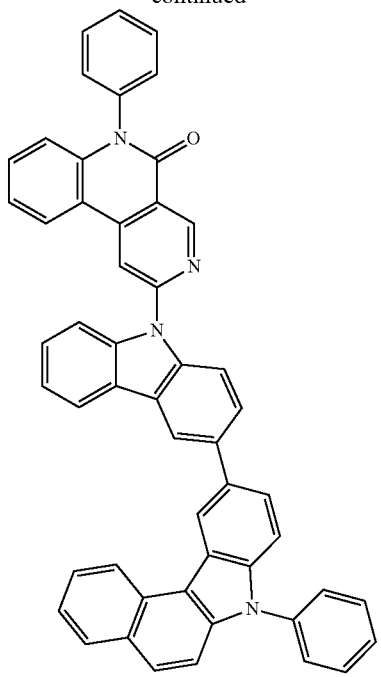
42
-continued
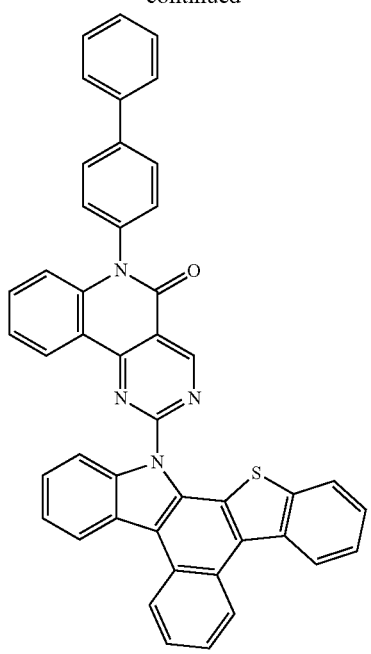
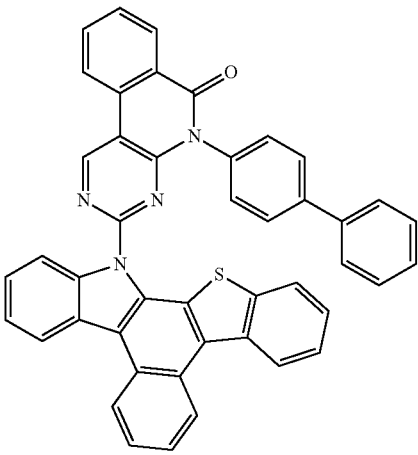
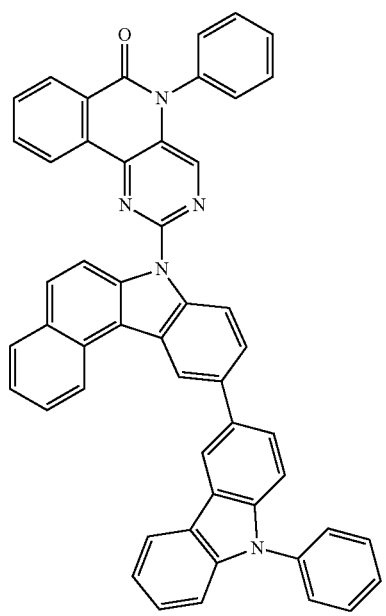
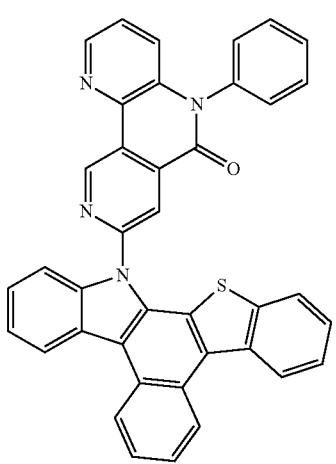

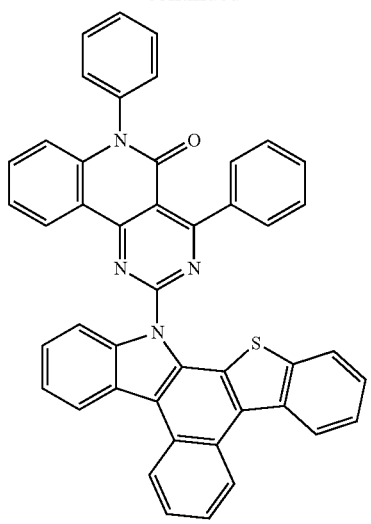
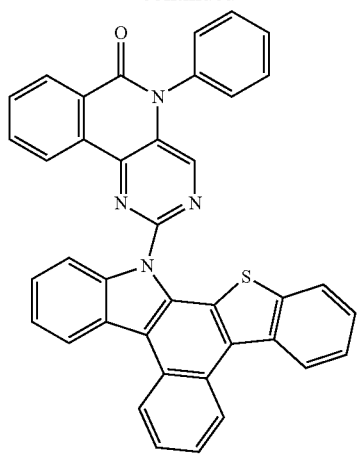
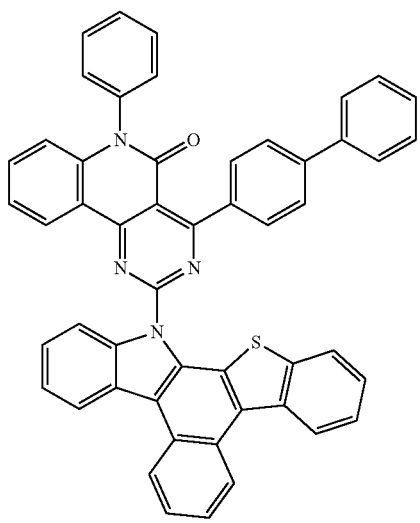
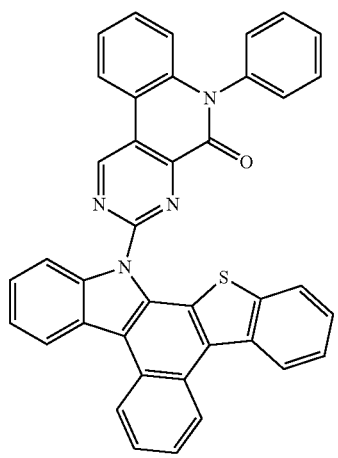
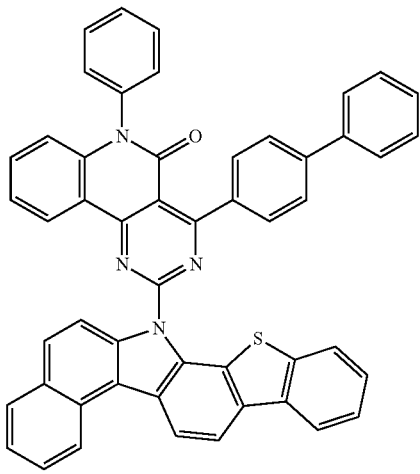
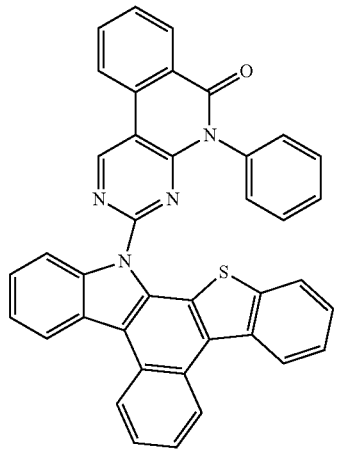

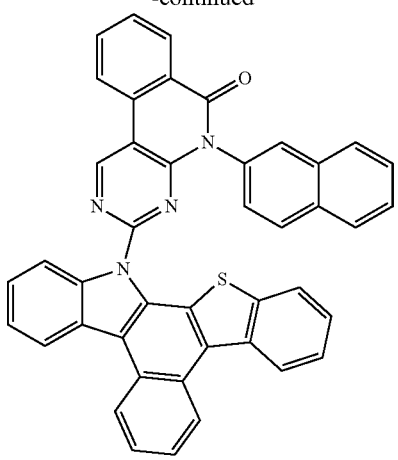
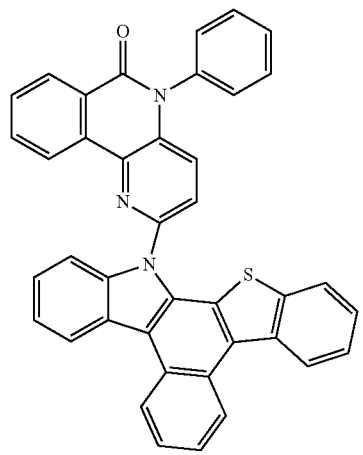
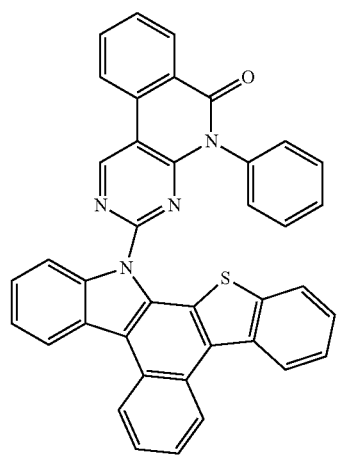
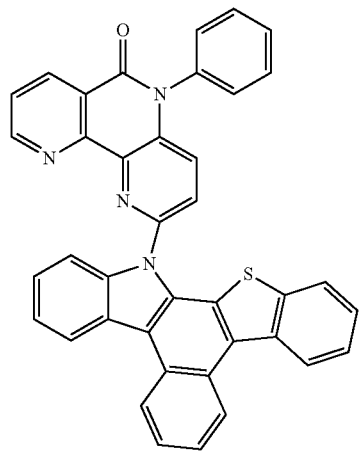
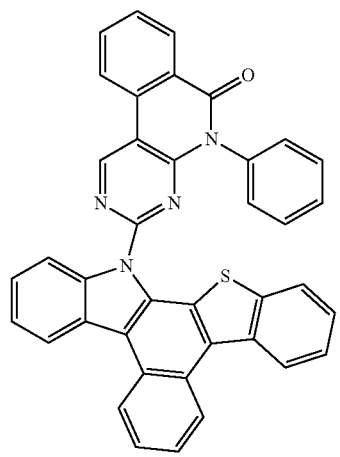
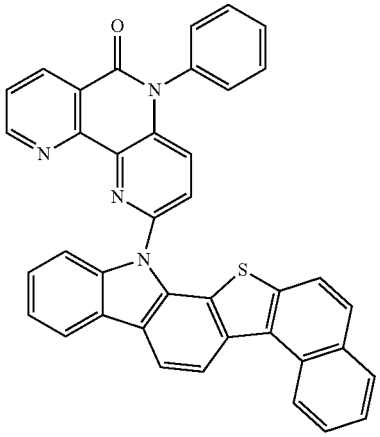

47
-continued
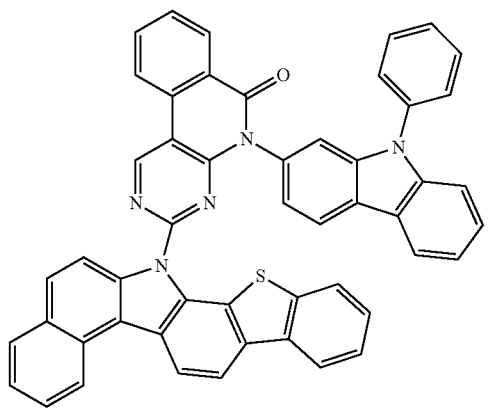
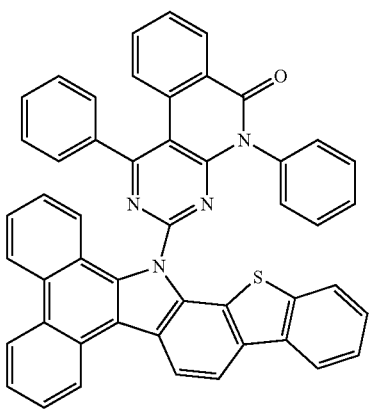
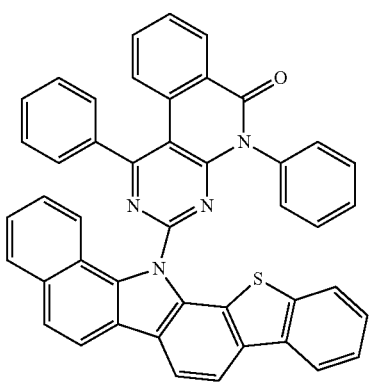
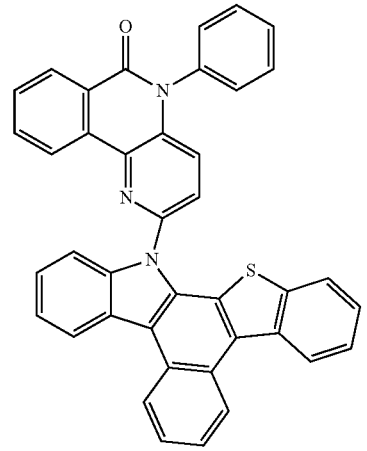
48
-continued
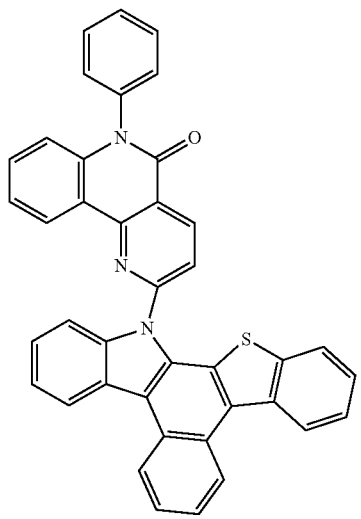
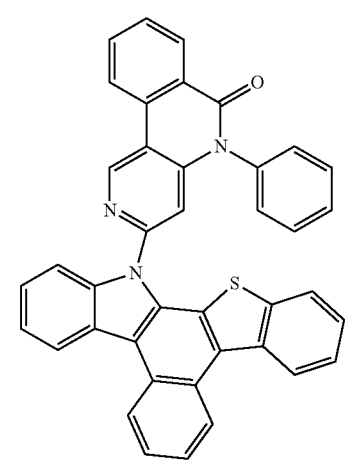
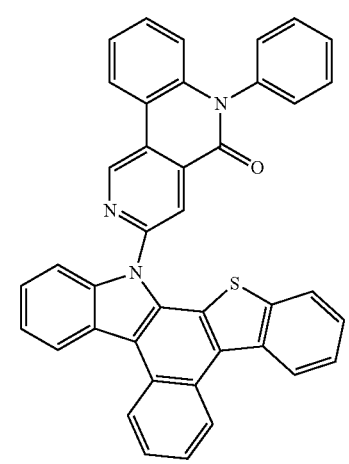

-continued
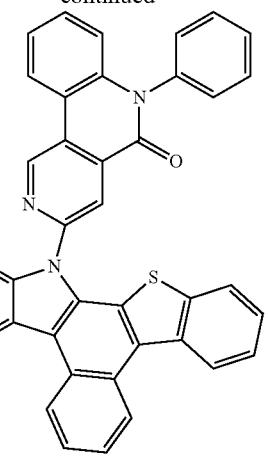
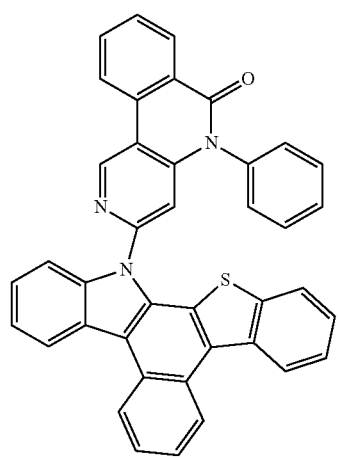
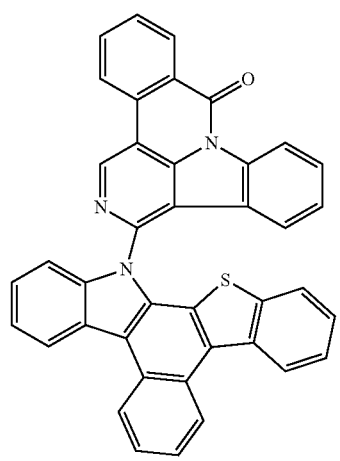
-continued
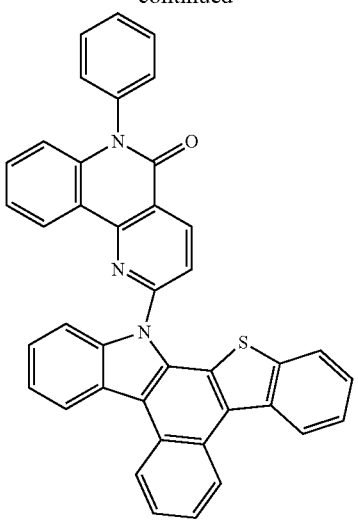
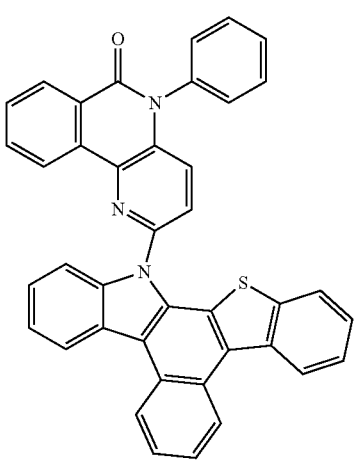
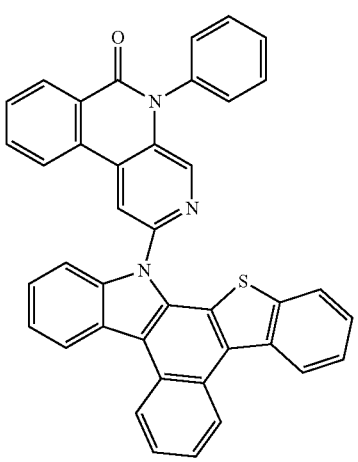

51
-continued
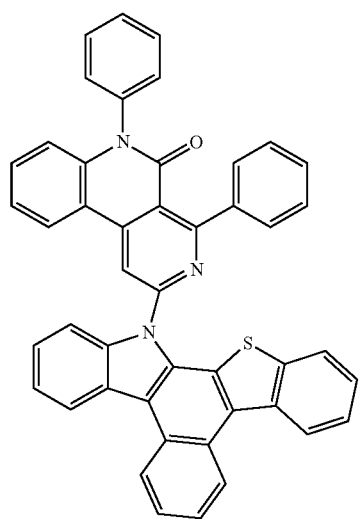
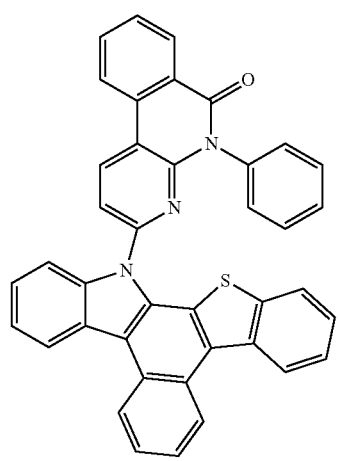
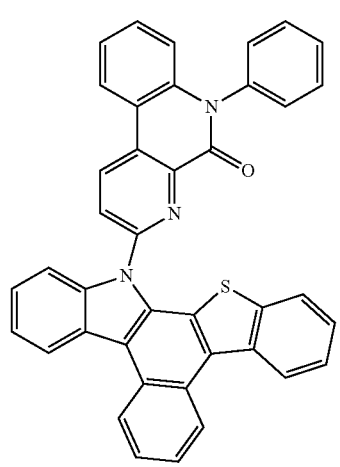
52
-continued
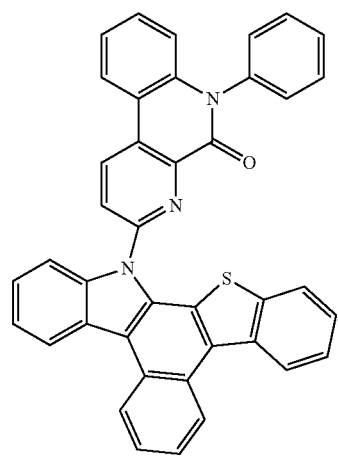
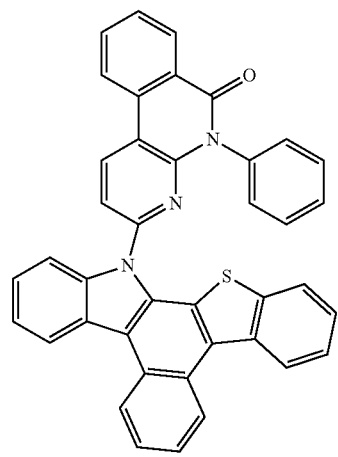
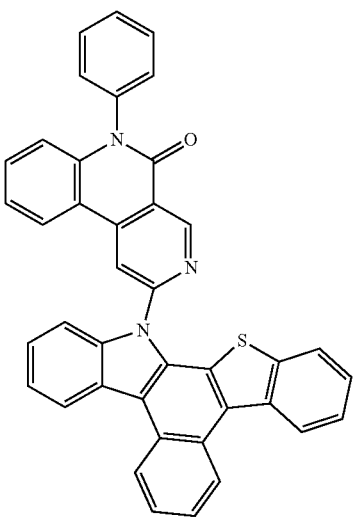

53
-continued
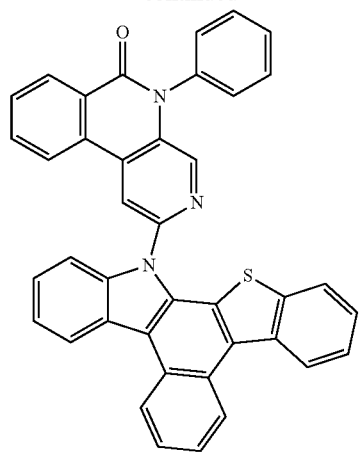
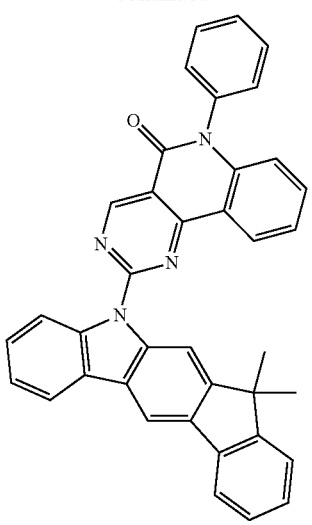
54
-continued
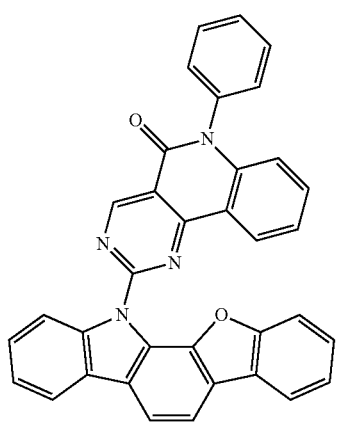
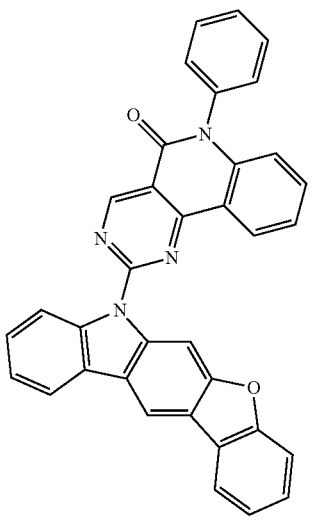

-continued
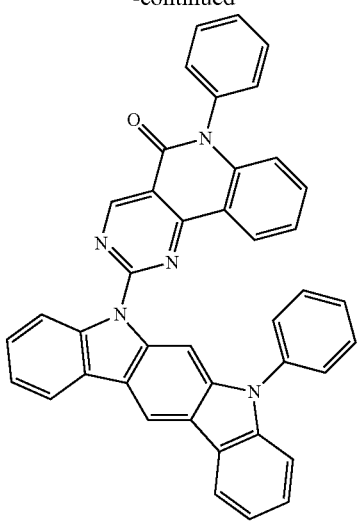
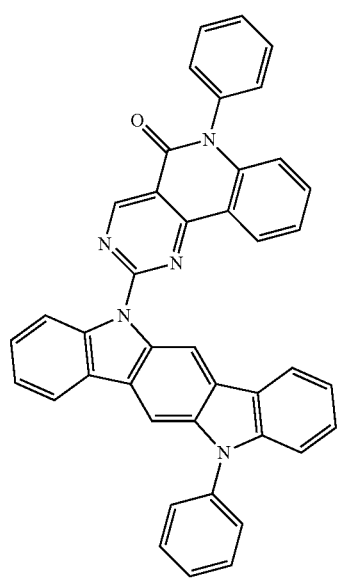
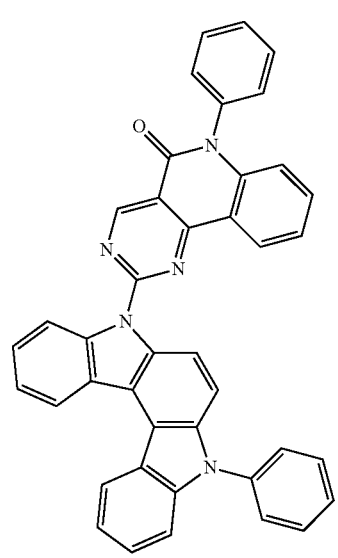
-continued
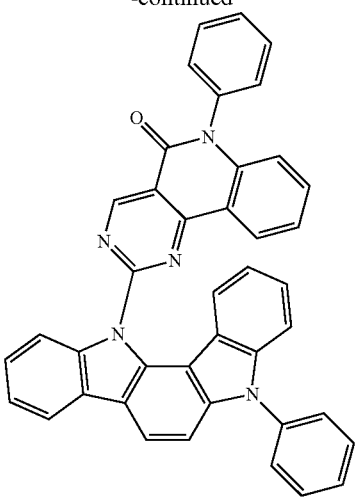
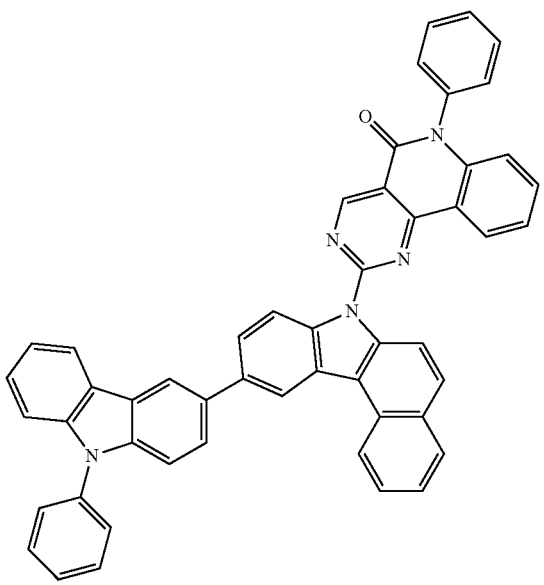
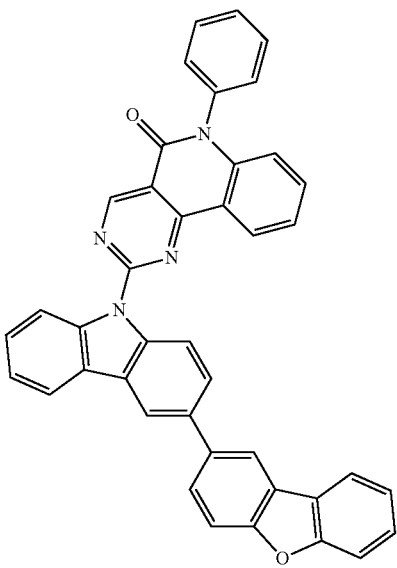

57
-continued
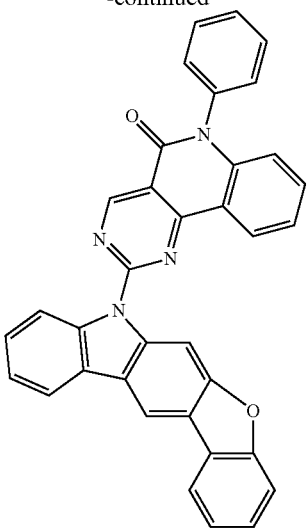
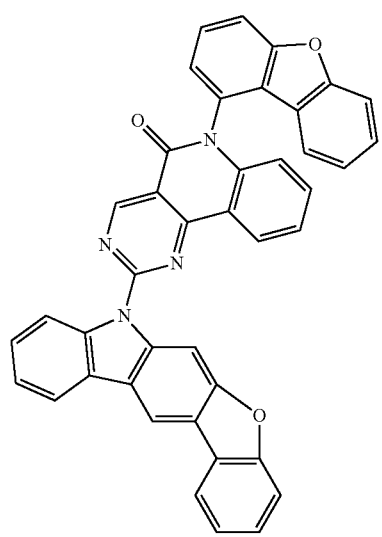
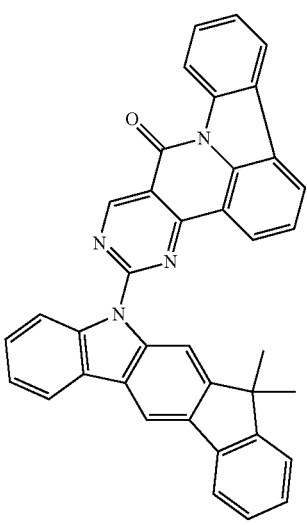
58
-continued
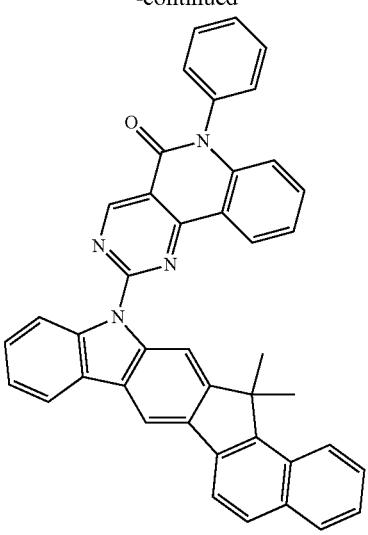
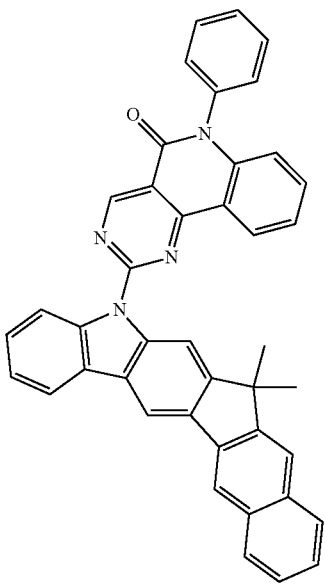
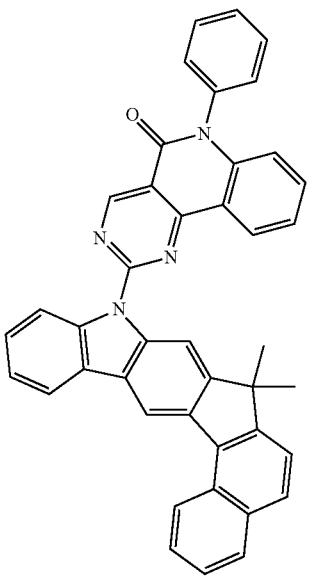

-continued

61
-continued
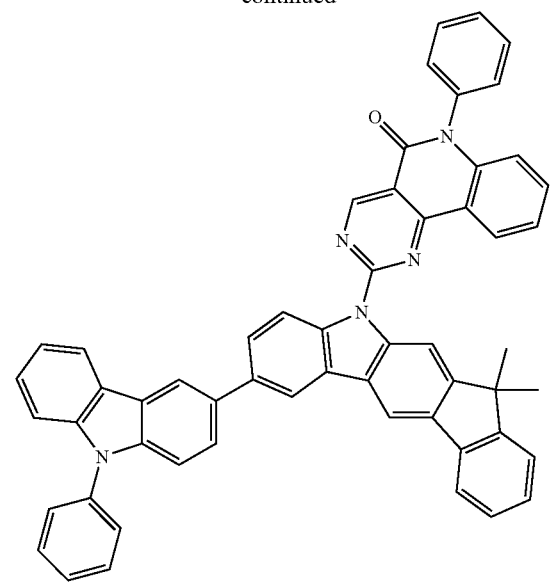
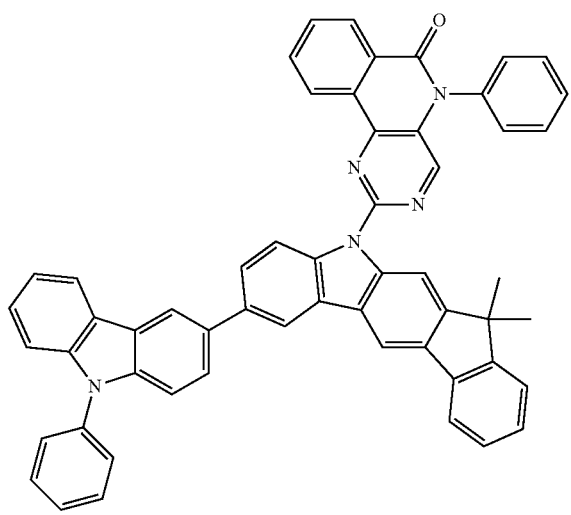
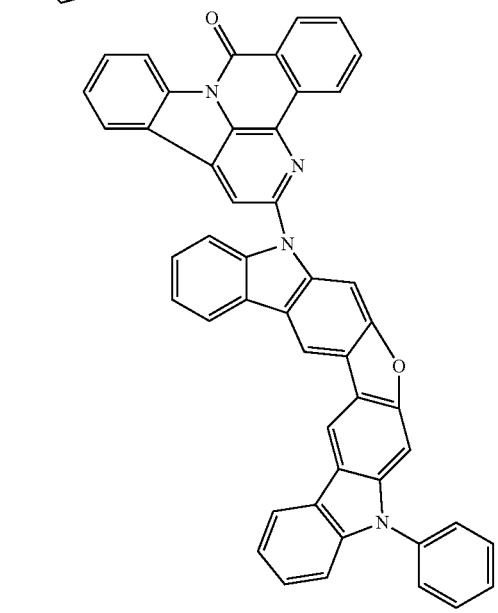
62
-continued
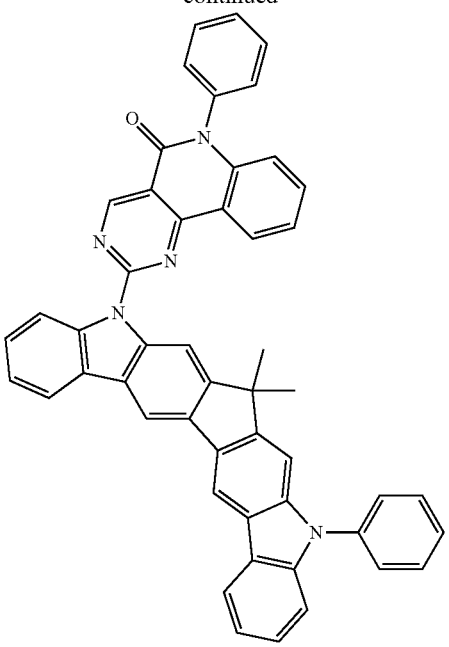
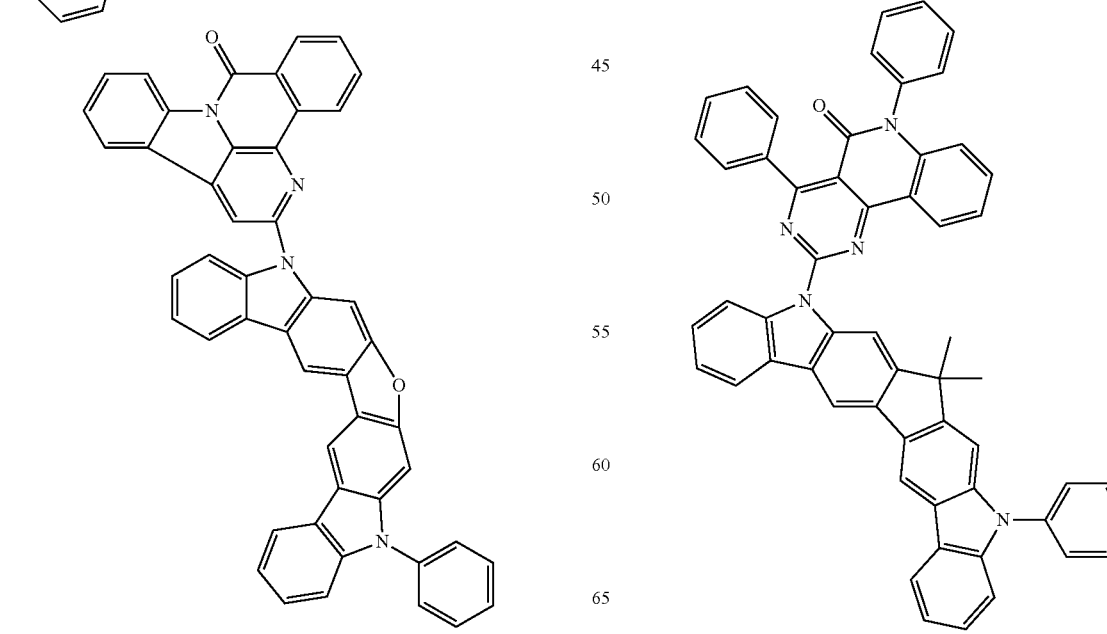

63
-continued
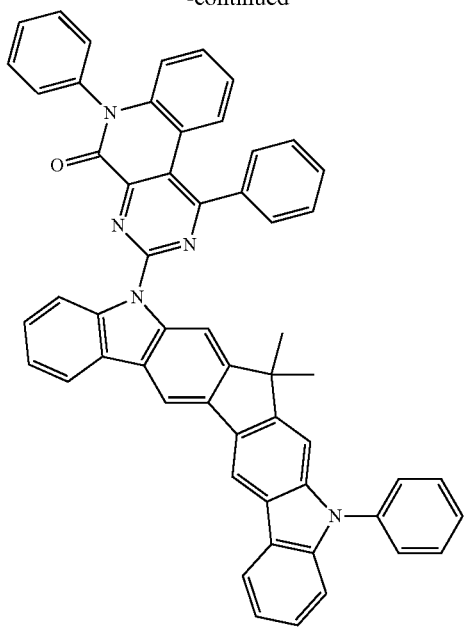
64
-continued
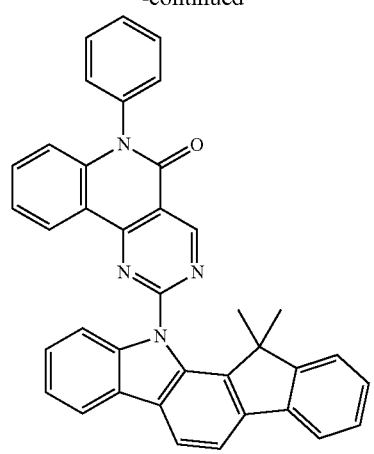
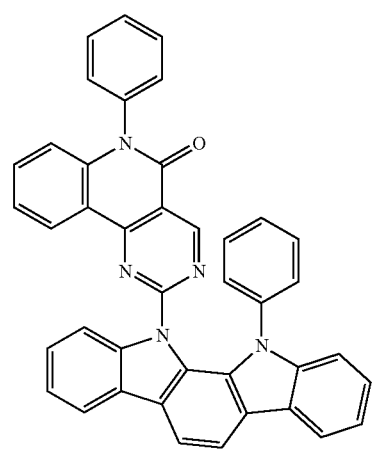
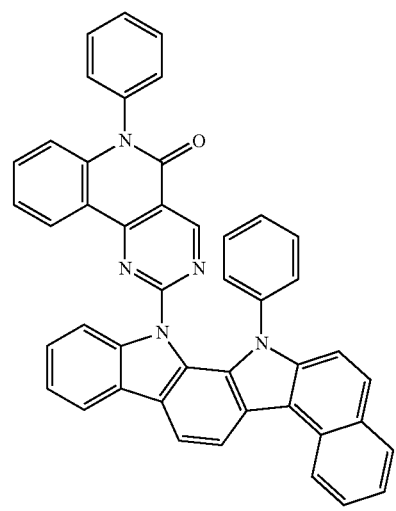
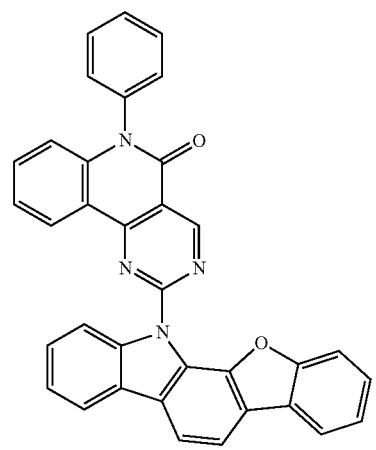
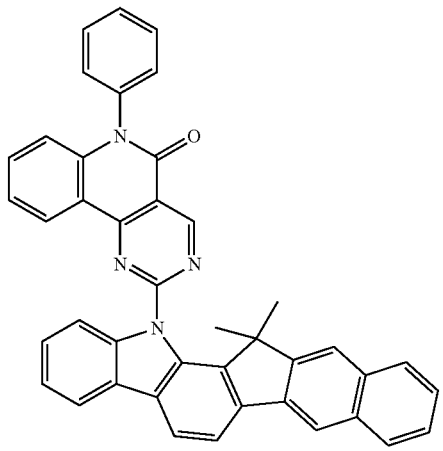

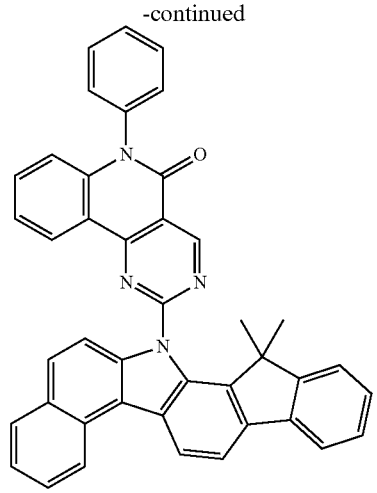
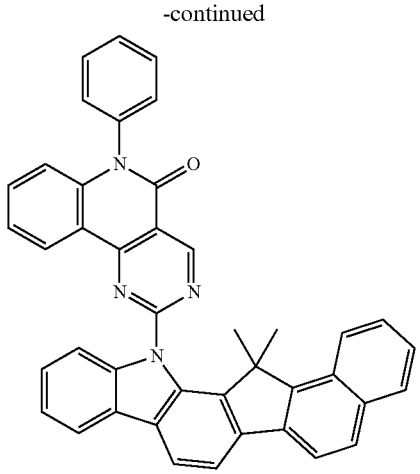
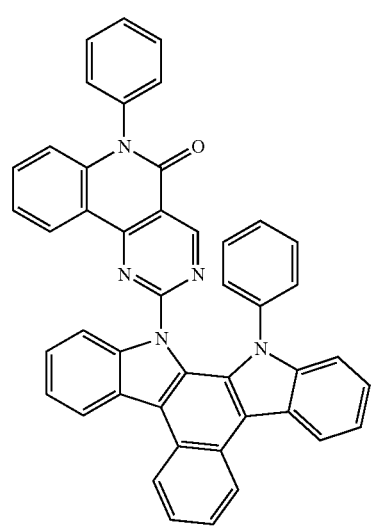
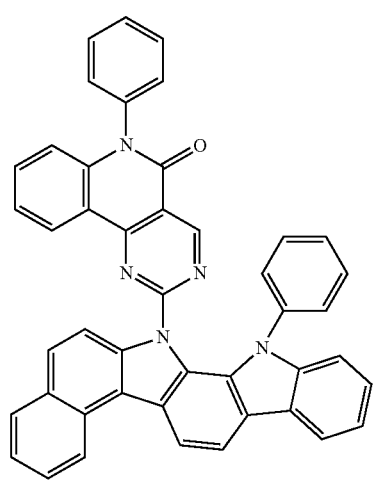

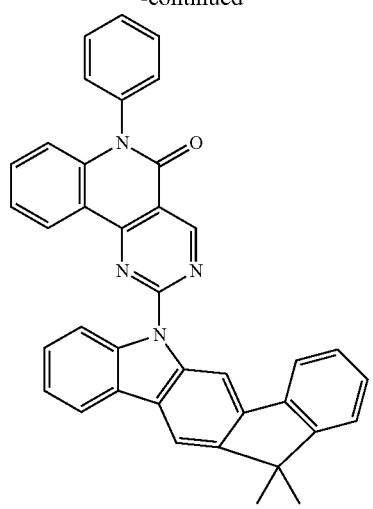
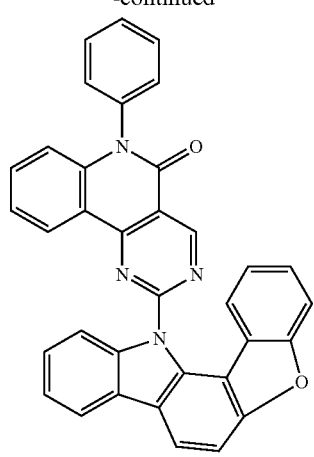
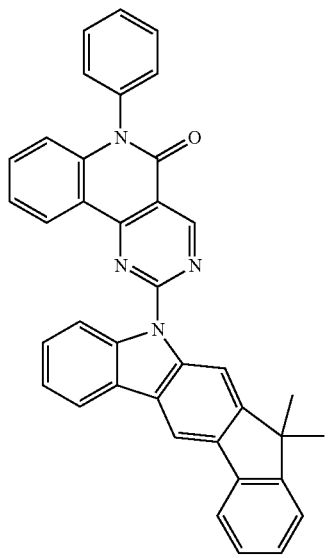
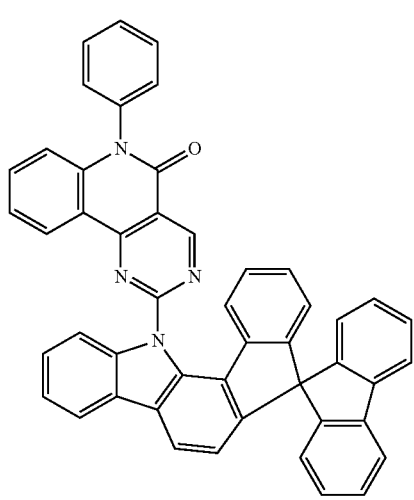

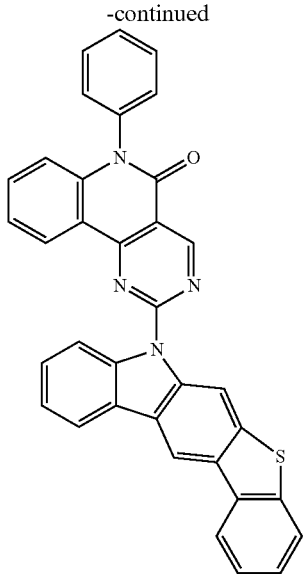
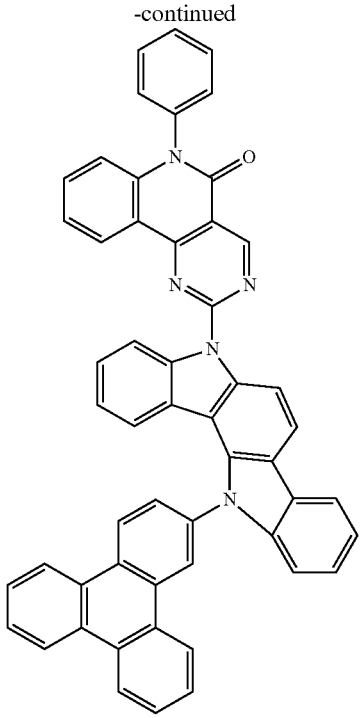
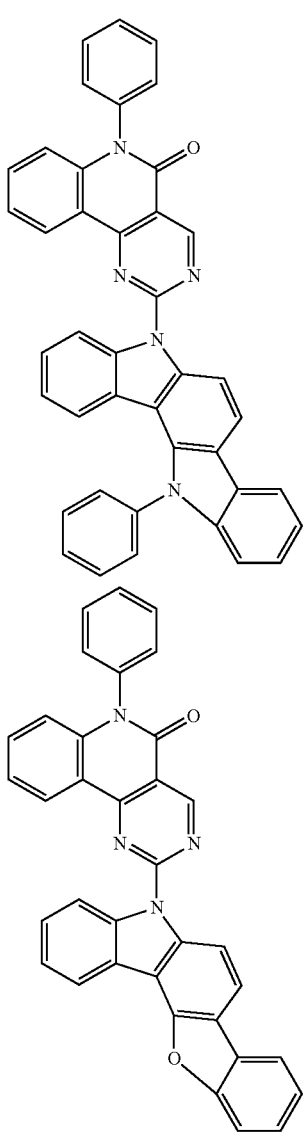
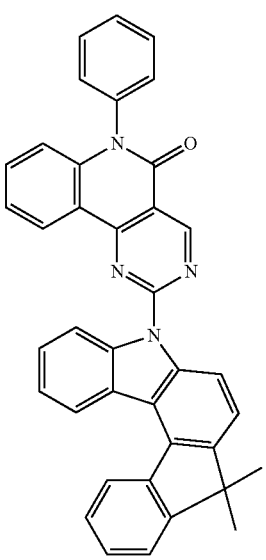

71
-continued
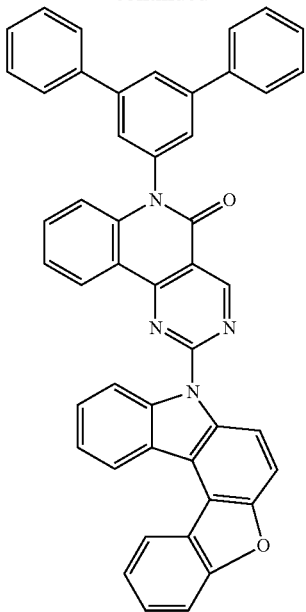
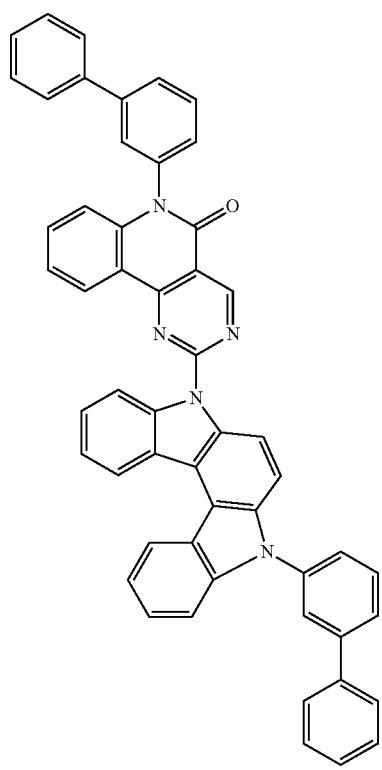 [SMILES: O=c1c2cnc(-n3c4ccccc4c4c5c6ccccc6n(-c6cccc(-c7ccccc7)c6)c5ccc43)nc2c2ccccc2n1-c1cccc(-c2ccccc2)c1]
72
-continued
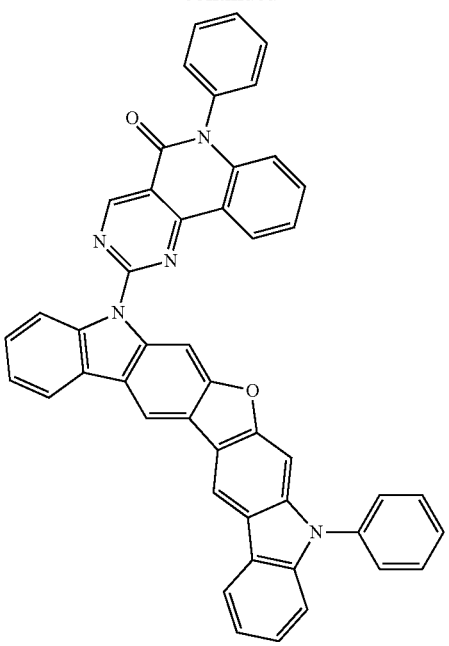
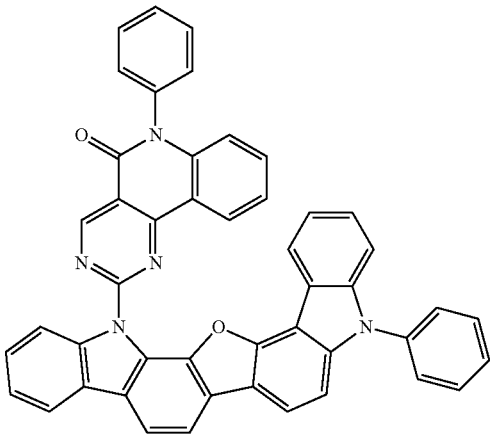
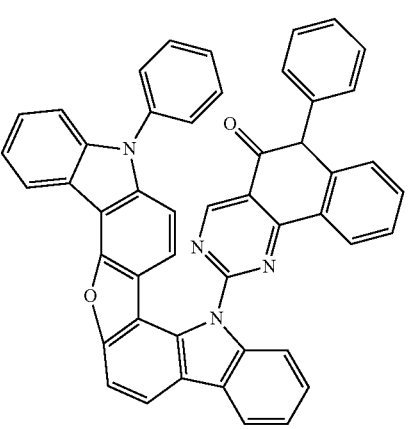

-continued

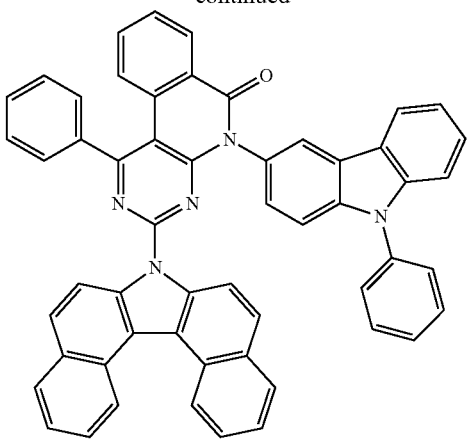

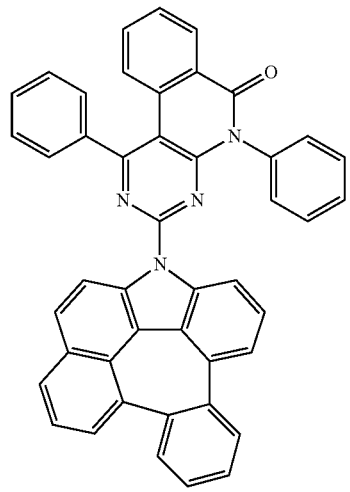

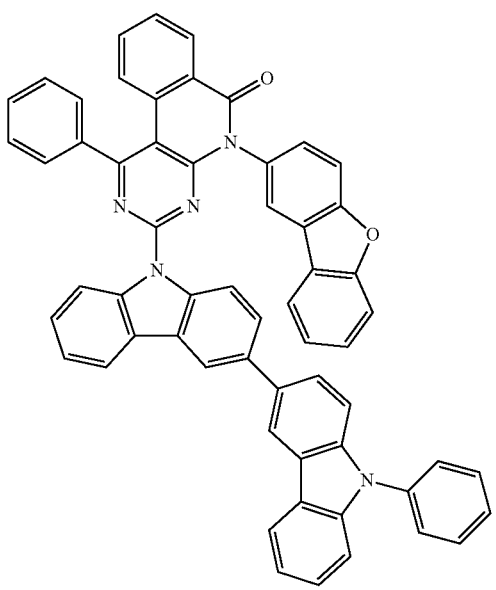

-continued

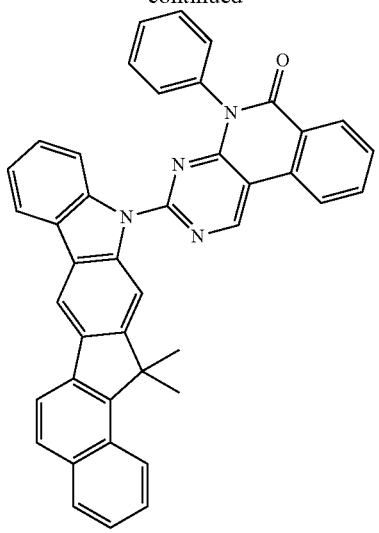

In a preferred process for preparing the compounds of the invention, the cyclic lactam base skeleton is first prepared, and this is then converted further to the compound of the invention in further reaction steps.

In a first preferred process for preparing the lactam base skeleton (scheme 1a), proceeding from an aromatic unit having an ester group and a halogen atom in vicinal position, and a further aromatic unit having an amino group and a boronic acid group in vicinal position, the cyclic lactam base skeleton is prepared by Suzuki coupling and ring closure to give the lactam. One of the two aromatic units has an alkyl thioether group, preferably a methyl thioether group, bonded to the aromatic ring. The halogen atom is preferably selected from Cl, Br and I, and is more preferably Cl.

Scheme 1a

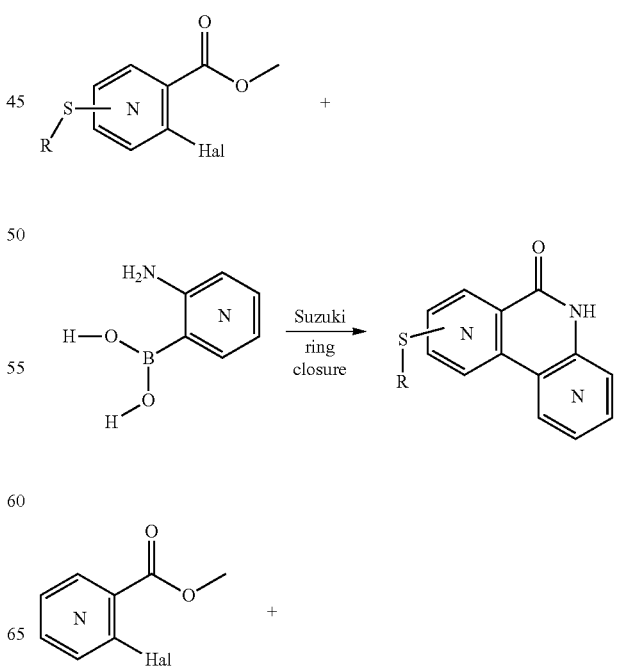

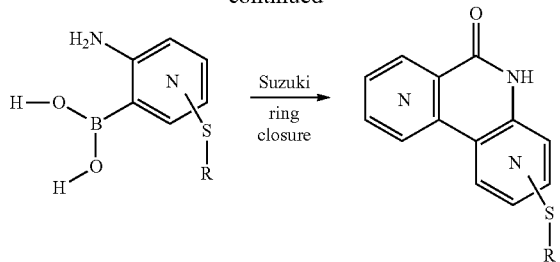

Hal=halogen, preferably Cl, Br, I
N in the ring: the ring may have one or more nitrogen atoms as ring members.

In a second preferred process (scheme 1b), proceeding from an aromatic unit having a carboxylic acid group and a boronic acid group in vicinal position, and a further aromatic unit having an amino group and a halogen atom in vicinal position, the cyclic lactam base skeleton is prepared by Suzuki coupling and ring closure to give the lactam. One of the two aromatic units has an alkyl thioether group, preferably a methyl thioether group, bonded to the aromatic ring. The halogen atom is preferably selected from Cl, Br and I, and is more preferably Cl.

Scheme 1b

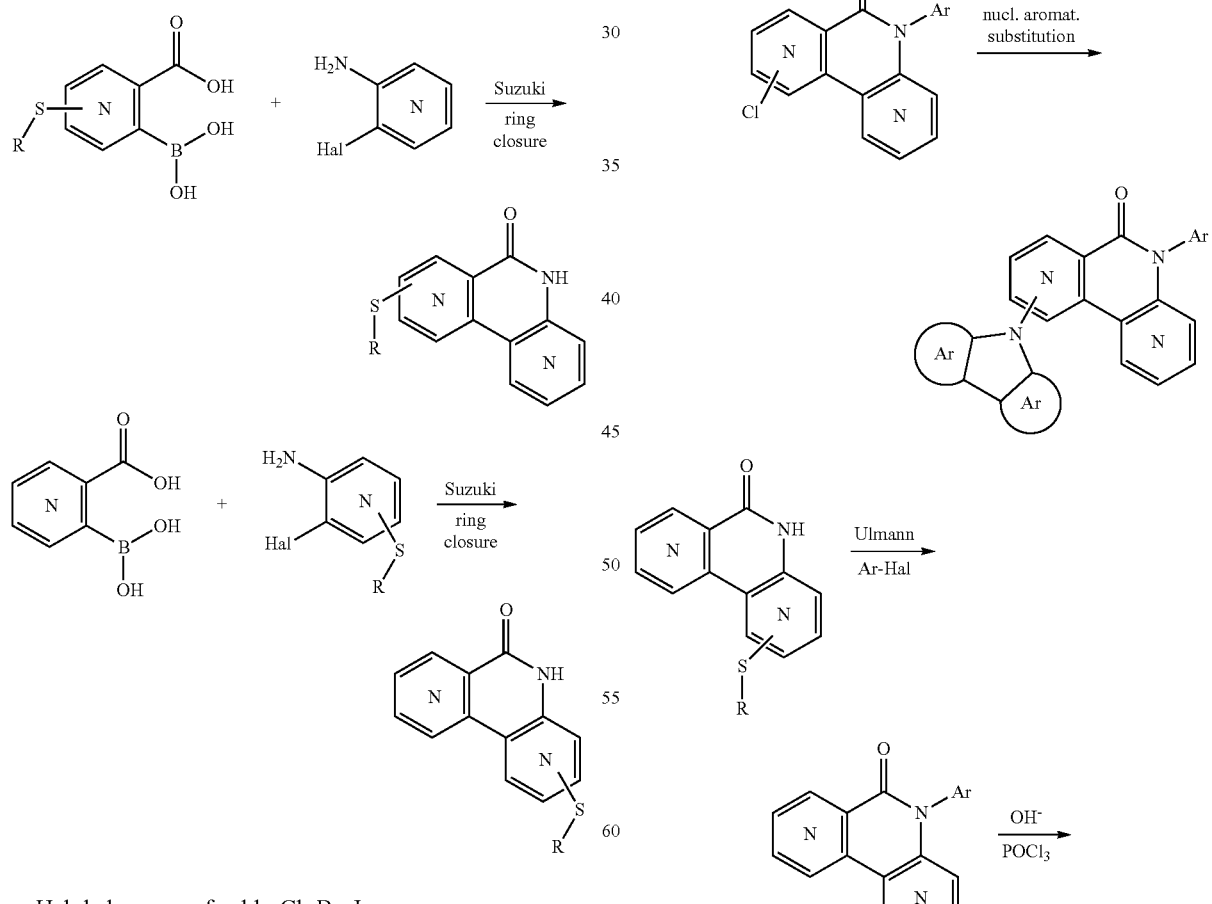

Hal=halogen, preferably Cl, Br, I
N in the ring: the ring may have one or more nitrogen atoms as ring members.

The compound obtained in scheme 1a or 1b is subsequently converted further by Ullmann coupling at the NH of the lactam. Then, in a further reaction, the alkyl thioether group is replaced by a chlorine atom. The corresponding reaction type is described in Ham et al., Tetrahedron Letters 2010, 51(35), 4609-4611. Subsequently, in a nucleophilic aromatic substitution, the N-bonded carbazole derivative is introduced at this chlorine atom (scheme 2).

Scheme 2

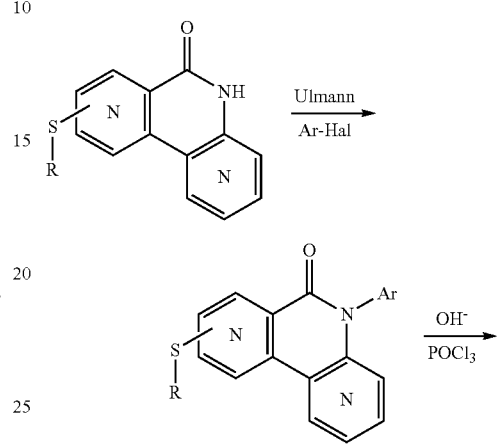

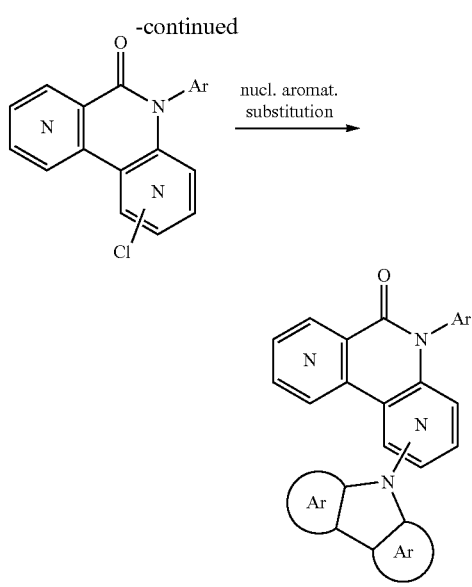

Ar = aromatic or heteroaromatic ring system

The compounds shown in the above schemes may be substituted by any organic radicals at the positions shown as unsubstituted.

The present application thus further provides a process for preparing a compound of the formula (I), characterized in that it comprises the following steps:
i) preparing a cyclic lactam from two aromatic units by Suzuki coupling and formation of an amide;
ii) Ullmann coupling of an aromatic unit to the nitrogen atom of the lactam group of the cyclic lactam;
iii) nucleophilic substitution of a halogen atom in the lactam base skeleton by the carbazole nitrogen atom of a carbazole derivative.

Steps i) to iii) are preferably conducted in the sequence specified. It is further preferable that the cyclic lactam at first has an alkyl thioether group which is exchanged for a halogen atom, preferably Cl, in a later step, where the nucleophilic substitution reaction takes place at the halogen atom mentioned.

The term "aromatic unit" in the context of the above-described syntheses encompasses both heteroaromatic and purely aromatic systems.

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$ or $R^3$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are selected from fluorenes, spirobifluorenes, paraphenylenes, carbazoles, thiophenes, dihydrophenanthrenes, cis- and trans-indenofluorenes, ketones, phenanthrenes or else two or more of these units. The polymers, oligomers and dendrimers typically contain still further units, for example emitting (fluorescent or phosphorescent) units, for example vinyltriarylamines or phosphorescent metal complexes, and/or charge transport units, especially those based on triarylamines.

The polymers, oligomers and dendrimers of the invention have advantageous properties, especially high lifetimes, high efficiencies and good color coordinates.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to C—C and C—N couplings are as follows:
(A) SUZUKI polymerization;
(B) YAMAMOTO polymerization;
(C) STILLE polymerization; and
(D) HARTWIG-BUCHWALD polymerization.

How the polymerization can be conducted by these methods and how the polymers can then be separated from the reaction medium and purified is known to those skilled in the art and is described in detail in the literature.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, alpha-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, or mixtures of these solvents.

The invention therefore further provides a formulation, especially a solution, dispersion or emulsion, comprising at least one compound of formula (I) or at least one polymer, oligomer or dendrimer containing at least one unit of formula (I) and at least one solvent, preferably an organic solvent. The way in which such solutions can be prepared is known to those skilled in the art.

In a preferred embodiment of the invention, the formulation, apart from the compound of the application, also contains at least one further matrix material and at least one phosphorescent emitter. The at least one further matrix material and the at least one phosphorescent emitter are selected from the embodiments specified as preferred below in each case. Application and evaporation of the solvent out of the formulation leaves the mixture of the materials as phosphorescent emitting layer with a mixed matrix.

The compounds of the application are suitable for use in electronic devices, especially in organic electroluminescent devices (OLEDs). Depending on the substitution, the compounds are used in different functions and layers.

The invention therefore further provides for the use of the compounds of the application in electronic devices. These electronic devices are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound as defined above. This electronic device is preferably selected from the abovementioned devices.

It is more preferably an organic electroluminescent device (OLED) comprising anode, cathode and at least one emitting layer, characterized in that at least one organic layer, which is preferably selected from emitting layers, electron transport layers and hole blocker layers, and which is more preferably selected from emitting layers, very particularly phosphorescent emitting layers, comprises at least one compound as defined above.

Apart from the cathode, anode and at least one emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers and/or organic or inorganic p/n junctions.

The sequence of layers in the organic electroluminescent device is preferably:

anode/hole injection layer/hole transport layer/optionally further hole transport layer(s)/electron blocker layer/emitting layer/hole blocker layer/electron transport layer/optionally further electron transport layer(s)/electron injection layer/cathode. It is additionally possible for further layers to be present in the OLED.

It is preferable when at least one hole-transporting layer of the apparatus is p-doped, i.e. contains at least one p-dopant. p-Dopants are preferably selected from electron acceptor compounds.

Particularly preferred p-dopants are selected from quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as binding site. Preference is further given to transition metal oxides as dopants, preferably oxides of rhenium, molybdenum and tungsten, more preferably $Re_2O_7$, $MoO_3$, $WO_3$ and $ReO_3$. Also preferred are bismuth complexes, especially Bi(III) complexes, especially bismuth complexes with benzoic acid derivatives as complex ligands.

The organic electroluminescent device of the invention may contain two or more emitting layers. More preferably, these emission layers have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, wherein one of the three layers in each case shows blue emission, one of the three layers in each case shows green emission, and one of the three layers in each case shows orange or red emission. The compounds of the invention are preferably present in the emitting layer. For the generation of white light, rather than multiple color-emitting emitter compounds, an emitter compound used individually that emits over a broad wavelength range may also be suitable.

It is preferable in accordance with the invention when the compounds are used in an electronic device comprising one or more phosphorescent emitting compounds in an emitting layer. The compounds are preferably present in the emitting layer in combination with the phosphorescent emitting compound, more preferably in a mixture with at least one further matrix material. The latter is preferably selected from hole-conducting matrix materials, electron-conducting matrix materials and matrix materials having both hole-conducting properties and electron-conducting properties (bipolar matrix materials), more preferably from electron-conducting matrix materials and bipolar matrix materials, most preferably from electron-conducting matrix materials.

The term "phosphorescent emitting compounds" preferably encompasses those compounds where the emission of light is effected through a spin-forbidden transition, for example a transition from an excited triplet state or a state having a higher spin quantum number, for example a quintet state.

In a preferred embodiment of the present invention, the compound of formula (I) is used in an emitting layer as matrix material in combination with one or more phosphorescent emitting compounds. The phosphorescent emitting compound is preferably a red- or green-phosphorescing emitter.

The total proportion of all matrix materials in the phosphorescent emitting layer in this case is between 50.0% and 99.9% by volume, preferably between 80.0% and 99.5% by volume, and more preferably between 85.0% and 97.0% by volume.

Correspondingly, the proportion of the phosphorescent emitting compound is between 0.1% and 50.0% by volume, preferably between 0.5% and 20.0% by volume, and more preferably between 3.0% and 15.0% by volume.

The emitting layer of the organic electroluminescent device preferably comprises two or more matrix materials (mixed matrix systems). The mixed matrix systems preferably comprise two or three different matrix materials, more preferably two different matrix materials.

In a preferred embodiment, one of the two matrix materials fulfills the function of a hole-transporting material, and the other of the two matrix materials fulfills the function of an electron-transporting material. More preferably, the compound of the formula (I) here is the electron-transporting material, and the further compound present in the emitting layer in a mixture with the compound of the formula (I) is the hole-transporting material.

In a further preferred embodiment of the invention, one of the two materials is a wide bandgap material, and one or two further matrix materials are present in the emitting layer, which fulfill an electron-transporting function and/or a hole-transporting function of the mixed matrix. In a preferred embodiment, this can be accomplished in that not only the wide bandgap material but also a further matrix material having electron-transporting properties is present in the emitting layer, and yet a further matrix material having hole-transporting properties is present in the emitting layer. Alternatively and more preferably, this can be accomplished in that not only the wide bandgap material but also a single further matrix material having both electron-transporting and hole-transporting properties is present in the emitting layer. Such matrix materials are also referred to as bipolar matrix materials.

In another alternative embodiment, as well as the wide bandgap matrix material, only a single further matrix material having either predominantly hole-transporting properties or predominantly electron-transporting properties may be present in the emitting layer.

In the preferred case that two different matrix materials are present in the emitting layer, these may be present in a volume ratio of 1:50 to 1:1, preferably 1:20 to 1:1, more preferably 1:10 to 1:1 and most preferably 1:4 to 1:1. Preferably, the compound of formula (I) is present in the same proportion as the further matrix compound, or it is present in a higher proportion than the further matrix compound.

The absolute proportion of the compound of formula (I) in the mixture of the emitting layer, in the case of use as matrix material in a phosphorescent emitting layer, is preferably 10% by volume to 85% by volume, more preferably 20% by volume to 85% by volume, even more preferably 30% by volume to 80% by volume, very especially preferably 20% by volume to 60% by volume and most preferably 30% by volume to 50% by volume. The absolute proportion of the second matrix compound in this case is preferably 15% by volume to 90% by volume, more preferably 15% by volume to 80% by volume, even more preferably 20% by volume to 70% by volume, very especially preferably 40% by volume to 80% by volume, and most preferably 50% by volume to 70% by volume.

For production of phosphorescent emitting layers of the mixed matrix type, in a preferred embodiment of the invention, a solution comprising the phosphorescent emitter and the two or more matrix materials may be produced. This can be applied by means of spin-coating, printing methods or other methods. Evaporation of the solvent in this case leaves the phosphorescent emitting layer of the mixed matrix type.

In an alternative, more preferred embodiment of the invention, the phosphorescent emitting layer of the mixed matrix type is produced by vapor phase deposition. For this purpose, there are two ways in which the layer can be applied. Firstly, each of the at least two different matrix materials may be initially charged in a material source, followed by simultaneous evaporation ("coevaporation") from the two or more different material sources. Secondly, the at least two matrix materials may be premixed and the mixture obtained may be initially charged in a single material source from which it is ultimately evaporated. The latter method is referred to as the premix method.

The present application therefore also provides a mixture comprising a compound of the above-specified formulae and at least one further compound selected from matrix compounds. In this respect, the preferred embodiments with regard to proportions of the matrix compounds and their chemical structure that are specified in this application are likewise considered to be preferable.

In an alternative preferred embodiment of the invention, the compound is used as electron-transporting material. This is especially true when the compound contains at least one group selected from electron-deficient heteroaryl groups, preferably azine groups, especially triazine groups, pyrimidine groups and pyridine groups, and benzimidazole groups.

When the compound is used as electron-transporting material, it is preferably used in a hole blocker layer, an electron transport layer or an electron injection layer. In a preferred embodiment, the layer comprising the compound of the formula (I) in that case is n-doped, or it is in a mixture with a further electron-transporting compound. The compound of the formula (I) may alternatively be present as a pure material in the layer selected from hole blocker layer, electron transport layer and electron injection layer.

In the present context, an n-dopant is understood to mean an organic or inorganic compound capable of releasing electrons (electron donor), i.e. a compound that acts as a reducing agent. The compounds used for n-doping can be used in the form of a precursor, in which case these precursor compounds release n-dopants through activation. Preferably, n-dopants are selected from electron-rich metal complexes; P=N compounds; N-heterocycles, more preferably naphthylenecarbodiimides, pyridines, acridines and phenazines; fluorenes and free-radical compounds.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 position. Aromatic pyreneamines, pyrenediamines, chryseneamines and chrysenediamines are defined analogously, where the diarylamino groups are bonded to the pyrene preferably in the 1 position or 1,6 position. Further preferred emitting compounds are indenofluoreneamines or -diamines, benzoindenofluoreneamines or -diamines, and dibenzoindenofluoreneamines or -diamines, and indenofluorene derivatives having fused aryl groups. Likewise preferred are pyrenearylamines. Likewise preferred are benzoindenofluoreneamines, benzofluoreneamines, extended benzoindenofluorenes, phenoxazines, and fluorene derivatives joined to furan units or to thiophene units.

Preferred matrix materials for fluorescent emitters are selected from the classes of the oligoarylenes (e.g. 2,2',7,7'-tetraphenylspirobifluorene), especially the oligoarylenes containing fused aromatic groups, the oligoarylenevinylenes, the polypodal metal complexes, the hole-conducting compounds, the electron-conducting compounds, especially ketones, phosphine oxides and sulfoxides; the atropisomers, the boronic acid derivatives or the benzanthracenes. Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

In general, all phosphorescent complexes as used for phosphorescent OLEDs according to the prior art and as known to those skilled in the art in the field of organic electroluminescent devices are suitable. Explicit examples of particularly suitable complexes are shown in the following table:

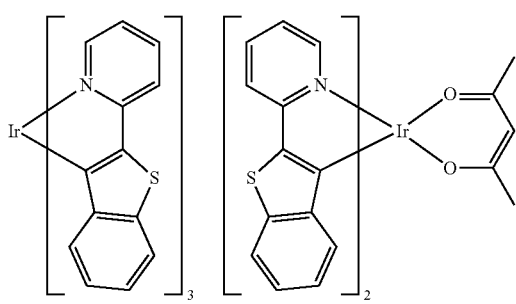

-continued

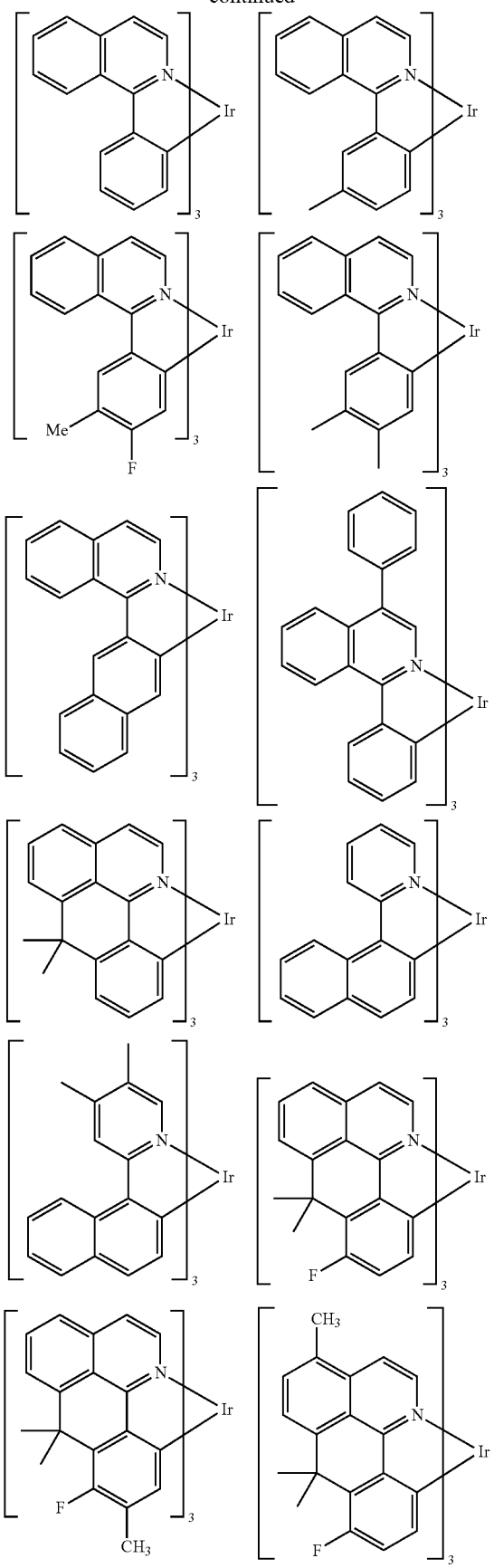

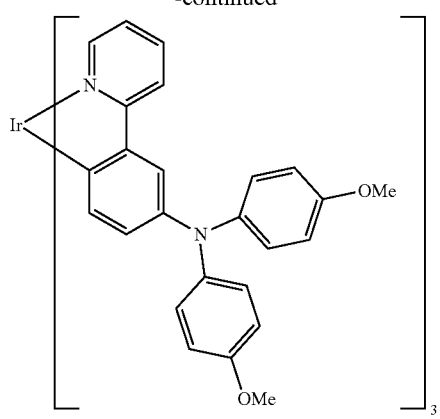
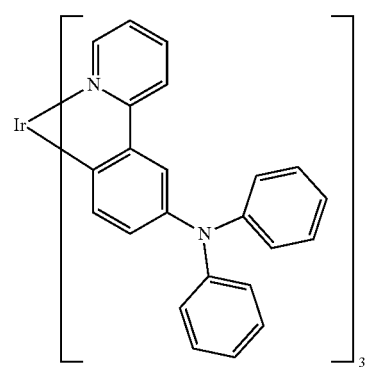
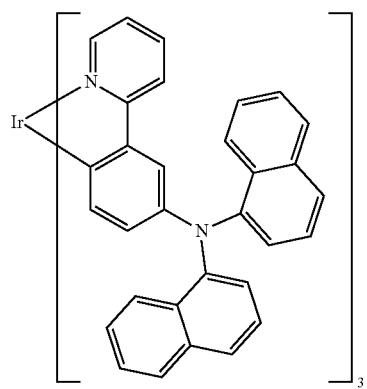
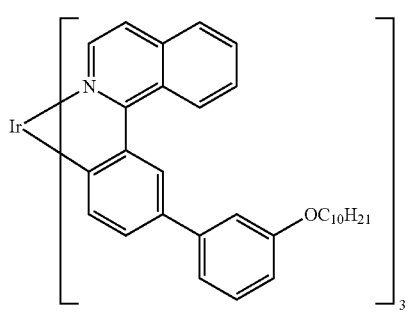
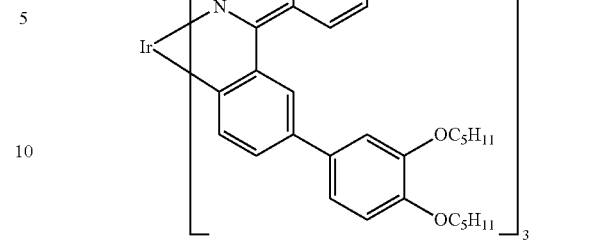
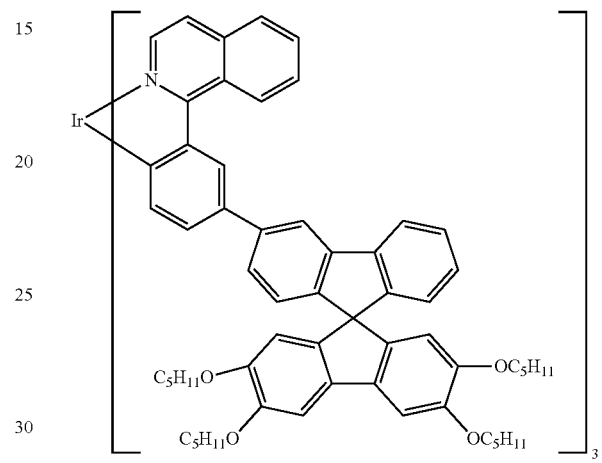
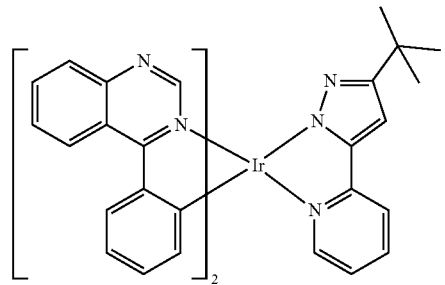
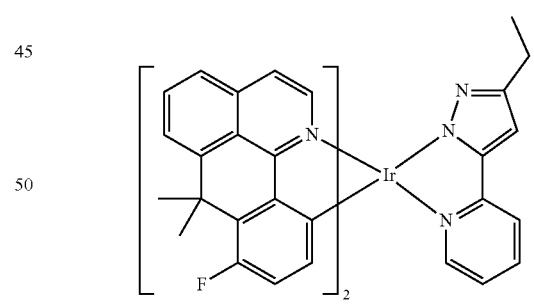
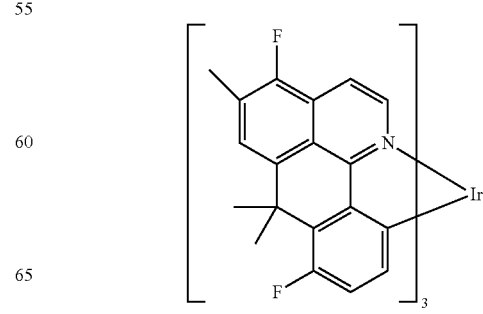

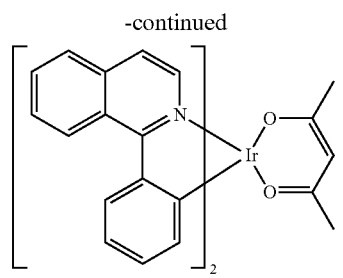
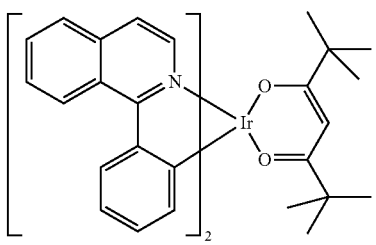
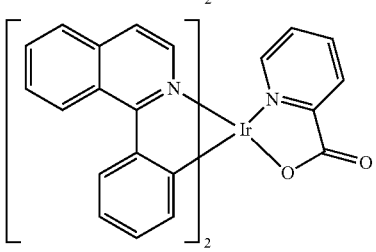
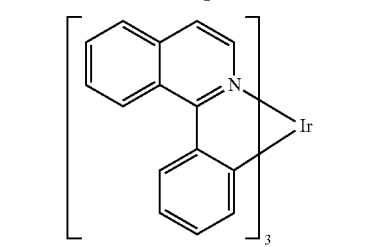
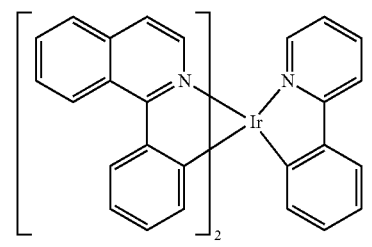
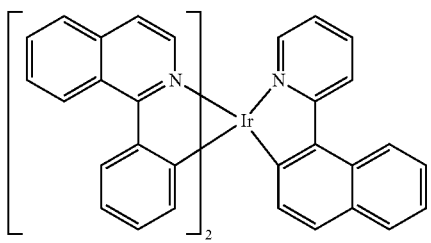
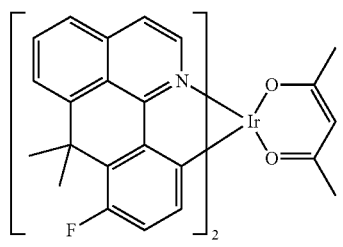
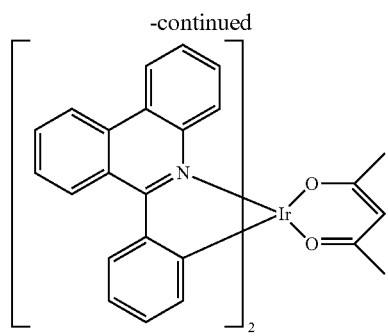
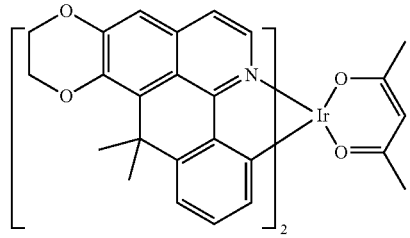
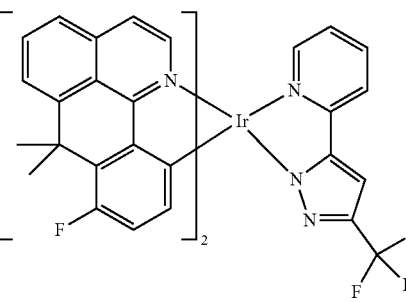
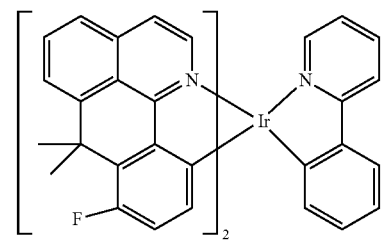
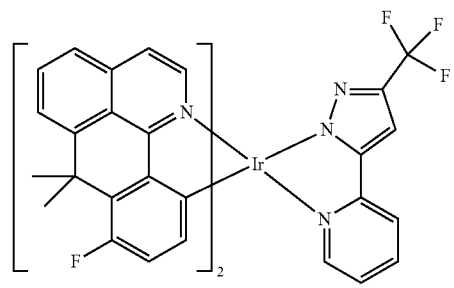

89
-continued
90
-continued
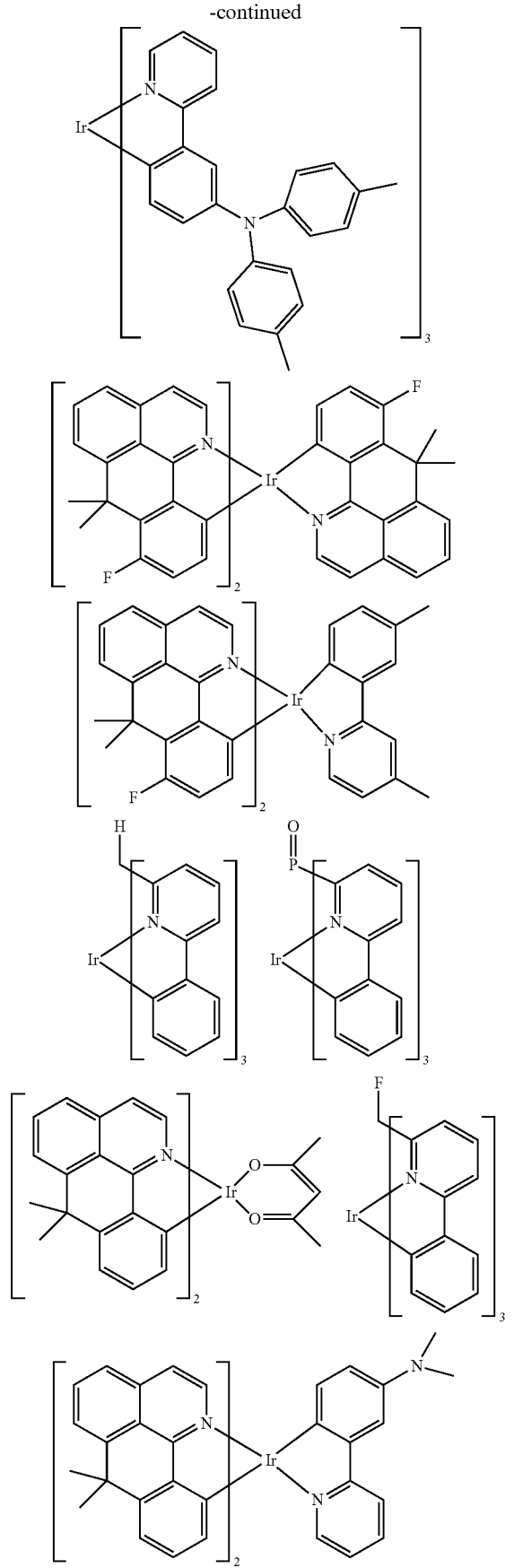
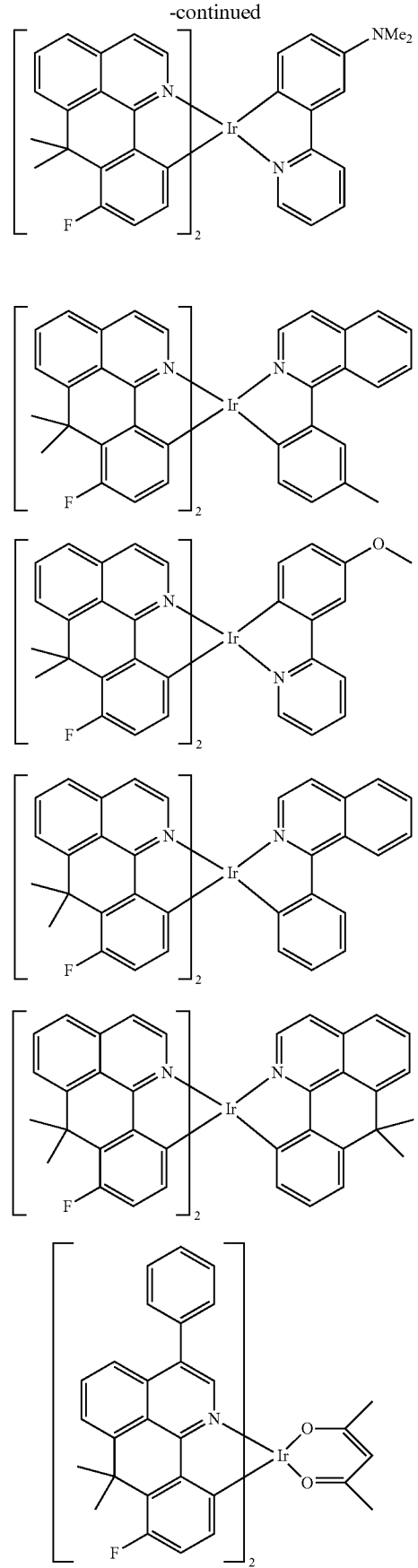

-continued
91
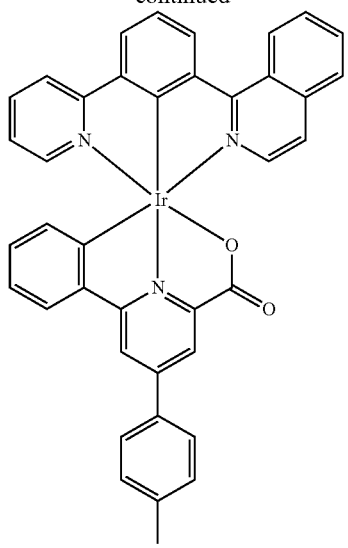
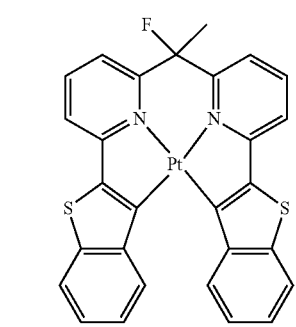
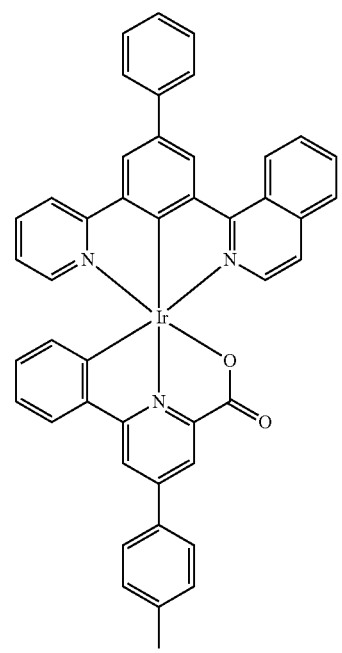
92
-continued
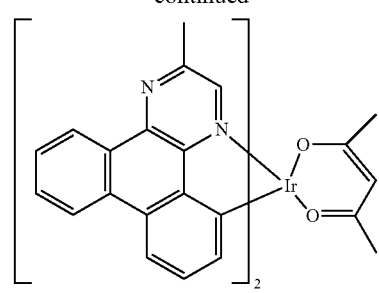
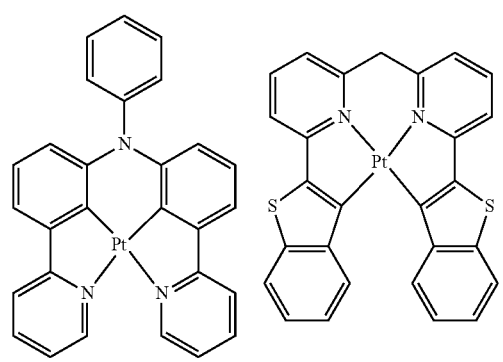
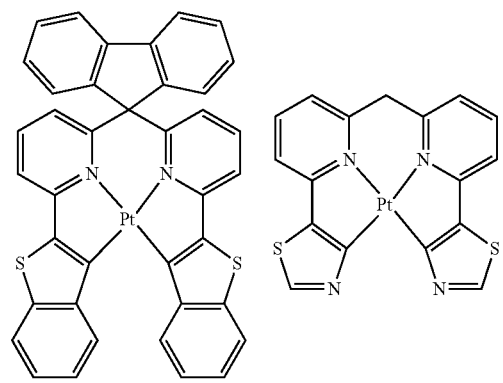
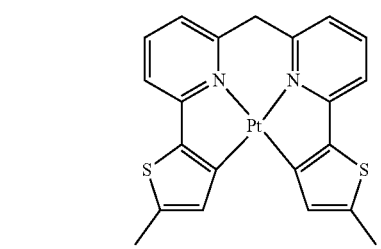
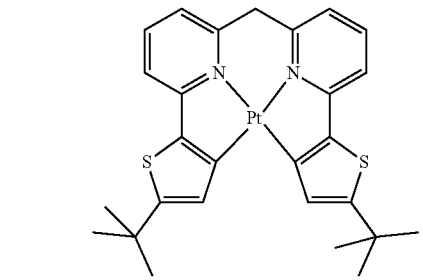

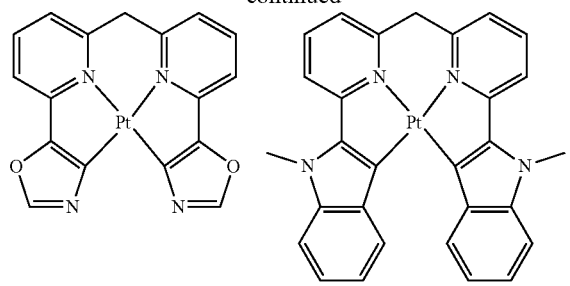
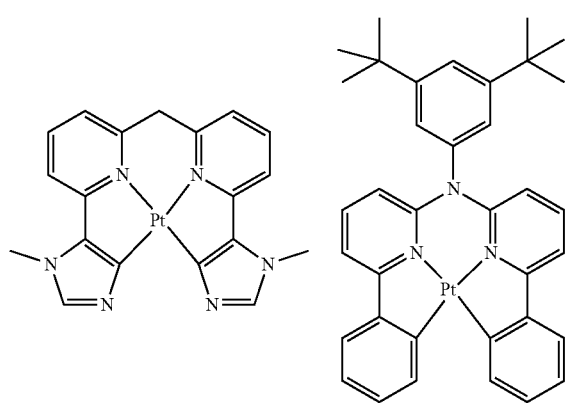
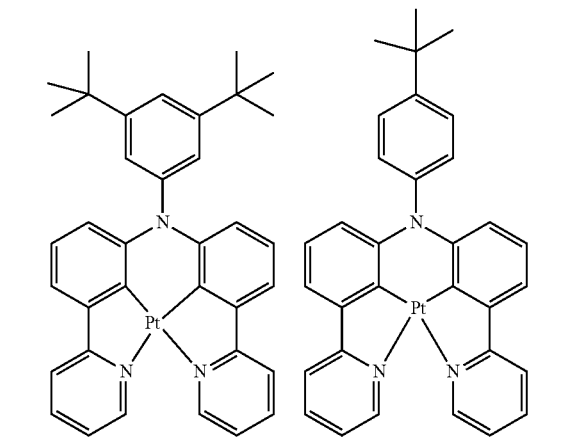
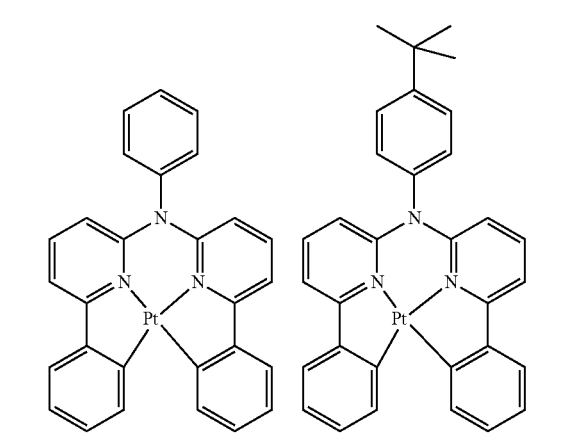
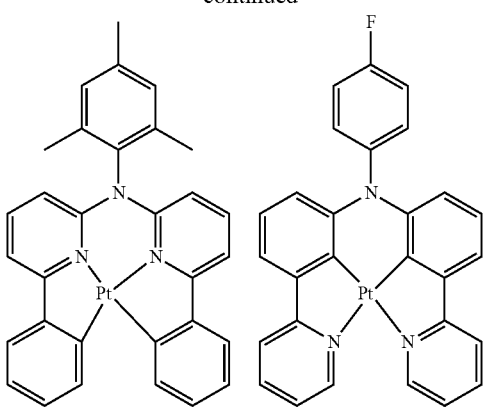

95
-continued
96
-continued
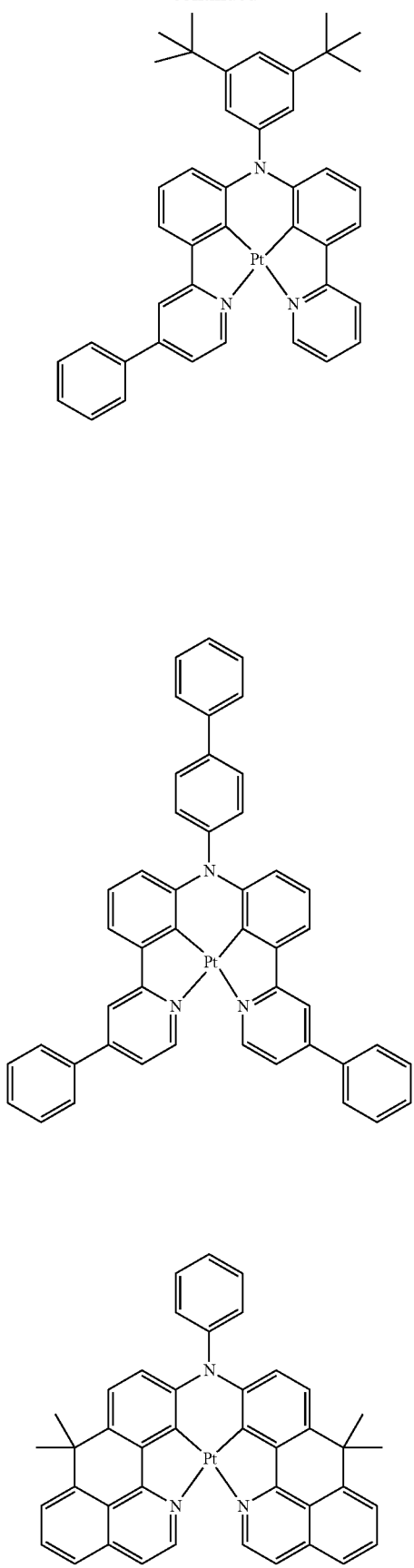
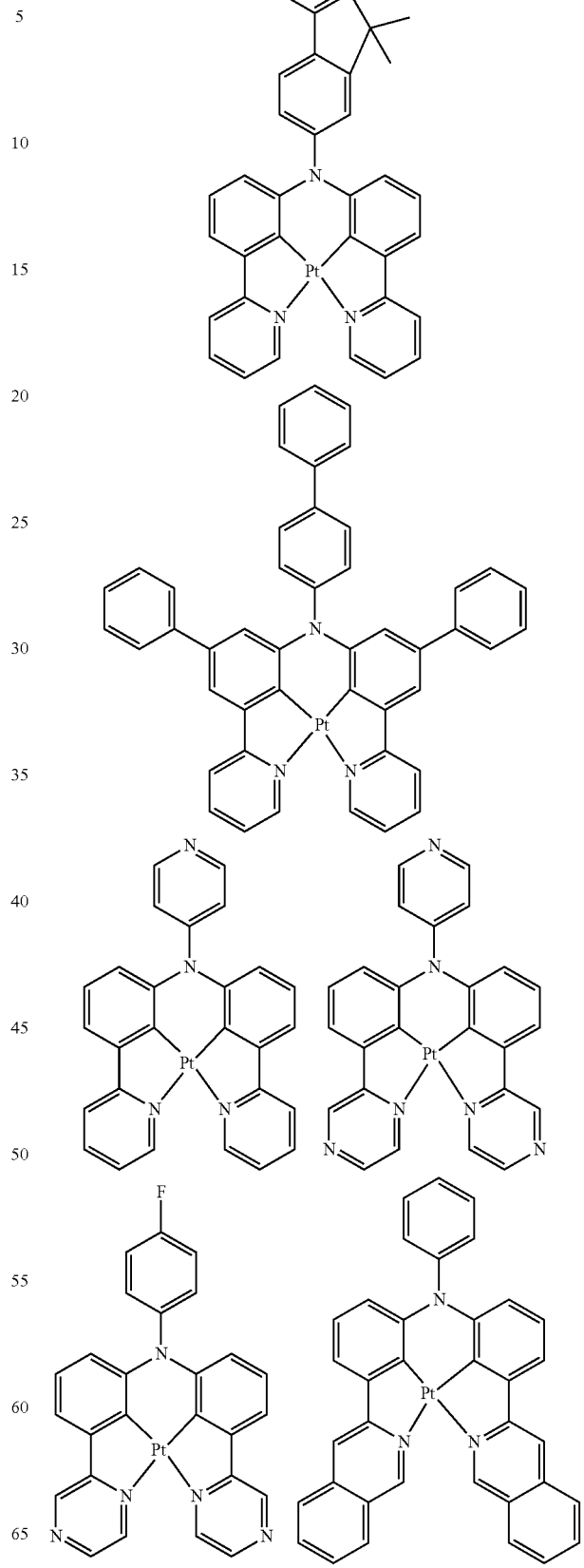

97
-continued
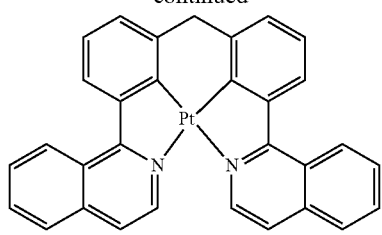
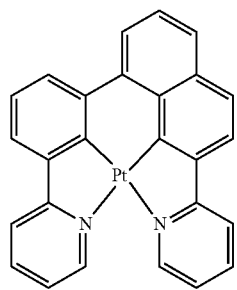
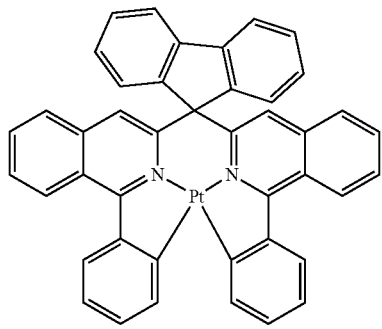
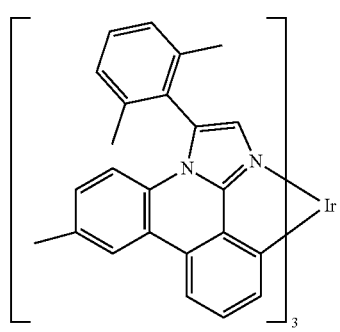
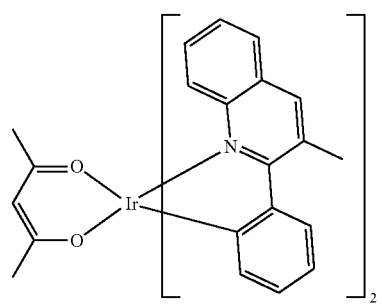
98
-continued
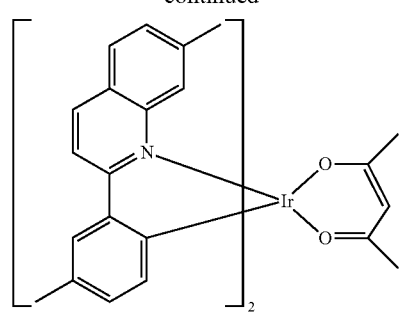
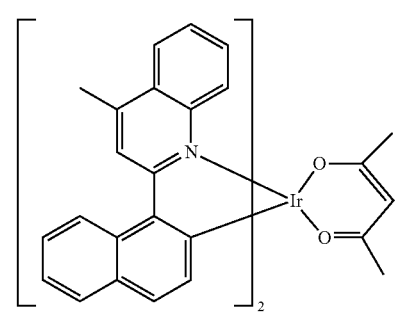
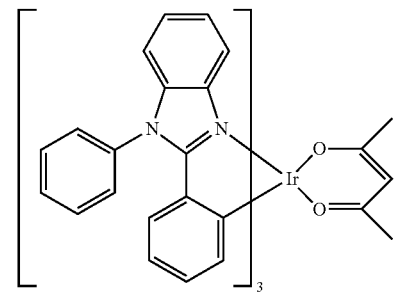
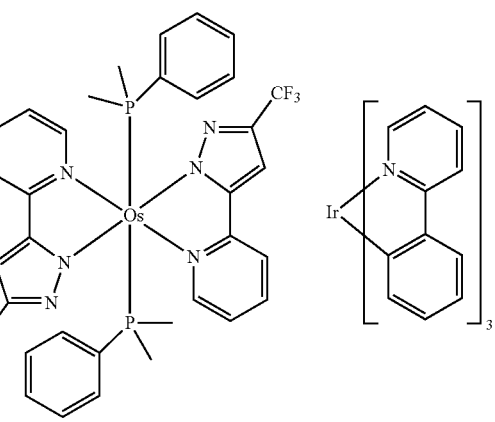
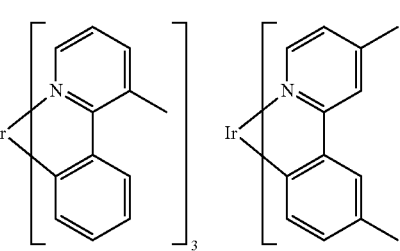

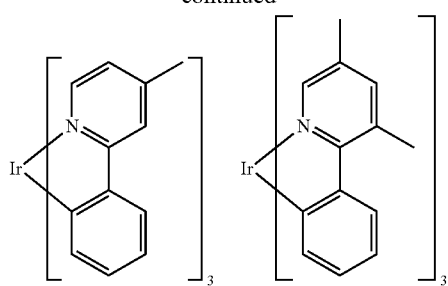
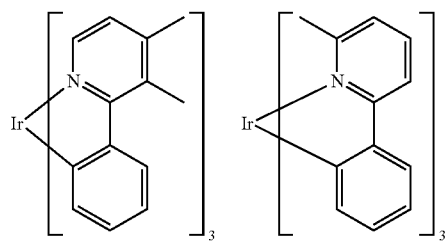
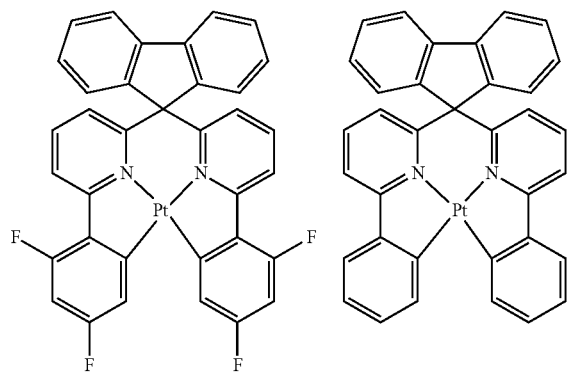
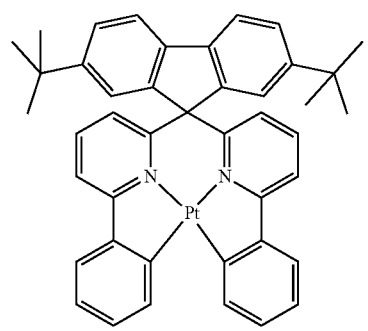
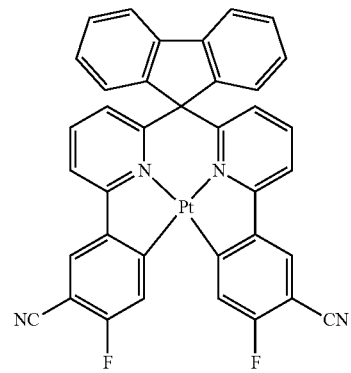
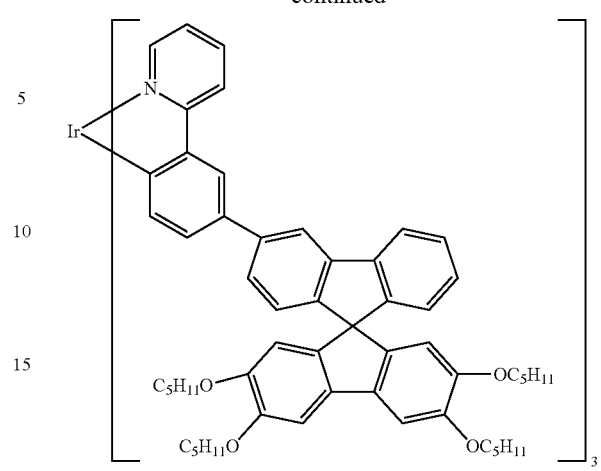
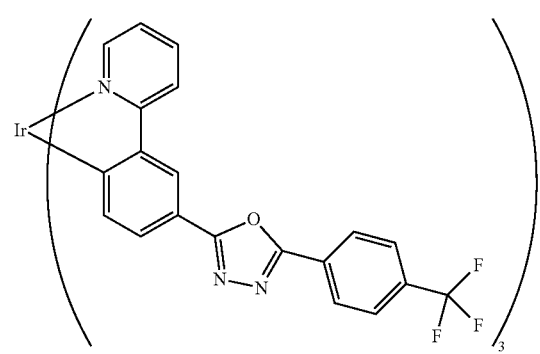
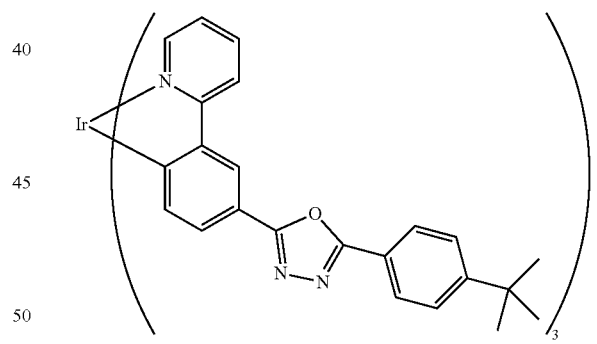
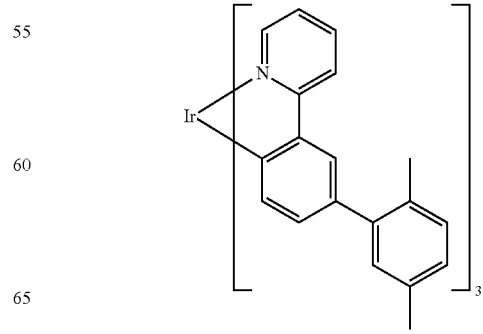

101
-continued
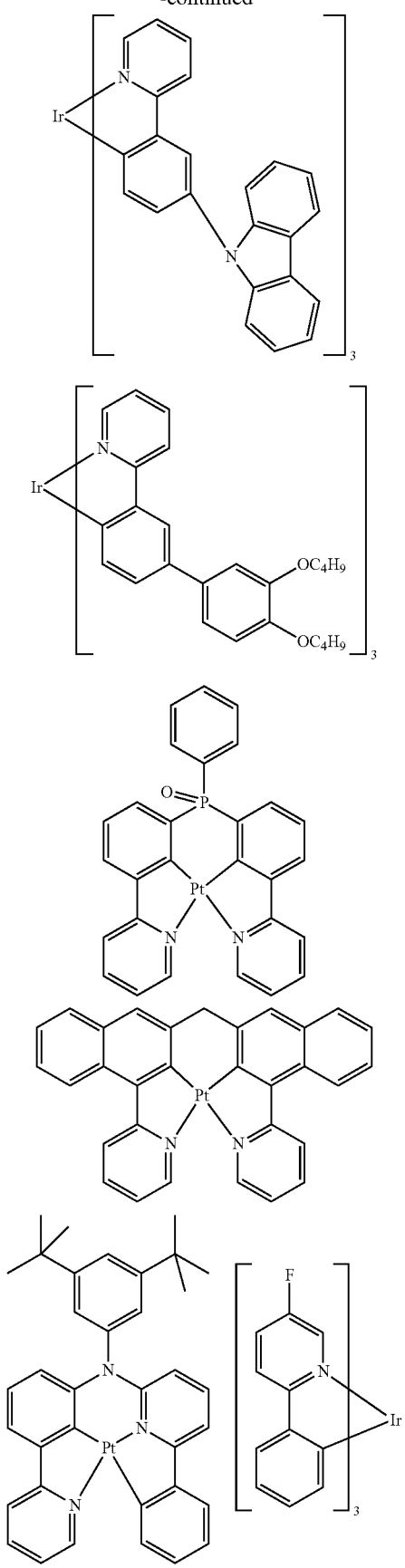
102
-continued
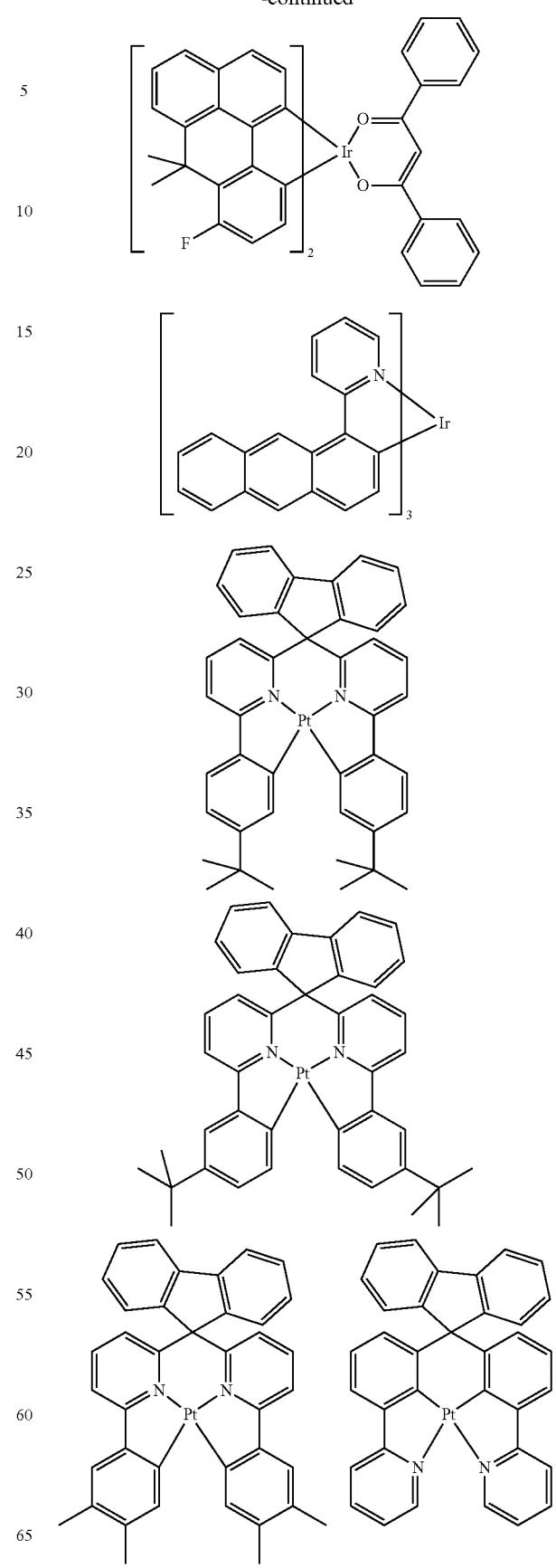

103
-continued
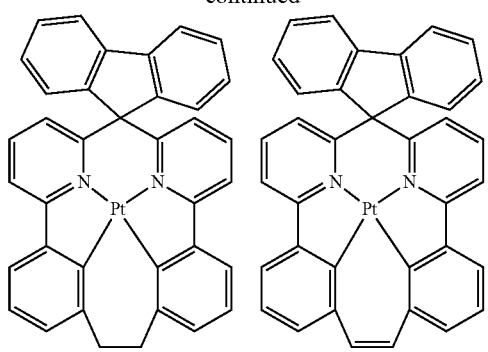
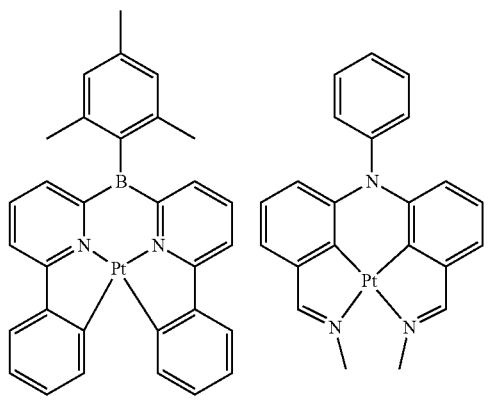
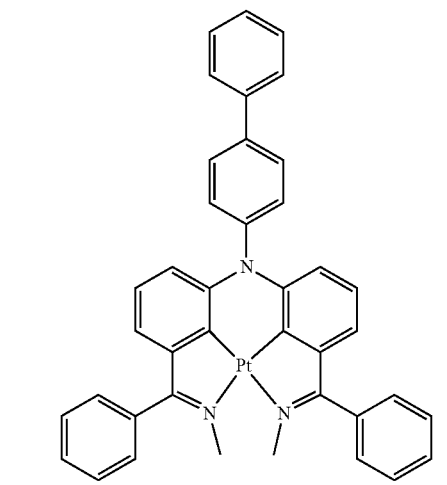
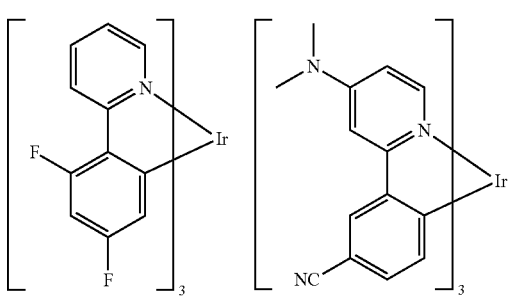
104
-continued
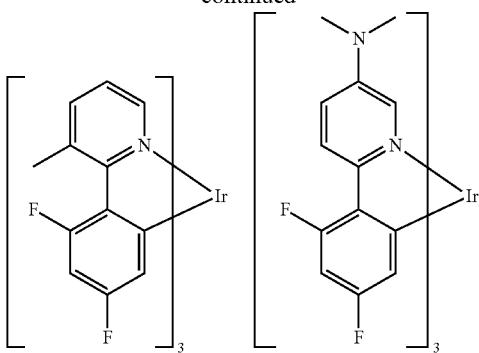
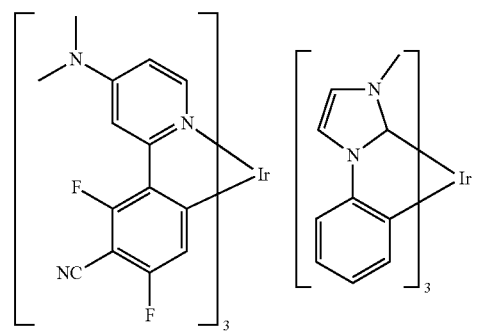
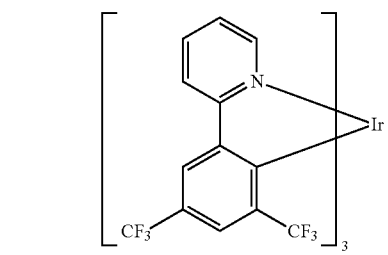
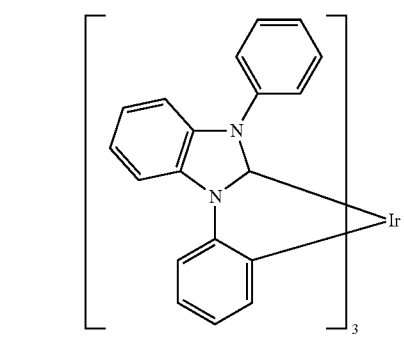
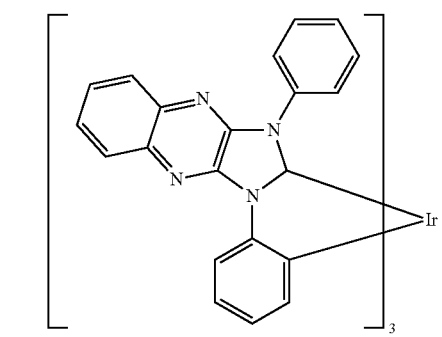

-continued
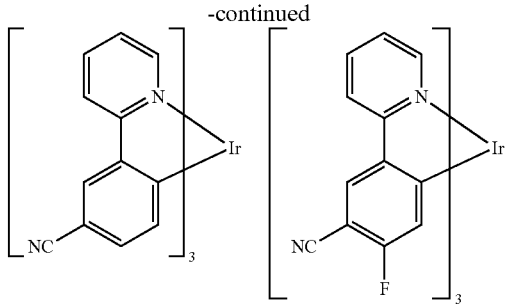
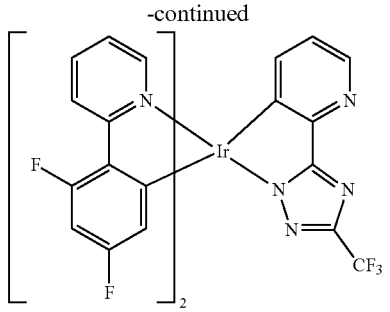
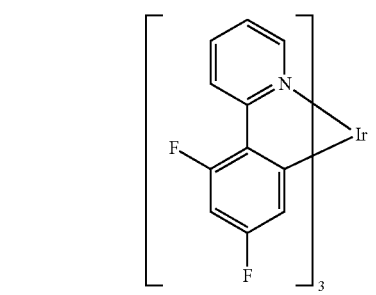
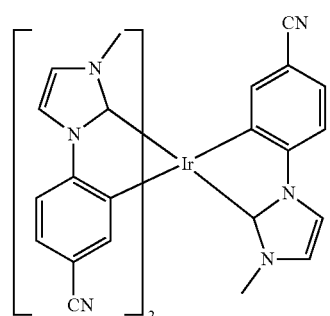
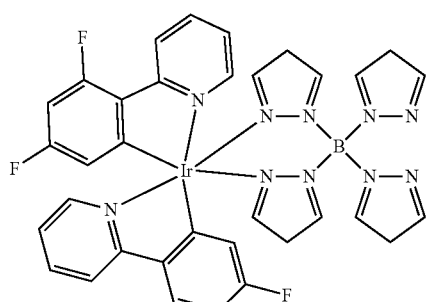
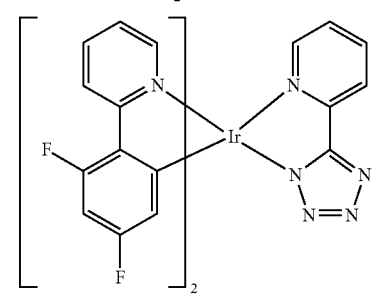
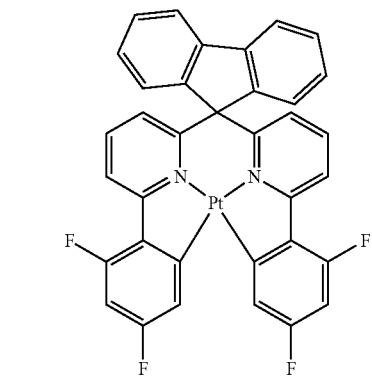
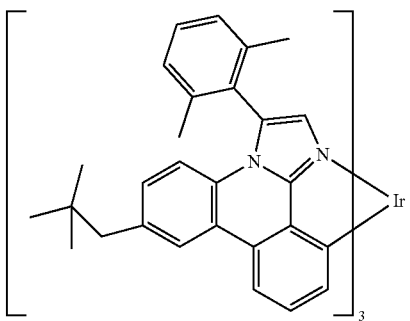
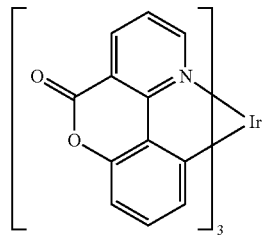
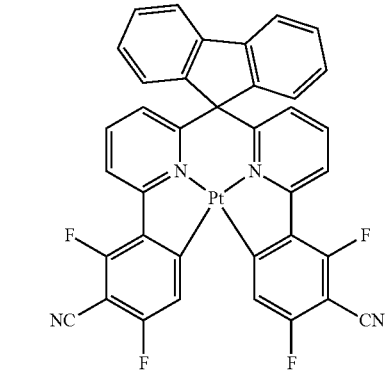
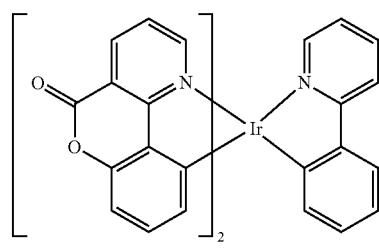

-continued
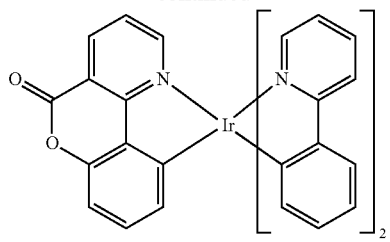
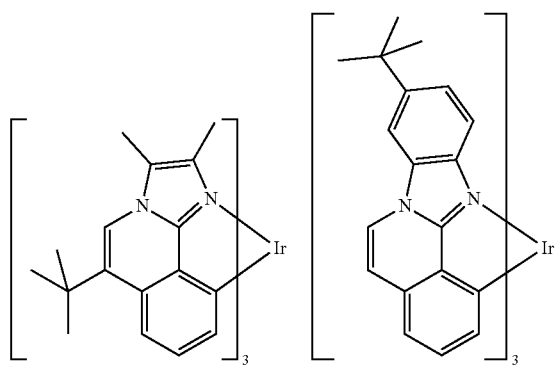
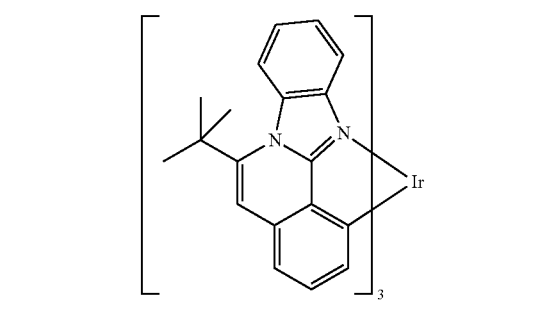
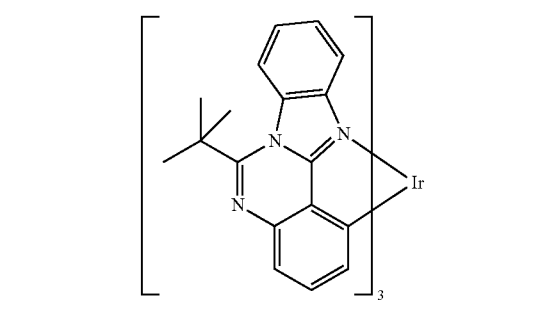
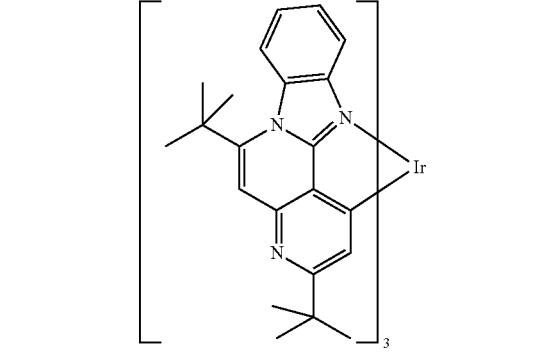
-continued
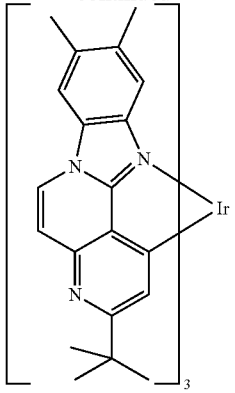
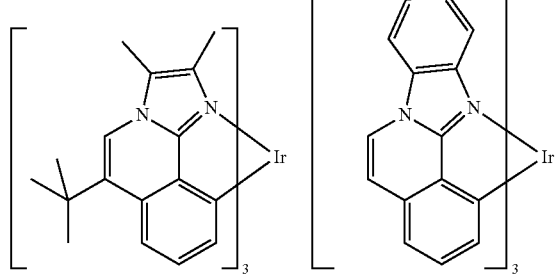
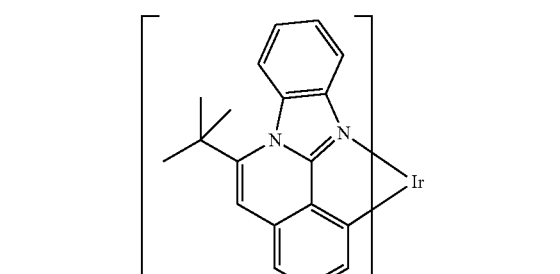
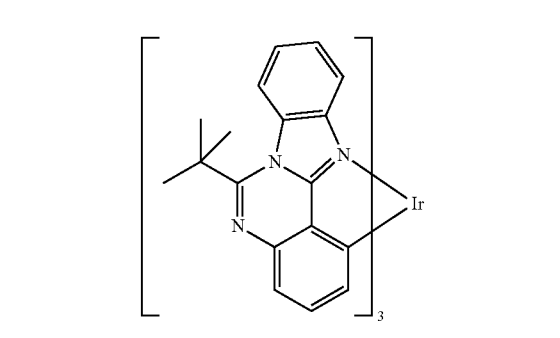
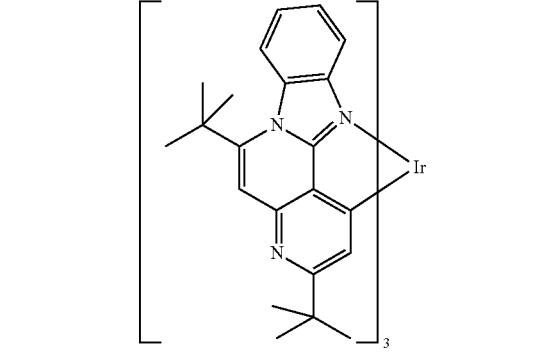

109
-continued
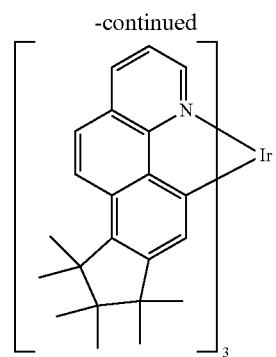
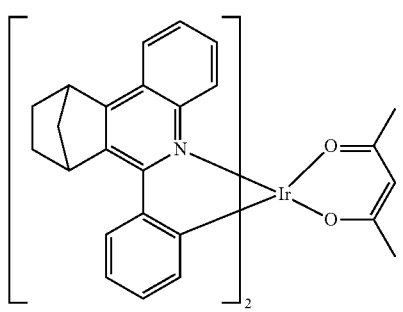
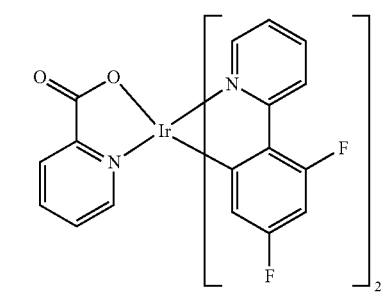
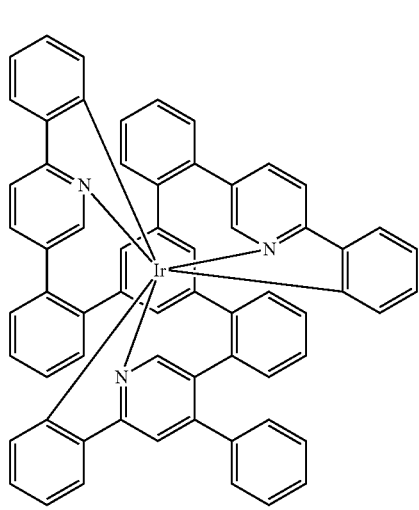
110
-continued
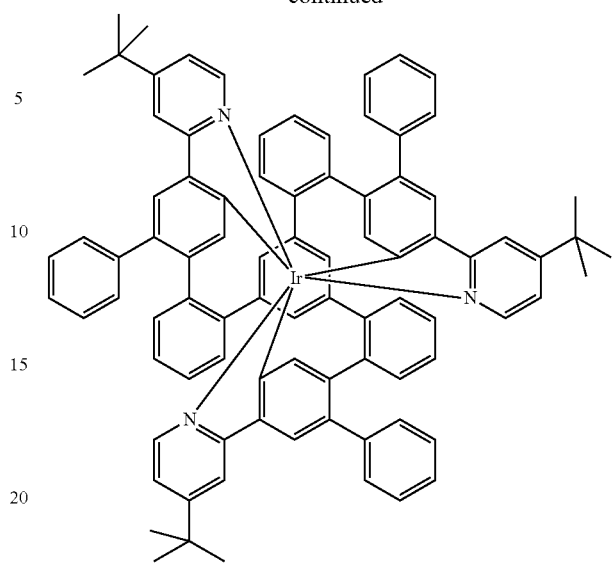
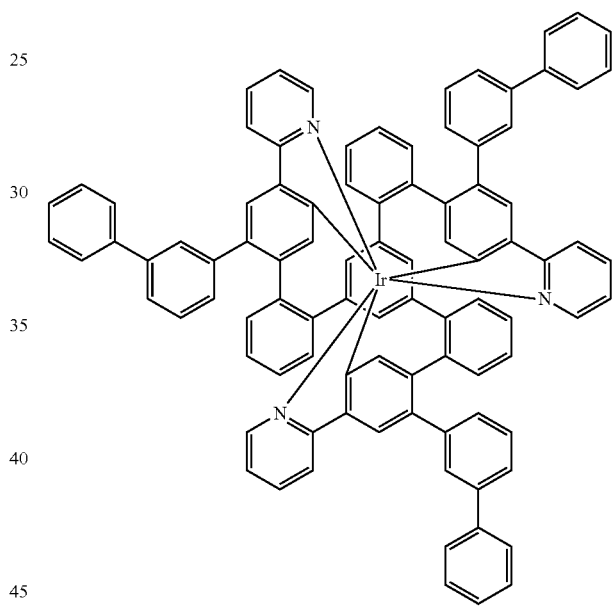

-continued

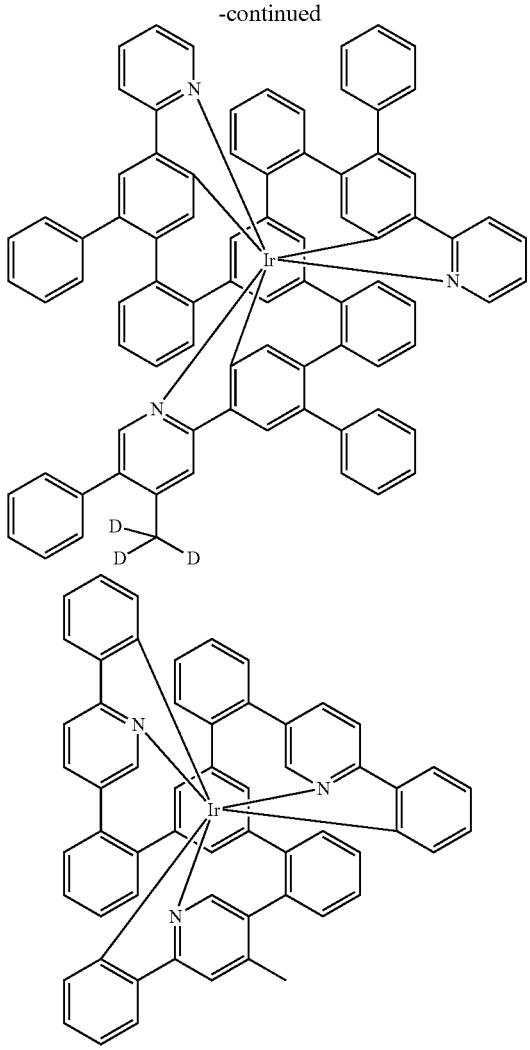

Preferred matrix materials for phosphorescent emitters, as well as the compounds of the application, are aromatic ketones, aromatic phosphine oxides or aromatic sulfoxides or sulfones, triarylamines, carbazole derivatives, e.g. CBP (N,N-biscarbazolylbiphenyl) or carbazole derivatives, indolocarbazole derivatives, indenocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives, bridged carbazole derivatives, triphenylene derivatives, or lactams. More preferably, the compound of the formula (I) is used in the emitting layer in combination with a phosphorescent emitter and a further matrix material which is preferably selected from the abovementioned preferred matrix materials and is more preferably selected from carbazole compounds, biscarbazole compounds, indolocarbazole compounds and indenocarbazole compounds.

Suitable charge transport materials as usable in the hole injection layer or hole transport layer or electron blocker layer or in the electron transport layer of the electronic device of the invention are, for example, the compounds disclosed in Y. Shirota et al., Chem. Rev. 2007, 107(4), 953-1010, or other materials as used in these layers according to the prior art.

Suitable materials for the electron-transporting layers of the device are especially aluminum complexes, for example Alq$_3$, zirconium complexes, for example Zrq$_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives.

Particularly preferred compounds for use in electron-transporting layers are shown in the following table:

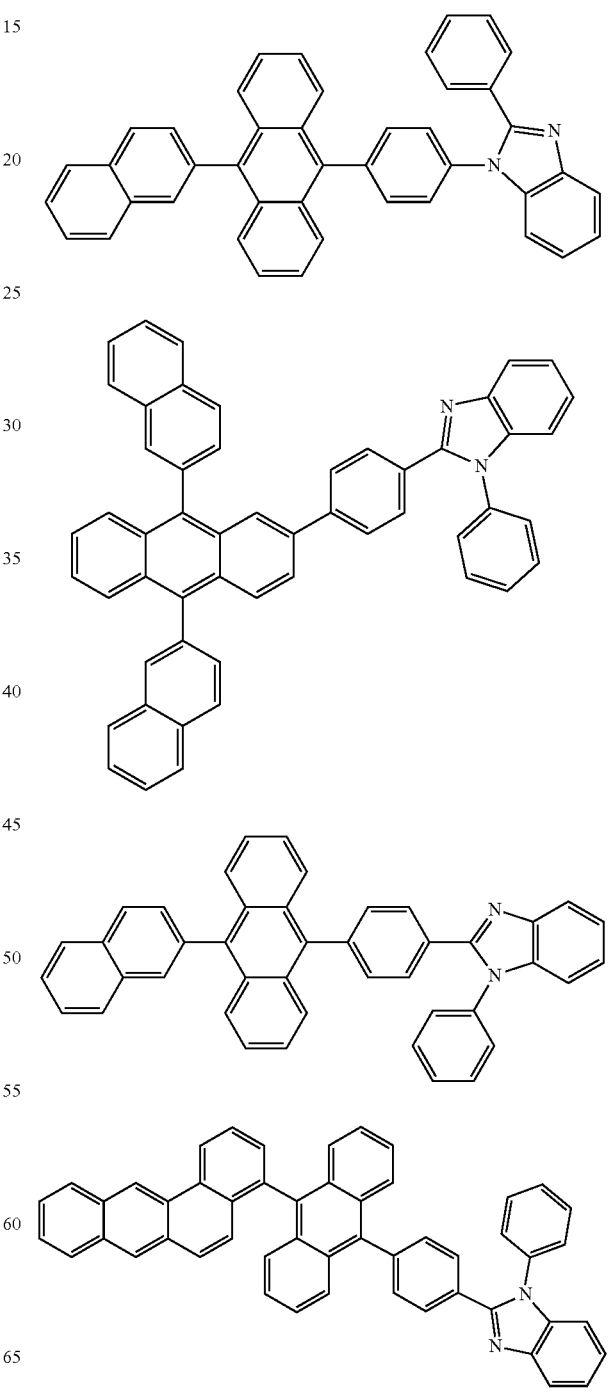

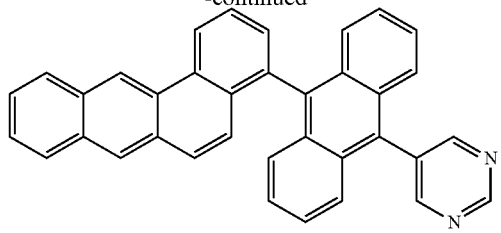
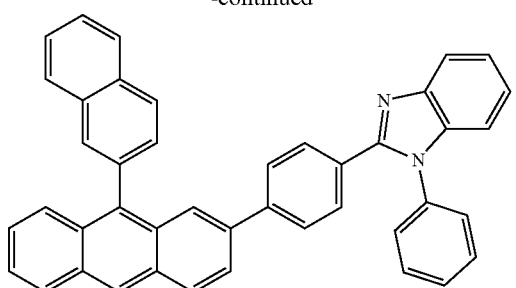
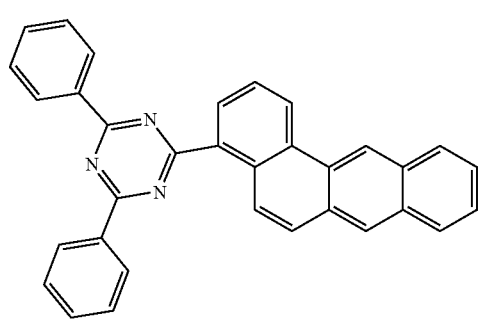
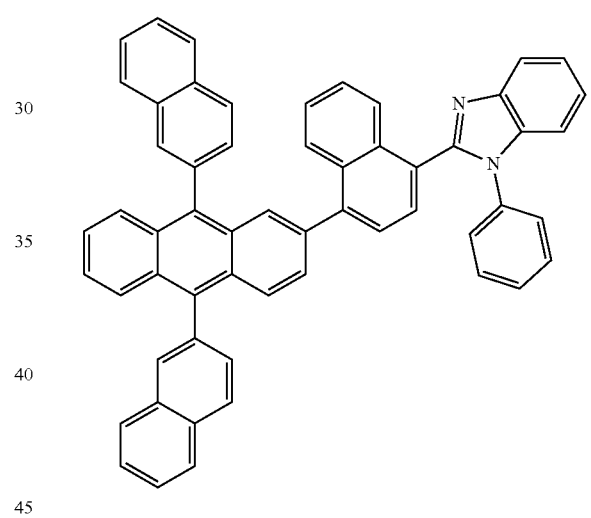
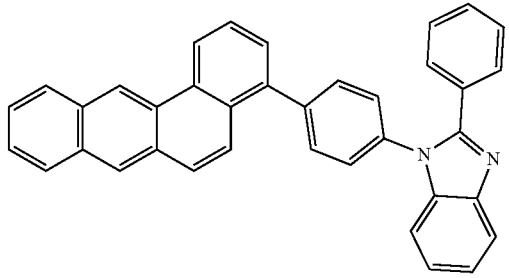
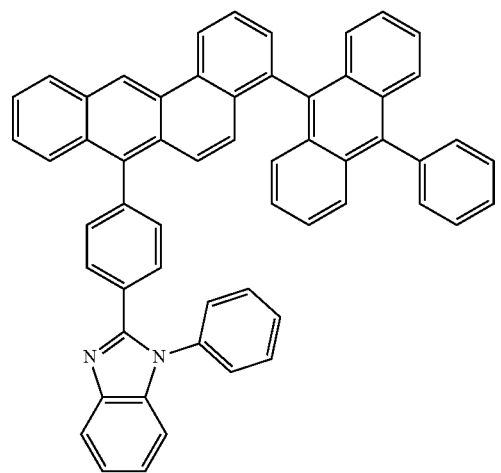
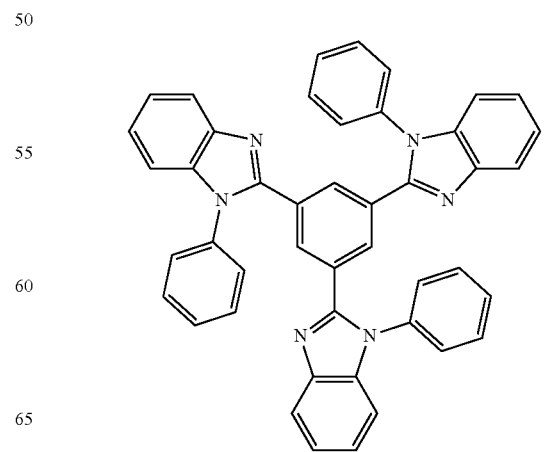

115
-continued
116
-continued
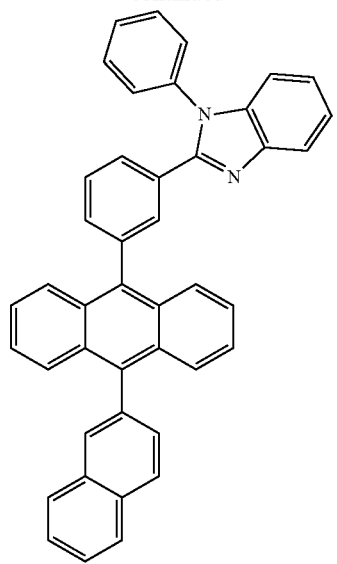

117
-continued
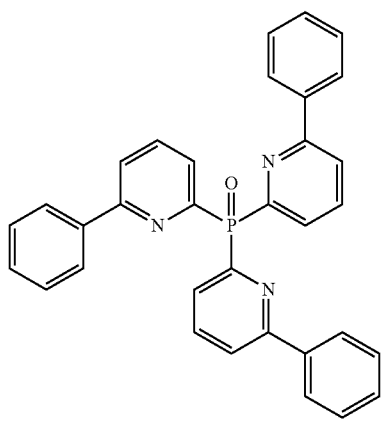
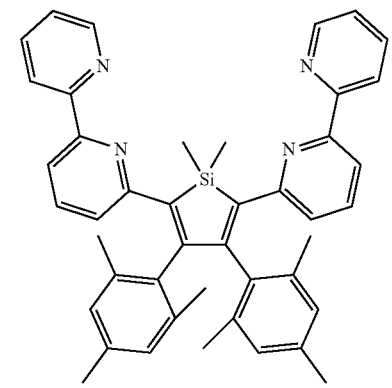
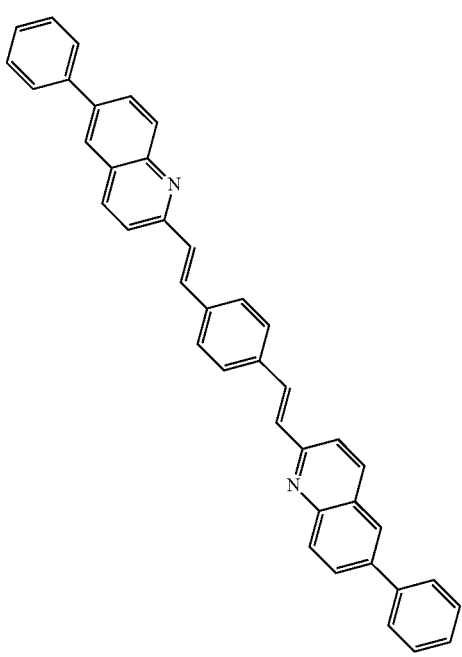
118
-continued
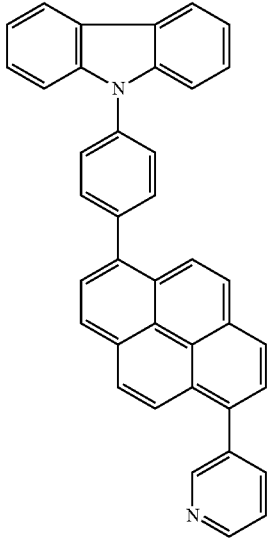
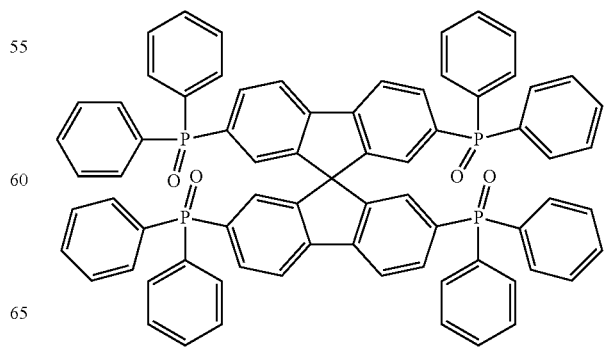

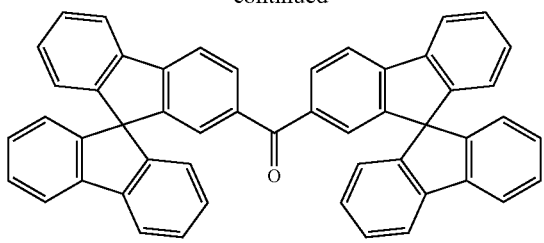

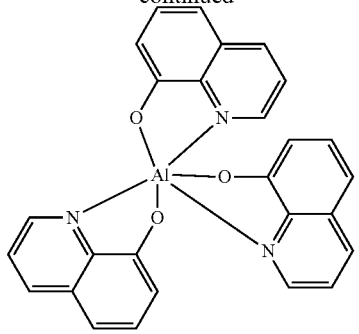

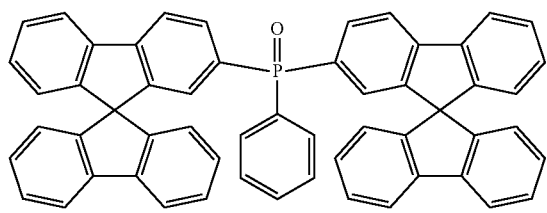

Materials used for hole-transporting layers of OLEDs may preferably be indenofluoreneamine derivatives, amine derivatives, hexaazatriphenylene derivatives, amine derivatives with fused aromatic systems, monobenzoindenofluoreneamines, dibenzoindenofluoreneamines, spirobifluoreneamines, fluoreneamines, spirodibenzopyranamines, dihydroacridine derivatives, spirodibenzofurans and spirodibenzothiophenes, phenanthrenediarylamines, spirotribenzotropolones, spirobifluorenes having meta-phenyldiamine groups, spirobisacridines, xanthenediarylamines, and 9,10-dihydroanthracene spiro compounds having diarylamino groups. More particularly, the following compounds are suitable for this purpose:

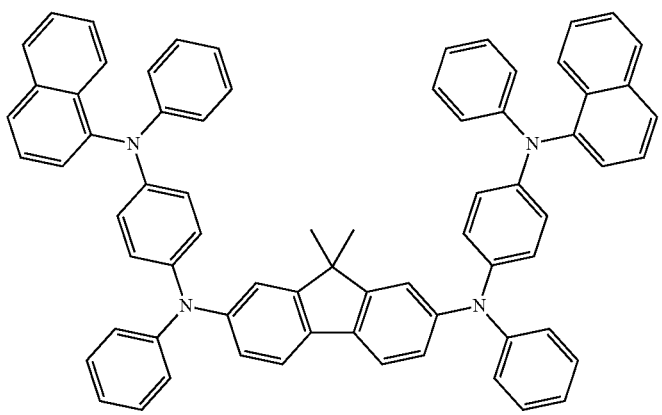

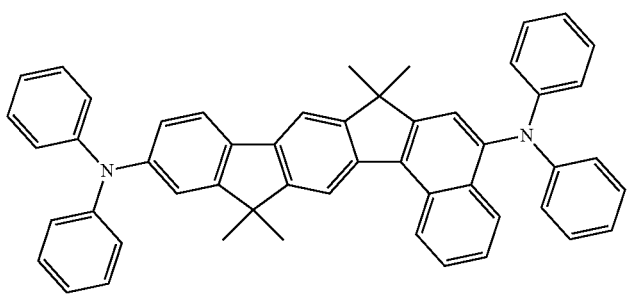

-continued
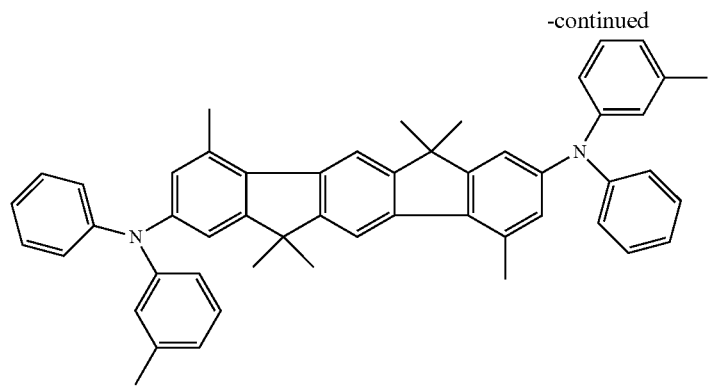
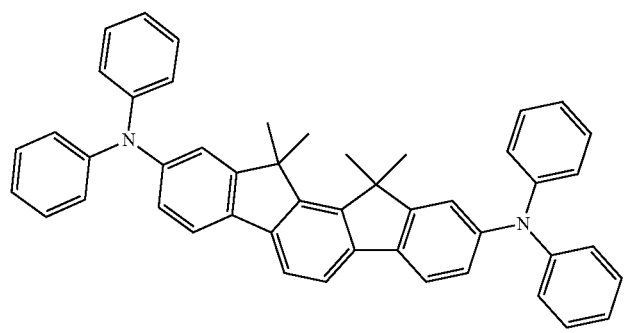
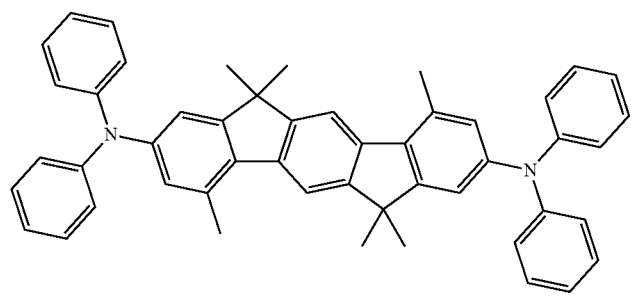
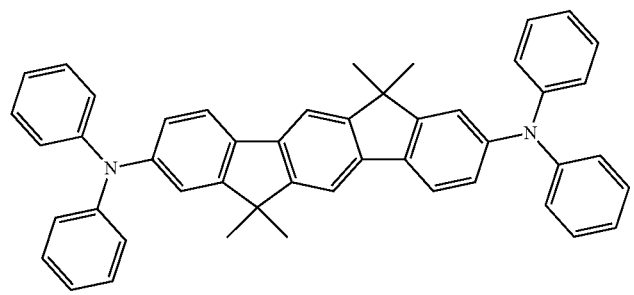

-continued
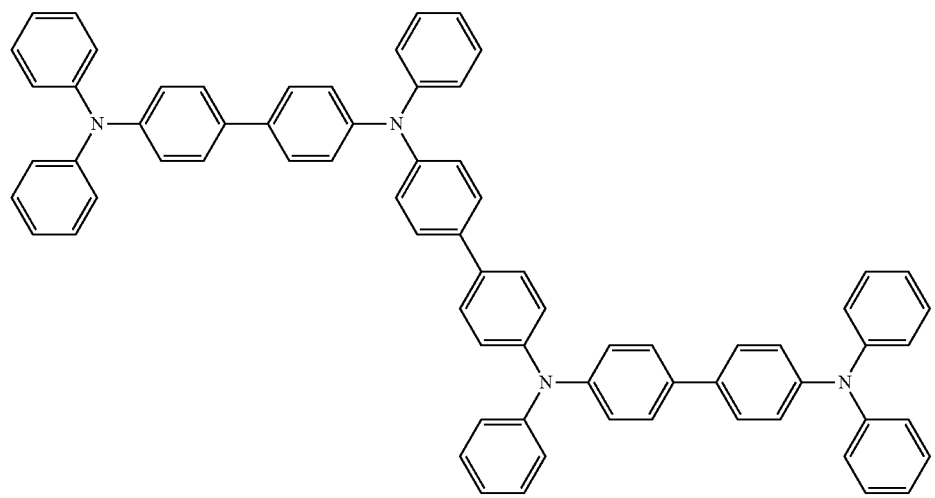
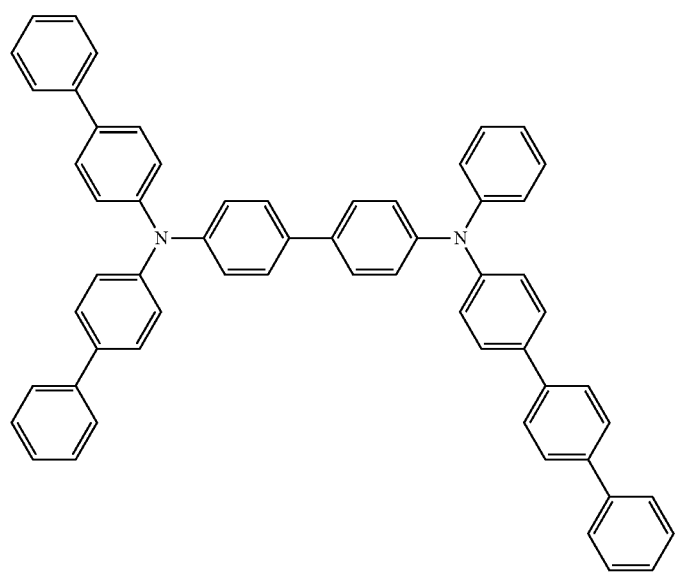
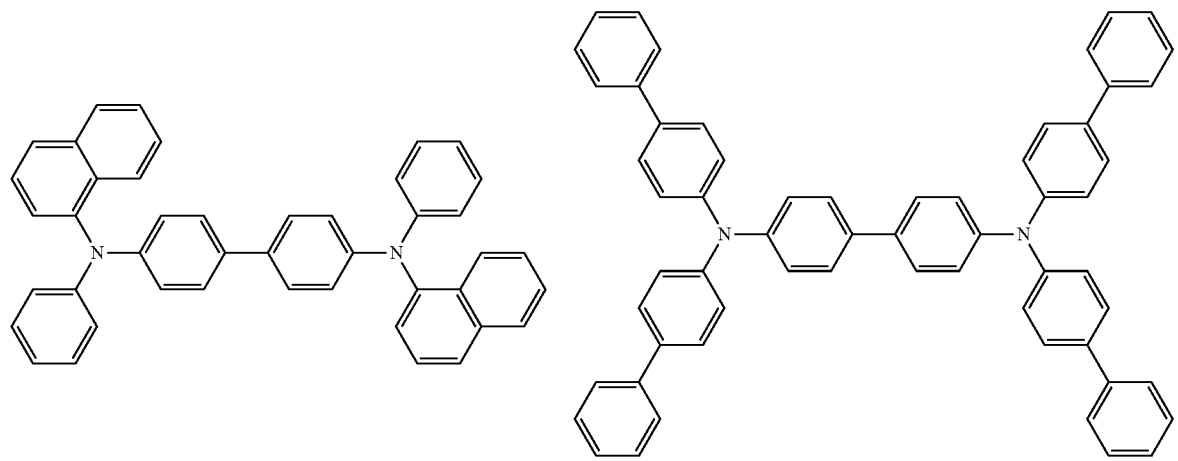

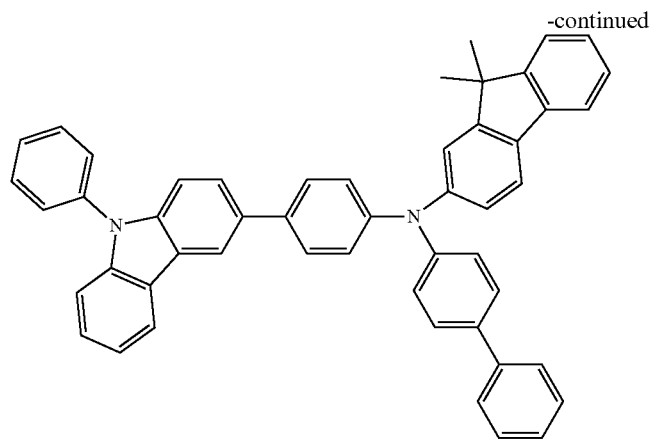
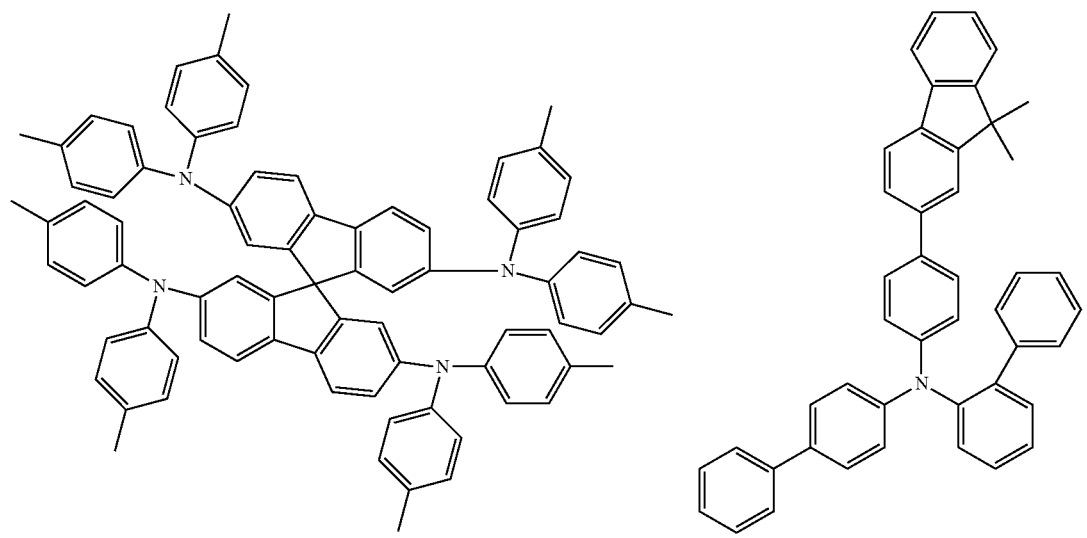
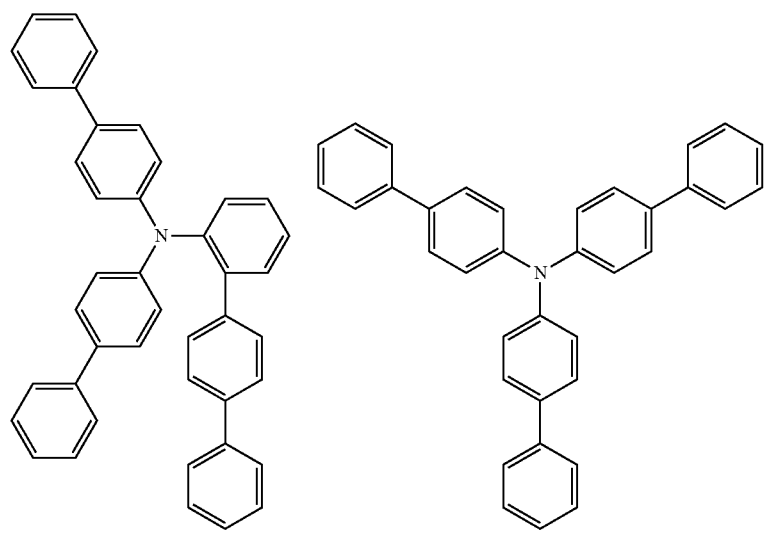

-continued
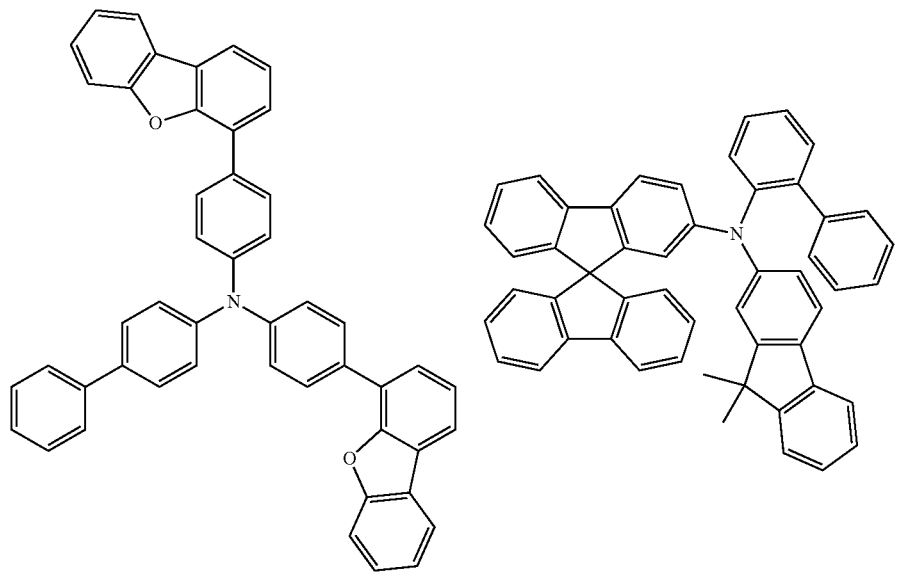
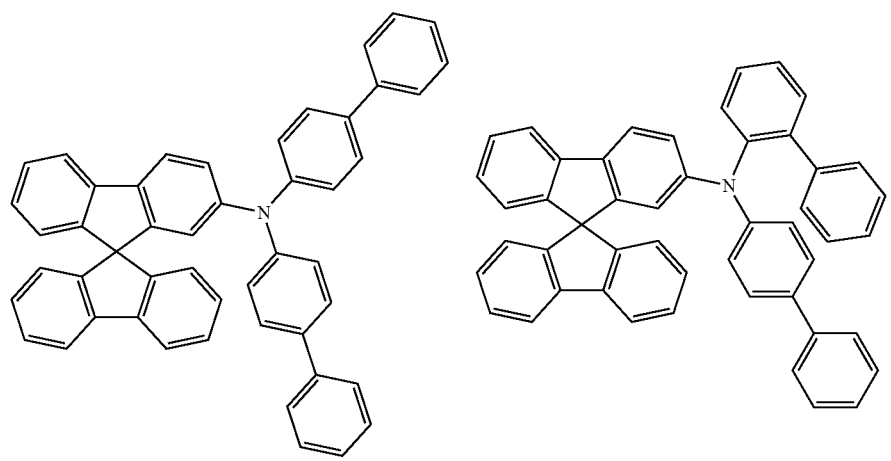
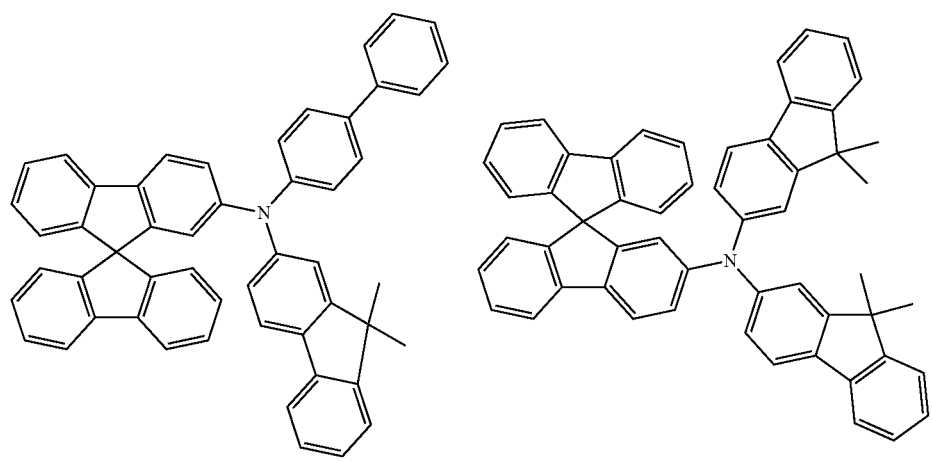

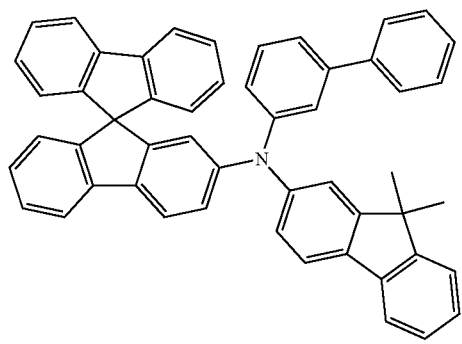
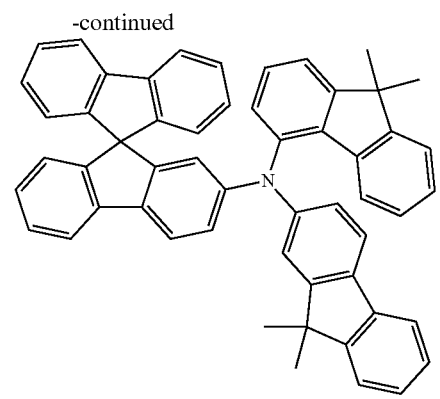
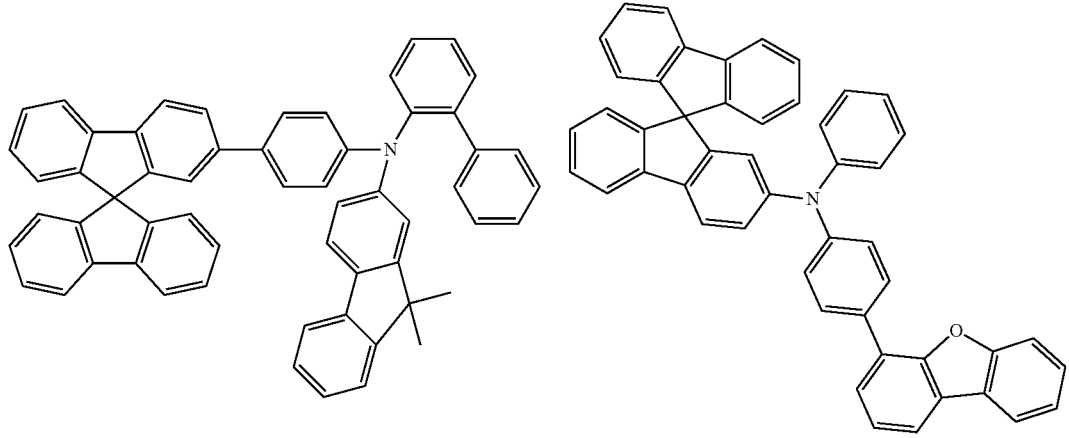
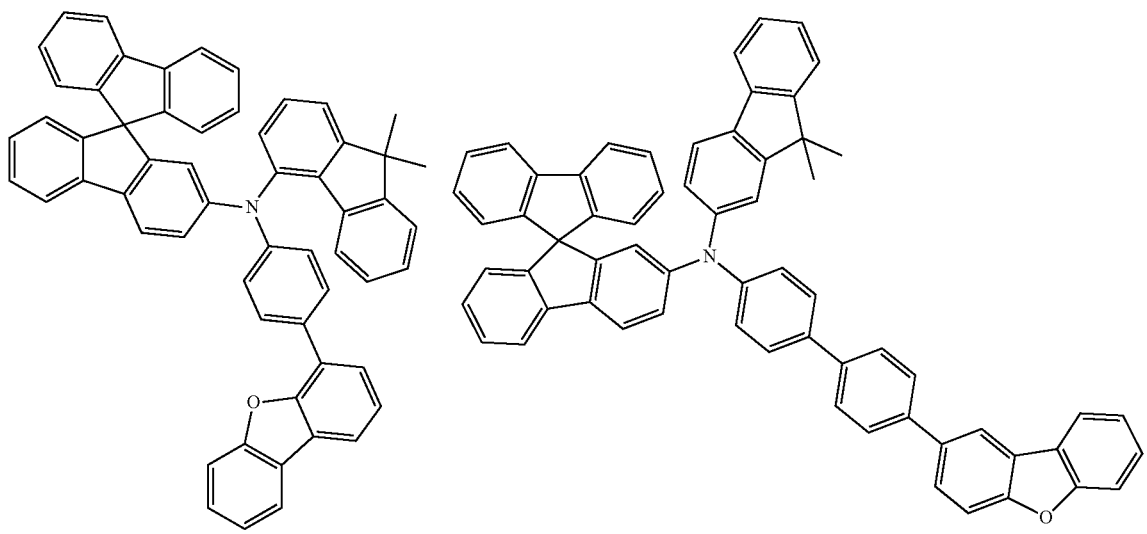

131
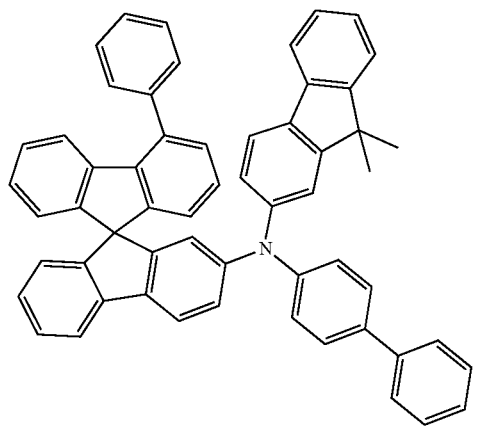
132
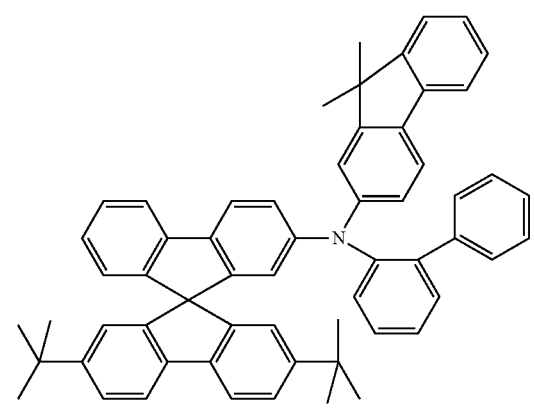
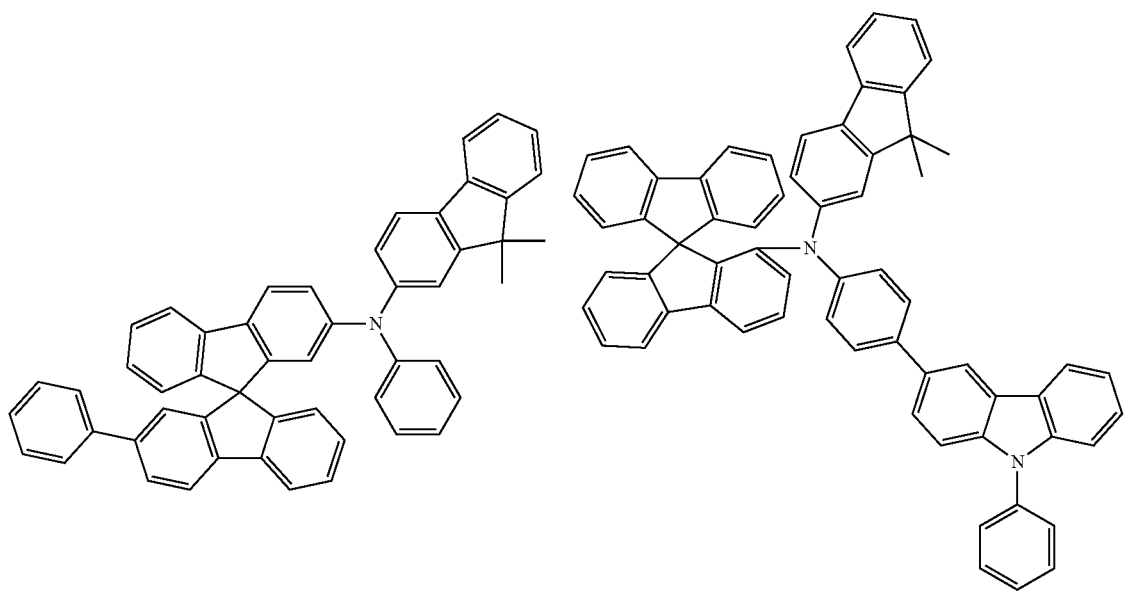
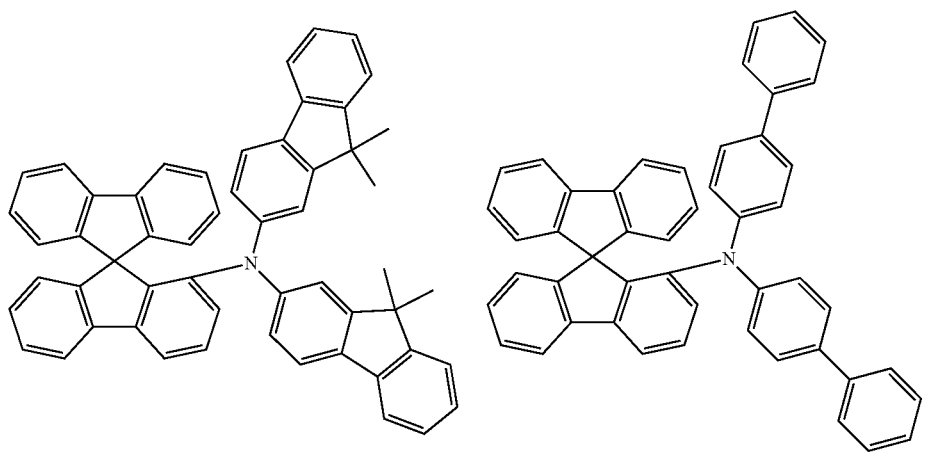

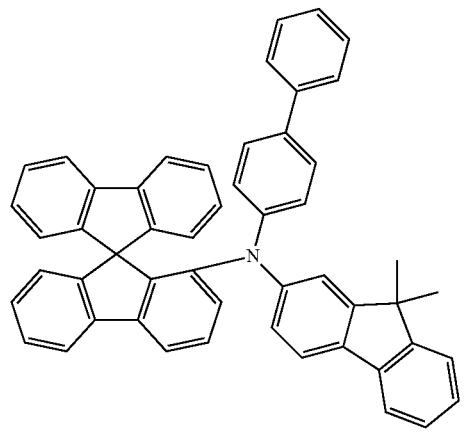
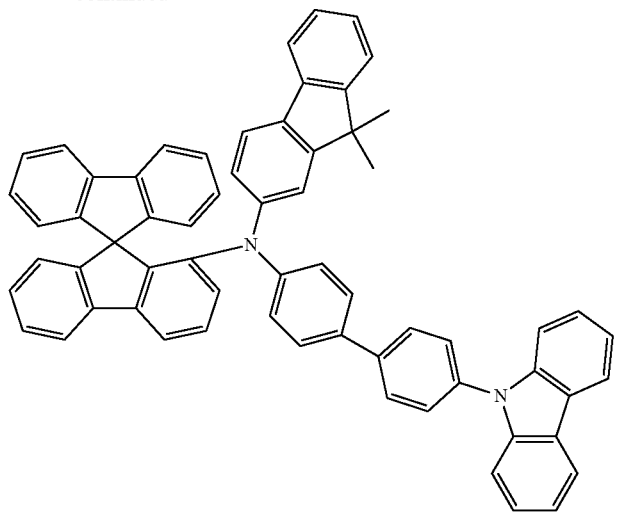
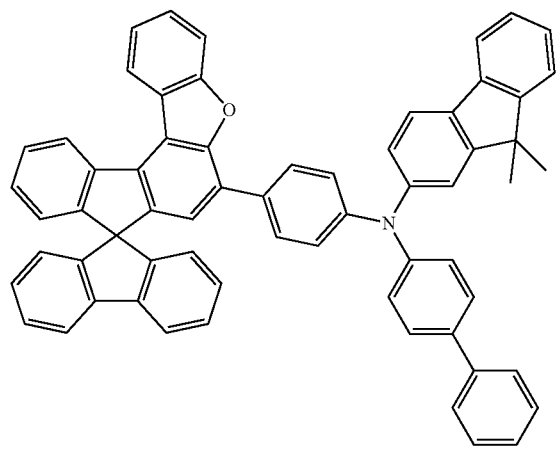
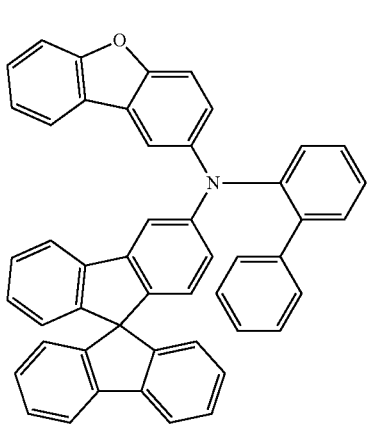
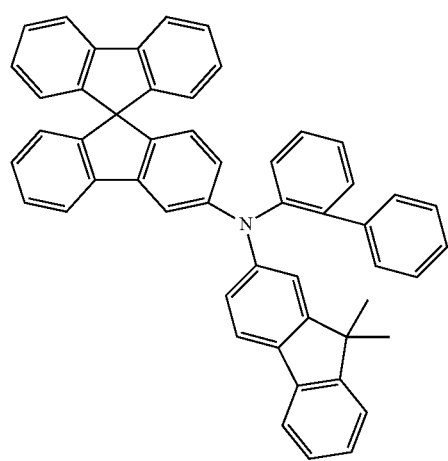
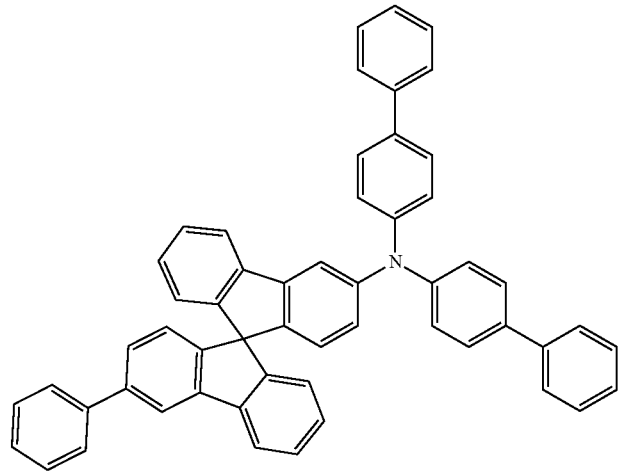

135 136
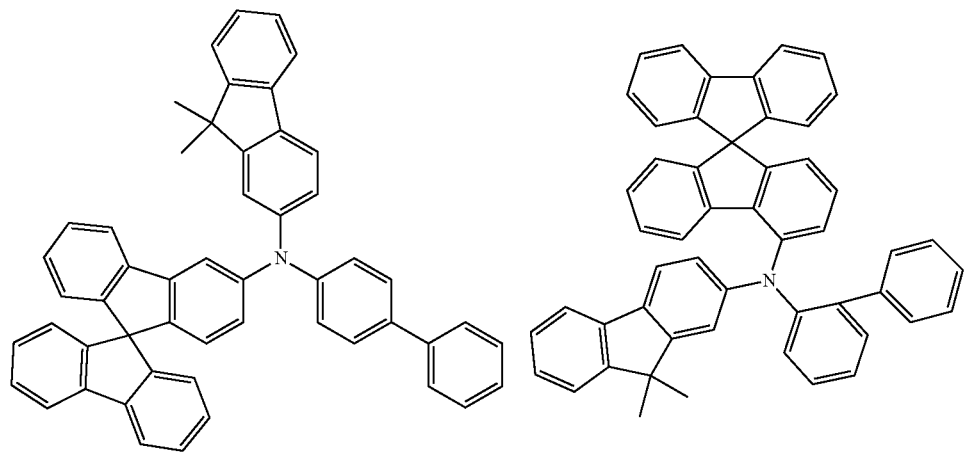
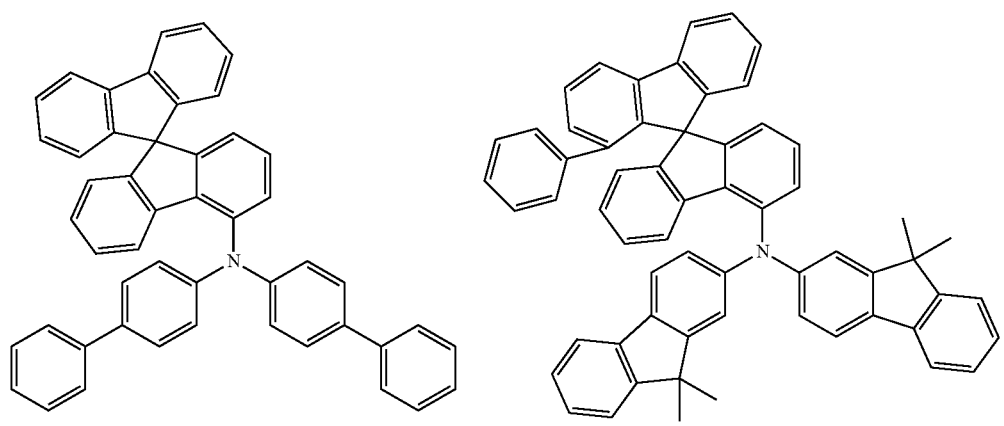
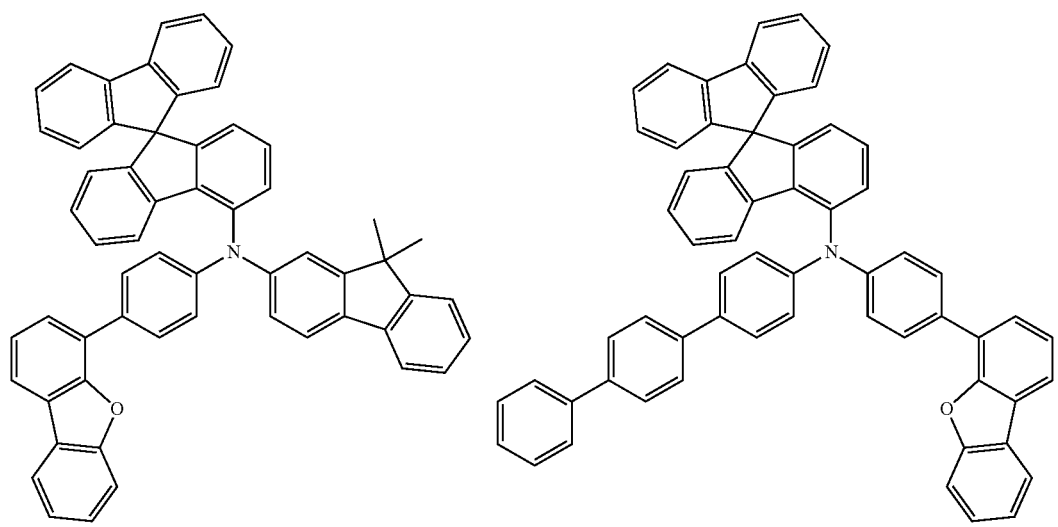

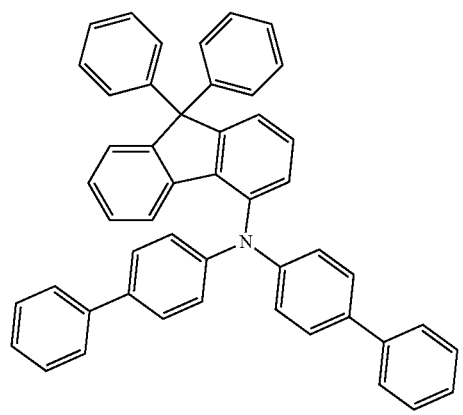
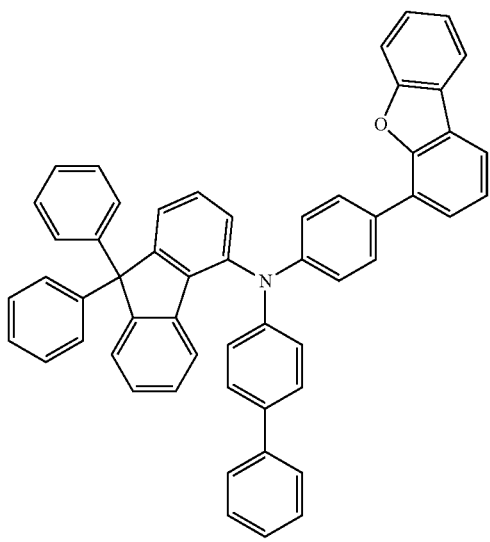
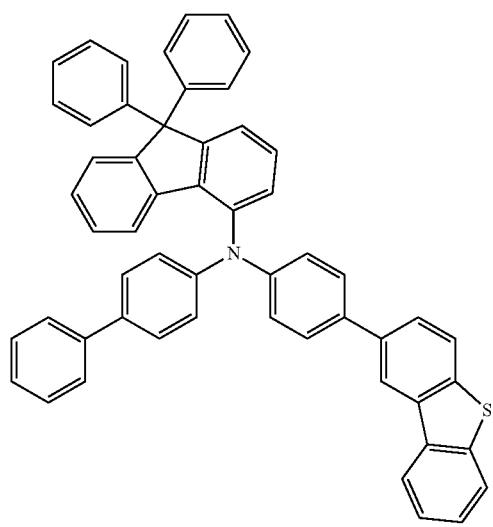
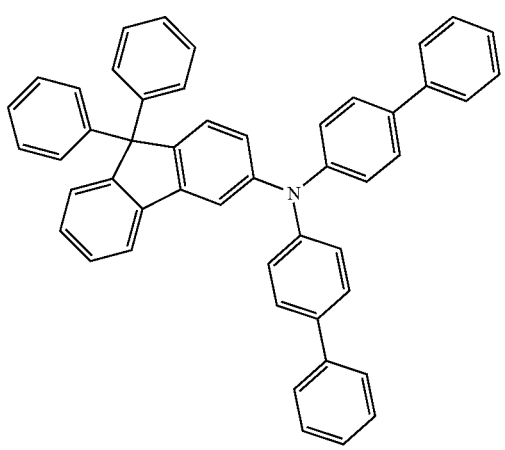
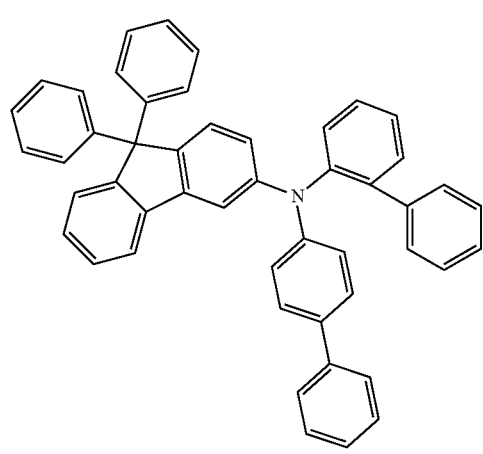
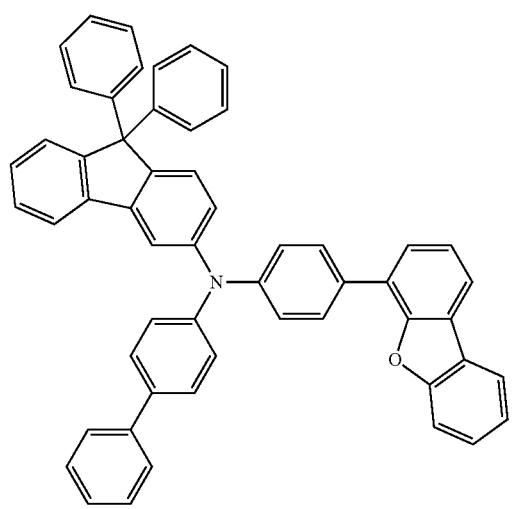

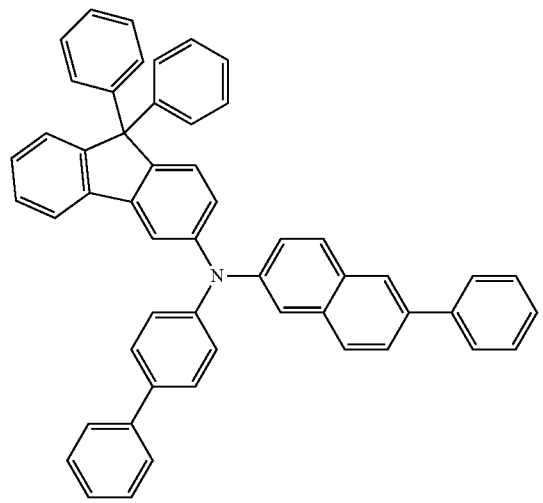
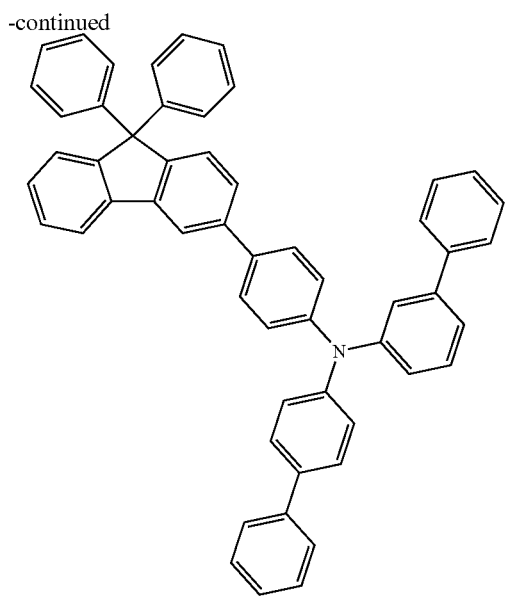
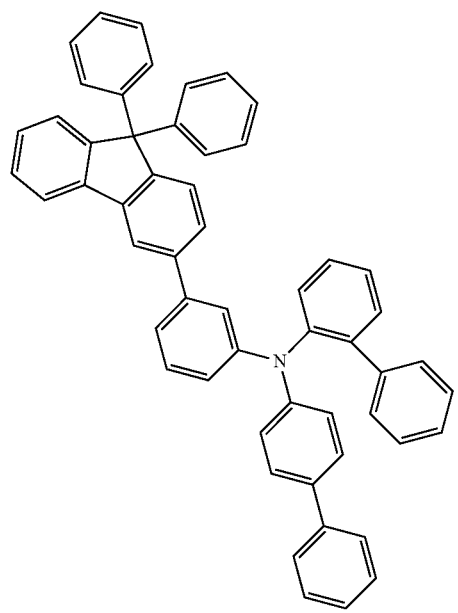
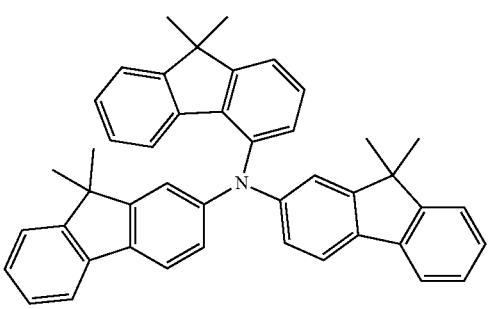
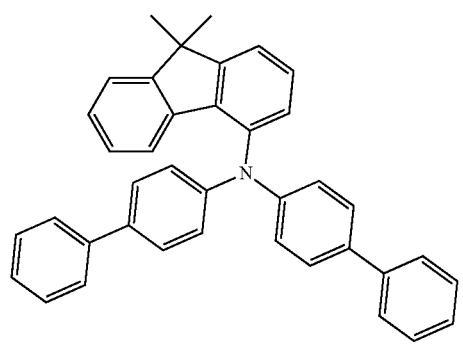
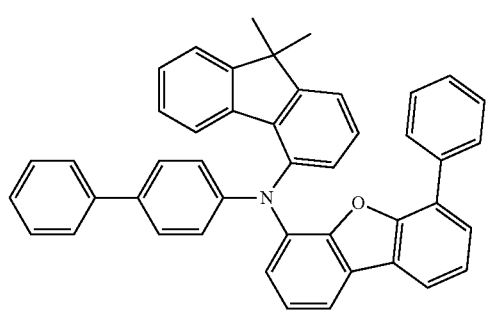

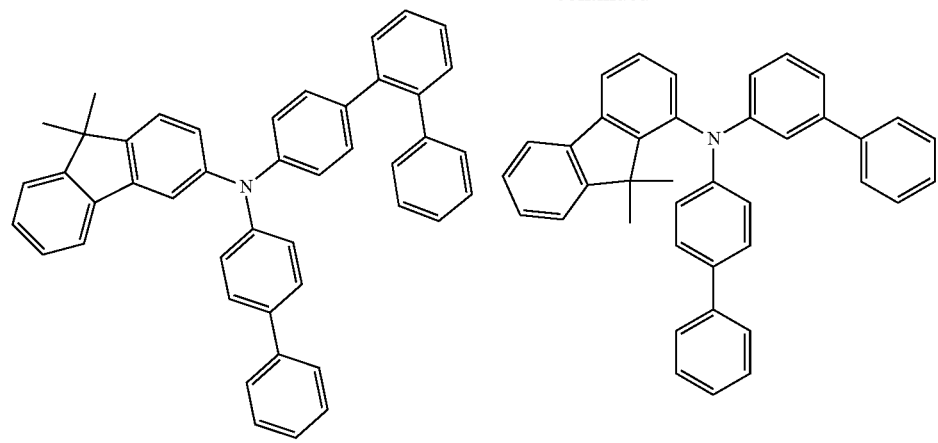
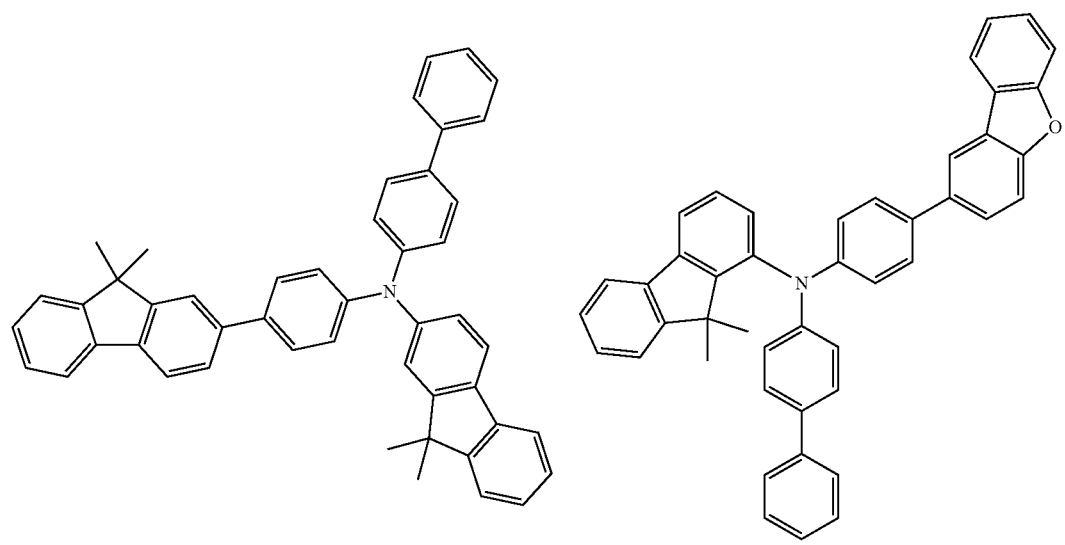
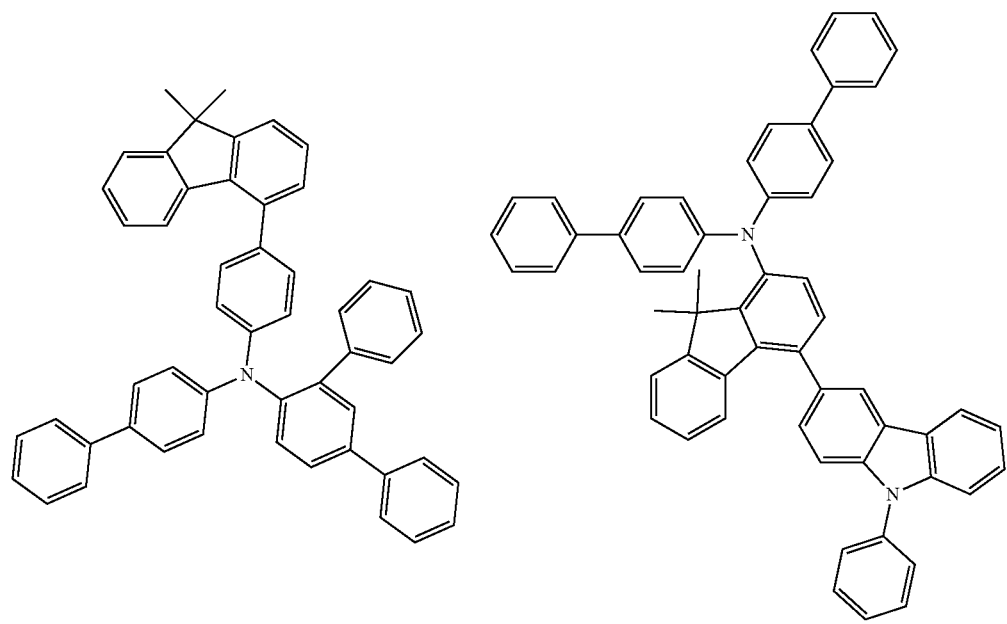

-continued
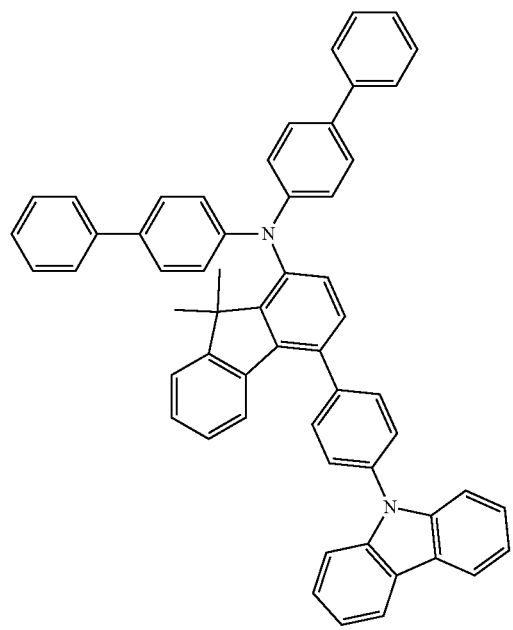
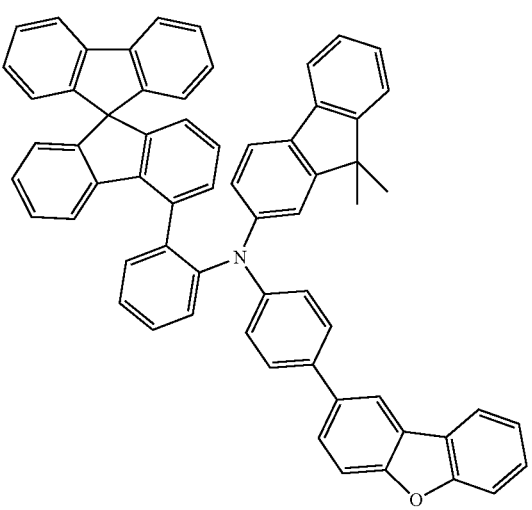
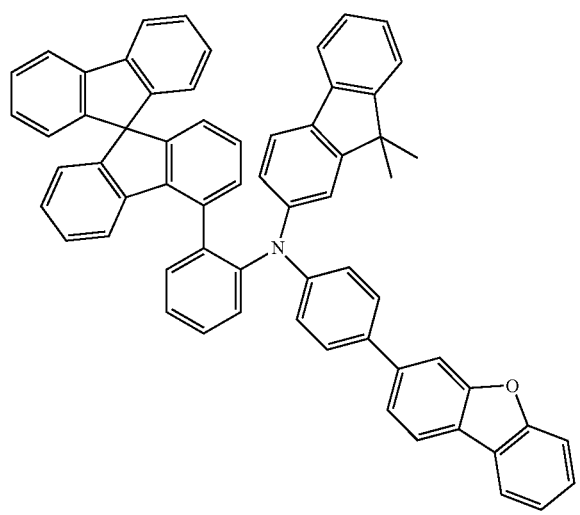
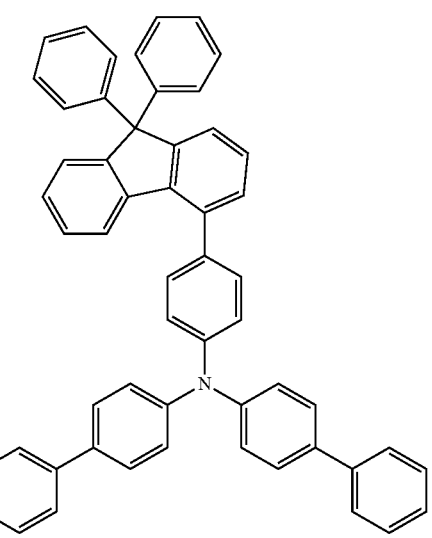
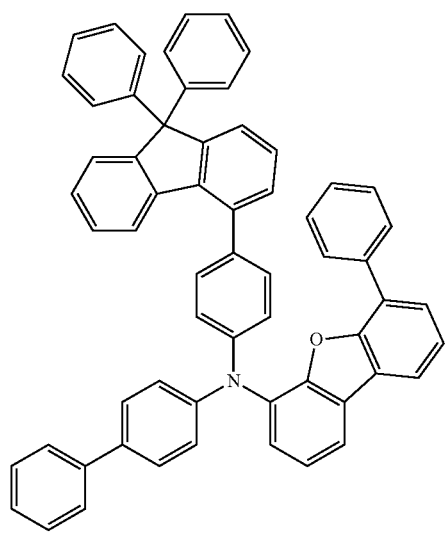

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects of water and air.

In a preferred embodiment, the electronic device is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds are needed. High solubility can be achieved by suitable substitution of the compounds.

It is further preferable that an electronic device of the invention is produced by applying one or more layers from solution and one or more layers by a sublimation method.

Electronic devices comprising one or more compounds as defined above are preferably used in displays, as light sources in lighting applications and as light sources in medical and/or cosmetic applications (e.g. light therapy).

WORKING EXAMPLES

A) Synthesis Examples

The syntheses which follow, unless stated otherwise, are conducted under a protective gas atmosphere in dried solvents. The compounds of the invention can be prepared by means of synthesis methods known to those skilled in the art.

a) Methyl 5-bromo-2-methylsulfanylpyrimidine-4-carboxylate

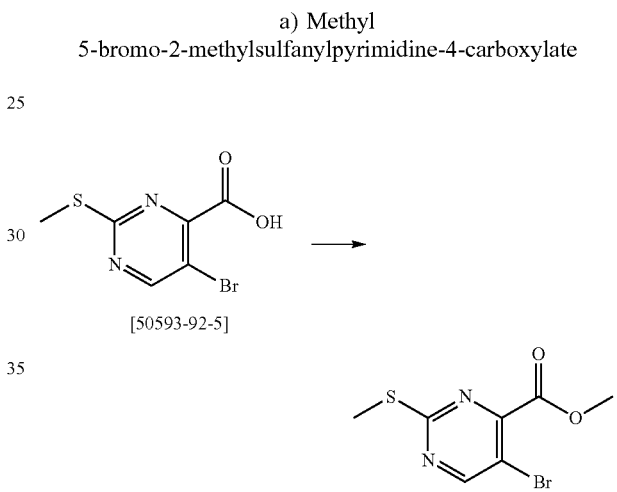

7.4 g (30 mmol) of 5-bromo-2-methylsulfanylpyrimidine-4-carboxylic acid is initially charged in 100 ml of $CH_2Cl_2$. To this solution are added 2.9 ml (33 mmol) of oxalyl chloride dropwise, and two drops of DMF, and the mixture is stirred at room temperature overnight. The mixture is concentrated under reduced pressure and heated with 50 ml of MeOH under reflux for two hours. The mixture is then concentrated and purified by chromatography (EA:heptane, 2:8).

Yield: 3.2 g (12.1 mmol); 42% of theory; purity: 97% by HPLC.

The following compounds can be prepared in an analogous manner:

| Ex. | Reactant 1 | Product | Yield |
|---|---|---|---|
| 1a | 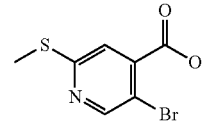 [1871987-15-3] | 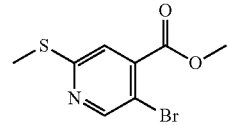 | 48% |

-continued

| Ex. | Reactant 1 | Product | Yield |
|---|---|---|---|
| 2a | [1183628-42-3] | | 51% |
| 3a | [1596116-38-9] | | 50% |
| 4a | [1936334-83-6] | | 56% |
| 5a | | | 55% |
| 6a | [50593-92-5] | | 61% |
| 7a | [1784048-83-4] | | 59% |
| 8a | [74840-34-9] | | 52% | b)₃-Methylsulfanyl-6H-pyrimido[4,5-c]quinolin-5-one

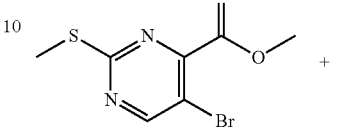

+

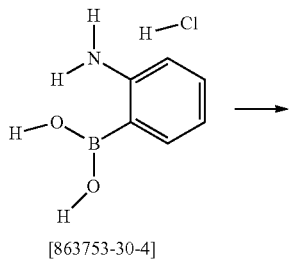

[863753-30-4]

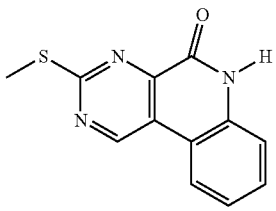

15.2 g (58 mmol) of methyl 5-bromo-2-methylsulfanylpyrimidine-4-carboxylate and 10 g (58 mmol) of 2-aminophenylboronic acid hydrochloride are dissolved in 100 ml of DMF, and the mixture is saturated with $N_2$. 19 g (230 mmol) of sodium acetate and 2.1 g (2.9 mmol) of 1,1'-bis(diphenylphosphine)ferrocenepalladium(II) chloride are added, and the mixture is heated to boiling for 18 h. The mixture is added to 300 ml of a saturated NaCl solution and extracted with $CH_2Cl_2$. After concentration under reduced pressure, the residue is recrystallized from toluene/n-heptane.

Yield: 2.8 g (4.1 mmol); 20% of theory; purity: 95% by HPLC.

The following compounds can be prepared in an analogous manner:
| Ex. | Reactant 1 | Reactant 1 | Product | Yield |
|---|---|---|---|---|
| 1b | 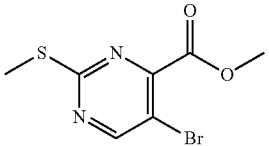 | 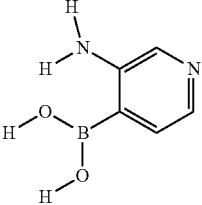 [2096337-23-2] | 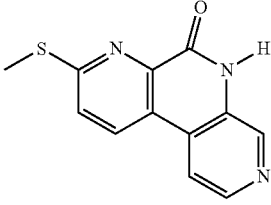 [SMILES: CSc1ccc2c(n1)c(=O)[nH]c1cnccc12] | 34% |
| 2b | 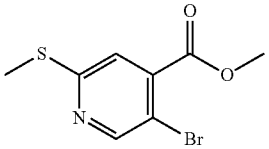 | 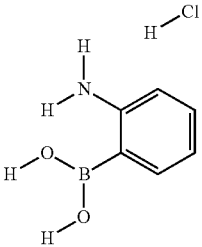 [863753-30-4] | 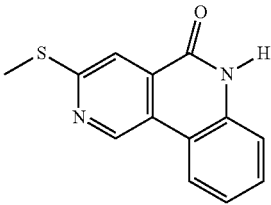 [SMILES: CSc1cc2c(=O)[nH]c3ccccc3c2cn1] | 30% |
| 3b |  | 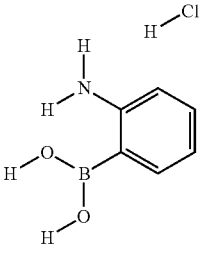 [863753-30-4] | 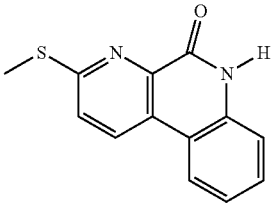 | 28% |
| 4b | 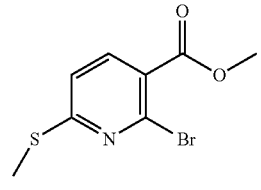 | 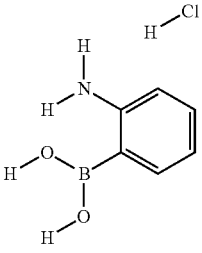 [863753-30-4] | 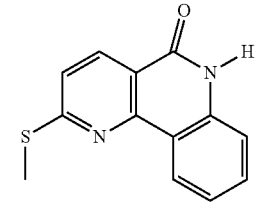 [SMILES: CSc1ccc2c(=O)[nH]c3ccccc3c2n1] | 26% |
| 5b | 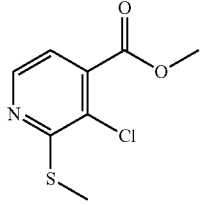 | 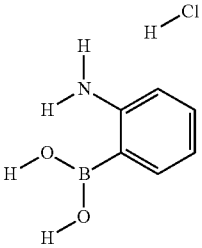 [863753-30-4] | 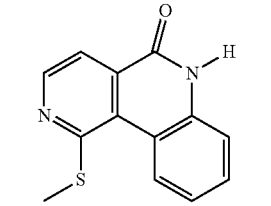 | 30% |

-continued
| Ex. | Reactant 1 | Reactant 1 | Product | Yield |
|---|---|---|---|---|
| 6b | 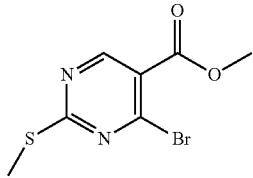 | 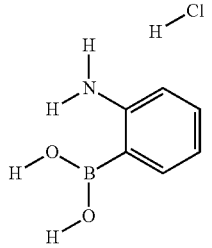  [863753-30-4] | 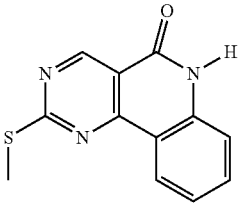 | 31% |
| 7b | 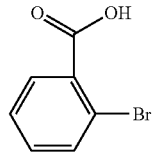  [610-94-6] | 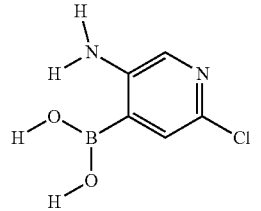  [1558927-18-6] | 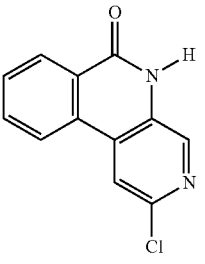 [SMILES: O=c1[nH]c2cnc(Cl)cc2c2ccccc12] | 24% |
| 8b | 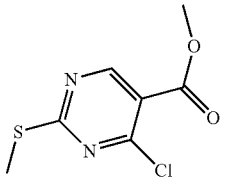 | 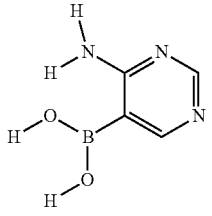  [1356054-72-2] | 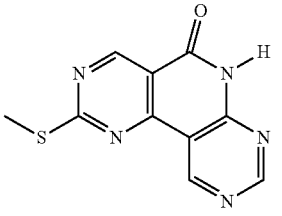 [SMILES: CSc1ncc2c(=O)[nH]c3ncncc3c2n1] | 20% |
| 9b | 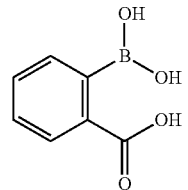  [374538-03-1] | 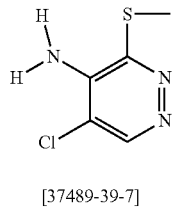  [37489-39-7] | 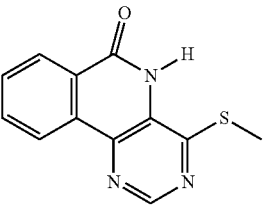 [SMILES: CSc1ncnc2c1[nH]c(=O)c1ccccc12] | 27% |
| 10b | 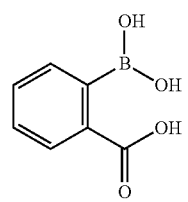  [374538-03-1] | 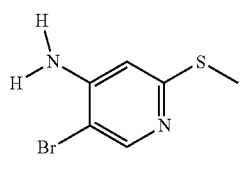  [1417620-74-6] | 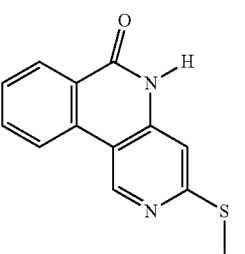 [SMILES: CSc1cc2[nH]c(=O)c3ccccc3c2cn1] | 26% |
| 11b | 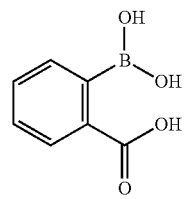  [374538-03-1] | 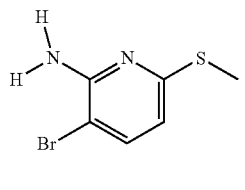  [1417416-47-7] | 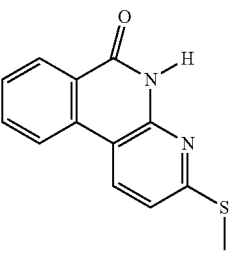 [SMILES: CSc1ccc2c(n1)[nH]c(=O)c1ccccc12] | 22% |

-continued
| Ex. | Reactant 1 | Reactant 1 | Product | Yield |
|---|---|---|---|---|
| 12b | 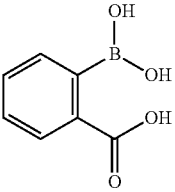 [374538-03-1] | 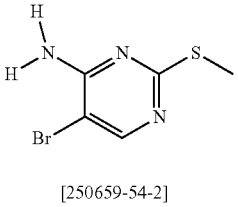 [250659-54-2] | 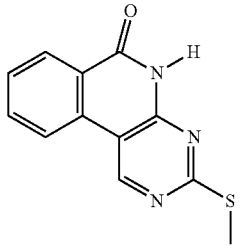 [SMILES: CSc1ncc2c(n1)[nH]c(=O)c1ccccc12] | 24% |
| 13b | 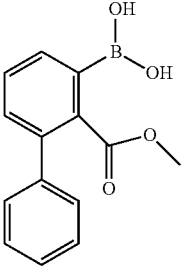 [2055742-91-9] | 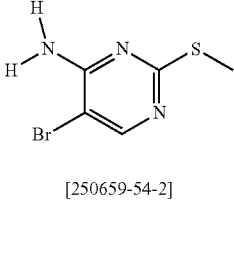 [250659-54-2] | 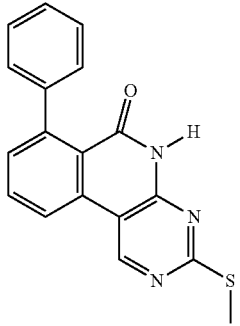 [SMILES: CSc1ncc2c(n1)[nH]c(=O)c1c(-c3ccccc3)cccc12] | 29% |
| 14b | 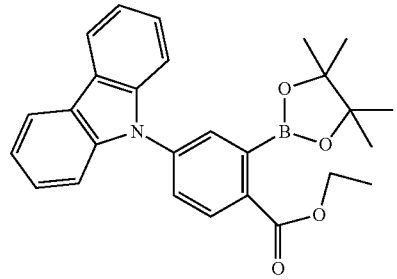 [1199798-73-6] | 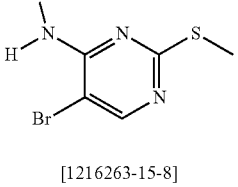 [1216263-15-8] | 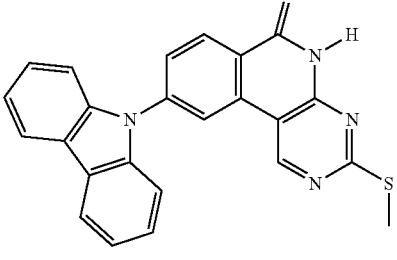 | 18% |
| 16b | 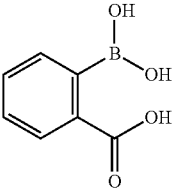 [374538-03-1] | 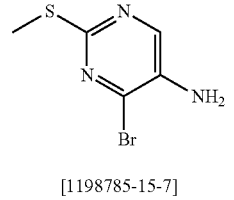 [1198785-15-7] | 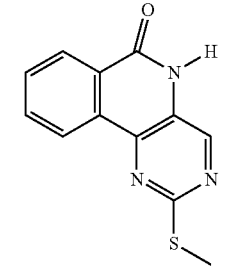 [SMILES: CSc1ncc2[nH]c(=O)c3ccccc3c2n1] | 38% |
| 17b | 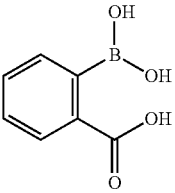 [374538-03-1] | 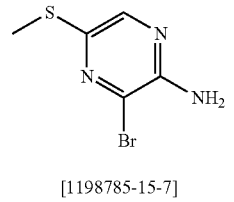 [1198785-15-7] | 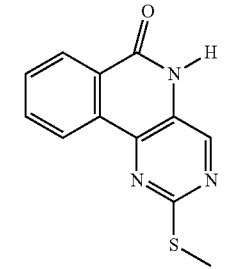 [SMILES: CSc1ncc2[nH]c(=O)c3ccccc3c2n1] | 31% |

-continued

| Ex. | Reactant 1 | Reactant 1 | Product | Yield |
|---|---|---|---|---|
| 18b | 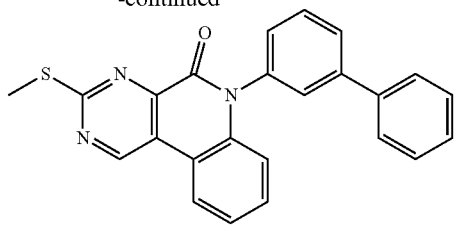 | 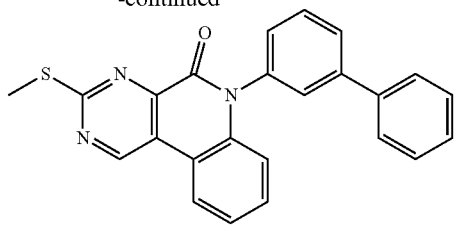  104830-06-0] | | 25% | c)3-Methylsulfanyl-6-(3-phenylphenyl)pyrimido[4,5]quinolin-5-one

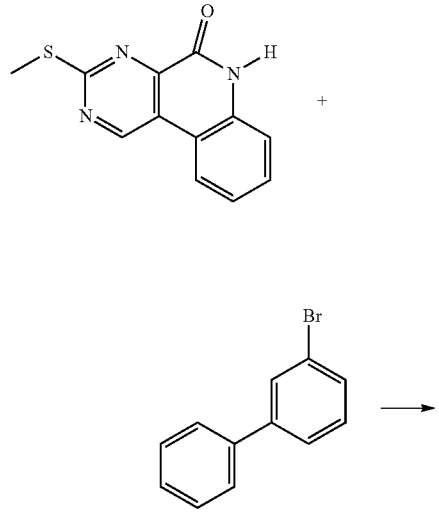

[2113-57-7]

An initial charge of 6 g (25 mmol, 1.00 eq.) of 3-methylsulfanyl-6H-pyrimido[4,5-c]quinolin-5-one, 21.3 ml (128 mmol, 5.2 eq.) of 3-bromobiphenyl and 7.20 g of potassium carbonate (52.1 mmol, 2.10 eq.) in 220 ml of dry DMF is inertized with argon. Subsequently, 0.62 g (2.7 mmol, 0.11 eq) of 1,3-di(2-pyridyl)propane-1,3-dione and 0.52 g (2.7 mmol, 0.11 eq) of copper(I) iodide are added and the mixture is heated at 140° C. for three days. After the reaction has ended, the mixture is concentrated cautiously on a rotary evaporator, and the precipitated solids are filtered off with suction and washed with water and ethanol. The crude product is purified twice by means of a hot extractor (toluene/heptane 1:1), and the solids obtained are recrystallized from toluene. After sublimation, 3.9 g (810.1 mmol, 42%) of the desired target compound is obtained.

The following compounds can be prepared in an analogous manner:

| Ex. | Reactant 1 | Reactant 1 |
|---|---|---|
| 1c | 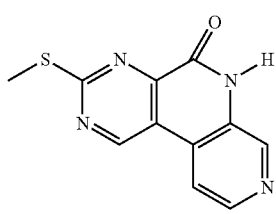 [SMILES: CSc1ncc2c(n1)c(=O)[nH]c1cnccc12] | 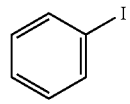 |
| 2c | 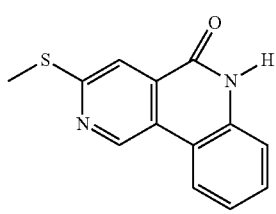 [SMILES: CSc1cc2c(=O)[nH]c3ccccc3c2cn1] | 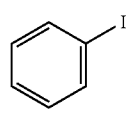 |

-continued
| | | |
|---|---|---|
| 3c | 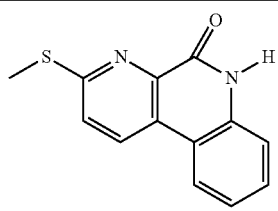 | 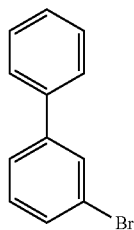 [SMILES: Brc1cccc(-c2ccccc2)c1] |
| 4c | 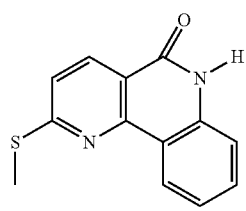 [SMILES: CSc1ccc2c(=O)[nH]c3ccccc3c2n1] | 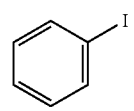 |
| 5c | 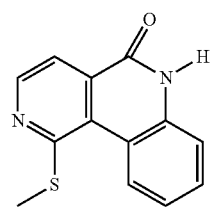 [SMILES: CSc1nccc2c(=O)[nH]c3ccccc3c12] | 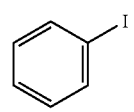 |
| 6c | 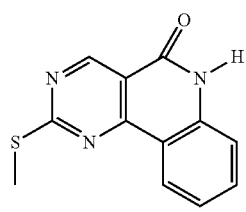 | 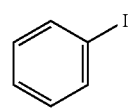 |
| 7c | 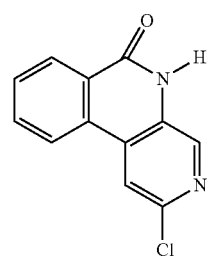 [SMILES: O=c1[nH]c2cnc(Cl)cc2c2ccccc12] | 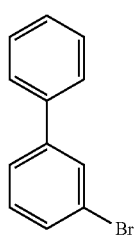 [SMILES: Brc1cccc(-c2ccccc2)c1] |
| 8c | 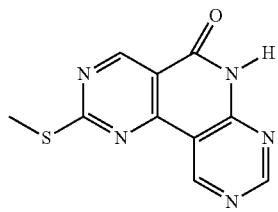 [SMILES: CSc1ncc2c(=O)[nH]c3ncncc3c2n1] | 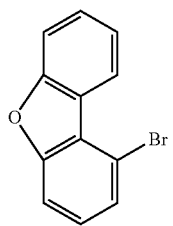 |
| 9c | 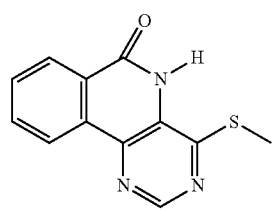 [SMILES: CSc1ncnc2c1[nH]c(=O)c1ccccc12] | 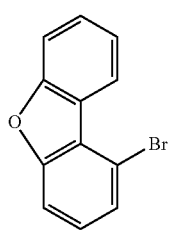 |

-continued
| | | |
|---|---|---|
| 10c | 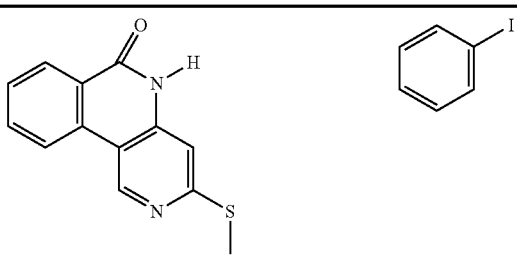 | 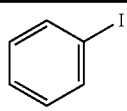 |
| 11c | 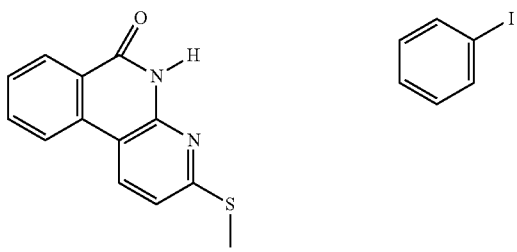 | 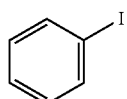 |
| 12c | 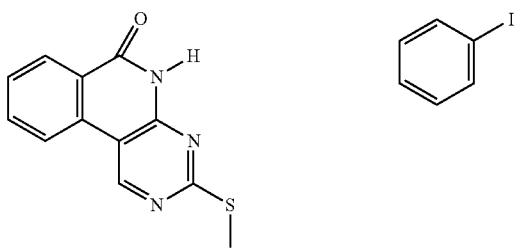 | 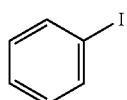 |
| 13c | 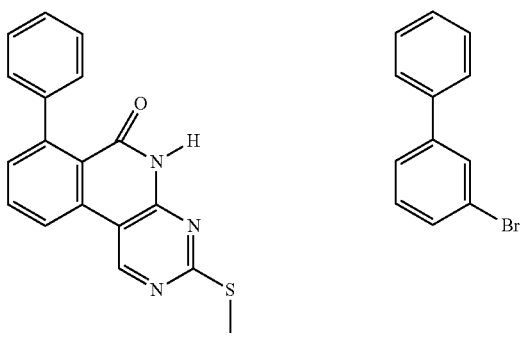 | 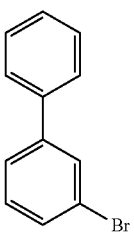 [SMILES: Brc1cccc(-c2ccccc2)c1] |
| 14c | 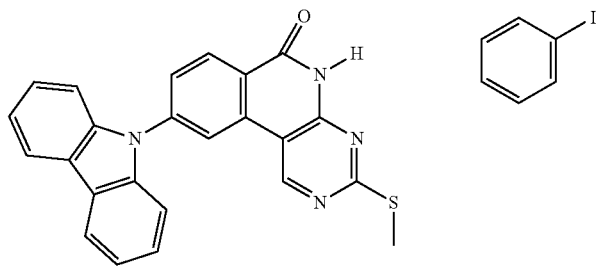 | 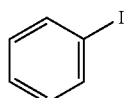 |
| 15c | 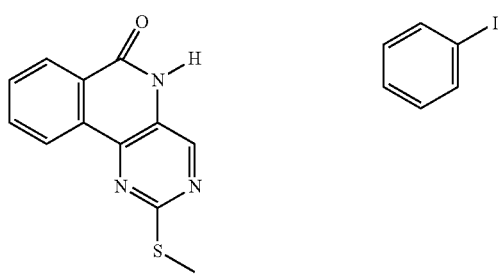 | 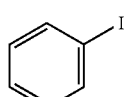 |

-continued
| | | |
|---|---|---|
| 16c | 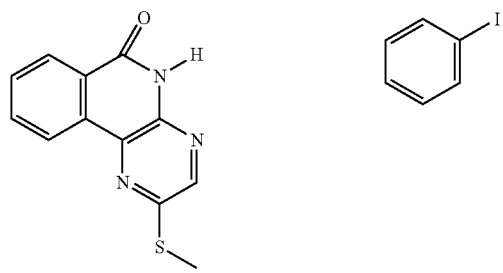 | 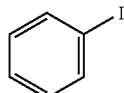 |
| 17c | 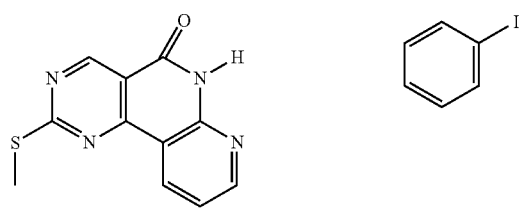 | 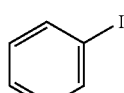 |
| 18c | 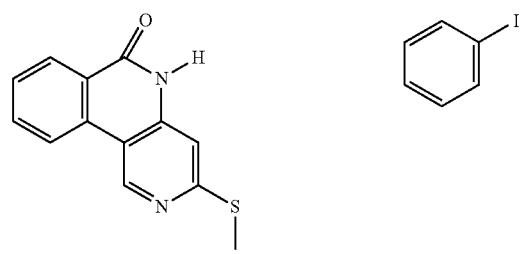 | 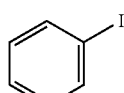 |
| 19c | 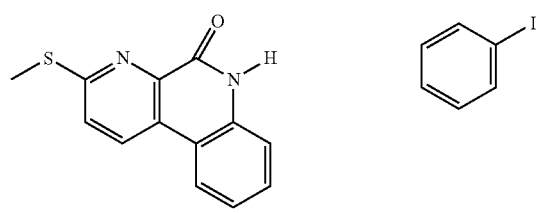 | 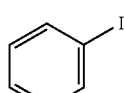 |
| Ex. | Product | Yield |
|---|---|---|
| 1c | 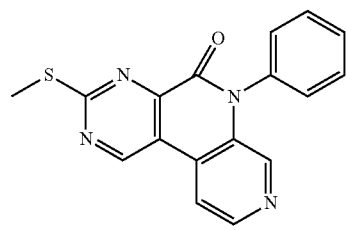 | 56% |
| 2c | 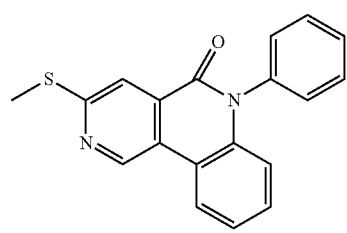 [SMILES: CSc1cc2c(=O)n(-c3ccccc3)c3ccccc3c2cn1] | 54% |

-continued
| | | |
|---|---|---|
| 3c | 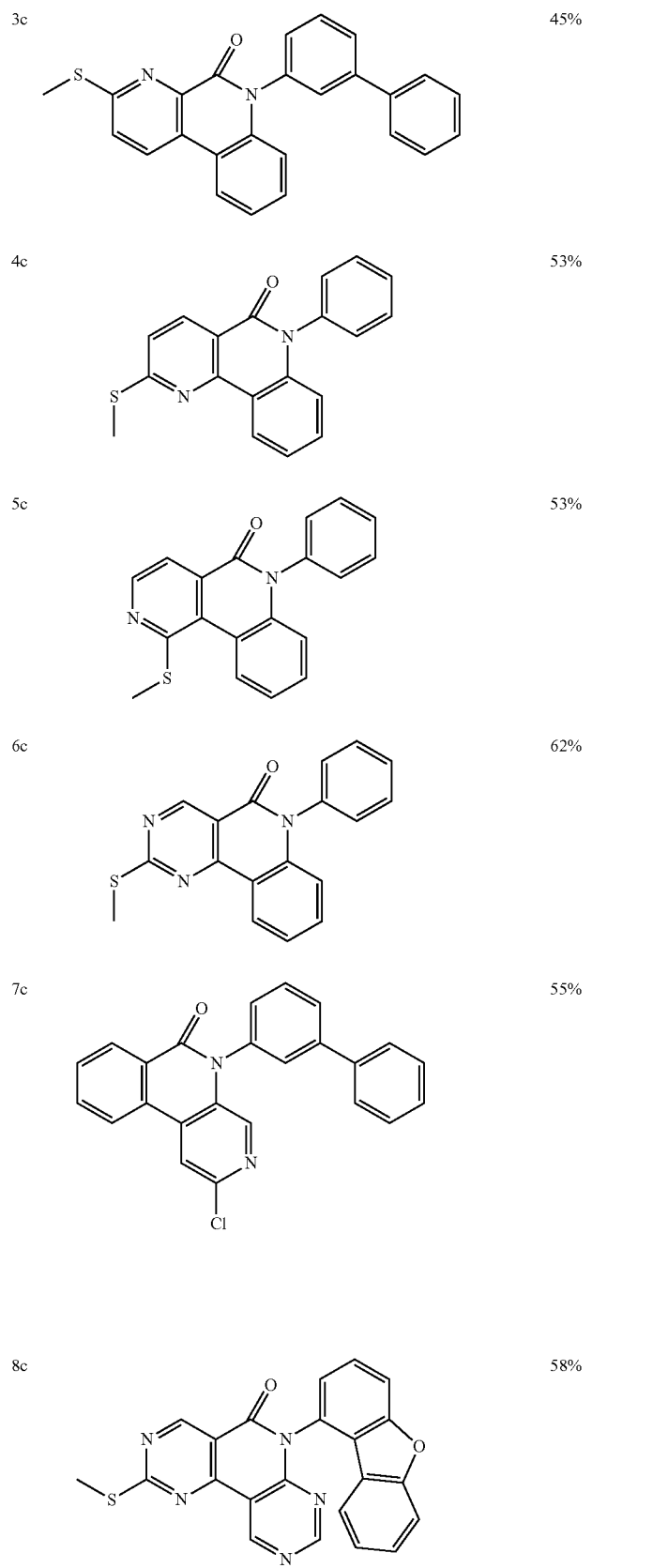 | 45% |
| 4c | | 53% |
| 5c | | 53% |
| 6c | | 62% |
| 7c | | 55% |
| 8c | | 58% |

| | | |
|---|---|---|
| 9c | 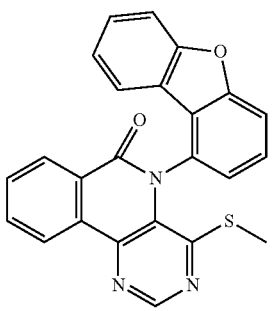 [SMILES: CSc1ncnc2c3ccccc3c(=O)n(-c3cccc4oc5ccccc5c34)c12] | 56% |
| 10c | 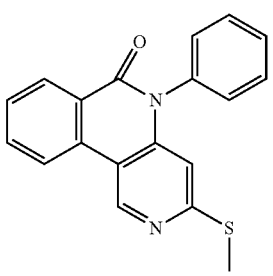 | 53% |
| 11c | 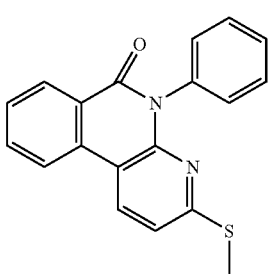 [SMILES: CSc1ccc2c3ccccc3c(=O)n(-c3ccccc3)c2n1] | 52% |
| 12c | 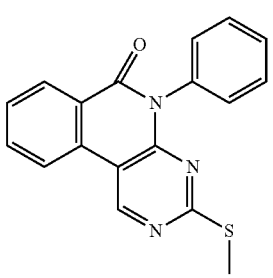 [SMILES: CSc1ncc2c3ccccc3c(=O)n(-c3ccccc3)c2n1] | 61% |
| 13c | 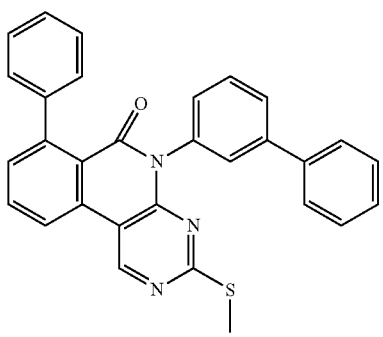 [SMILES: CSc1ncc2c3cccc(-c4ccccc4)c3c(=O)n(-c3cccc(-c4ccccc4)c3)c2n1] | 52% |

-continued
| | | |
|---|---|---|
| 14c | 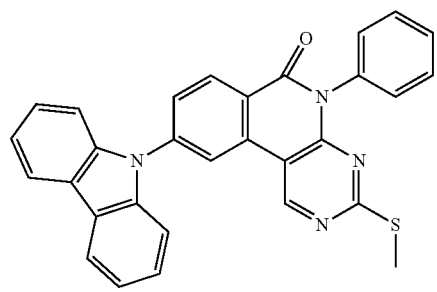 [SMILES: CSc1ncc2c3cc(-n4c5ccccc5c5ccccc54)ccc3c(=O)n(-c3ccccc3)c2n1] | 50% |
| 15c | 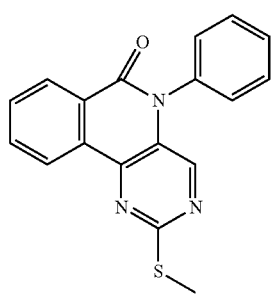 [SMILES: CSc1ncc2c(n1)c1ccccc1c(=O)n2-c1ccccc1] | 58% |
| 16c | 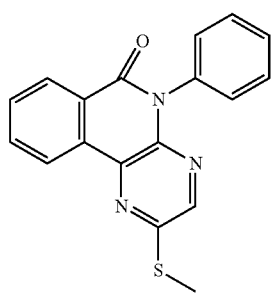 [SMILES: CSc1cnc2c(n1)c1ccccc1c(=O)n2-c1ccccc1] | 56% |
| 17c | 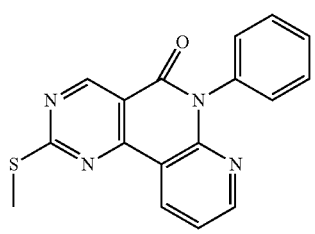 [SMILES: CSc1ncc2c(=O)n(-c3ccccc3)c3ncccc3c2n1] | 54% |
| 18c | 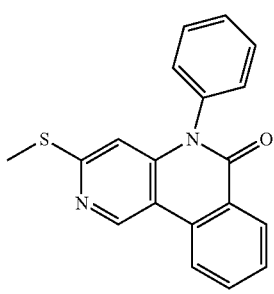 [SMILES: CSc1cc2c(cn1)c1ccccc1c(=O)n2-c1ccccc1] | 52% |

| 19c | 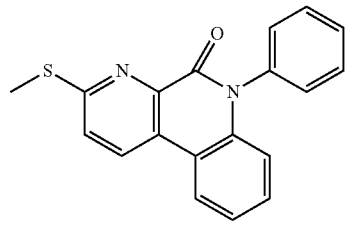 [SMILES: CSc1ccc2c(n1)c(=O)n(-c1ccccc1)c1ccccc21] | 57% | d)₂-Methylsulfanyl-4,5-diphenylpyrimido[5,4-c]isoquinolin-6-one

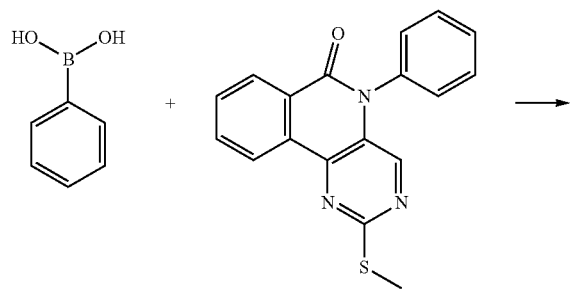

To a solution of 2-methylsulfanyl-5-phenylpyrimido[5,4-c]isoquinolin-6-one (7.9 g, 25 mmol, 1.0 equiv.) in 125 ml of dichloromethane is added 0.1 ml of trifluoroacetic acid (25 mmol, 1.0 equiv.). This is followed by addition of 37.5 mmol of phenylboronic acid and 75 ml of water. Then 8.5 g (5 mmol) of silver(I) nitrate dissolved in 50 ml of water is added. Finally, $K_2S_2O_8$ (0.2 g, 75 mmol) is added and the mixture is stirred vigorously at room temperature for four hours. Subsequently, the same amount of silver nitrate and potassium persulfate as in the previous steps is added again, and the mixture is stirred for a further 24 hours.

Then 300 ml of dichloromethane and 200 ml of 2 M NaOH solution are added to the mixture, and the organic phase is removed. The crude product is purified by column chromatography using the eluent specified. The identity and purity of the product are confirmed by GC-MS, 1H NMR and 13C NMR.

Yield: 8.8 g (20 mmol); 90% of theory; purity: 98% by HPLC.

The following compounds can be prepared in an analogous manner:

| Ex. | Reactant 1 | Reactant 2 | Product | Yield |
|---|---|---|---|---|
| 1d | | | | 62% |

| Ex. | Reactant 1 | Reactant 2 | Product | Yield |
|---|---|---|---|---|
| 2d | | | | 61% |
| 3d | | | | 56% | e) 3-Chloro-6-(3-phenylphenyl)pyrimido[4,5-c]qui-nolin-5-one

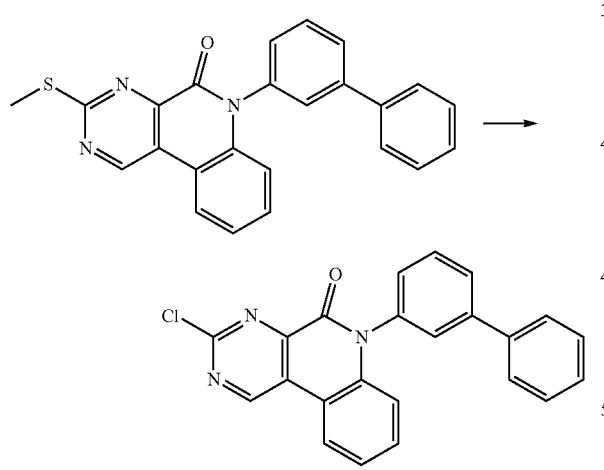

10 g (26 mmol) of 3-methylsulfanyl-6-(3-phenylphenyl)pyrimido[4,5-c]quinolin-5-one and 34 g (88 mmol) of KOH are dissolved in 50 ml of EtOH and heated to boiling for 1 h. After cooling, the mixture is concentrated under reduced pressure, and HCl solution is added until a pH of 4 has been attained. Subsequently, 30 ml of POCl₃ and 30 ml of thionyl chloride are added to the mixture, which is heated under reflux for 2 h. Then the solvent is removed by distillation and the product is recrystallized from toluene.

Yield: 8.9 g (23 mmol), 92% of theory; purity: 95% by NMR.

The following compounds can be prepared in an analogous manner:

| Ex. | Reactant 1 | Product | Yield |
|---|---|---|---|
| 1e | | | 90% |

-continued

| Ex. | Reactant 1 | Product | Yield |
|---|---|---|---|
| 2e | | | 89% |
| 3e | | | 68% |
| 4e | | | 93% |
| 5e | | | 90% |
| 6e | | | 92% |
| 7e | | | 87% |

-continued

| Ex. | Reactant 1 | Product | Yield |
|---|---|---|---|
| 8e | | | 82% |
| 9e | | | 87% |
| 10e | | | 91% |
| 11e | | | 93% |
| 12e | | | 86% |

| Ex. | Reactant 1 | Product | Yield |
|---|---|---|---|
| 13e | | | 80% |
| 14e | | | 76% |
| 15e | | | 93% |
| 16e | | | 97% |
| 17e | | | 85% |

-continued

| Ex. | Reactant 1 | Product | Yield |
|---|---|---|---|
| 18e | | | 84% |
| 19e | | | 81% |
| 20e | | | 80% |
| 21e | | | 76% |

-continued
| Ex. | Reactant 1 | Product | Yield |
|---|---|---|---|
| 22e | | | 71% |
| 23e | | | 82% |
f) Nucleophilic Substitution
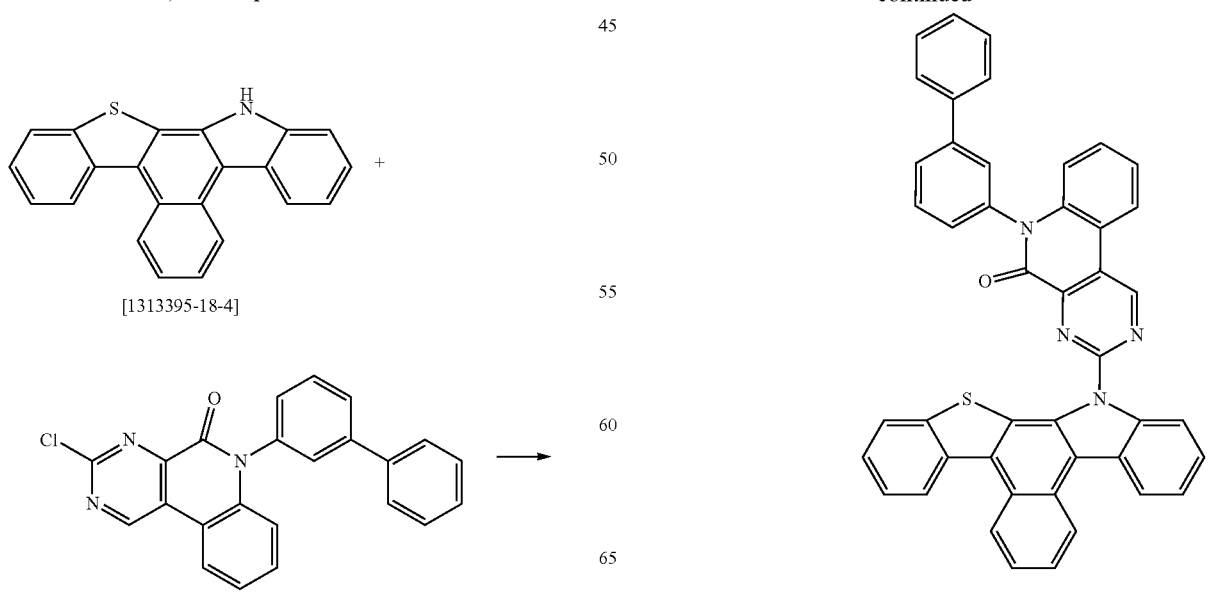
[1313395-18-4]

16.5 g (61 mmol) of 14H-13-thia-14-azabenzo[c]indeno[2,1-a]fluorene is dissolved in 300 ml of dimethylformamide under a protective gas atmosphere, and 3 g of NaH, 60% in mineral oil, 75 mmol, is added. After 1 h at room temperature, a solution of 24 g (63 mmol) of 3-chloro-6-(3-phenylphenyl)pyrimido[4,5-c]quinolin-5-one in 150 ml of dimethylformamide is added dropwise. The reaction mixture is then stirred at room temperature for 12 h. After this time, the reaction mixture is poured onto ice and extracted three times with dichloromethane. The combined organic phases are dried over $Na_2SO_4$ and concentrated. The residue is recrystallized with toluene and finally fractionally sublimed twice (p about $10^{-6}$ mbar, T=395-420° C.).

Yield: 22 g (40 mmol), 80% of theory; purity: 99.9% by HPLC.

The following compounds can be prepared in an analogous manner:

| Ex. | Reactant 1 | Reactant 2 |
|---|---|---|
| 1f | [1313395-18-4] | |
| 2f | [1313395-18-4] | |
| 3f | [1313395-18-4] | |
| 4f | [1313395-18-4] | |
| 5f | [1345202-03-0] | |

-continued
6f
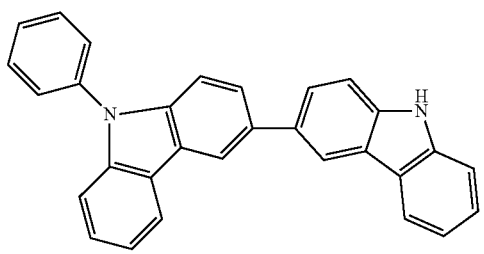
[1345202-03-0]
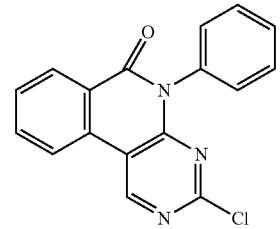 [SMILES: O=c1c2ccccc2c2cnc(Cl)nc2n1-c1ccccc1]
7f
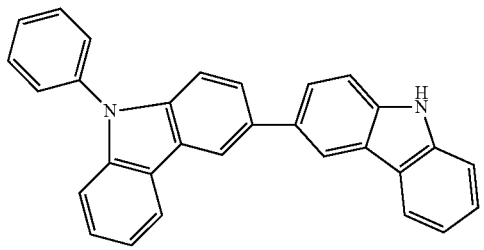
[1345202-03-0]
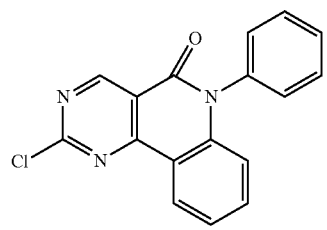 [SMILES: O=c1c2cnc(Cl)nc2c2ccccc2n1-c1ccccc1]
8f
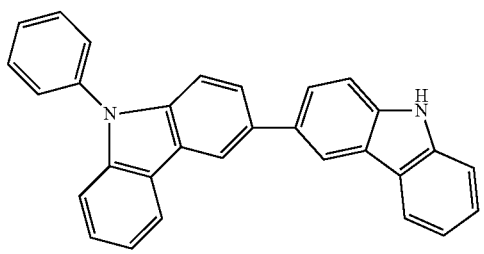
[1345202-03-0]
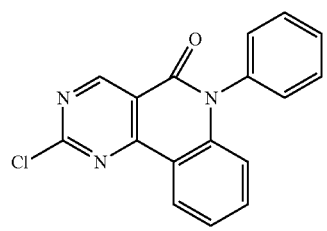 [SMILES: O=c1c2cnc(Cl)nc2c2ccccc2n1-c1ccccc1]
9f
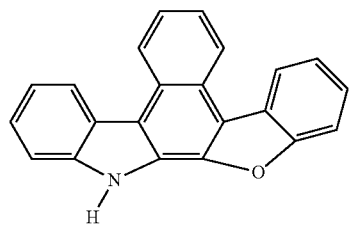
[1678511-52-8]
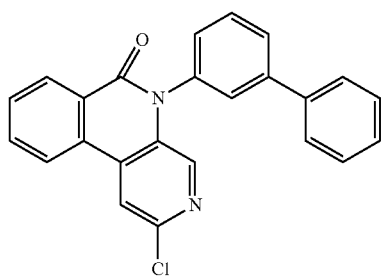 [SMILES: O=c1c2ccccc2c2cc(Cl)ncc2n1-c1cccc(-c2ccccc2)c1]
10f
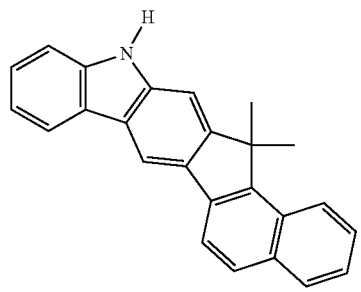
[2137465-59-7]
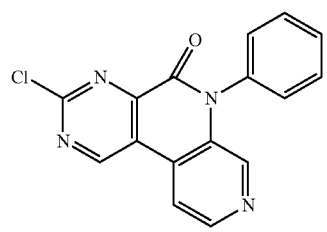 [SMILES: O=c1c2nc(Cl)ncc2c2ccncc2n1-c1ccccc1]

-continued
11f
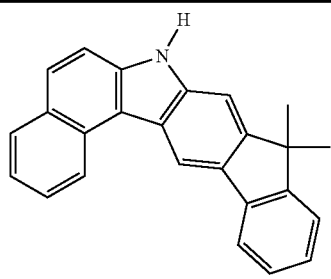
[2137465-43-9]
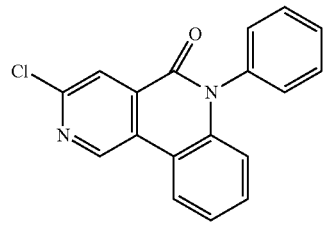 [SMILES: O=c1c2cc(Cl)ncc2c2ccccc2n1-c1ccccc1]
12f
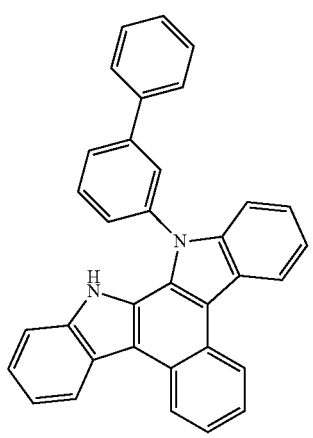
[1639394-10-7]
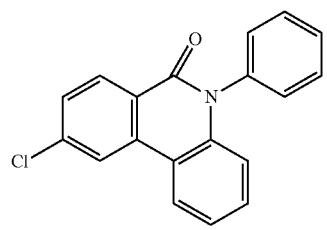 [SMILES: O=c1c2ccc(Cl)cc2c2ccccc2n1-c1ccccc1]
13f
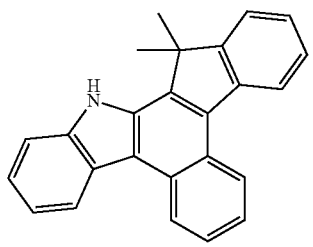
[1447709-49-0]
14f
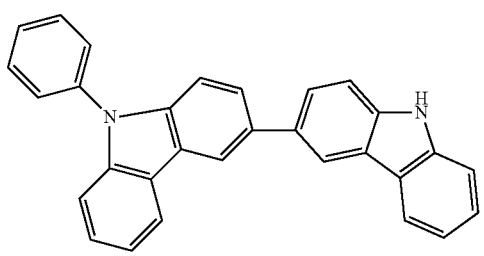
[1345202-03-0]
15f
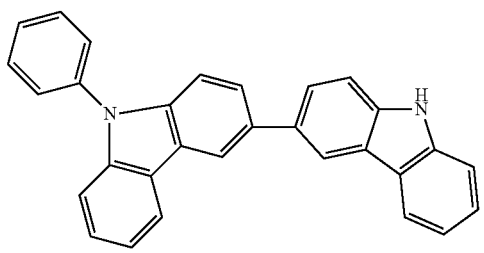
[1345202-03-0]
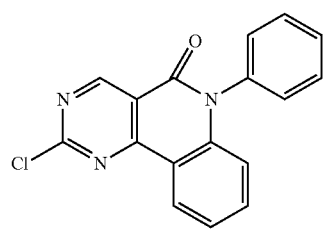 [SMILES: O=c1c2cnc(Cl)nc2c2ccccc2n1-c1ccccc1]

16f 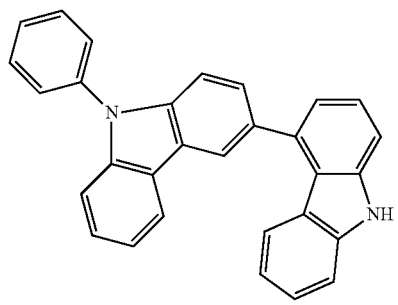
[1407183-66-7]
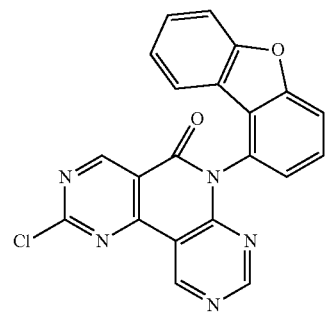 [SMILES: O=c1c2cnc(Cl)nc2c2cncnc2n1-c1cccc2oc3ccccc3c12]
17f 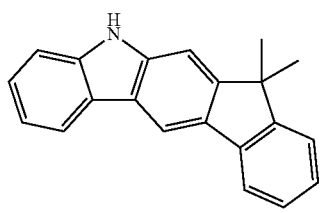
[1257220-47-5]
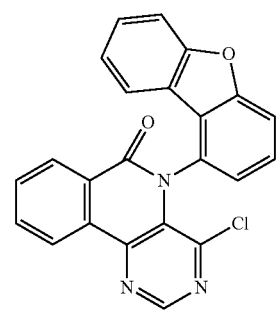 [SMILES: O=c1c2ccccc2c2ncnc(Cl)c2n1-c1cccc2oc3ccccc3c12]
18f 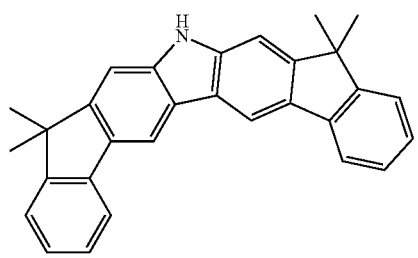
[137328-72-1]
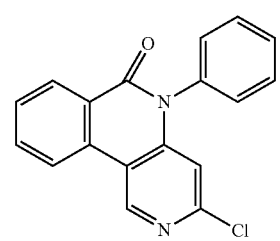 [SMILES: O=c1c2ccccc2c2cnc(Cl)cc2n1-c1ccccc1]
19f 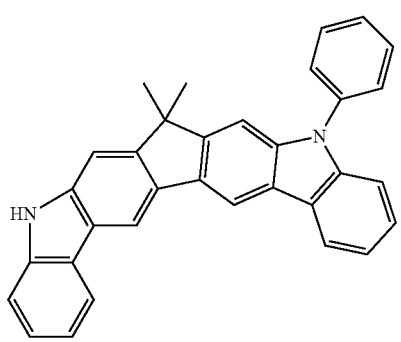
[1618097-04-3]
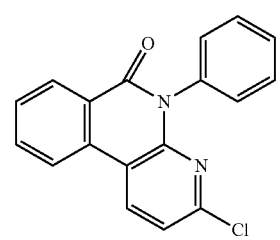 [SMILES: O=c1c2ccccc2c2ccc(Cl)nc2n1-c1ccccc1]
20f 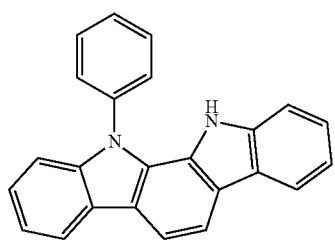
[1024598-06-8]
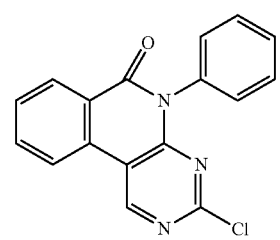 [SMILES: O=c1c2ccccc2c2cnc(Cl)nc2n1-c1ccccc1]

-continued
| | | |
|---|---|---|
| 21f | 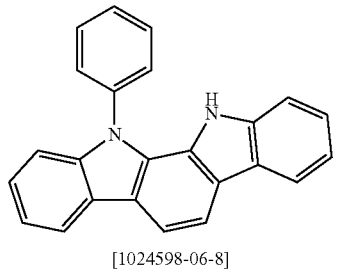 [SMILES: c1ccc(-n2c3ccccc3c3ccc4c5ccccc5[nH]c4c32)cc1]<br>[1024598-06-8] | 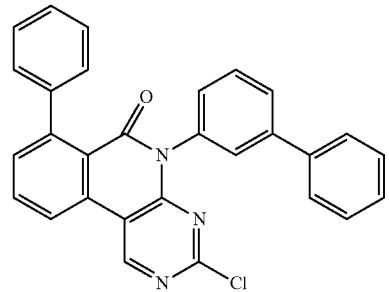 [SMILES: O=c1c2c(-c3ccccc3)cccc2c2cnc(Cl)nc2n1-c1cccc(-c2ccccc2)c1] |
| 22f | 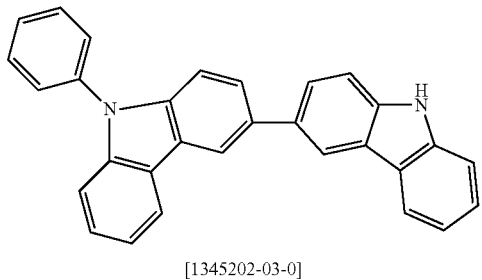 [SMILES: c1ccc(-n2c3ccccc3c3cc(-c4ccc5[nH]c6ccccc6c5c4)ccc32)cc1]<br>[1345202-03-0] | 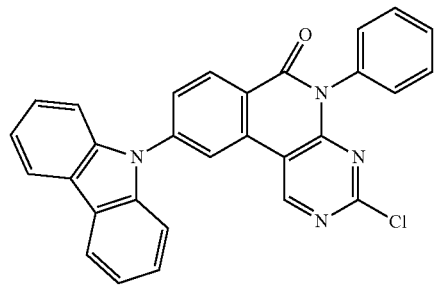 [SMILES: O=c1c2ccc(-n3c4ccccc4c4ccccc43)cc2c2cnc(Cl)nc2n1-c1ccccc1] |
| 23f | 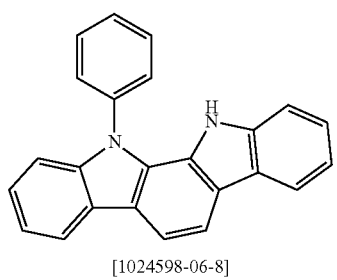 [SMILES: c1ccc(-n2c3ccccc3c3ccc4c5ccccc5[nH]c4c32)cc1]<br>[1024598-06-8] | 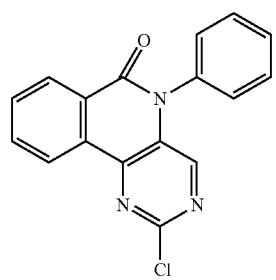 [SMILES: O=c1c2ccccc2c2nc(Cl)ncc2n1-c1ccccc1] |
| 24f | 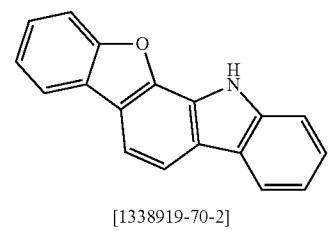 [SMILES: c1ccc2c(c1)[nH]c1c2ccc2c3ccccc3oc21]<br>[1338919-70-2] | 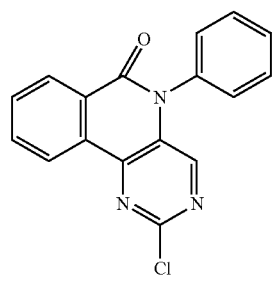 [SMILES: O=c1c2ccccc2c2nc(Cl)ncc2n1-c1ccccc1] |
| 25f | 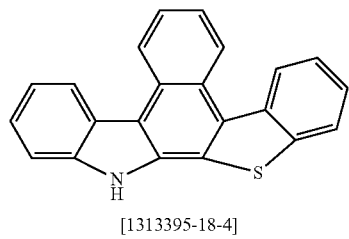 [SMILES: c1ccc2c(c1)[nH]c1c3sc4ccccc4c3c3ccccc3c21]<br>[1313395-18-4] | 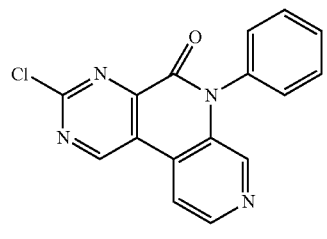 [SMILES: O=c1c2nc(Cl)ncc2c2ccncc2n1-c1ccccc1] |
| 26f | 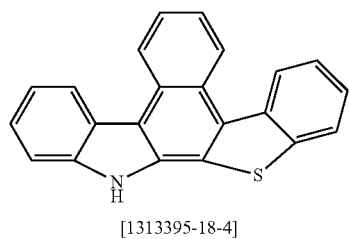 [SMILES: c1ccc2c(c1)[nH]c1c3sc4ccccc4c3c3ccccc3c21]<br>[1313395-18-4] | 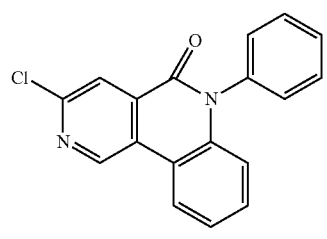 [SMILES: O=c1c2cc(Cl)ncc2c2ccccc2n1-c1ccccc1] |

27f 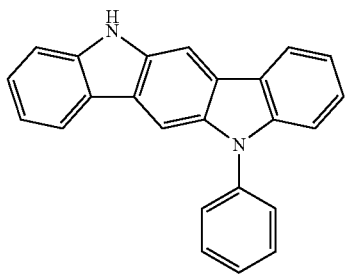
[1316311-27-9]
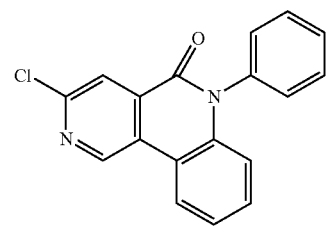 [SMILES: O=c1c2cc(Cl)ncc2c2ccccc2n1-c1ccccc1]
28f 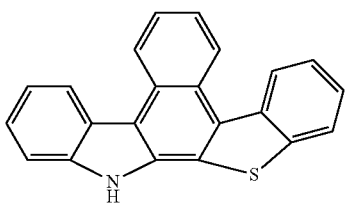
[1313395-18-4]
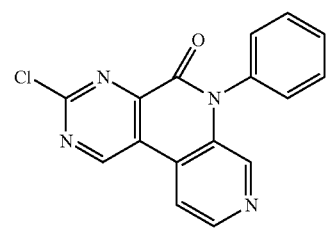 [SMILES: O=c1c2nc(Cl)ncc2c2ccncc2n1-c1ccccc1]
29f 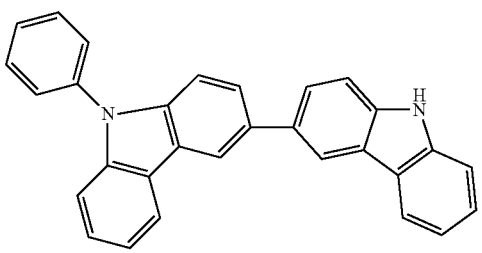
[1345202-03-0]
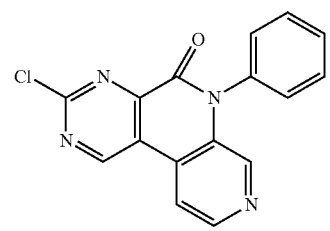 [SMILES: O=c1c2nc(Cl)ncc2c2ccncc2n1-c1ccccc1]
30f 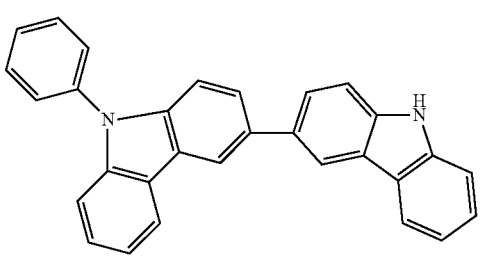
[1345202-03-0]
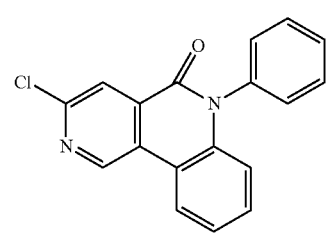 [SMILES: O=c1c2cc(Cl)ncc2c2ccccc2n1-c1ccccc1]
31f 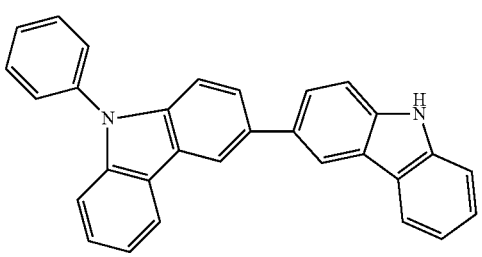
[1345202-03-0]
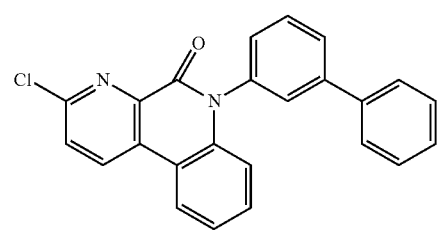 [SMILES: O=c1c2nc(Cl)ccc2c2ccccc2n1-c1cccc(-c2ccccc2)c1]

-continued
32f 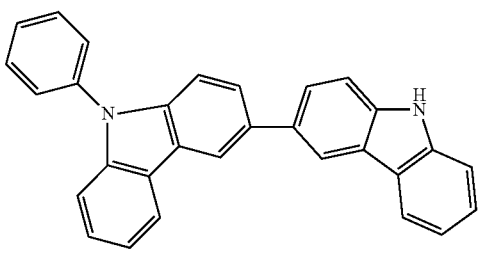
[1345202-03-0]
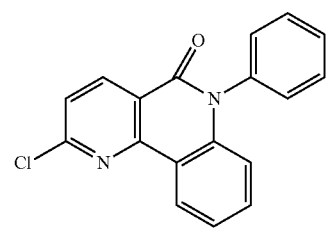 [SMILES: O=c1c2ccc(Cl)nc2c2ccccc2n1-c1ccccc1]
33f 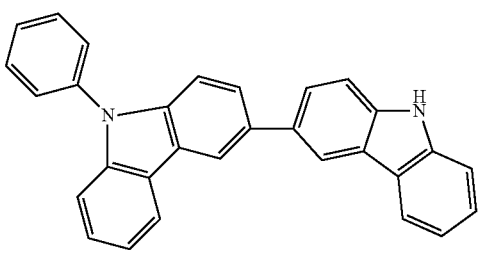
[1345202-03-0]
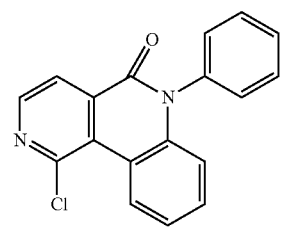 [SMILES: O=c1c2ccnc(Cl)c2c2ccccc2n1-c1ccccc1]
34f 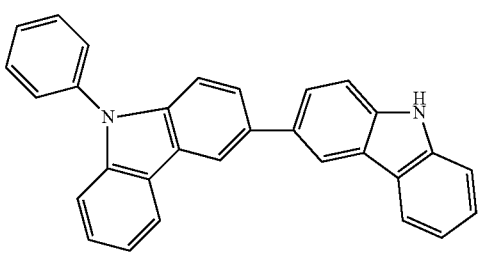
[1345202-03-0]
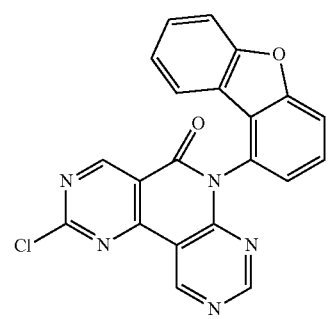 [SMILES: O=c1c2cnc(Cl)nc2c2cncnc2n1-c1cccc2oc3ccccc3c12]
35f 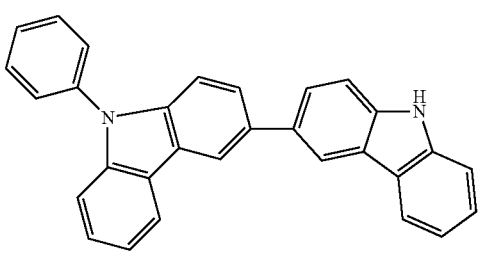
[1345202-03-0]
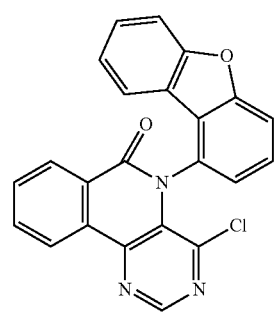 [SMILES: O=c1c2ccccc2c2ncnc(Cl)c2n1-c1cccc2oc3ccccc3c12]
36f 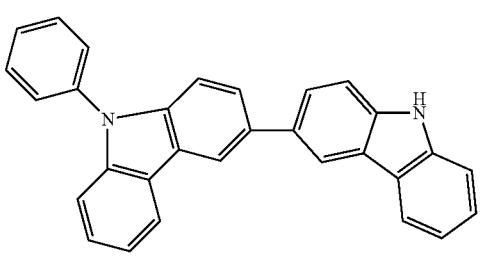
[1345202-03-0]
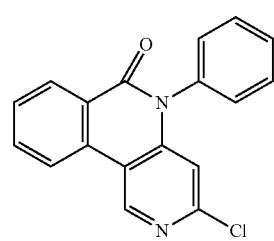 [SMILES: O=c1c2ccccc2c2cnc(Cl)cc2n1-c1ccccc1]

-continued
| | | |
|---|---|---|
| 37f | 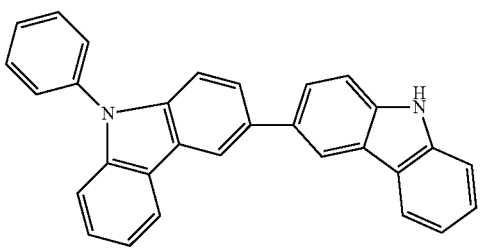 [1345202-03-0] | 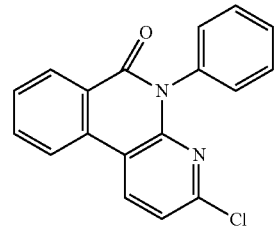 [SMILES: O=c1c2ccccc2c2ccc(Cl)nc2n1-c1ccccc1] |
| 38f | 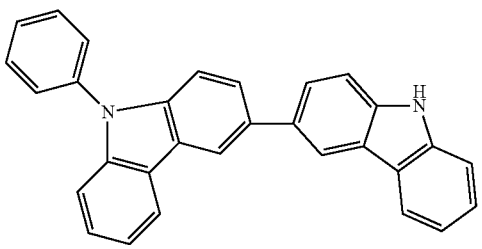 [1345202-03-0] | 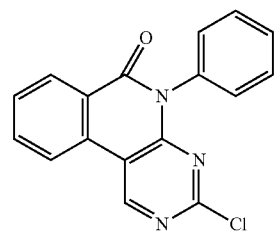 [SMILES: O=c1c2ccccc2c2cnc(Cl)nc2n1-c1ccccc1] |
| 39f | 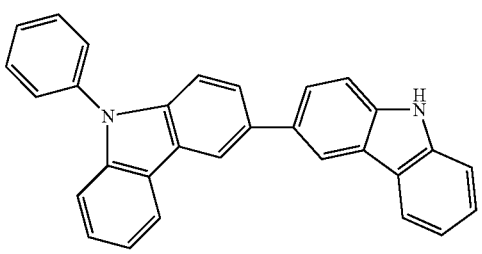 [1345202-03-0] | 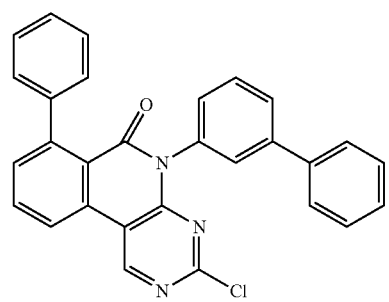 [SMILES: O=c1c2c(-c3ccccc3)cccc2c2cnc(Cl)nc2n1-c1cccc(-c2ccccc2)c1] |
| 40f | 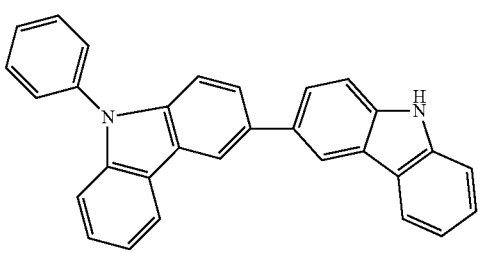 [1345202-03-0] | 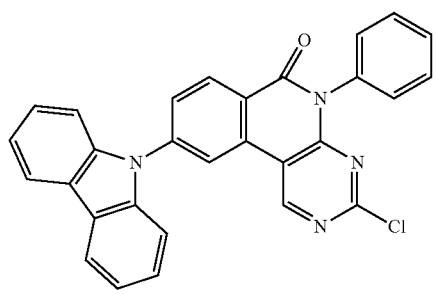 [SMILES: O=c1c2ccc(-n3c4ccccc4c4ccccc43)cc2c2cnc(Cl)nc2n1-c1ccccc1] |
| 41f | 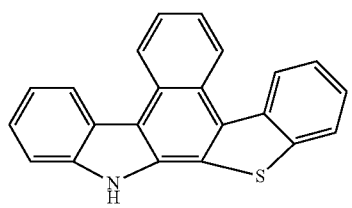 [1313395-18-4] | 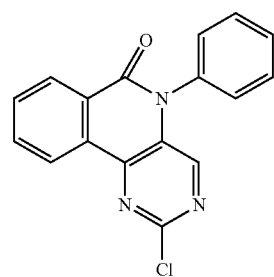 [SMILES: O=c1c2ccccc2c2nc(Cl)ncc2n1-c1ccccc1] |

-continued
42f 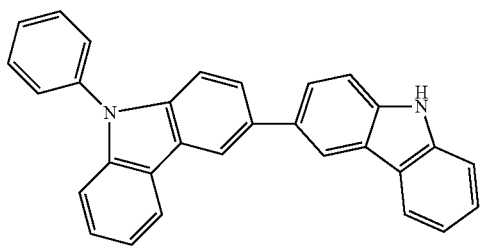
[1345202-03-0]
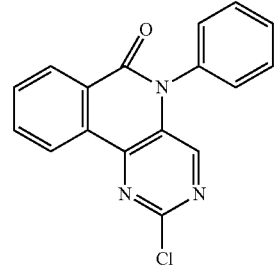 [SMILES: O=c1c2ccccc2c2nc(Cl)ncc2n1-c1ccccc1]
43f 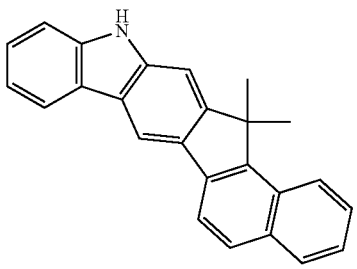
[2137465-59-7]
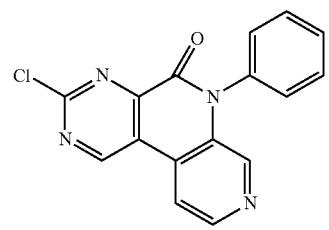 [SMILES: O=c1c2nc(Cl)ncc2c2ccncc2n1-c1ccccc1]
44f 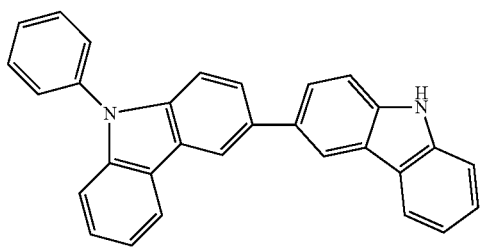
[1345202-03-0]
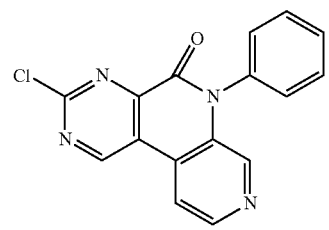 [SMILES: O=c1c2nc(Cl)ncc2c2ccncc2n1-c1ccccc1]
45f 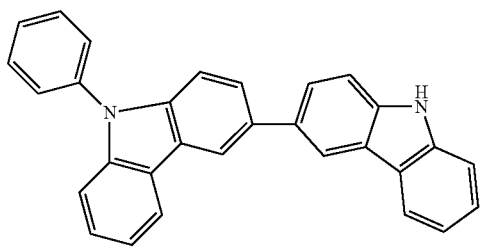
[1345202-03-0]
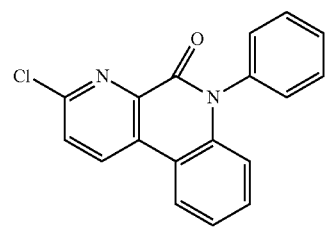 [SMILES: O=c1c2nc(Cl)ccc2c2ccccc2n1-c1ccccc1]
46f 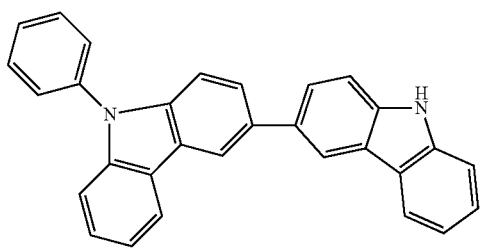
[1345202-03-0]
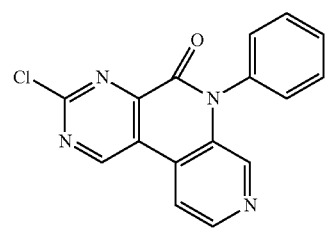 [SMILES: O=c1c2nc(Cl)ncc2c2ccncc2n1-c1ccccc1]

| | 201 | 202 |
|---|---|---|
| 47f | 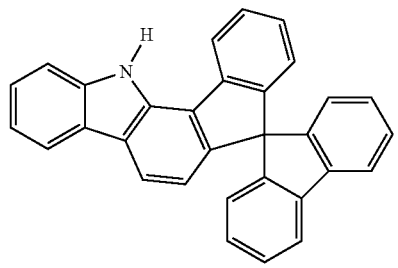 [1615703-28-0] | 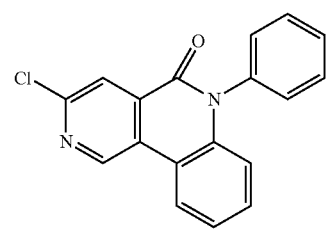 [SMILES: O=c1c2cc(Cl)ncc2c2ccccc2n1-c1ccccc1] |
| 48f | 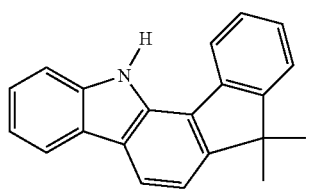 [1616231-39-0] | 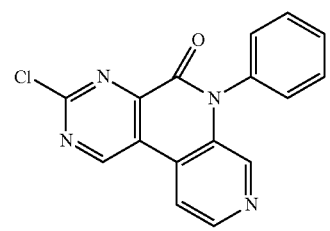 [SMILES: O=c1c2nc(Cl)ncc2c2ccncc2n1-c1ccccc1] |
| 49f | 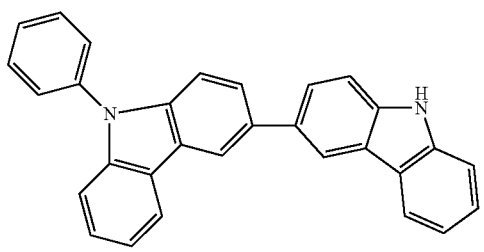 [1345202-03-0] | 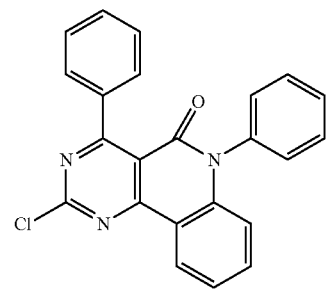 [SMILES: O=c1c2c(-c3ccccc3)nc(Cl)nc2c2ccccc2n1-c1ccccc1] |
| 50f | 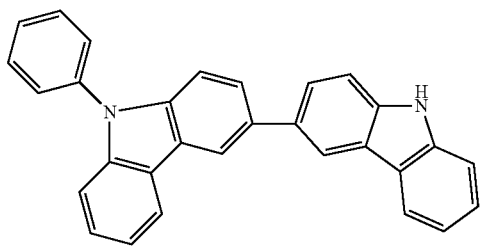 [1345202-03-0] | 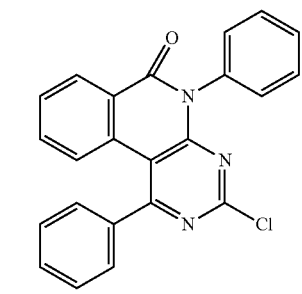 [SMILES: O=c1c2ccccc2c2c(-c3ccccc3)nc(Cl)nc2n1-c1ccccc1] |
| 51f | 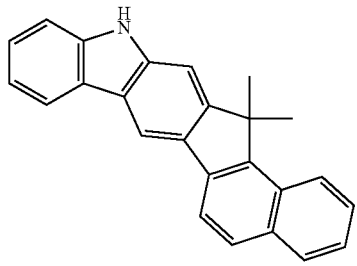 [2137465-59-7] | 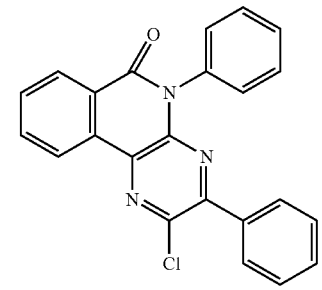 [SMILES: O=c1c2ccccc2c2nc(Cl)c(-c3ccccc3)nc2n1-c1ccccc1] |

-continued
| | | |
|---|---|---|
| 52f | 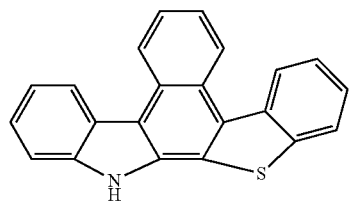\
[1313395-18-4] | 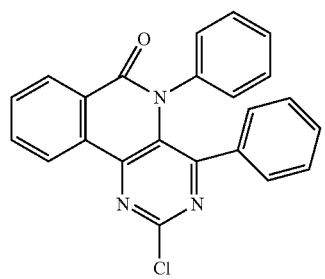 [SMILES: O=c1c2ccccc2c2nc(Cl)nc(-c3ccccc3)c2n1-c1ccccc1] |
| 53f | 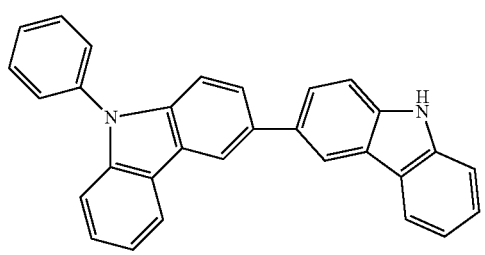\
[1345202-03-0] | 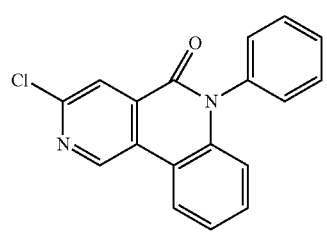 [SMILES: O=c1c2cc(Cl)ncc2c2ccccc2n1-c1ccccc1] |
| 54f | 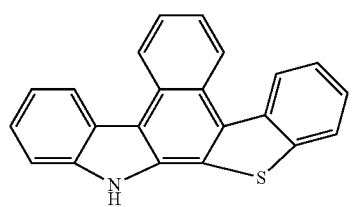\
[1313395-18-4] | 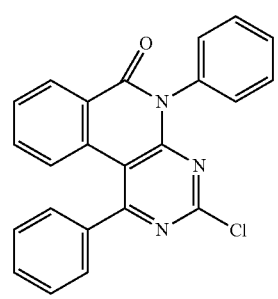 [SMILES: O=c1c2ccccc2c2c(-c3ccccc3)nc(Cl)nc2n1-c1ccccc1] |
| Ex. | Product | Yield |
|---|---|---|
| 1f | | 75% |

-continued
| | | |
|---|---|---|
| 2f | 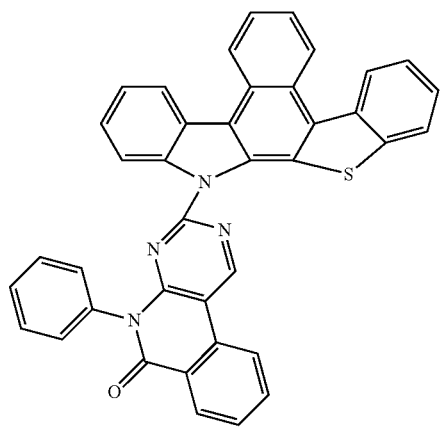 [SMILES: O=c1c2ccccc2c2cnc(-n3c4ccccc4c4c5ccccc5c5c6ccccc6sc5c43)nc2n1-c1ccccc1] | 81% |
| 3f | 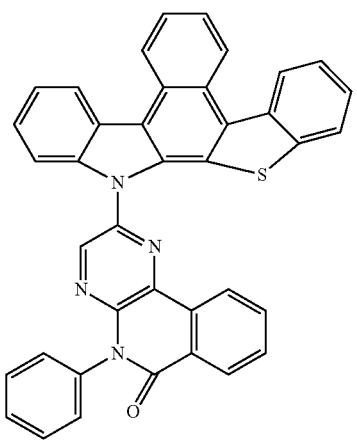 [SMILES: O=c1c2ccccc2c2nc(-n3c4ccccc4c4c5ccccc5c5c6ccccc6sc5c43)cnc2n1-c1ccccc1] | 80% |
| 4f | 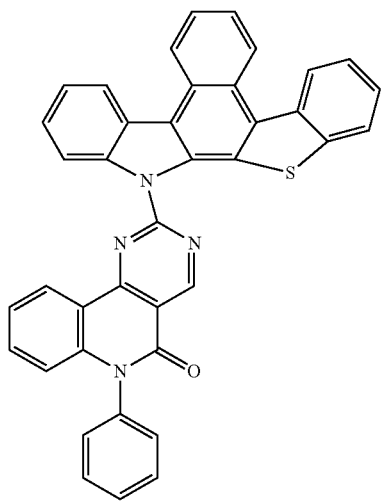 [SMILES: O=c1c2cnc(-n3c4ccccc4c4c5ccccc5c5c6ccccc6sc5c43)nc2c2ccccc2n1-c1ccccc1] | 76% |

| | | |
|---|---|---|
| 5f | 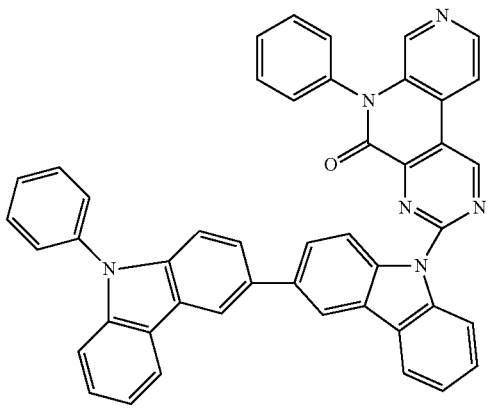 [SMILES: O=c1c2nc(-n3c4ccccc4c4cc(-c5ccc6c(c5)c5ccccc5n6-c5ccccc5)ccc43)ncc2c2ccncc2n1-c1ccccc1] | 84% |
| 6f | 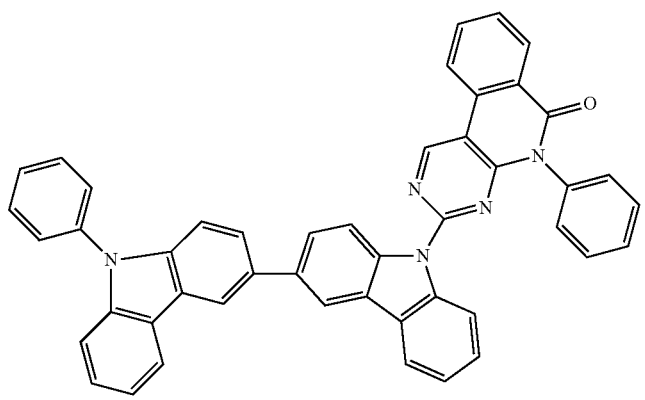 [SMILES: O=c1c2ccccc2c2cnc(-n3c4ccccc4c4cc(-c5ccc6c(c5)c5ccccc5n6-c5ccccc5)ccc43)nc2n1-c1ccccc1] | 83% |
| 7f | 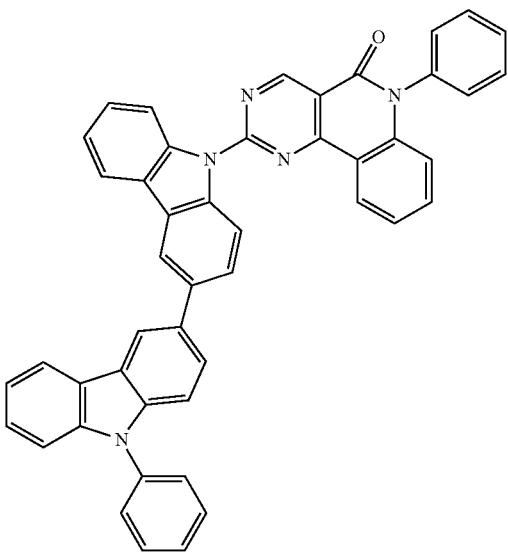 [SMILES: O=c1c2cnc(-n3c4ccccc4c4cc(-c5ccc6c(c5)c5ccccc5n6-c5ccccc5)ccc43)nc2c2ccccc2n1-c1ccccc1] | 81% |

-continued
| | | |
|---|---|---|
| 8f | 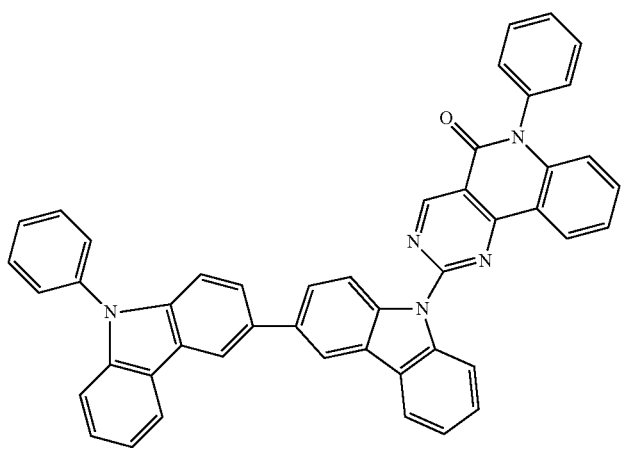 [SMILES: O=c1c2cnc(-n3c4ccccc4c4cc(-c5ccc6c(c5)c5ccccc5n6-c5ccccc5)ccc43)nc2c2ccccc2n1-c1ccccc1] | 78% |
| 9f | 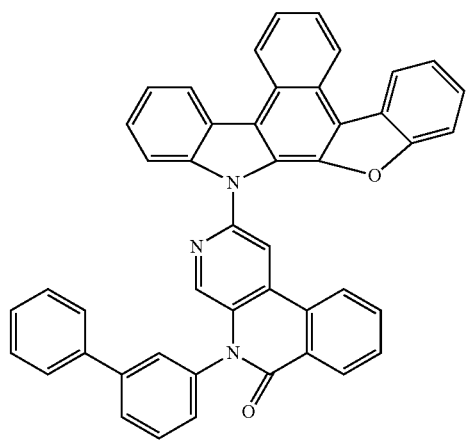 [SMILES: O=c1c2ccccc2c2cc(-n3c4ccccc4c4c5ccccc5c5c6ccccc6oc5c43)ncc2n1-c1cccc(-c2ccccc2)c1] | 69% |
| 10f | 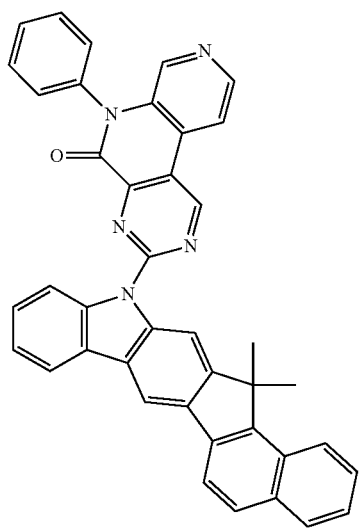 [SMILES: CC1(C)c2cc3c(cc2-c2ccc4ccccc4c21)c1ccccc1n3-c1ncc2c(n1)c(=O)n(-c1ccccc1)c1cnccc21] | 67% |

| | | |
|---|---|---|
| 11f | 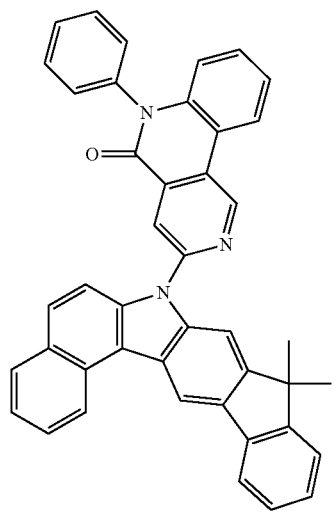 [SMILES: CC1(C)c2ccccc2-c2cc3c4c5ccccc5ccc4n(-c4cc5c(=O)n(-c6ccccc6)c6ccccc6c5cn4)c3cc21] | 83% |
| 12f | 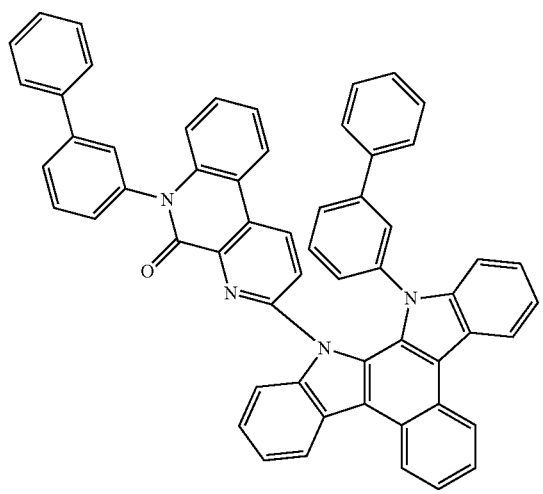 [SMILES: O=c1c2nc(-n3c4ccccc4c4c5ccccc5c5c6ccccc6n(-c6cccc(-c7ccccc7)c6)c5c43)ccc2c2ccccc2n1-c1cccc(-c2ccccc2)c1] | 86% |
| 13f | 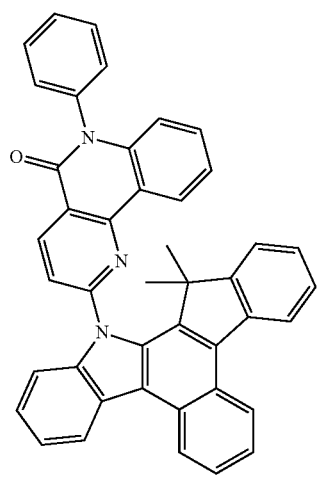 [SMILES: CC1(C)c2ccccc2-c2c1c1c(c3ccccc23)c2ccccc2n1-c1ccc2c(=O)n(-c3ccccc3)c3ccccc3c2n1] | 81% |

14f 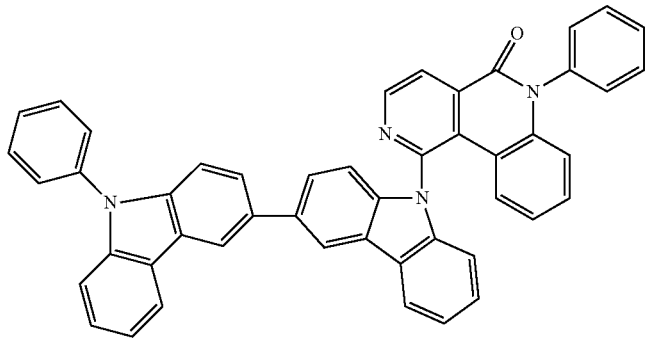 [SMILES: O=c1c2ccnc(-n3c4ccccc4c4cc(-c5ccc6c(c5)c5ccccc5n6-c5ccccc5)ccc43)c2c2ccccc2n1-c1ccccc1] 82%
15f 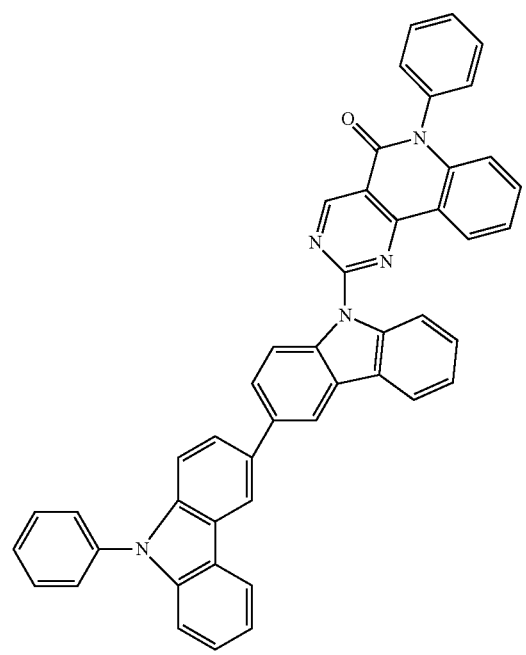 [SMILES: O=c1c2cnc(-n3c4ccccc4c4cc(-c5ccc6c(c5)c5ccccc5n6-c5ccccc5)ccc43)nc2c2ccccc2n1-c1ccccc1] 78%

| | | |
|---|---|---|
| 16f | 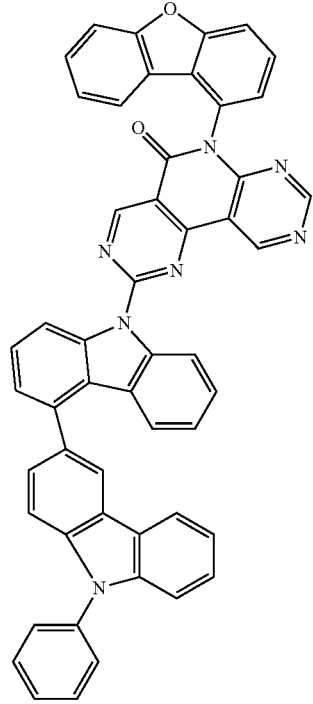 [SMILES: O=c1c2cnc(-n3c4ccccc4c4c(-c5ccc6c(c5)c5ccccc5n6-c5ccccc5)cccc43)nc2c2cncnc2n1-c1cccc2oc3ccccc3c12] | 75% |
| 17f | 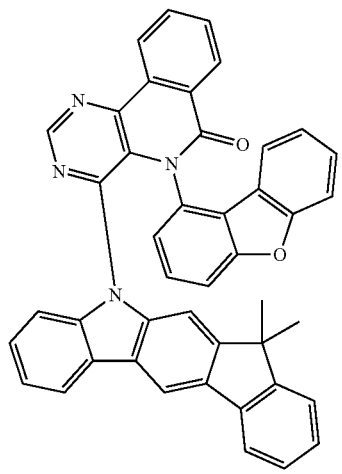 [SMILES: CC1(C)c2ccccc2-c2cc3c4ccccc4n(-c4ncnc5c6ccccc6c(=O)n(-c6cccc7oc8ccccc8c67)c45)c3cc21] | 76% |
| 18f | 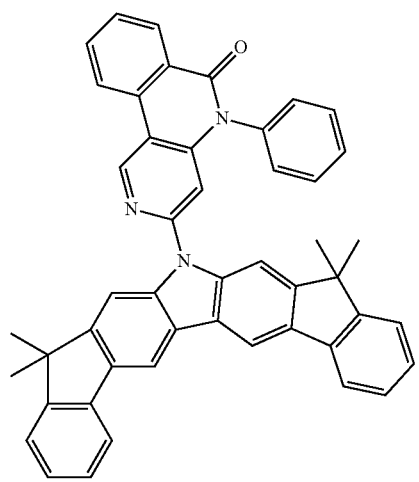 [SMILES: CC1(C)c2ccccc2-c2cc3c4cc5c(cc4n(-c4cc6c(cn4)c4ccccc4c(=O)n6-c4ccccc4)c3cc21)C(C)(C)c1ccccc1-5] | 80% |

19f 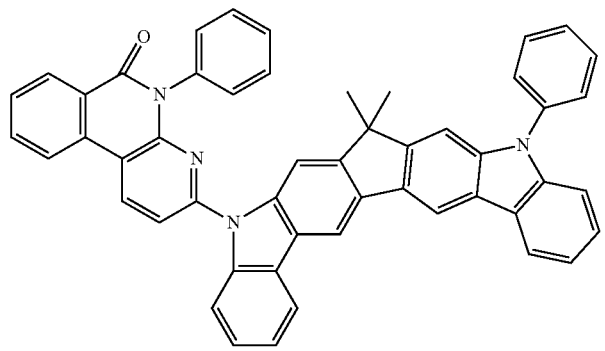 [SMILES: CC1(C)c2cc3c(cc2-c2cc4c5ccccc5n(-c5ccc6c7ccccc7c(=O)n(-c7ccccc7)c6n5)c4cc21)c1ccccc1n3-c1ccccc1] 77%
20f 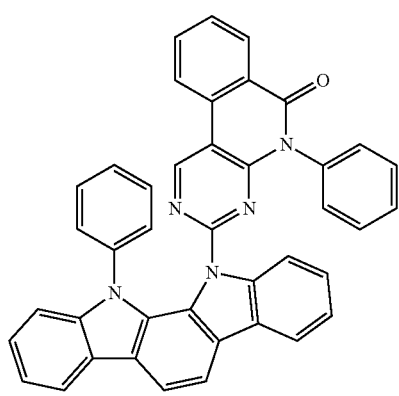 [SMILES: O=c1c2ccccc2c2cnc(-n3c4ccccc4c4ccc5c6ccccc6n(-c6ccccc6)c5c43)nc2n1-c1ccccc1] 84%
21f 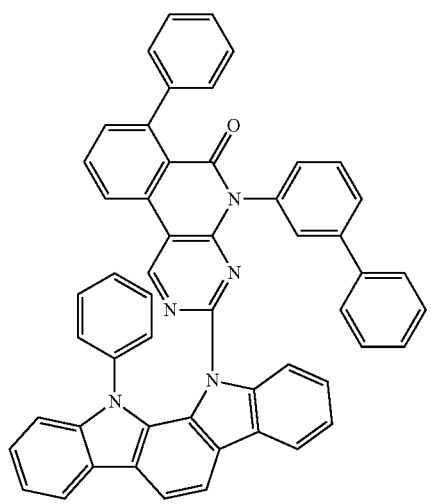 [SMILES: O=c1c2c(-c3ccccc3)cccc2c2cnc(-n3c4ccccc4c4ccc5c6ccccc6n(-c6ccccc6)c5c43)nc2n1-c1cccc(-c2ccccc2)c1] 87%

| | | |
|---|---|---|
| 22f | 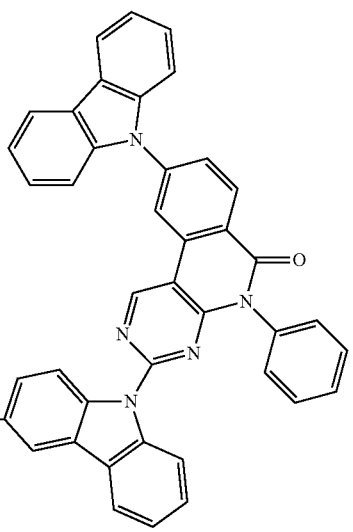 | 85% |
| 23f | 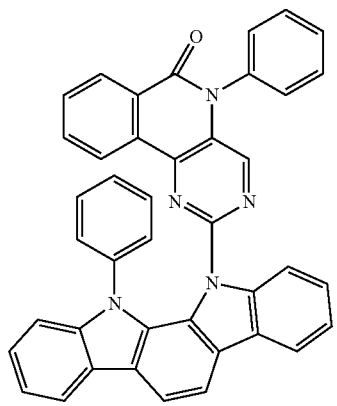 [SMILES: O=c1c2ccccc2c2nc(-n3c4ccccc4c4ccc5c6ccccc6n(-c6ccccc6)c5c43)ncc2n1-c1ccccc1] | 83% |
| 24f | 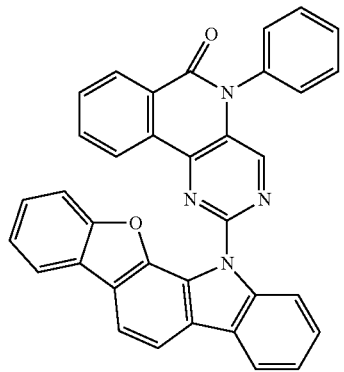 [SMILES: O=c1c2ccccc2c2nc(-n3c4ccccc4c4ccc5c6ccccc6oc5c43)ncc2n1-c1ccccc1] | 83% |

| | | |
|---|---|---|
| 25f | 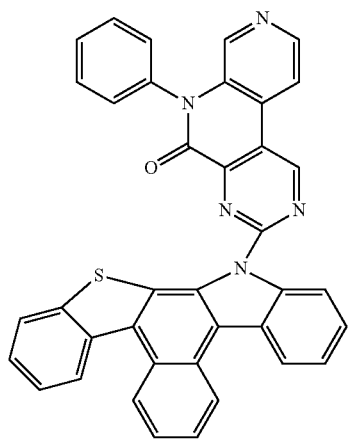 [SMILES: O=c1c2nc(-n3c4ccccc4c4c5ccccc5c5c6ccccc6sc5c43)ncc2c2ccncc2n1-c1ccccc1] | 85% |
| 26f | 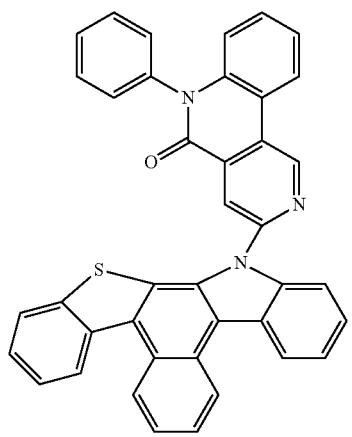 [SMILES: O=c1c2cc(-n3c4ccccc4c4c5ccccc5c5c6ccccc6sc5c43)ncc2c2ccccc2n1-c1ccccc1] | 73% |
| 27f | 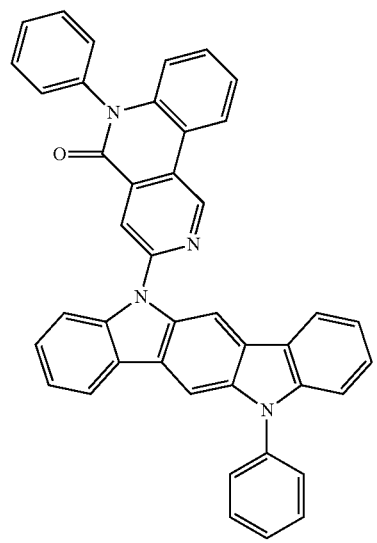 [SMILES: O=c1c2cc(-n3c4ccccc4c4cc5c(cc43)c3ccccc3n5-c3ccccc3)ncc2c2ccccc2n1-c1ccccc1] | 74% |

| | | |
|---|---|---|
| 28f | 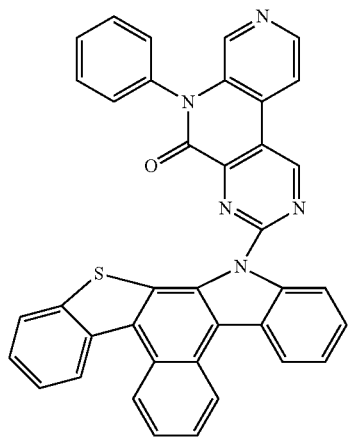 [SMILES: O=c1c2nc(-n3c4ccccc4c4c5ccccc5c5c6ccccc6sc5c43)ncc2c2ccncc2n1-c1ccccc1] | 77% |
| 29f | 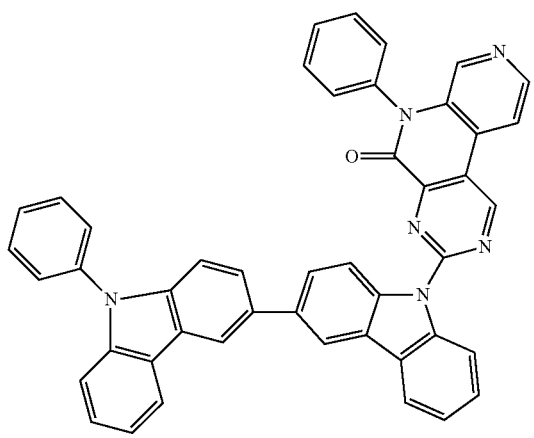 | 75% |
| 30f | 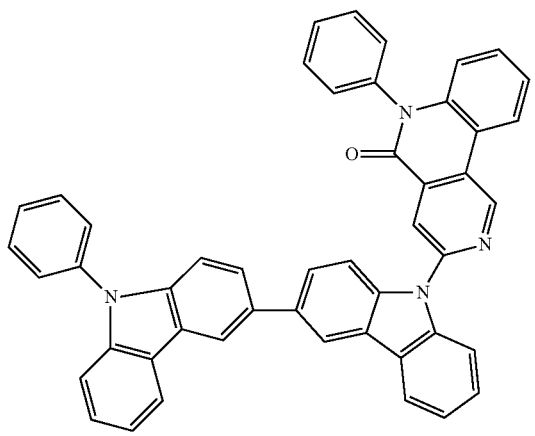 [SMILES: O=c1c2cc(-n3c4ccccc4c4cc(-c5ccc6c(c5)c5ccccc5n6-c5ccccc5)ccc43)ncc2c2ccccc2n1-c1ccccc1] | 77% |

| | | |
|---|---|---|
| 31f | 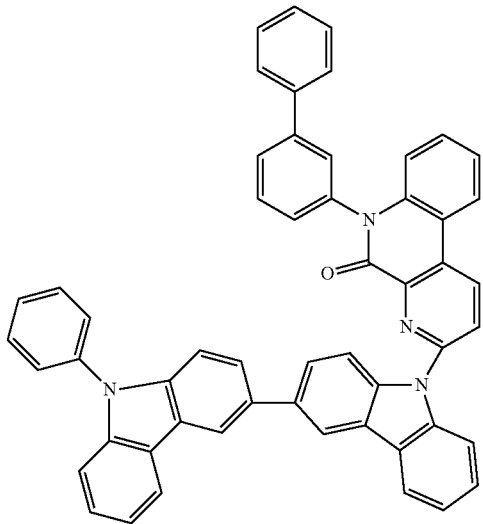 [SMILES: O=c1c2nc(-n3c4ccccc4c4cc(-c5ccc6c(c5)c5ccccc5n6-c5ccccc5)ccc43)ccc2c2ccccc2n1-c1cccc(-c2ccccc2)c1] | 80% |
| 32f | 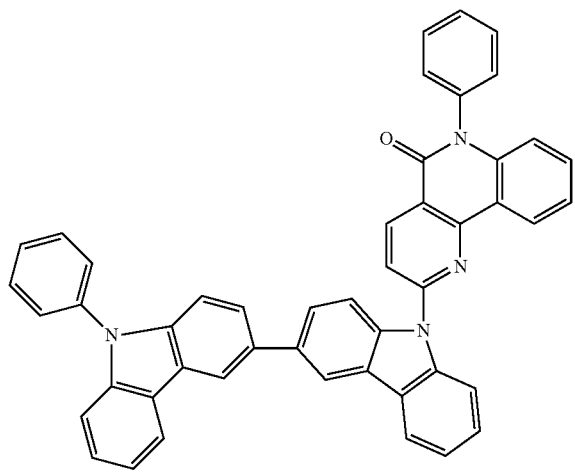 [SMILES: O=c1c2ccc(-n3c4ccccc4c4cc(-c5ccc6c(c5)c5ccccc5n6-c5ccccc5)ccc43)nc2c2ccccc2n1-c1ccccc1] | 72% |
| 33f | 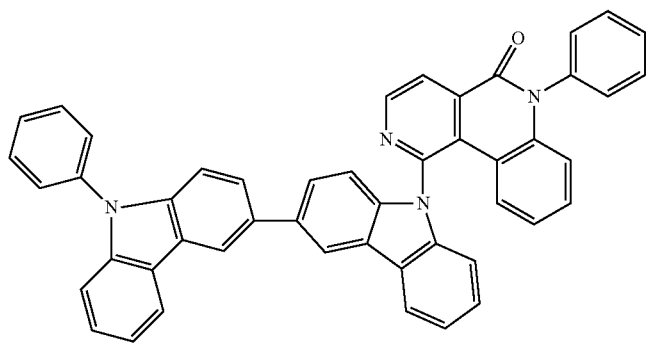 [SMILES: O=c1c2ccnc(-n3c4ccccc4c4cc(-c5ccc6c(c5)c5ccccc5n6-c5ccccc5)ccc43)c2c2ccccc2n1-c1ccccc1] | 70% |

| | | |
|---|---|---|
| 34f | 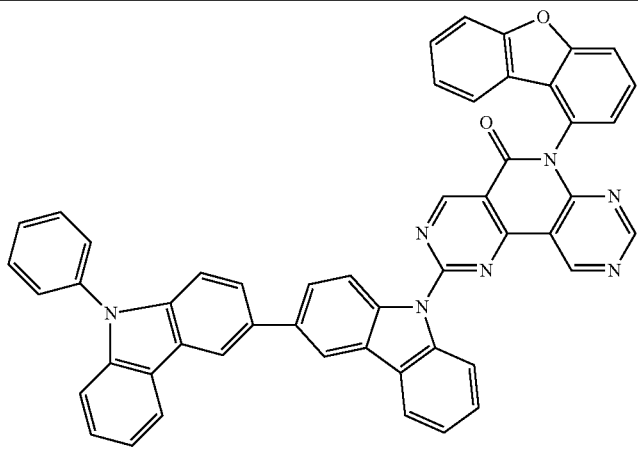 | 69% |
| 35f | 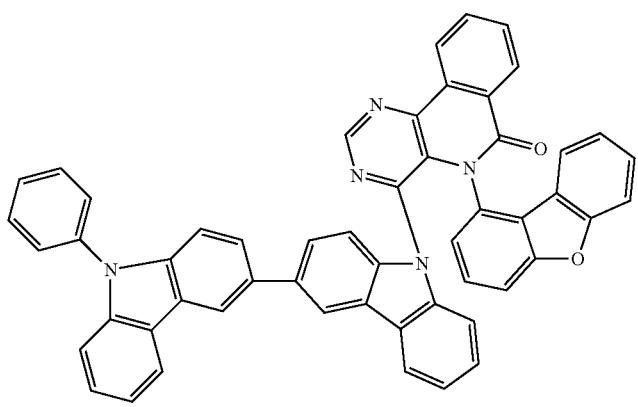 [SMILES: O=c1c2ccccc2c2ncnc(-n3c4ccccc4c4cc(-c5ccc6c(c5)c5ccccc5n6-c5ccccc5)ccc43)c2n1-c1cccc2oc3ccccc3c12] | 87% |
| 36f | 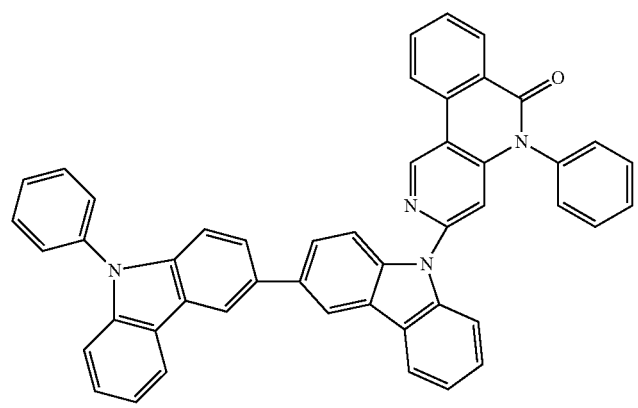 | 72% |
| 37f | 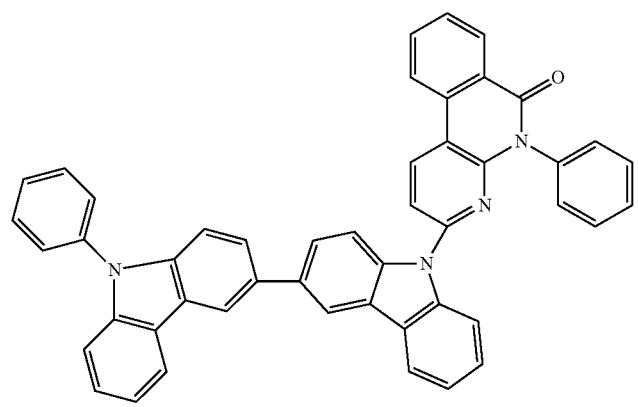 [SMILES: O=c1c2ccccc2c2ccc(-n3c4ccccc4c4cc(-c5ccc6c(c5)c5ccccc5n6-c5ccccc5)ccc43)nc2n1-c1ccccc1] | 70% |

-continued
38f 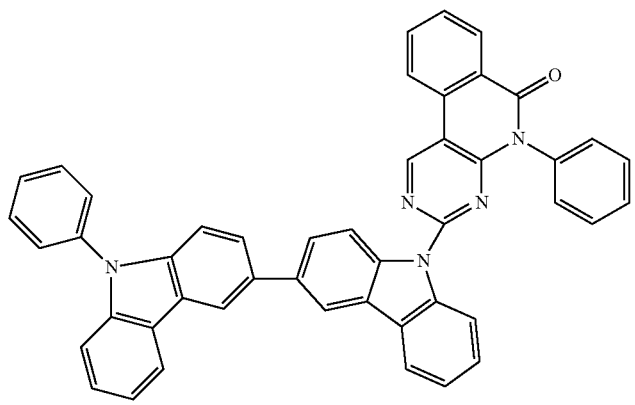 [SMILES: O=c1c2ccccc2c2cnc(-n3c4ccccc4c4cc(-c5ccc6c(c5)c5ccccc5n6-c5ccccc5)ccc43)nc2n1-c1ccccc1] 81%
39f 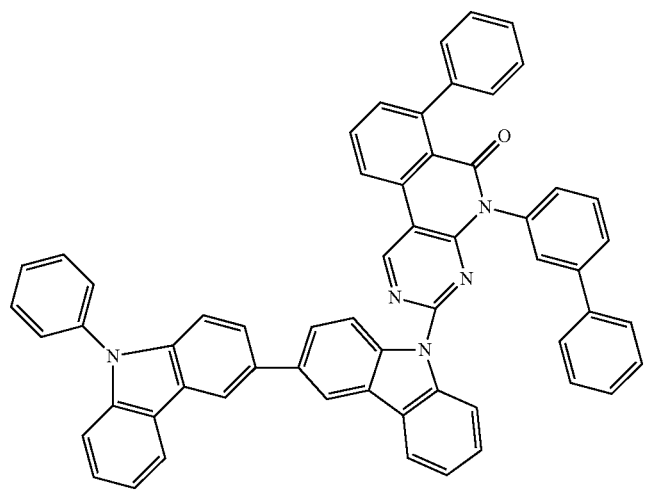 [SMILES: O=c1c2c(-c3ccccc3)cccc2c2cnc(-n3c4ccccc4c4cc(-c5ccc6c(c5)c5ccccc5n6-c5ccccc5)ccc43)nc2n1-c1cccc(-c2ccccc2)c1] 78%
40f 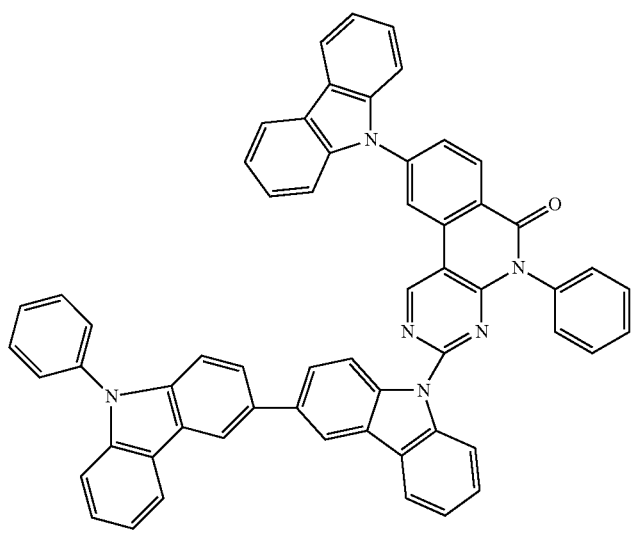 [SMILES: O=c1c2ccc(-n3c4ccccc4c4ccccc43)cc2c2cnc(-n3c4ccccc4c4cc(-c5ccc6c(c5)c5ccccc5n6-c5ccccc5)ccc43)nc2n1-c1ccccc1] 76%

| | | |
|---|---|---|
| 41f | 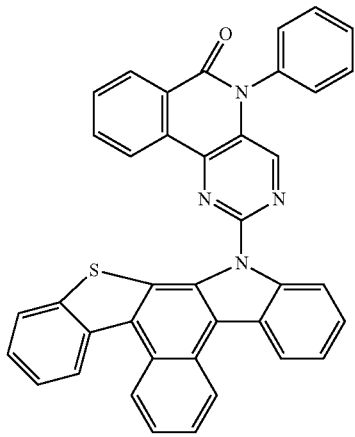 [SMILES: O=c1c2ccccc2c2nc(-n3c4ccccc4c4c5ccccc5c5c6ccccc6sc5c43)ncc2n1-c1ccccc1] | 77% |
| 42f | 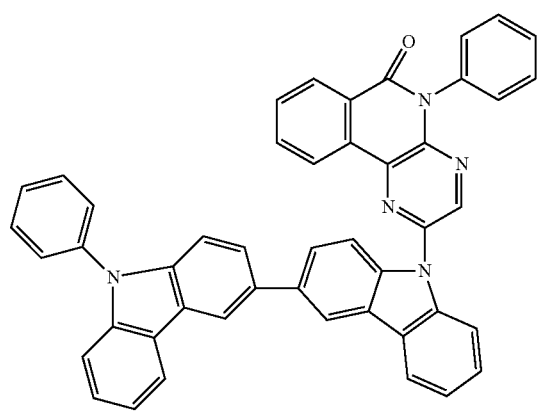 [SMILES: O=c1c2ccccc2c2nc(-n3c4ccccc4c4cc(-c5ccc6c(c5)c5ccccc5n6-c5ccccc5)ccc43)cnc2n1-c1ccccc1] | 71% |
| 43f | 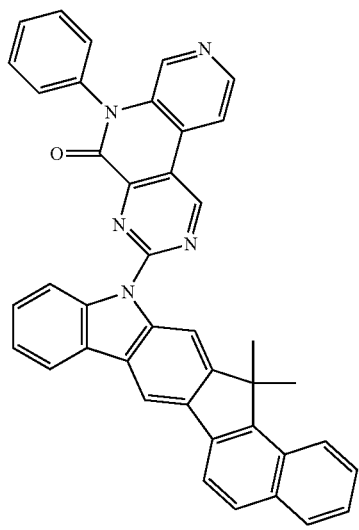 [SMILES: CC1(C)c2cc3c(cc2-c2ccc4ccccc4c21)c1ccccc1n3-c1ncc2c(n1)c(=O)n(-c1ccccc1)c1cnccc21] | 69% |

| | | |
|---|---|---|
| 44f | 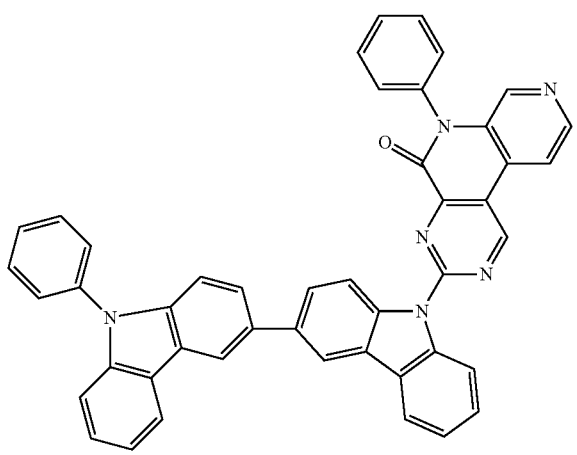 [SMILES: O=c1c2nc(-n3c4ccccc4c4cc(-c5ccc6c(c5)c5ccccc5n6-c5ccccc5)ccc43)ncc2c2ccncc2n1-c1ccccc1] | 60% |
| 45f | 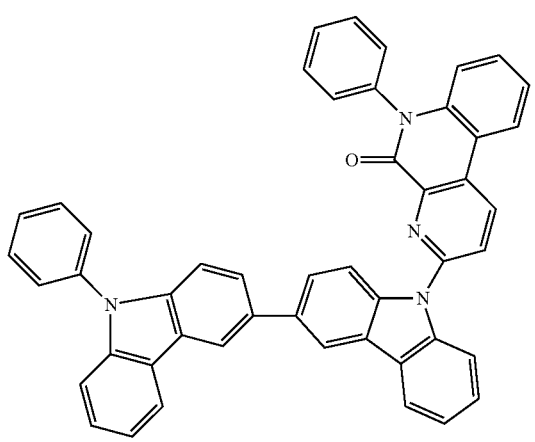 | 74% |
| 46f | 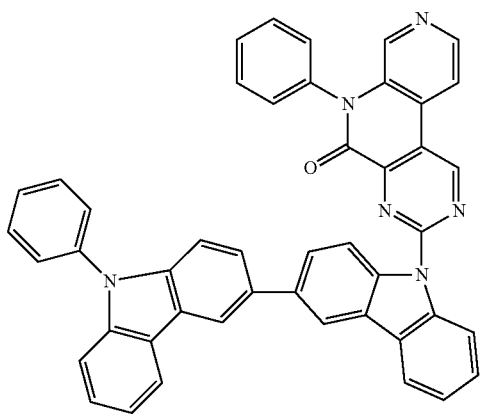 [SMILES: O=c1c2nc(-n3c4ccccc4c4cc(-c5ccc6c(c5)c5ccccc5n6-c5ccccc5)ccc43)ncc2c2ccncc2n1-c1ccccc1] | 72% |

| | | |
|---|---|---|
| 47f | 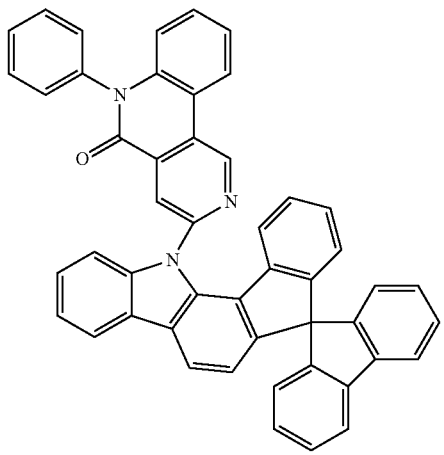 [SMILES: O=c1c2cc(-n3c4ccccc4c4ccc5c(c43)-c3ccccc3C53c4ccccc4-c4ccccc43)ncc2c2ccccc2n1-c1ccccc1] | 70% |
| 48f | 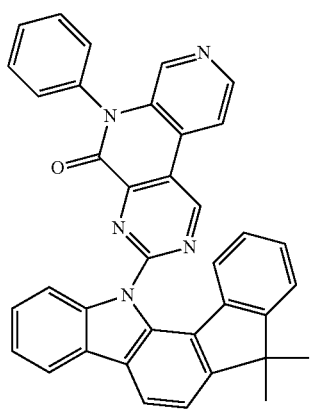 [SMILES: CC1(C)c2ccccc2-c2c1ccc1c3ccccc3n(-c3ncc4c(n3)c(=O)n(-c3ccccc3)c3cnccc43)c21] | 67% |
| 49f | 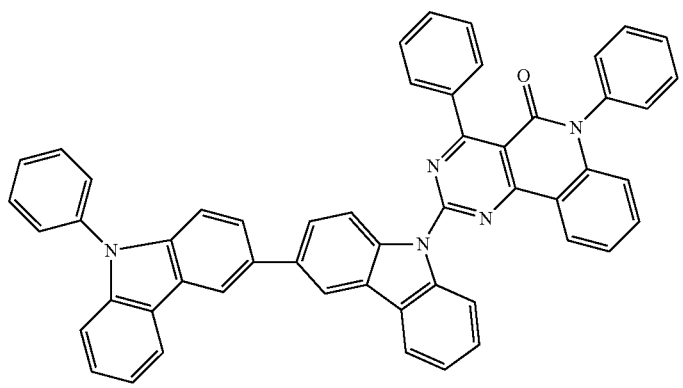 [SMILES: O=c1c2c(-c3ccccc3)nc(-n3c4ccccc4c4cc(-c5ccc6c(c5)c5ccccc5n6-c5ccccc5)ccc43)nc2c2ccccc2n1-c1ccccc1] | 64% |
| 50f | 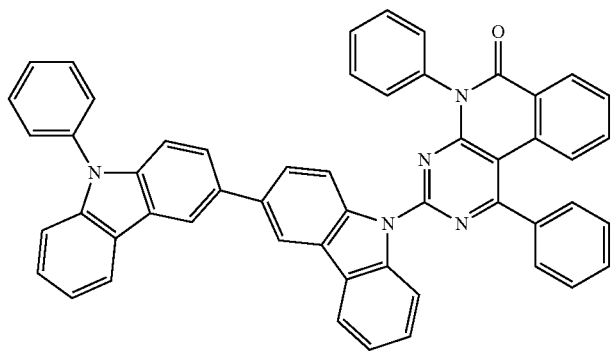 [SMILES: O=c1c2ccccc2c2c(-c3ccccc3)nc(-n3c4ccccc4c4cc(-c5ccc6c(c5)c5ccccc5n6-c5ccccc5)ccc43)nc2n1-c1ccccc1] | 68% |

| | | |
|---|---|---|
| 51f | 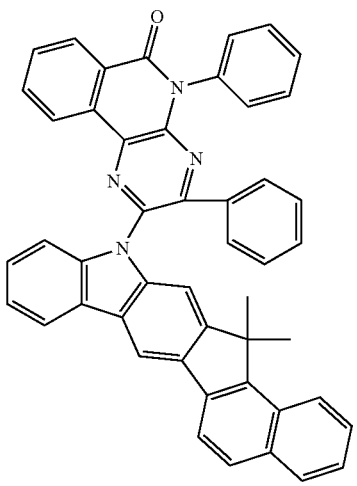 [SMILES: CC1(C)c2cc3c(cc2-c2ccc4ccccc4c21)c1ccccc1n3-c1nc2c3ccccc3c(=O)n(-c3ccccc3)c2nc1-c1ccccc1] | 59% |
| 52f | 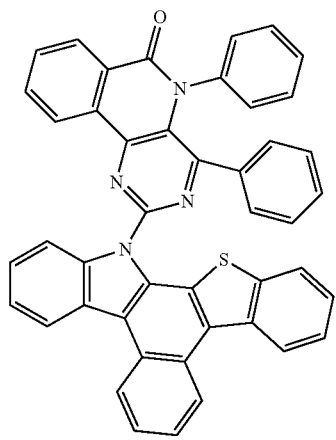 [SMILES: O=c1c2ccccc2c2nc(-n3c4ccccc4c4c5ccccc5c5c6ccccc6sc5c43)nc(-c3ccccc3)c2n1-c1ccccc1] | 73% |
| 53f | 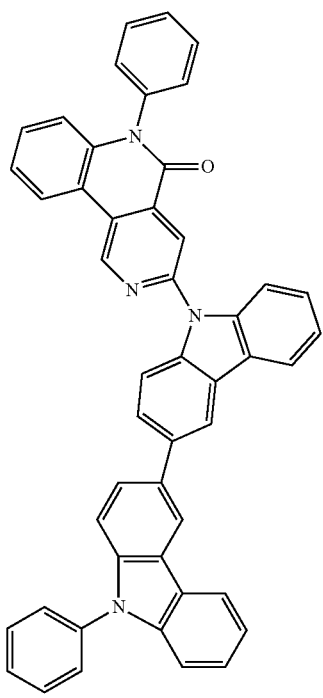 [SMILES: O=c1c2cc(-n3c4ccccc4c4cc(-c5ccc6c(c5)c5ccccc5n6-c5ccccc5)ccc43)ncc2c2ccccc2n1-c1ccccc1] | 79% |

| | | |
|---|---|---|
| 54f | 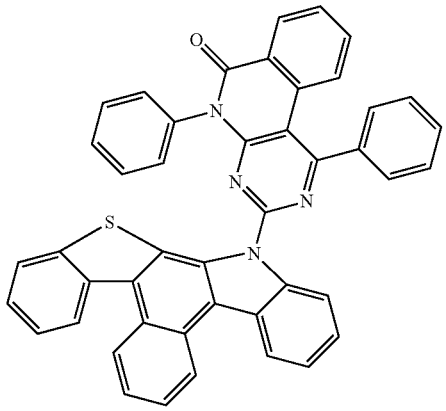 [SMILES: O=c1c2ccccc2c2c(-c3ccccc3)nc(-n3c4ccccc4c4c5ccccc5c5c6ccccc6sc5c43)nc2n1-c1ccccc1] | 81% |

B) Device Examples

Examples E1 to E6 which follow (see table 1) present the use of the materials of the invention in OLEDs.

Glass plates coated with structured ITO (indium tin oxide) of thickness 50 nm are treated prior to coating, first with an oxygen plasma, followed by an argon plasma. These plasma-treated glass plates form the substrates to which the OLEDs are applied.

The OLEDs have the following layer structure: substrate/ hole injection layer (HIL)/hole transport layer (HTL)/electron blocker layer (EBL)/emission layer (EML)/hole blocker layer (HBL)/electron transport layer (ETL)/electron injection layer (EIL) and finally a cathode. The cathode is formed by an aluminum layer of thickness 100 nm. The exact structure of the OLEDs can be found in tables 1a and 1b. The data of the OLEDs are listed in tables 2a and 2b. The materials required for production of the OLEDs are shown in table 3.

The OLEDs are characterized in a standard manner. For this purpose, the electroluminescence spectra, operating voltage and external quantum efficiency (EQE, measured in %) as a function of luminance, calculated from current-voltage-luminance characteristics assuming Lambertian emission characteristics, are determined. The electroluminescence spectra are determined at a luminance of 1000 cd/m$^2$, and the CIE 1931 x and y color coordinates are calculated therefrom. The parameter U1000 in table 3 refers to the voltage which is required for a luminance of 1000 cd/m$^2$. EQE1000 denotes the external quantum efficiency which is attained at 1000 cd/m$^2$.

The materials EG1 and EG2 of the invention are used in examples E1 and E2 as matrix material in the emission layer of green-phosphorescing OLEDs.

TABLE 1a

Structure of the OLEDs

| Ex. | HIL thickness | HTL thickness | EBL thickness | EML thickness | HBL thickness | ETL thickness | EIL thickness |
|---|---|---|---|---|---|---|---|
| E1 | HATCN 5 nm | SpMA1 215 nm | SpMA2 20 nm | EG1:IC2:TEG1 (49%:44%:7%) 30 nm | ST2 10 nm | ST2:LiQ (50%:50%) 30 nm | LiQ 1 nm |
| E2 | HATCN 5 nm | SpMA1 215 nm | SpMA2 20 nm | EG2:IC2:TEG1 (49%:44%:7%) 30 nm | ST2 10 nm | ST2:LiQ (50%:50%) 30 nm | LiQ 1 nm |

All materials are applied by thermal vapor deposition in a vacuum chamber. In this case, the emission layer always consists of at least one matrix material (host material) and an emitting dopant (emitter) which is added to the matrix material(s) in a particular proportion by volume by coevaporation. Details given in such a form as EG1:IC2:TEG1 (45%:45%:10%) mean here that the material EG1 is present in the layer in a proportion of 45%, IC2 in a proportion of 45%, and TEG1 in a proportion of 10%. Analogously, the electron transport layer may also consist of a mixture of two materials.

Both compounds of the invention give very good results for external quantum efficiency.

| Ex. | U1000 (V) | EQE 1000 (%) | CIE x/y at 1000 cd/m$^2$ |
|---|---|---|---|
| E1 | 3.6 | 21.1 | 0.36/0.61 |
| E2 | 3.3 | 22 | 0.35/0.61 |

The materials EG1 and EG3 to EG5 of the invention are used in examples E3 to E6 as matrix material in the emission layer of red-phosphorescing OLEDs.

TABLE 1b

Structure of the OLEDs

| Ex. | HIL thickness | HTL thickness | EBL thickness | EML thickness | HBL thickness | ETL thickness | EIL thickness |
|---|---|---|---|---|---|---|---|
| E3 | HATCN 5 nm | SpMA1 125 nm | SpMA2 10 nm | EG1:TER5 (97%:3%) 35 nm | ST2 10 nm | ST2:LiQ (50%:50%) 30 nm | LiQ 1 nm |
| E4 | HATCN 5 nm | SpMA1 125 nm | SpMA2 10 nm | EG3:IC2:TER5 (57%:40%:3%) 35 nm | ST2 10 nm | ST2:LiQ (50%:50%) 30 nm | LiQ 1 nm |
| E5 | HATCN 5 nm | SpMA1 125 nm | SpMA2 10 nm | EG4:IC2:TER5 (57%:40%:3%) 35 nm | ST2 10 nm | ST2:LiQ (50%:50%) 30 nm | LiQ 1 nm |
| E6 | HATCN 5 nm | SpMA1 125 nm | SpMA2 10 nm | EG5:IC2:TER5 (57%:40%:3%) 35 nm | ST2 10 nm | ST2:LiQ (50%:50%) 30 nm | LiQ 1 nm |

All four compounds of the invention give very good results for external quantum efficiency.

| Ex. | U1000 (V) | EQE 1000 (%) | CIE x/y at 1000 cd/m$^2$ |
|---|---|---|---|
| E3 | 3.6 | 24.7 | 0.66/0.34 |
| E4 | 3.7 | 24.1 | 0.66/0.34 |
| E5 | 3.4 | 25.7 | 0.67/0.34 |
| E6 | 3.3 | 25.6 | 0.66/0.34 |

TABLE 2

Structural formulae of the materials for the OLEDs

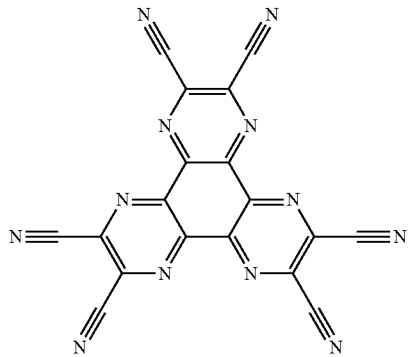 [SMILES: N#Cc1nc2c3nc(C#N)c(C#N)nc3c3nc(C#N)c(C#N)nc3c2nc1C#N]

HATCN

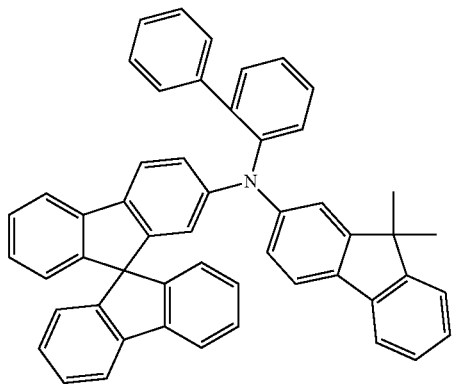 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

SpMA1

TABLE 2-continued
Structural formulae of the materials for the OLEDs
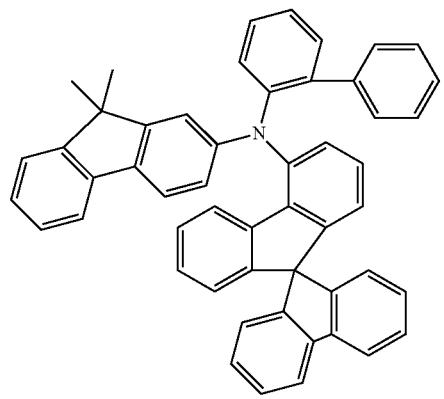 [SMILES: CC1(C)c2ccccc2-c2ccc(N(c3ccccc3-c3ccccc3)c3cccc4c3-c3ccccc3C43c4ccccc4-c4ccccc43)cc21]
SpMA2
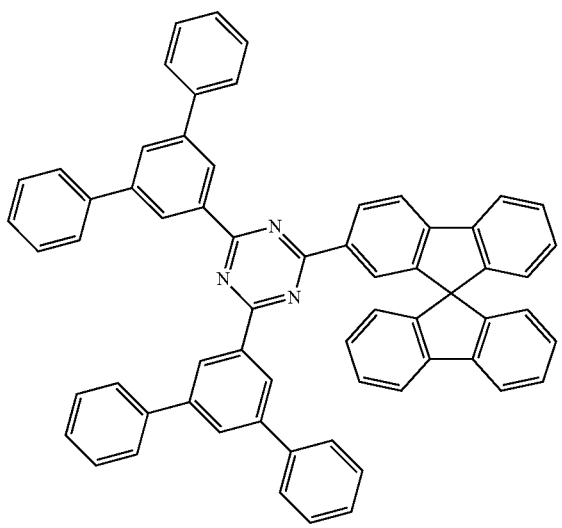 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
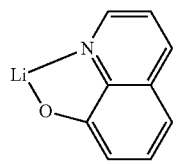
LiQ
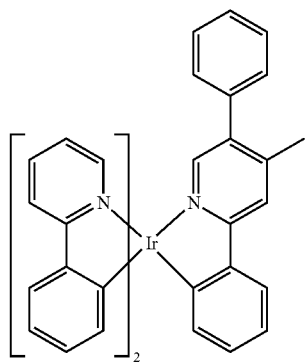
TEG1

TABLE 2-continued
Structural formulae of the materials for the OLEDs
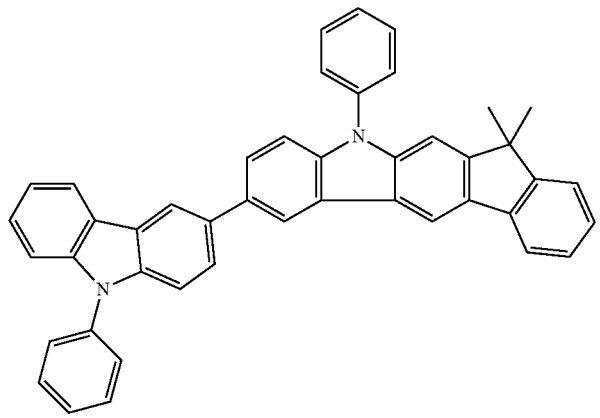 [SMILES: CC1(C)c2ccccc2-c2cc3c4cc(-c5ccc6c(c5)c5ccccc5n6-c5ccccc5)ccc4n(-c4ccccc4)c3cc21]
IC2
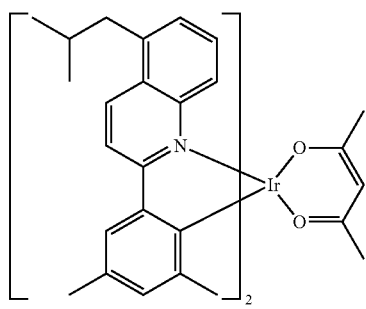
TER5
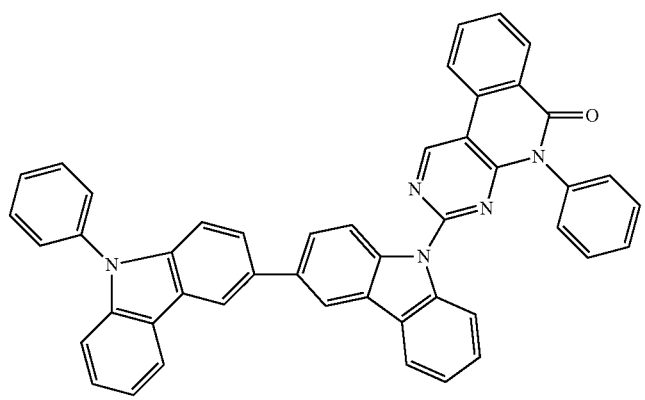 [SMILES: O=c1c2ccccc2c2cnc(-n3c4ccccc4c4cc(-c5ccc6c(c5)c5ccccc5n6-c5ccccc5)ccc43)nc2n1-c1ccccc1]
EG1

TABLE 2-continued
Structural formulae of the materials for the OLEDs
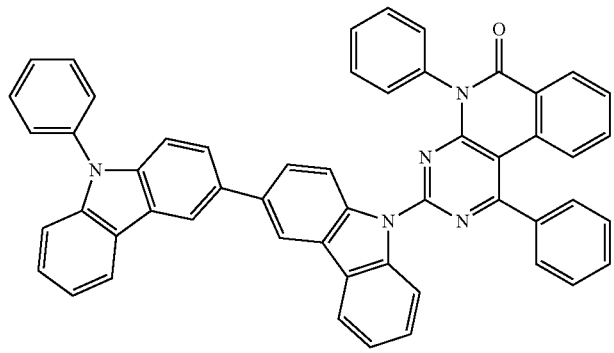 [SMILES: O=c1c2ccccc2c2c(-c3ccccc3)nc(-n3c4ccccc4c4cc(-c5ccc6c(c5)c5ccccc5n6-c5ccccc5)ccc43)nc2n1-c1ccccc1]
EG2
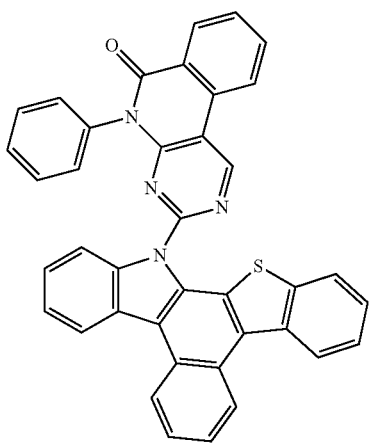 [SMILES: O=c1c2ccccc2c2cnc(-n3c4ccccc4c4c5ccccc5c5c6ccccc6sc5c43)nc2n1-c1ccccc1]
EG3
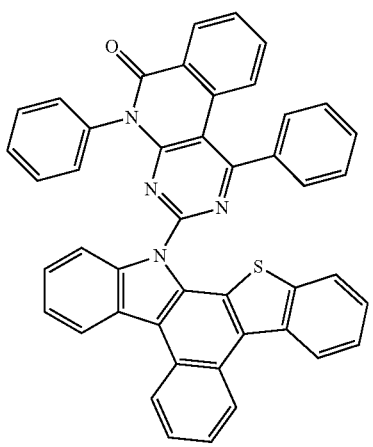 [SMILES: O=c1c2ccccc2c2c(-c3ccccc3)nc(-n3c4ccccc4c4c5ccccc5c5c6ccccc6sc5c43)nc2n1-c1ccccc1]
EG4 (54e)

TABLE 2-continued

Structural formulae of the materials for the OLEDs

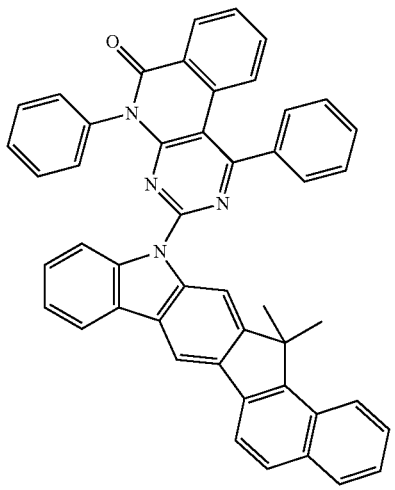 [SMILES: CC1(C)c2cc3c(cc2-c2ccc4ccccc4c21)c1ccccc1n3-c1nc(-c2ccccc2)c2c3ccccc3c(=O)n(-c3ccccc3)c2n1]

EG5 (51e)

The invention claimed is:

1. A compound of a formula (I)

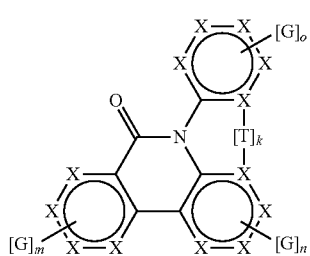

Formula (I)

where

G is the same or different at each instance and is selected from a group of the formula (G-1)

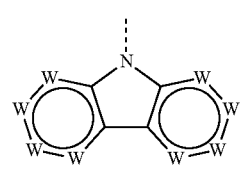

Formula (G-1)

attached via the dotted bond, where, in formula (G-1), W is the same or different at each instance and is $CR^2$ or N; or one or more units from any two adjacent W groups are the same or different at each instance and are selected from units of the formulae (W-1) to (W-2)

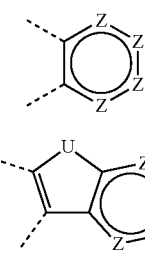

Formula (W-1)

Formula (W-2)

where the dotted bonds represent the bonds to the rest of the formula (G-1);

where U is the same or different at each instance and is selected from O, S, $NR^3$ and $C(R^3)_2$; and where, in formula (W-1) to (W-2), V is the same or different at each instance and is $CR^2$ or N; or one or more units from any two adjacent V groups are the same or different at each instance and are selected from units of the formulae (V-1) to (V-2)

Formula (V-1)

Formula (V-2)

where the dotted bonds represent the bonds to the rest of the formulae (W-1) to (W-2);

where Z is the same or different at each instance and is $CR^2$ or N;

X, when no G or T is bonded thereto, is the same or different at each instance and is N or $CR^1$; and X, when G or T is bonded thereto, is C;

T is a single bond that connects the X groups in question;

$R^1$ is the same or different at each instance and is selected from H, D, F, Cl, Br, I, C(=O)R$^4$, CN, Si(R$^4$)$_3$, N(R$^4$)$_2$, P(=O)(R$^4$)$_2$, OR$^4$, S(=O)R$^4$, S(=O)$_2$R$^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R$^1$ radicals may be joined to one another and may form a ring; where the alkyl, alkoxy, alkenyl and alkynyl groups and the aromatic ring systems and heteroaromatic ring systems are each substituted by R$^4$ radicals; and where one or more CH$_2$ groups in the alkyl, alkoxy, alkenyl and alkynyl groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$;

$R^2$ is the same or different at each instance and is selected from H, D, F, Cl, Br, I, C(=O)R$^4$, CN, Si(R$^4$)$_3$, N(R$^4$)$_2$, P(=O)(R$^4$)$_2$, OR$^4$, S(=O)R$^4$, S(=O)$_2$R$^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R$^2$ radicals may be joined to one another and may form a ring; where the alkyl, alkoxy, alkenyl and alkynyl groups and the aromatic ring systems and heteroaromatic ring systems are each substituted by R$^4$ radicals; and where one or more CH$_2$ groups in the alkyl, alkoxy, alkenyl and alkynyl groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$;

$R^3$ is the same or different at each instance and is selected from H, D, F, Cl, Br, I, CN, Si(R$^4$)$_3$, N(R$^4$)$_2$, straight-chain alkyl groups having 1 to 20 carbon atoms, branched or cyclic alkyl groups having 3 to 20 carbon atoms, aromatic ring systems having 6 to 40 aromatic ring atoms, and heteroaromatic ring systems having 5 to 40 aromatic ring atoms; where two or more R$^3$ radicals may be joined to one another and may form a ring; where the alkyl groups and the aromatic ring systems and heteroaromatic ring systems are each substituted by R$^4$ radicals;

$R^4$ is the same or different at each instance and is selected from H, D, F, Cl, Br, I, C(=O)R$^5$, CN, Si(R$^5$)$_3$, N(R$^5$)$_2$, P(=O)(R$^5$)$_2$, OR$^5$, S(=O) R$^5$, S(=O)$_2$R$^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R$^4$ radicals may be joined to one another and may form a ring; where the alkyl, alkoxy, alkenyl and alkynyl groups and the aromatic ring systems and heteroaromatic ring systems are each substituted by R$^5$ radicals; and where one or more CH$_2$ groups in the alkyl, alkoxy, alkenyl and alkynyl groups may be replaced by —R$^5$C=CR$^5$—, —C≡C—, Si(R$^5$)$_2$, C=O, C=NR$^5$, —C(=O)O—, —C(=O) NR$^5$—, NR$^5$, P(=O)(R$^5$), —O—, —S—, SO or SO$_2$;

$R^5$ is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more R$^5$ radicals may be joined to one another and may form a ring; and where the alkyl, alkoxy, alkenyl and alkynyl groups, aromatic ring systems and heteroaromatic ring systems may be substituted by one or more radicals selected from F and CN;

k is 0 or 1, where, when k is 0, T is absent, and the X groups in question are not bonded to one another;

m, n, o is the same or different at each instance and is selected from 0 and 1, where at least one of the indices m, n and o must be 1;

where at least one X group in at least one of the rings to which a G group is bonded is N.

2. A compound as claimed in claim 1, wherein one, two, three or four, X groups in formula (I) are N.

3. A compound as claimed in claim 1, wherein, in a ring to which a G group binds, exactly one or two, X groups are N.

4. A compound as claimed in claim 1, wherein, in a ring to which a G group binds, one or two X groups adjacent to the bond to G are N.

5. A compound as claimed in claim 1, wherein k is 0.

6. A compound as claimed in claim 1, wherein the sum total of the indices m, n and o is 1.

7. A compound as claimed in claim 1, wherein one of the indices m and n is 1 and the other of the indices m and n is 0, and in that the index o is 0.

8. A compound as claimed in claim 1, wherein in a ring in formula (I) to which a G group binds, all R$^1$ radicals are selected from aromatic ring systems that have 6 to 40 aromatic ring atoms and are substituted by one or more R$^4$ radicals, and heteroaromatic ring systems that have 5 to 40 aromatic ring atoms and are substituted by one or more R$^4$ radicals.

9. A compound as claimed in claim 1, wherein $R^1$ is the same or different at each instance and is selected from H, aromatic ring systems that have 6 to 40 aromatic ring atoms and are substituted by R$^4$ radicals, and heteroaromatic ring systems that have 5 to 40 aromatic ring atoms and are substituted by R$^4$ radicals; and $R^2$ is the same or different at each instance and is selected from H, aromatic ring systems that have 6 to 40 aromatic ring atoms and are substituted by R$^4$ radicals, and heteroaromatic ring systems that have 5 to 40 aromatic ring atoms and are substituted by R$^4$ radicals; and $R^3$ is the same or different at each instance and is selected from H, straight-chain alkyl groups having 1 to 20 carbon atoms, branched or cyclic alkyl groups having 3 to 20 carbon atoms, aromatic ring systems having 6 to 40 aromatic ring atoms, and heteroaromatic ring systems having 5 to 40 aromatic ring atoms; where two R$^3$ radicals that are phenyl substituted by R$^4$ radicals and constituents of a U group that is C (R$^3$)$_2$ may be joined to one another and may form a ring, so as to form a spirobifluorene unit; and where the alkyl groups and the aromatic ring systems and heteroaromatic ring systems are each substituted by R$^4$ radicals; and $R^4$ is the same or different at each instance and is selected from H, aromatic ring systems that have 6 to 40 aromatic ring atoms and are substituted by R$^5$ radicals, and heteroaromatic ring systems that have 5 to 40 aromatic ring atoms and are substituted by $R^5$ radicals.

10. A compound as claimed in claim 1, wherein groups of the formula (G-1) conform to one of the following formulae:

Formula (G-1-1)
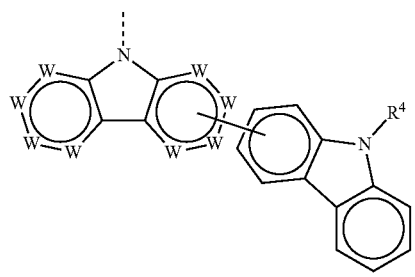

Formula (G-1-2)
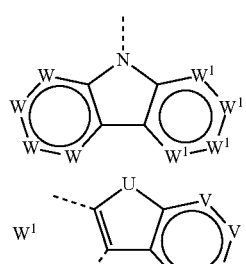
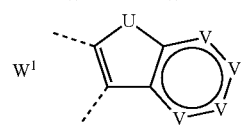

Formula (G-1-3)
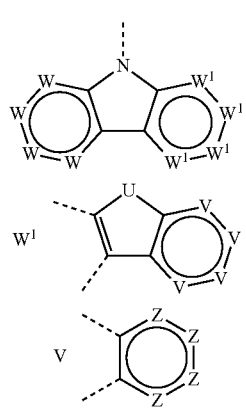

Formula (G-1-4)
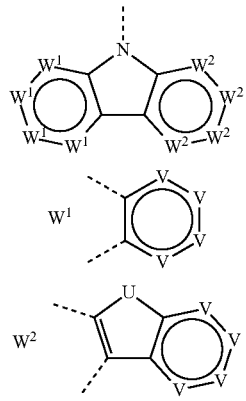

Formula (G-1-5)
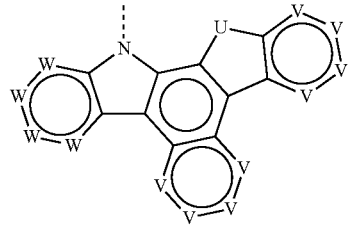

Formula (G-1-6)
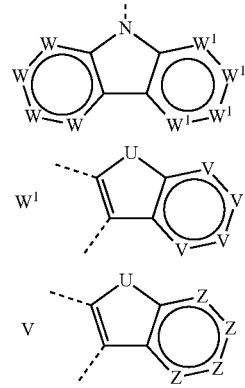

Formula (G-1-7)
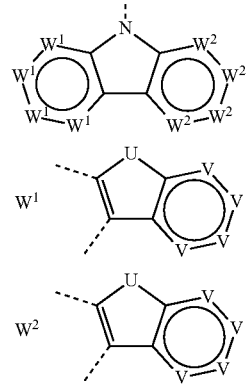

where, in formula (G-1-1), W is as defined in claim 1, and where the positions shown as unsubstituted in formula (G-1-1) are substituted by $R^4$ radicals;

where, in formula (G-1-2), a $W^1$-$W^1$ unit is selected from the lower formula, where the dotted lines are the bonds of the unit to the rest of the formula (G-1-2), and where the remaining $W^1$ groups are the same or different and are selected from $CR^2$ and N; and where W is as defined in claim 1; and where U is as defined in claim 1; and where V is as defined in claim 1;

where, in formula (G-1-3), a $W^1$-$W^1$ unit is selected from the middle formula, where the dotted lines are the bonds of the unit to the rest of the formula (G-1-3), and where the remaining $W^1$ groups are the same or different and are selected from $CR^2$ and N; and where W is as defined in claim 1; and where, in formula (G-1-3), a V-V unit is selected from the lower formula, where the dotted lines are the bonds of the unit to the rest of the formula (G-1-3), and where the remaining V groups are the same or different and are selected from $CR^2$ and N; and where U is as defined in claim 1; and where Z is as defined in claim 1;

where, in formula (G-1-4), a $W^1$-$W^1$ unit is selected from the middle formula, where the dotted lines are the bonds of the unit to the rest of the formula (G-1-4), and where the remaining $W^1$ groups are the same or different and are selected from $CR^2$ and N; and where a $W^2$-$W^2$ unit is selected from the lower formula, where the dotted lines are the bonds of the unit to the rest of the formula (G-1-4), and where the remaining $W^2$ groups are the same or different and are selected from $CR^2$ and N; and where V is as defined in claim 1, and V is preferably the same or different and is selected from $CR^2$ and N; and where U is as defined in claim 1;

where, in formula (G-1-5), W is as defined in claim 1; and where U is as defined in claim 1; and where V is as defined in claim 1;

where, in formula (G-1-6), a $W^1$-$W^1$ unit is selected from the middle formula, where the dotted lines are the bonds of the unit to the rest of the formula (G-1-6), and where the remaining $W^1$ groups are the same or different and are selected from $CR^2$ and N; and where W is as defined in claim 1; and where, in formula (G-1-6), a V-V unit is selected from the lower formula, where the dotted lines are the bonds of the unit to the rest of the formula (G-1-6), and where the remaining V groups are the same or different and are selected from $CR^2$ and N; and where U is as defined in claim 1; and where Z is as defined in claim 1;

where, in formula (G-1-7), a $W^1$-$W^1$ unit is selected from the middle formula, where the dotted lines are the bonds of the unit to the rest of the formula (G-1-7), and where the remaining W groups are the same or different and are selected from $CR^2$ and N; and where, in formula (G-1-7), a $W^2$-$W^2$ unit is selected from the lower formula, where the dotted lines are the bonds of the unit to the rest of the formula (G-1-7), and where the remaining $W^2$ groups are the same or different and are selected from $CR^2$ and N; and where U is as defined in claim 1;

and where V is as defined in claim 1.

11. A compound as claimed in one or more of claims 1 to 10, wherein the compound of the formula (I) corresponds to one of the following formulae:

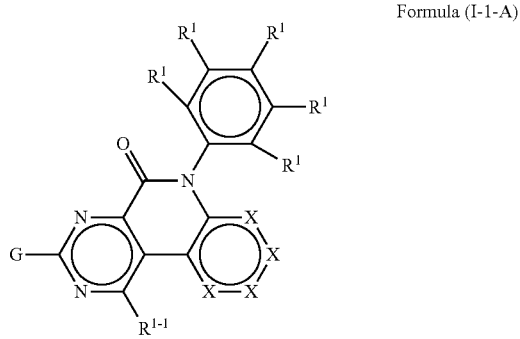

Formula (I-1-A)

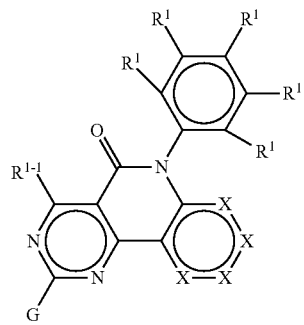

Formula (I-1-B)

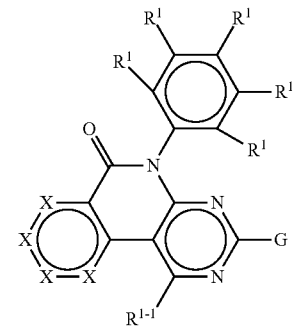

Formula (I-2-A)

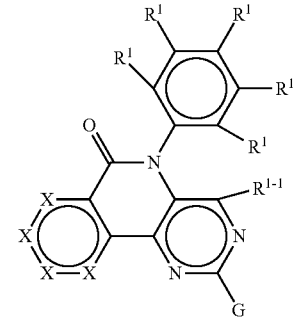

Formula (I-2-B)

where $R^{1-1}$ is as defined for $R^1$.

12. A process for preparing a compound as claimed in claim 1, wherein the process comprises the following steps:
i) preparing a cyclic lactam from two aromatic units by Suzuki coupling and formation of an amide;
ii) Ullmann coupling of an aromatic unit to the nitrogen atom of the lactam group of the cyclic lactam;
iii) nucleophilic substitution of a halogen atom in the lactam base skeleton by the carbazole nitrogen atom of a carbazole derivative.

13. An oligomer, polymer or dendrimer containing one or more compounds of formula (I) as claimed in claim 1, wherein the bond(s) to the polymer, oligomer or dendrimer may be localized at any position substituted by $R^1$ or $R^2$ or $R^3$ in formula (I).

14. A formulation comprising at least one compound as claimed in claim 1, and at least one solvent.

15. An electronic device comprising at least one compound as claimed in claim 1.

16. The electronic device as claimed in claim 15, wherein the device is an organic electroluminescent device and comprises anode, cathode and at least one emitting layer, and wherein the compound is present in an emitting layer together with at least one phosphorescent emitter, or in that the compound is present in a layer selected from hole blocker layers, electron transport layers and electron injection layers.

17. The organic electroluminescent device as claimed in claim 16, wherein the compound is present in an emitting layer of the device together with at least one phosphorescent emitter and at least one further compound, where the further compound is a matrix material.

18. A method comprising incorporating the compound as claimed in claim 1 in an electronic device.

19. A mixture comprising at least one compound as claimed in claim 1 and at least one further compound selected from matrix materials for phosphorescent emitters.

* * * * *